(12) United States Patent
Lou et al.

(10) Patent No.: US 12,024,531 B2
(45) Date of Patent: Jul. 2, 2024

(54) IMMUNOPROTEASOME INHIBITORS

(71) Applicant: Principia Biopharma Inc., South San Francisco, CA (US)

(72) Inventors: Yan Lou, Pleasanton, CA (US); Timothy Duncan Owens, Redwood City, CA (US); Kenneth Albert Brameld, Menlo Park, CA (US); David Michael Goldstein, Redwood City, CA (US)

(73) Assignee: Principia Biopharma Inc., Bridgewater, NJ (US)

( * ) Notice: Subject to any disclaimer, the term of this patent is extended or adjusted under 35 U.S.C. 154(b) by 1060 days.

(21) Appl. No.: 16/764,199

(22) PCT Filed: Nov. 14, 2018

(86) PCT No.: PCT/US2018/061132
§ 371 (c)(1),
(2) Date: May 14, 2020

(87) PCT Pub. No.: WO2019/099576
PCT Pub. Date: May 23, 2019

(65) Prior Publication Data
US 2023/0133165 A1      May 4, 2023

Related U.S. Application Data

(60) Provisional application No. 62/587,375, filed on Nov. 16, 2017.

(51) Int. Cl.
*C07F 5/02*        (2006.01)
(52) U.S. Cl.
CPC .................................. *C07F 5/027* (2013.01)
(58) Field of Classification Search
CPC ....................................................... C07F 5/027
See application file for complete search history.

(56) References Cited

U.S. PATENT DOCUMENTS

| | | | |
|---|---|---|---|
| 4,963,655 A | 10/1990 | Kinder et al. | |
| 11,225,493 B2 | 1/2022 | Lou et al. | |

FOREIGN PATENT DOCUMENTS

| | | | |
|---|---|---|---|
| CA | 2860142 A1 | 6/2013 | |
| CN | 107001391 A | 8/2017 | |
| CN | 111491938 A | 8/2020 | |
| JP | H10510245 A | 10/1998 | |
| JP | 2007502304 A | 2/2007 | |
| KR | 20060120585 A | 11/2006 | |
| KR | 20130016435 A | 2/2013 | |
| WO | WO 95/09634 | 4/1995 | |
| WO | 9613266 A1 | 5/1996 | |
| WO | WO 2005/021558 | 5/2005 | |
| WO | 2005082348 A2 | 9/2005 | |
| WO | 2013092979 A1 | 6/2013 | |
| WO | WO 2016/050358 | 4/2016 | |
| WO | WO 2018/136401 | 7/2018 | |
| WO | WO 2019/099582 | 5/2019 | |

OTHER PUBLICATIONS

Vardiman "The World Health Organization (WHO) classification of the myeloid neoplasms" Blood (2002), 100(7), 2292-2302.*
Huber "A Nut for Every Bolt: Subunit-Selective Inhibitors of the Immunoproteasome and Their Therapeutic Potential" Cells 2021, 10, 1929.*
Pui "Treatment of Acute Lymphoblastic Leukemia" New England Journal of Medicine 2006, 354, 166-78.*
Ettari R"Immunoproteasome-selective and non-selective inhibitors: A promising approach for the treatment of multiple myeloma." Pharmacol Ther (2018) 182:176-92.*
Kisselev "Site-Specific Proteasome Inhibitors" Biomolecules 2022, 12, 54, p. 14 Table 7, CLL see Besse "Immunoproteasome Activity in Chronic Lymphocytic Leukemia as a Target of the Immunoproteasome-Selective Inhibitors" Cells 2022, 11, 838.*
University of Cambridge John van Geest Centre for Brain Repair School of Clinical Medicine "Alzheimer's disease and tauopathy" Online "http://www.brc.cam.ac.uk/research/alzheimers-disease-and-tauopathy/" accessed Sep. 10, 2015.*
Tomohiro Chiba "Emerging Therapeutic Strategies in Alzheimer's Disease" Intech 2013, 181-225.*
Argollo "Novel therapeutic targets for inflammatory bowel disease" Journal of Autoimmunity (2017), 85, 103-116.*
Chaichian "Targeted Therapies in Systemic Lupus Erythematosus: A State-of-the-Art Review" J Clin Cell Immunol 2013, S6, 1-8.*
Mahieu "A critical review of clinical trials in systemic lupus erythematosus" Lupus (2016) 25, 1122-1140.*
Communication dated May 6, 2020 for EP Application No. 18716009.8 (4 pages).
Examination Report dated Jun. 14, 2019 for PK Application No. 0036/2018 (23 pages)
International Preliminary Report on Patentability dated May 19, 2020 for PCT Application No. PCT/US2018/061140 (9 pages).
International Preliminary Report on Patentability dated Jul. 23, 2019 for PCT Application No. PCT/US2018/013823 (8 pages).
International Search Report and Written Opinion dated Jan. 25, 2019 for PCT Application No. PCT/US2018/061140 (28 pages).
International Search Report and Written Opinion dated Jun. 26, 2018 for PCT Application No. PCT/US2018/013823 (15 pages).
Pending U.S. Appl. No. 16/478,788, filed Jul. 17, 2019 (not enclosed).
Pending U.S. Appl. No. 16/764,136, filed May 14, 2020 (not enclosed).

(Continued)

*Primary Examiner* — David K O'Dell
(74) *Attorney, Agent, or Firm* — McNeill Baur PLLC

(57) ABSTRACT

Provided herein are compounds, such as a compound of Formula (I), or a pharmaceutically acceptable salt thereof that are immunoproteasome (such as LMP2 and LMP7) inhibitors. The compounds described herein can be useful for the treatment of diseases treatable by inhibition of immunoproteasomes. Also provided herein are pharmaceutical compositions containing such compounds and processes for preparing such compounds.

21 Claims, No Drawings

(56) References Cited

OTHER PUBLICATIONS

International Search Report and Written Opinion dated Feb. 14, 2019 for PCT Application No. PCT/US2018/061132 filed Nov. 14, 2018, dated Feb. 14, 2019.
International Preliminary Report on Patentability dated May 19, 2020 for PCT Application No. PCT/US2018/061132 filed Nov. 14, 2018, dated Feb. 14, 2019.

* cited by examiner

IMMUNOPROTEASOME INHIBITORS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6., including U.S. Provisional Application No. 62/587,375, filed Nov. 16, 2017. This application is a U.S. national stage filing of International Application No. PCT/US2018/061132, filed Nov. 14, 2018 which claims priority to U.S. Provisional Application No. 62/587,375, filed Nov. 16, 2017, each of which is incorporated by reference in its entirety.

BACKGROUND OF THE DISCLOSURE

In eukaryotes, protein degradation is mediated through the ubiquitin pathway in which proteins targeted for destruction are ligated to the 76 amino acid polypeptide ubiquitin. Ubiquitinated proteins then serve as substrates for the 26S proteasome, a multicatalytic protease, which cleaves proteins into short peptides through the action of its three major proteolytic activities. Proteasome-mediated degradation plays a key role in many processes such as antigen presentation in the context of the major histocompatibility complex (MHC) class I, apoptosis and cell viability, antigen processing, NF-KB activation, and transduction of pro-inflammatory signals.

The 20S proteasome is a 700 kDa cylinder-shaped multicatalytic protease complex comprised of 28 subunits, classified as alpha- and beta-type, that are arranged in 4 stacked heptameric rings. In yeast and other eukaryotes, 7 different subunits form the outer rings and 7 different subunits comprise the inner rings. The alpha subunits serve as binding sites for the 19S and llS regulatory complexes, as well as a physical barrier for the inner proteolytic chamber formed by the two subunit rings. Thus, in vivo, the proteasome is believed to exist as a 26S particle. In vivo experiments have shown that inhibition of the 20S form of the proteasome can be readily correlated to inhibition of the 26S proteasome.

In addition to the constitutive proteasome, which is ubiquitously expressed, there is an alternative complex, the immunoproteasome, which can be found in immune cells and/or in cells exposed to inflammatory cytokines, such as IFN-γ and TNF-α. The immunoproteasome differs from the constitutive proteasome in its subunit composition. It contains subunits with chymotrypsin-like (β5i/LMP7), caspase-like (β1i/LMP2) and trypsin-like (β2i) protease activity that replace their counterparts in the constitutive proteasome (β5c, β1c, and β2c respectively). When all three IFN-γ-inducible subunits are present, the proteasome is referred to as the "immunoproteasome." Thus, eukaryotic cells can possess two forms of proteasomes in varying ratios. The immunoproteasome plays an essential role in the generation of antigenic peptide repertoire and shaping MHC class I restricted CD8+ T cell response (see Basler et al. Immunoproteasomes down-regulate presentation of a subdominant T cell epitope from lymphocytic choriomeningitis virus. *J. Immunol* 173:3925-3934 (2004); Moebius, J., M. et al. 2010. Immunoproteasomes are essential for survival and expansion of T cells in virus-infected mice. Eur J Immunol 40:3439-3449).

The immunoproteasome function is not only limited to MHC class I presentation, but it is also involved in a number of pathological disorders including hematological malignancies, inflammatory and autoimmune diseases. The commercially available proteasome inhibitors Bortezomib and Carfilzomib, which have been validated in multiple myeloma and other diseases, appear to target both the constitutive and immunoproteasomes indiscriminately. This lack of specificity may, in part, explain some of the side effects of these agents. It may, however, be possible to keep the therapeutic efficacies (such as antilymphoma and antimyeloma efficacies) of these immunoproteasomes unchanged, and at the same time, increase the therapeutic index, by selectively targeting the immunoproteasome. Therefore, inhibitors which selectively inhibit the immunoproteasome are of interest.

LMP7/β5i is an essential subunit of the immunoproteasome. It regulates inflammatory cytokine production and immune cell functions beyond its role in the generation of MHC class I-restricted epitopes. A small molecule LMP7 inhibitor, PR-957, has been shown to potently block both human and mouse Th1/17 differentiation (see Muchamuel, T., et al. 2009. A selective inhibitor of the immunoproteasome subunit LMP7 blocks cytokine production and attenuates progression of experimental arthritis. Nat Med 15:781-787; Kalim, K. W., et al. 2012. Immunoproteasome Subunit LMP7 Deficiency and Inhibition Suppresses Th1 and Th17 but Enhances Regulatory T Cell Differentiation. J. Immunol. 189:4182-4293) and B cell effector functions and production of proinflammatory cytokines (IL-6, TNF-α, IL-23) (see Basler, M., et al. 2010. Prevention of experimental colitis by a selective inhibitor of the immunoproteasome. J Immunol 185:634-641). In addition, LMP7 inhibition with PR-957 has been demonstrated to produce therapeutic benefits in several preclinical autoimmune disease models. For example, PR-957 was shown to significantly inhibit disease activity in murine collagen-induced arthritis, including significant reduction of inflammation and bone erosion (see Muchamuel, T., et al. 2009. A selective inhibitor of the immunoproteasome subunit LMP7 blocks cytokine production and attenuates progression of experimental arthritis. Nat Med 15:781-787). PR-957 also reduced plasma cell numbers and anti-dsDNA IgG levels in the MRL/lpr lupus model, and prevented disease progression. (see Ichikawa, H. T., et al. 2012. Beneficial effect of novel proteasome inhibitors in murine lupus via dual inhibition of type I interferon and autoantibody-secreting cells. Arthritis Rheum 64:493-503). In addition, PR-957 reduced inflammation and tissue destruction in a murine DSS-induced colitis model (see Basler, M., et al. 2010. Prevention of experimental colitis by a selective inhibitor of the immunoproteasome. J Immunol 185:634-641). Also, PR-957 has been shown to be efficacious in an autoantibody-driven Hashimoto's thyroiditis model (see Nagayama, Y., et al. 2012. Prophylactic and therapeutic efficacies of a selective inhibitor of the immunoproteasome for Hashimoto's thyroiditis, but not for Graves' hyperthyroidism, in mice. Clin Exp Immunol. 168: 268-273). In addition, LMP7 knockout mice are protected from disease in IBD models (see Basler, M., et al. 2010. Prevention of experimental colitis by a selective inhibitor of the immunoproteasome. J. Immunol. 185:634-641; Kalim, K. W., et al. 2012. Immunoproteasome Subunit LMP7 Deficiency and Inhibition Suppresses Th1 and Th17 but Enhances Regulatory T Cell Differentiation. J Immunol. 189:4182-4293; Schmidt, N., et al. 2010. Targeting the proteasome: partial inhibition of the proteasome by bortezomib or deletion of the immunosubunit LMP7 attenuates experimental colitis. Gut 59:896-906). Additionally, inhibition of LMP7 with the selective inhibitor PR-924 has been shown to inhibit growth of multiple myeloma cell lines and primary patient tumor cells, including those resistant to conventional and novel prior therapies (see Singh, A. V., et al. 2011. PR-924, a Selective Inhibitor of the Immunoproteasome Subunit LMP-7, Blocks Multiple Myeloma Cell Growth both in Vitro and in Vivo. Br J Haematol. 2011 January; 152(2): 155-163).

An additional immunoproteasome subunit LMP2/β1i has been shown to regulate antiviral and innate immune responses in addition to its contribution to antigen processing (see Hensley, S. E., et al. 2010. Unexpected role for the immunoproteasome subunit LMP2 in antiviral humoral and innate immune responses. J. Immunol 184:4115-4122). A small molecule inhibitor, ISPI-001, which preferentially targets LMP2/pli, inhibited in vitro proliferation of peripheral blood mononuclear cells (PBMC) isolated from myeloma patients (see Kuhn, D. J., et al. 2009. Targeted inhibition of the immunoproteasome is a potent strategy against models of multiple myeloma that overcomes resistance to conventional drugs and nonspecific immunoproteasome inhibitors. Blood 113:4667-4676). An additional small molecule inhibitor, UK-101, which selectively targets LMP2/β1i, induced apoptosis of an prostate PC-3 cell line in vitro and significantly suppressed tumor growth in vivo (see Wehenkel, M., et al. 2012. A selective inhibitor of the immunoproteasome subunit LMP2 induced apoptosis in PC-3 cells and suppresses tumor growth in nude mice. Br J Cancer 107:53-62).

WO 2016/050358 A1 discloses inhibitors of LMP7, which are boronic acid derivatives, that can be used for the treatment of autoimmune disorder or hematological malignancies.

WO 2015/195950 A1 discloses inhibitors of LMP7, and methods of treating various diseases using these inhibitors.

SUMMARY OF THE DISCLOSURE

Some embodiments provided herein are directed to a compound of Formula (I):

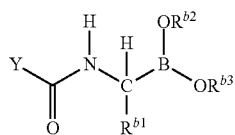

and/or a pharmaceutically acceptable salt thereof, wherein:

Y can be —OR$^2$, —N(R')R$^2$, or a group of formula

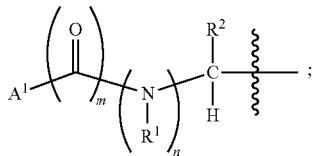

A$^1$ can be hydrogen, hydroxy, optionally substituted alkyl, optionally substituted aryl, optionally substituted heteroaryl, optionally substituted heterocyclyl, or —S(=O)$_2$-alkyl, where said alkyl of said —S(=O)$_2$-alkyl is optionally substituted;

R' can be H or optionally substituted alkyl;

each R$^1$ can be H or optionally substituted alkyl;

each R$^2$ independently can be a group of Formula (a) or (b):

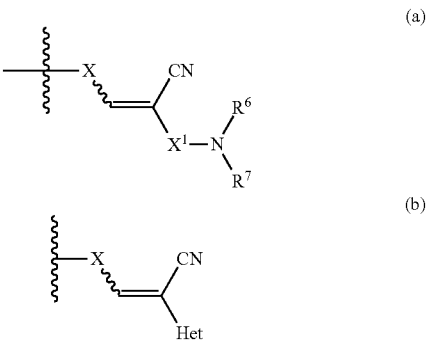

wherein:

each X independently can be -alkyl-, -alkyl-cycloalkyl-, -alkyl-aryl-, -alkyl-heteroaryl-, -alkyl-heterocyclyl-, -alkyl-heterocyclenyl-, -alkyl-O-alkyl-, -alkyl-O-cycloalkyl-, -alkyl-O-aryl-, -alkyl-O-heteroaryl-, -alkyl-O-heterocyclyl-, -alkyl-O-heterocyclenyl-, -alkyl-N(R)-alkyl-, -alkyl-N(R)-cycloalkyl-, -alkyl-N(R)-aryl-, -alkyl-N(R)-heteroaryl-, -alkyl-N(R)-heterocyclyl-, -alkyl-N(R)-heterocyclenyl-, -alkyl-O-alkyl-cycloalkyl-, -alkyl-O-alkyl-aryl-, -alkyl-O-alkyl-heteroaryl-, -alkyl-O-alkyl-heterocyclyl-, -alkyl-O-alkyl-heterocyclenyl-, -alkyl-N(R)-alkyl-cycloalkyl-, -alkyl-N(R)-alkyl-aryl-, -alkyl-N(R)-alkyl-heteroaryl-, -alkyl-N(R)-alkyl-heterocyclyl-, -alkyl-N(R)-alkyl-heterocyclenyl-, -cycloalkyl-aryl-, -heterocyclyl-alkyl-, -heterocyclyl-cycloalkyl-, -heterocyclyl-aryl-, -heterocyclyl-heteroaryl-, -heterocyclyl-heterocyclyl-, -heterocyclyl-heterocyclenyl-, —O-alkyl-, —O-cycloalkyl-, —O-aryl-, —O-heteroaryl-, —O-heterocyclyl-, —O-heterocyclenyl-, —N(R)-alkyl-, —N(R)-cycloalkyl-, —N(R)-aryl-, —N(R)-heteroaryl-, —N(R)— heterocyclyl-, —N(R)-heterocyclenyl-, —O-alkyl-cycloalkyl-, —O-alkyl-aryl-, —O-alkyl-heteroaryl-, —O-alkyl-heterocyclyl-, —O-alkyl-heterocyclenyl-, —N(R)-alkyl-cycloalkyl-, —N(R)-alkyl-aryl-, —N(R)-alkyl-heteroaryl-, —N(R)-alkyl-heterocyclyl-, —N(R)-alkyl-heterocyclenyl-, -aryl-aryl-, or

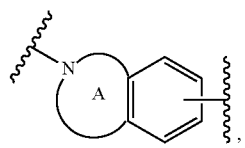

wherein each instance of alkyl, aryl, heteroaryl, cycloalkyl, heterocyclyl, and heterocyclenyl is optionally substituted;

ring A with the ring nitrogen atom shown is an optionally substituted five- to six-membered heterocyclyl that is benzofused as shown, wherein said benzofused ring A is optionally substituted;

X' can be —C(=O)— or —S(=O)$_2$—;

R$^6$ can be hydrogen, optionally substituted alkyl, optionally substituted heterocyclyl, or optionally substituted heteroaryl;

R[7] can be hydrogen, optionally substituted alkyl, optionally substituted cycloalkyl, optionally substituted aryl, optionally substituted heterocyclyl, or optionally substituted heteroaryl; or R[6] and R[7] together with the nitrogen atom to which they are shown attached can form an optionally substituted heterocyclyl or optionally substituted heterocyclenyl;

Het can be an optionally substituted aryl or optionally substituted heteroaryl;

each R independently can be H or optionally substituted alkyl;

R[b1] can be optionally substituted alkyl, optionally substituted aryl, optionally substituted heteroaryl, optionally substituted cycloalkyl, or optionally substituted heterocyclyl;

R[b2] and R[b3] independently can be hydrogen or optionally substituted alkyl; or R[b2] and R[b3] together with the boron atom to which they are shown attached can form a cyclic boronic ester having 2 to 20 carbons, and optionally containing one or two additional cyclic heteroatoms chosen from N, O and S; and m and n independently can be 0 or 1.

Some embodiments described herein also provides a pharmaceutical composition comprising a compound of Formula (I) (or any of the embodiments thereof described herein), and/or a pharmaceutically acceptable salt thereof; and a pharmaceutically acceptable excipient.

Some embodiments described herein also provides a method of treating a disease (such as an autoimmune disease, an inflammatory disease, and/or a hematological disorder), treatable by inhibition of LMP2 and/or LMP7 in a patient which method comprises administering to the patient in need thereof, a therapeutically effective amount of a compound of Formula (I) (or any of the embodiments thereof described herein) and/or a pharmaceutically acceptable salt thereof.

DETAILED DESCRIPTION OF THE DISCLOSURE

Definitions

Unless otherwise stated, the following terms used in the specification and claims are defined for the purposes of this Application and have the following meaning. All undefined technical and scientific terms used in this Application have the meaning as commonly understood by one of ordinary skill in the art.

As used herein, "a" or "an" entity refers to one or more of that entity; for example, a compound refers to one or more compounds or at least one compound unless stated otherwise. As such, the terms "a" (or "an"), "one or more", and "at least one" can be used interchangeably herein.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%.

"Patient" includes both human and animals. "Patient" and "subject" are used interchangeably herein.

"Mammal" means humans and other mammalian animals.

"X" in Formula (I) is read left to right, wherein the right hand point of attachment is connected to the alkenyl moiety of Formula (a) and (b), i.e., to

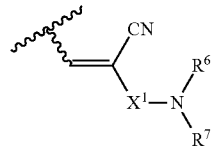

in Formula (a), and to

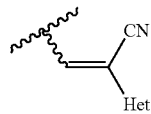

in Formula (b).

"Alkyl" means an aliphatic hydrocarbon group which may be straight or branched and comprising 1 to 20 carbon atoms in the chain. Preferred alkyl groups contain 1 to 12 carbon atoms in the chain. More preferred alkyl groups contain about 1 to 6 carbon atoms in the chain. Branched means that one or more lower alkyl groups such as methyl, ethyl or propyl, are attached to a linear alkyl chain. "Lower alkyl" means a group having about 1 to 6 carbon atoms in the chain which may be straight or branched. "Optionally substituted alkyl" means an alkyl group that can be optionally substituted by one or more (e.g., one, two, or three) substituents which may be the same or different, each substituent being independently chosen from halo, optionally substituted aryl, optionally substituted heterocyclyl, optionally substituted heterocyclenyl, optionally substituted heteroaryl, optionally substituted cycloalkyl, optionally substituted cycloalkenyl, cyano, hydroxy, alkoxy, aryloxy, heteroaryloxy, cycloalkyloxy, alkylthio, amino, oxime (e.g., =N—OH), —NH(alkyl), —NH(aryl), —N(alkyl)(aryl), —NH(heteroaryl), —N(alkyl)(heteroaryl), —NH(cycloalkyl), —N(alkyl)$_2$, —NH—C(=O)-alkyl, —N(alkyl)-C(=O)-alkyl, —NH—C(=O)-aryl, —N(alkyl)-C(=O)-aryl, —NH—C(=O)-cycloalkyl, —N(alkyl)-C(=O)-cycloalkyl, —O—C(O)-alkyl, —O—C(O)-aryl, —O—C(O)-cycloalkyl, —SF$_5$, carboxy and —C(O)O-alkyl. Non-limiting examples of suitable alkyl groups include methyl, ethyl, n-propyl, isopropyl, n-butyl, iso-butyl, and t-butyl.

"Alkenyl" means an aliphatic hydrocarbon group containing at least one carbon-carbon double bond, which may be straight or branched, and comprising about 2 to about 15 carbon atoms in the chain. Preferred alkenyl groups have 2 to 12 carbon atoms in the chain; and more preferably 2 to 6 carbon atoms in the chain. Branched means that one or more lower alkyl groups such as methyl, ethyl or propyl, are attached to a linear alkenyl chain. "Lower alkenyl" means 2 to 6 carbon atoms in the chain which may be straight or branched. "Optionally substituted alkenyl" means an alkenyl group that can be optionally substituted by one or more (e.g., one, two or three) substituents which may be the same or different, each substituent being independently chosen from halo, optionally substituted aryl, optionally substituted cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond, which may be straight or branched, and comprising 2 to 15 carbon atoms in the chain. Preferred alkynyl groups have 2 to 12 carbon atoms in the chain; and more preferably 2 to 4 carbon atoms in the chain. Branched means that one or more lower alkyl groups such as methyl, ethyl or propyl, are attached to a linear alkynyl chain. "Lower alkynyl" means 2 to 6 carbon atoms in the chain which may be straight or branched. "Optionally substituted alkynyl" means an alkynyl group which can be optionally substituted by one or more (e.g., one or two) substituents which may be the same or different, each substituent being independently chosen from aryl and cycloalkyl. Non-limiting examples of suitable alkynyl groups include ethynyl, propynyl, 2-butynyl and 3-methylbutynyl.

"Aryl" means an aromatic monocyclic or multicyclic (e.g., bicyclic, tricyclic) ring system comprising 6 to 14 carbon atoms, preferably 6 to 10 carbon atoms. "Optionally substituted aryl" means an aryl group which can be optionally substituted with one or more (e.g., one, two, three, or four) "ring system substituents" which may be the same or different, and are as defined herein. Non-limiting examples of suitable aryl groups include phenyl and naphthyl.

"Heteroaryl" means an aromatic monocyclic or multicyclic (e.g., bicyclic, tricyclic) ring system comprising 5 to 14 ring atoms, preferably 5 to 10 ring atoms, in which one or more of the ring atoms is an element other than carbon, for example, nitrogen, oxygen or sulfur, alone or in combination. Preferred heteroaryls contain 5 to 6 ring atoms. "Optionally substituted heteroaryl" means a heteroaryl group which can be optionally substituted by one or more (e.g., one, two, three, or four) "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, 1H-Indazolyl azaindolyl, benzimidazolyl, benzothienyl, quinolinyl, isoquinolinyl, imidazolyl, thienopyridyl, quinazolinyl, quinoxalinyl, phthalazinyl, naphthrydinyl, thienopyrimidyl, pyrrolopyridyl, imidazopyridyl, isoquinolinyl, benzoazaindolyl, 1,2,4-triazinyl, benzothiazolyl and the like. "Heteroaryl" also includes a heteroaryl ring as described above wherein an oxo (=O) group is also part of the ring, provided the ring is aromatic. For example,

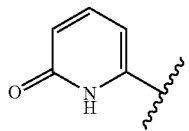 [SMILES: *c1cccc(=O)[nH]1]

is a heteroaryl group.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Cycloalkyl" means a non-aromatic mono- or multicyclic (e.g., bicyclic, tricyclic) ring system comprising 3 to 10 carbon atoms, preferably 5 to 10 carbon atoms. Preferred cycloalkyl rings contain 5 to 7 ring atoms. "Optionally substituted cycloalkyl" means a cycloalkyl group which can be optionally substituted with one or more (e.g., one, two, three, or four) "ring system substituents" which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkenyl" means a non-aromatic mono or multicyclic (e.g., bicyclic, tricyclic) ring system comprising 3 to 10 carbon atoms, preferably 5 to 10 carbon atoms which contains at least one carbon-carbon double bond. Preferred cycloalkenyl rings contain 5 to 7 ring atoms. "Optionally substituted cycloalkenyl" means a cycloalkenyl group which can be optionally substituted with one or more (e.g., one, two, three, or four) "ring system substituents" which may be the same or different, and are as defined herein. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Halogen" or "Halo" means fluorine, chlorine, bromine, or iodine. Preferred are fluorine, chlorine and bromine.

"Haloalkyl" means alkyl radical as defined above, which is substituted with one or more halogen atoms, preferably one to five halogen atoms, preferably fluorine or chlorine, including those substituted with different halogens, e.g., —CH$_2$Cl, —CF$_3$, —CHF$_2$, —CClF$_2$, —CH$_2$CF$_3$, —CF$_2$CF$_3$, —CF(CH$_3$)$_2$, and the like. When the alkyl is substituted with only fluoro, it can be referred to in this Application as fluoroalkyl.

"Hydroxyalkyl" means a HO-alkyl- group in which alkyl is as previously described. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Cycloalkyloxy" means a cycloalkyl-O— group in which the cycloalkyl group is as previously described. Non-limiting examples of suitable cycloalkyloxy groups include cyclopentyloxy and cyclohexyloxy. The bond to the parent moiety is through the ether oxygen.

"Heteroaryloxy" means a heteroaryl-O— group in which the heteroaryl group is as previously described. Non-limiting examples of suitable heteroaryloxy groups include pyridyloxy and thiophenyloxy. The bond to the parent moiety is through the ether oxygen.

"Heterocyclyloxy" means a heterocyclyl-O— group in which the heterocyclyl group is as described herein. Non-limiting examples of suitable heterocyclyloxy groups include piperazinyloxy and morpholinyloxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—C(=O)— group in which the alkyl group is as previously described. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(=O)— group in which the aryl group is as previously described. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(=O)— group in which the aralkyl group is as previously described. Non-limiting example of a suitable aralkoxycarbonyl group is benzyloxycarbonyl. The bond to the parent moiety is through the carbonyl.

"Alkylsulfonyl" means an alkyl-S(=O)$_2$— group in which the alkyl group is as previously described. Preferred groups are those in which the alkyl group is lower alkyl. The bond to the parent moiety is through the sulfonyl.

"Arylsulfonyl" means an aryl-S(O$_2$)— group in which the aryl group is as previously described. The bond to the parent moiety is through the sulfonyl.

"Ring system substituent" means a substituent attached to an aromatic or non-aromatic ring system (for example, cycloalkyl, cycloalkenyl, aryl, heteroaryl, heterocyclyl, heterocyclenyl) which, for example, replaces an available hydrogen on the ring system. Ring system substituents may be the same or different, each being independently chosen from alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, alkoxyalkyl, aryloxy, heteroaryloxy, cycloalkyloxy, aralkoxy, acyl, aroyl, halo, haloalkyl, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SF$_5$, —OSF$_5$ (for aryl), —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(O)NY$_1$Y$_2$, —SO$_2$NY$_1$Y$_2$ and —SO$_2$NY$_1$Y$_2$, wherein Y$_1$ and Y$_2$ can be the same or different and are independently chosen from hydrogen, alkyl, aryl, heteroaryl, cycloalkyl, and aralkyl. "Ring system substituent" may also mean a single moiety which simultaneously replaces two available hydrogens on two adjacent carbon atoms (one H on each carbon, and form a fused ring) or replaces two available hydrogens on a single carbon atom (i.e., a spiro ring or an oxo (=O) group) on a ring system. Examples of the former, i.e., a moiety replacing two hydrogens on adjacent carbon atoms are methylene dioxy, ethylenedioxy, —C(CH$_3$)$_2$— and the like which form moieties such as, for example:

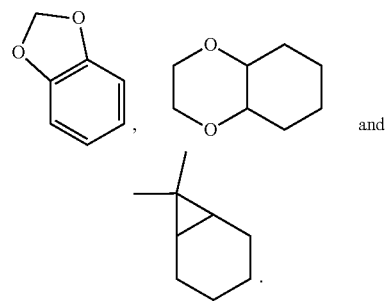

An example of the latter, i.e., a moiety replacing two hydrogens on a single carbon atom (i.e., spiro ring) is

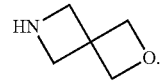

"Heterocyclyl" means a non-aromatic saturated monocyclic or multicyclic (e.g., bicyclic, tricyclic) ring system comprising 3 to 10 ring atoms, preferably 4 to 7 ring atoms, or 5 to 10 ring atoms, in which one or more of the atoms in the ring system is an element other than carbon, for example, nitrogen, oxygen or sulfur, alone or in combination. There are no adjacent oxygen and/or sulfur atoms present in the ring system. Preferred heterocyclyls contain 4 to 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; and are part of the heterocyclyl. "Optionally substituted heterocyclyl" means a heterocyclyl group which can be optionally substituted by one or more (e.g., one, two, three, or four) "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidinyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom.

"Heterocyclenyl" means a non-aromatic monocyclic or multicyclic (e.g., bicyclic, tricyclic) ring system comprising 3 to 10 ring atoms, preferably 5 to 10 ring atoms, in which one or more of the atoms in the ring system is an element other than carbon, for example, nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain 5 to 6 ring atoms. The prefix aza, oxa or thia before the heterocyclenyl root name means that at least a nitrogen, oxygen or sulfur atom respectively is present as a ring atom. "Optionally substituted heterocyclenyl" means a heterocyclenyl group which can be optionally substituted by one or more (e.g., one, two, three, or four) ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom.

It should be noted that in hetero-atom containing ring systems described herein, there are no hydroxyl groups on carbon atoms adjacent to a N, O or S, as well as there are no N or S groups on carbon adjacent to another heteroatom. Thus, for example, in the ring:

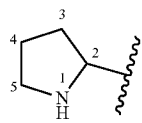

there is no —OH attached directly to carbons marked 2 and 5.

It should also be noted that tautomeric forms such as, for example, the moieties:

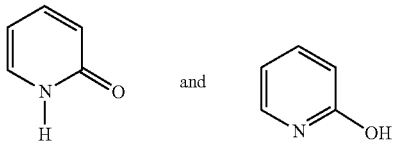 [SMILES: O=c1cccc[nH]1 ; Oc1ccccn1]

are considered equivalent unless otherwise specified.

As used herein, the structure

indicates that the configuration of groups on the double bond can be either E or Z. Thus, for example,

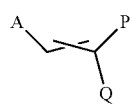

has the same meaning as

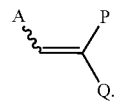

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution (i.e., unsubstituted or substituted) with the specified groups, radicals or moieties. When a list of optional substituents is not explicitly provided, the optional substituents provided in the definitions of various terms (such as "alkyl", "cycloalkyl", "heterocyclyl", "aryl", and "heteroaryl") are to be used.

As used herein, the term "composition" is intended to encompass a product comprising the specified ingredients in the specified amounts, as well as any product which results, directly or indirectly, from combination of the specified ingredients in the specified amounts.

"Effective amount" or "therapeutically effective amount" is meant to describe an amount of compound or a composition described herein that is effective in inhibiting the above-noted diseases and thus producing the desired therapeutic, ameliorative, inhibitory and/or preventative effect.

Unless otherwise specified, reference to an Embodiment number refers to all the subparts of the Embodiment. Thus for example, reference to "Embodiment 12", refers to Embodiment 12, as well as Embodiments 9A-9J. However, this construction does not apply to a subpart within an Embodiment. Thus, for example, reference to "Embodiment 9" in Embodiment 9G only refers to "Embodiment 9" and not to Embodiments 9, and 9A-I unless specified otherwise.

EMBODIMENTS

Examples of embodiments of the present application include the following:

Embodiment 1

A compound of Formula (I):

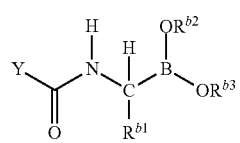

and/or a pharmaceutically acceptable salt thereof, wherein:

Y is —OR², —N(R')R², or a group of formula

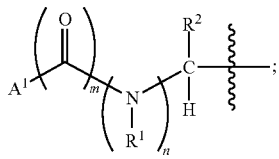

$A^1$ is hydrogen, hydroxy, optionally substituted alkyl, optionally substituted aryl, optionally substituted heteroaryl, optionally substituted heterocyclyl, or —S(=O)₂-alkyl, where said alkyl of said —S(=O)₂-alkyl is optionally substituted;

R' is H or optionally substituted alkyl;

each $R^1$ is H or optionally substituted alkyl;

each $R^2$ independently is a group of Formula (a) or (b):

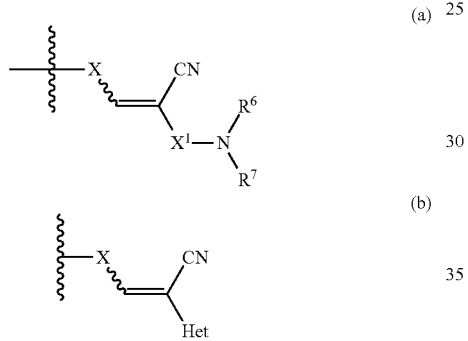

wherein:

each X independently is -alkyl-, -alkyl-cycloalkyl-, -alkyl-aryl-, -alkyl-heteroaryl-, -alkyl-heterocyclyl-, -alkyl-heterocyclenyl-, -alkyl-O-alkyl-, -alkyl-O-cycloalkyl-, -alkyl-O-aryl-, -alkyl-O-heteroaryl-, -alkyl-O-heterocyclyl-, -alkyl-O-heterocyclenyl-, -alkyl-N(R)-alkyl-, -alkyl-N(R)-cycloalkyl-, -alkyl-N(R)-aryl-, -alkyl-N(R)-heteroaryl-, -alkyl-N(R)-heterocyclyl-, -alkyl-N(R)-heterocyclenyl-, -alkyl-O-alkyl-cycloalkyl-, -alkyl-O-alkyl-aryl-, -alkyl-O-alkyl-heteroaryl-, -alkyl-O-alkyl-heterocyclyl-, -alkyl-O-alkyl-heterocyclenyl-, -alkyl-N(R)-alkyl-cycloalkyl-, -alkyl-N(R)-alkyl-aryl-, -alkyl-N(R)-alkyl-heteroaryl-, -alkyl-N(R)-alkyl-heterocyclyl-, -alkyl-N(R)-alkyl-heterocyclenyl-, -cycloalkyl-aryl-, -heterocyclyl-alkyl-, -heterocyclyl-cycloalkyl-, -heterocyclyl-aryl-, -heterocyclyl-heteroaryl-, -heterocyclyl-heterocyclyl-, -heterocyclyl-heterocyclenyl-, —O-alkyl-, —O-cycloalkyl-, —O-aryl-, —O-heteroaryl-, —O-heterocyclyl-, —O-heterocyclenyl-, —N(R)-alkyl-, —N(R)-cycloalkyl-, —N(R)-aryl-, —N(R)-heteroaryl-, —N(R)— heterocyclyl-, —N(R)-heterocyclenyl-, —O-alkyl-cycloalkyl-, —O-alkyl-aryl-, —O-alkyl-heteroaryl-, —O-alkyl-heterocyclyl-, —O-alkyl-heterocyclenyl-, —N(R)-alkyl-cycloalkyl-, —N(R)-alkyl-aryl-, —N(R)-alkyl-heteroaryl-, —N(R)-alkyl-heterocyclyl-, —N(R)-alkyl-heterocyclenyl-, -aryl-aryl-, or

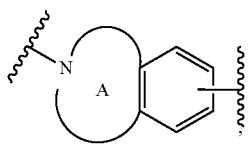

wherein each instance of alkyl, aryl, heteroaryl, cycloalkyl, heterocyclyl, and heterocyclenyl is optionally substituted;

ring A with the ring nitrogen atom shown is an optionally substituted five- to six-membered heterocyclyl that is benzofused as shown, wherein said benzofused ring A is optionally substituted;

$X^1$ is —C(=O)— or —S(=O)₂—;

$R^6$ is hydrogen, optionally substituted alkyl, optionally substituted heterocyclyl, or optionally substituted heteroaryl;

$R^7$ is hydrogen, optionally substituted alkyl, optionally substituted cycloalkyl, optionally substituted aryl, optionally substituted heterocyclyl, or optionally substituted heteroaryl; or $R^6$ and $R^7$ together with the nitrogen atom to which they are shown attached form an optionally substituted heterocyclyl or optionally substituted heterocyclenyl;

Het is an optionally substituted aryl or optionally substituted heteroaryl;

each R independently is H or optionally substituted alkyl;

$R^{b1}$ is optionally substituted alkyl, optionally substituted aryl, optionally substituted heteroaryl, optionally substituted cycloalkyl, or optionally substituted heterocyclyl;

$R^{b2}$ and $R^{b3}$ are independently hydrogen or optionally substituted alkyl; or $R^{b2}$ and $R^{b3}$ together with the boron atom to which they are shown attached form a cyclic boronic ester having 2 to 20 carbons, and optionally containing one or two additional cyclic heteroatoms chosen from N, O and S; and m and n are independently 0 or 1.

Embodiment 2

A compound of Formula (I'):

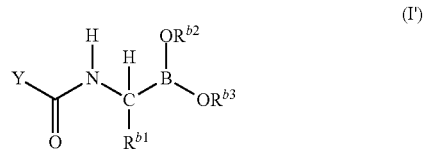

and/or a pharmaceutically acceptable salt thereof, wherein:

Y is —OR², —N(R')R², or a group of formula

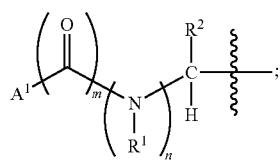

$A^1$ is hydrogen, hydroxy, alkyl, aryl, heteroaryl, heterocyclyl, or —S(=O)$_2$-alkyl, wherein each of said aryl, heteroaryl, and heterocyclyl is optionally substituted with 1-3 substituents independently chosen from halo, hydroxy, alkyl, alkoxy, cyano, haloalkyl, —NH$_2$, —NH(alkyl), —N(alkyl)$_2$, heterocyclyl, aryl, and heteroaryl, and wherein said alkyl and the "alkyl" portion of said —S(=O)$_2$-alkyl is optionally substituted with 1-3 substituents independently chosen from halo, hydroxy, alkoxy, cyano, —NH$_2$, —NH(alkyl), —N(alkyl)$_2$, heterocyclyl, aryl, and heteroaryl;

R' is H or alkyl;

each $R^1$ is H or alkyl;

each $R^2$ independently is a group of Formula (a) or (b):

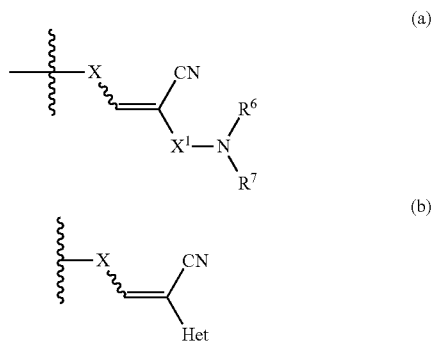

wherein:

each X independently is -alkyl-aryl-, -alkyl-O-aryl-, or

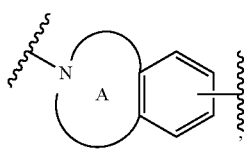

wherein the "aryl" portion of each of said -alkyl-aryl- and -alkyl-O-aryl- is optionally independently substituted with 1-2 substituents chosen from halo, alkoxy, hydoxyalkyl, and cyano;

ring A with the ring nitrogen atom shown is a five- to six-membered heterocyclyl that is benzofused as shown;

$X^1$ is —C(=O)— or —S(=O)$_2$—;

$R^6$ is hydrogen, alkyl, or heterocyclyl;

$R^7$ is alkyl which is optionally substituted with 1-2 substituents chosen from halo and alkoxy; heterocyclyl; or aryl; or $R^6$ and $R^7$ together with the nitrogen atom to which they are shown attached form a heterocyclyl which is optionally substituted with 1-2 substituents chosen from alkyl and heterocyclyl;

Het is a heteroaryl which is optionally substituted with 1-2 substituents chosen from halo, haloalkyl, alkoxy, and cyano;

$R^{b1}$ is alkyl which is optionally substituted with an aryl or heteroaryl, wherein each of said aryl or heteroaryl is optionally substituted with 1-2 substituents chosen from halo, hydroxy, alkyl, alkoxy, cyano, haloalkyl, —NH$_2$, —NH(alkyl), and —N(alkyl)$_2$; and $R^{b2}$ and $R^{b3}$ are independently hydrogen; and m and n are independently 0 or 1.

Embodiment 3

The compound and/or a pharmaceutically acceptable salt thereof of embodiment 1 or 2, wherein Y is

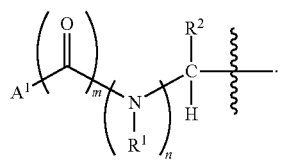

Embodiment 4

The compound and/or a pharmaceutically acceptable salt thereof of Embodiment 1 or 2, wherein Y is OR$^2$.

Embodiment 5

The compound and/or a pharmaceutically acceptable salt thereof of Embodiment 1 or 2, wherein Y is —N(R')R$^2$.

Embodiment 6

The compound and/or a pharmaceutically acceptable salt thereof of Embodiment 3, wherein m and n are each 0.

Embodiment 7

The compound and/or a pharmaceutically acceptable salt thereof of Embodiment 3, wherein m and n are each 1.

Embodiment 8

The compound and/or a pharmaceutically acceptable salt thereof of Embodiment 3, wherein m is 0 and n is 1.

Embodiment 9

The compound and/or pharmaceutically acceptable salt of Embodiment 6, wherein $A^1$ is H.

Embodiment 10

The compound and/or pharmaceutically acceptable salt of Embodiment 7 or 8, wherein $A^1$ is alkyl, aryl or heteroaryl, each of which is optionally independently substituted with 1-3 substituents independently chosen from halo, hydroxy, alkyl, alkoxy, cyano, haloalkyl, —NH$_2$, —NH(alkyl), —N(alkyl)$_2$, optionally substituted heterocyclyl, optionally substituted aryl, and optionally substituted heteroaryl.

Embodiment 10A

The compound and/or pharmaceutically acceptable salt of Embodiment 10, wherein $A^1$ is alkyl, which is optionally independently substituted with 1-3 substituents independently chosen from halo, hydroxy, alkoxy, cyano, —NH$_2$, —NH(alkyl), —N(alkyl)$_2$, optionally substituted heterocyclyl, optionally substituted aryl, and optionally substituted heteroaryl.

Embodiment 10B

The compound and/or pharmaceutically acceptable salt of Embodiment 10A, wherein A$^1$ is alkyl, which is optionally substituted with one to three halo substituents.

Embodiment 10C

The compound and/or pharmaceutically acceptable salt of Embodiment 10B, wherein said optionally substituted alkyl of A$^1$ is —CH$_2$CF$_3$.

Embodiment 10D

The compound and/or pharmaceutically acceptable salt of Embodiment 10, wherein said A$^1$ is aryl, which is optionally substituted with 1-3 substituents chosen from halo, hydroxy, alkyl, alkoxy, cyano, haloalkyl, —NH$_2$, —NH(alkyl), —N(alkyl)$_2$, heterocyclyl, aryl, and heteroaryl.

Embodiment 10E

The compound and/or pharmaceutically acceptable salt of Embodiment 10D, wherein said aryl of A$^1$ is phenyl, which is optionally substituted with 1-3 substituents chosen from halo, hydroxy, alkyl, alkoxy, cyano, haloalkyl, —NH$_2$, —NH(alkyl), —N(alkyl)$_2$, optionally substituted heterocyclyl, optionally substituted aryl, and optionally substituted heteroaryl.

Embodiment 10F

The compound and/or pharmaceutically acceptable salt of Embodiment 10E, wherein said aryl of A$^1$ is 2,5-dichlorophenyl.

Embodiment 10G

The compound and/or pharmaceutically acceptable salt of Embodiment 10, wherein said A$^1$ is heteroaryl, which is optionally substituted with 1-3 substituents chosen from halo, hydroxy, alkyl, alkoxy, cyano, haloalkyl, —NH$_2$, —NH(alkyl), —N(alkyl)$_2$, heterocyclyl, aryl, and heteroaryl.

Embodiment 10H

The compound and/or pharmaceutically acceptable salt of Embodiment 10G, wherein said heteroaryl of A$^1$ is a 4-6 membered monocyclic heteroaryl, which is optionally substituted with 1-3 substituents chosen from halo, hydroxy, alkyl, alkoxy, cyano, haloalkyl, —NH$_2$, —NH(alkyl), —N(alkyl)$_2$, heterocyclyl, aryl, and heteroaryl.

Embodiment 10I

The compound and/or pharmaceutically acceptable salt of Embodiment 10H, wherein said heteroaryl of A$^1$ is 2-pyrazinyl.

Embodiment 10J

The compound and/or pharmaceutically acceptable salt of Embodiment 10G, wherein said heteroaryl of A$^1$ is a multicyclic (e.g., bicyclic, tricyclic) heteroaryl.

Embodiment 11

The compound and/or pharmaceutically acceptable salt of any of Embodiments 1-10, wherein R$^2$ is a group of Formula (a).

Embodiment 12

The compound and/or pharmaceutically acceptable salt of any of Embodiments 1-10, wherein R$^2$ is a group of Formula (b).

Embodiment 13

The compound and/or pharmaceutically acceptable salt of any of Embodiments 1, and 3-12, wherein each X independently is -alkyl-O-aryl-, -alkyl-aryl-, -alkyl-O-alkyl-aryl-, -alkyl-O-heteroaryl-, -alkyl-heteroaryl-, -alkyl-O-alkyl-heteroaryl-, -alkyl-N(R)-aryl-, -alkyl-N(R)-alkyl-aryl-, -alkyl-N(R)-heteroaryl-, -alkyl-N(R)-alkyl-heteroaryl-, —O-alkyl-aryl-, —O-alkyl-heteroaryl-, —N(R)-alkyl-aryl-, -cycloalkyl-aryl-, -heterocyclyl-aryl-, -aryl-aryl-, -alkyl-heterocyclyl-, -alkyl-heterocyclenyl, or

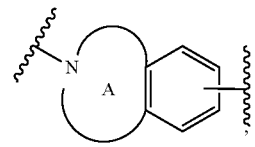

wherein each instance of alkyl, aryl, heteroaryl, cycloalkyl, heterocyclyl, and heterocyclenyl is optionally substituted, and said benzofused ring A is optionally substituted.

Embodiment 13A

The compound and/or pharmaceutically acceptable salt of Embodiment 2 or 13, wherein X is -alkyl-O-aryl-, wherein each of said alkyl and aryl of said -alkyl-O-aryl- is optionally substituted; and when said -aryl- of -alkyl-O-aryl- has two adjacent substituents, said substituents together with the carbon atoms to which they are attached form an optionally substituted five- or six-membered heteroaryl.

Embodiment 13B

The compound and/or pharmaceutically acceptable salt of Embodiment 13A, wherein said -alkyl-O-aryl- of X is —(CH$_2$)$_{1-2}$—O-phenyl-,

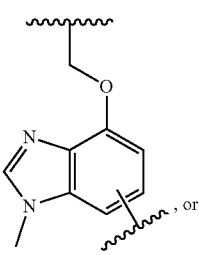

, or

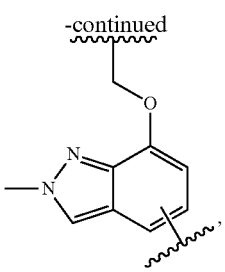

wherein each phenyl of X is optionally substituted.

Embodiment 13C

The compound and/or pharmaceutically acceptable salt of Embodiment 13B, wherein each phenyl of each X is optionally independently substituted with 1-3 substituents chosen from alkyl, halo, cyano, haloalkyl, and alkoxy.

Embodiment 13D

The compound and/or pharmaceutically acceptable salt of Embodiment 13, wherein X is -alkyl-aryl-, wherein each of said alkyl and aryl of said -alkyl-aryl- is optionally substituted.

Embodiment 13E

The compound and/or pharmaceutically acceptable salt of Embodiment 13D, wherein said -alkyl-aryl- of X is —$(CH_2)_{1-2}$-phenyl-.

Embodiment 13F

The compound and/or pharmaceutically acceptable salt of Embodiments 13, wherein X is -alkyl-O-alkyl-aryl-, wherein each of said alkyl and aryl is optionally substituted.

Embodiment 13G

The compound and/or pharmaceutically acceptable salt of Embodiment 13F, wherein said -alkyl-O-alkyl-aryl- of X is —$(CH_2)_{1-2}$—O—$(CH_2)_{1-2}$-phenyl-.

Embodiment 13H

The compound and/or pharmaceutically acceptable salt of Embodiment 13, wherein X is -alkyl-O-heteroaryl-, wherein each of said alkyl and heteroaryl is optionally substituted.

Embodiment 13I

The compound and/or pharmaceutically acceptable salt of Embodiment 13H, wherein said -alkyl-O-heteroaryl- of X is —$(CH_2)_{1-2}$—O-pyridyl, wherein said pyridyl is optionally substituted.

Embodiment 13J

The compound and/or pharmaceutically acceptable salt of Embodiment 13H, wherein said —$(CH_2)_{1-2}$—O-pyridyl- is or

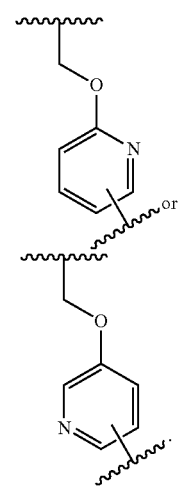

Embodiment 13K

The compound and/or pharmaceutically acceptable salt of Embodiment 13, wherein X is -alkyl-N(R)-aryl-, wherein each of said alkyl and aryl is optionally substituted, and R is hydrogen or alkyl.

Embodiment 13L

The compound and/or pharmaceutically acceptable salt of Embodiment 13K, wherein said -alkyl-N(R)-aryl- is —$(CH_2)_{1-2}$—N(R)-phenyl, wherein said phenyl is optionally substituted, and R is hydrogen or alkyl.

Embodiment 13M

The compound and/or pharmaceutically acceptable salt of Embodiment 13L, wherein said —$(CH_2)_{1-2}$—N(R)-phenyl- is

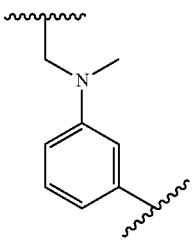 [SMILES: *CN(C)c1cccc(*)c1]

wherein said phenyl is optionally substituted.

Embodiment 13N

The compound and/or pharmaceutically acceptable salt of Embodiment 13, wherein X is —O-alkyl-aryl-, wherein each of said alkyl and aryl is optionally substituted.

Embodiment 13O

The compound and/or pharmaceutically acceptable salt of Embodiment 13N, wherein said —O-alkyl-aryl- is —O—$(CH_2)_{1-2}$-phenyl-, wherein said phenyl is optionally substituted.

Embodiment 13P

The compound and/or pharmaceutically acceptable salt of Embodiment 13, wherein X is —N(R)-alkyl-aryl-, wherein each of said alkyl and aryl is optionally substituted.

Embodiment 13Q

The compound and/or pharmaceutically acceptable salt of Embodiment 13P, wherein said —N(R)-alkyl-aryl- is —N(R)—(CH$_2$)$_{1-2}$-phenyl-, wherein said phenyl is optionally substituted.

Embodiment 13R

The compound and/or pharmaceutically acceptable salt of Embodiment 13Q, wherein said —N(R)—(CH$_2$)$_{1-2}$-phenyl is

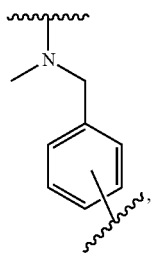

wherein said phenyl is optionally substituted.

Embodiment 13S

The compound and/or pharmaceutically acceptable salt of Embodiment 13, wherein X is -cycloalkyl-aryl-, wherein each of said cycloalkyl and aryl is optionally substituted, and said -aryl- is optionally substituted -phenyl-.

Embodiment 13T

The compound and/or pharmaceutically acceptable salt of Embodiment 13S, wherein said-cycloalkyl-aryl- is -cyclopropyl-phenyl- or -cyclopentyl-phenyl-.

Embodiment 13U

The compound and/or pharmaceutically acceptable salt of Embodiment 13T, wherein said -cyclopentyl-phenyl- is

Embodiment 13V

The compound and/or pharmaceutically acceptable salt of Embodiment 12, wherein X is -heterocyclyl-aryl-, wherein each of said heterocyclyl and aryl is optionally substituted, and said optionally substituted aryl is optionally substituted phenyl.

Embodiment 13W

The compound and/or pharmaceutically acceptable salt of Embodiment 13W, wherein said -heterocyclyl-aryl- is

Embodiment 13X

The compound and/or pharmaceutically acceptable salt of Embodiment 13, wherein X is -aryl-aryl-, wherein each of said aryl is optionally substituted phenyl.

Embodiment 13Y

The compound and/or pharmaceutically acceptable salt of Embodiment 13X, wherein said -aryl-aryl- is

Embodiment 13Z

The compound and/or pharmaceutically acceptable salt of Embodiment 13, wherein said -alkyl-heterocyclenyl- is —(CH$_2$)$_{1-2}$-1,2,3,4-tetrahydroisoquinolinyl-.

Embodiment 13Z1

The compound and/or pharmaceutically acceptable salt of Embodiment 13Z, wherein said —(CH$_2$)$_{1-2}$-1,2,3,4-tetrahydroisoquinolinyl- has the structure:

Embodiment 13Z2

The compound and/or pharmaceutically acceptable salt of Embodiment 13, wherein said

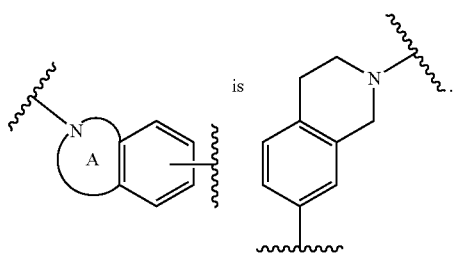

Embodiment 14

The compound and/or pharmaceutically acceptable salt of Embodiment 13, wherein X is -alkyl-O-aryl-, -alkyl-aryl-, or -alkyl-O-alkyl-aryl-, wherein each of said alkyl and aryl is optionally substituted, and each aryl independently is optionally substituted phenyl; wherein said -alkyl-O—, -alkyl-, or -alkyl-O-alkyl- portion respectively of said -alkyl-O-phenyl-, -alkyl-phenyl-, or -alkyl-O-alkyl-phenyl-, and said

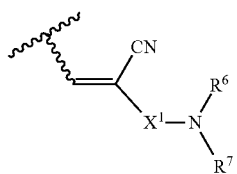

are in 1,3-position with respect to each other on the phenyl ring; i.e., $R^2$ is represented respectively by:

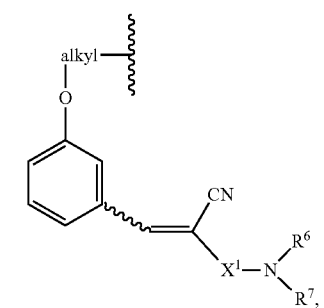

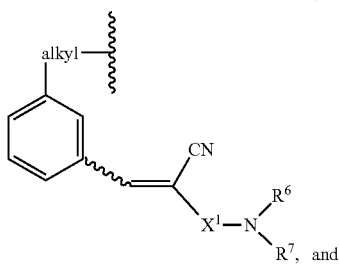

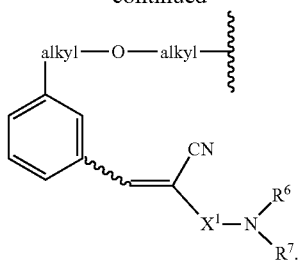

Embodiment 15

The compound and/or pharmaceutically acceptable salt of Embodiment 13 wherein X is -alkyl-O-aryl-, -alkyl-aryl-, or -alkyl-O-alkyl-aryl-, wherein each of said alkyl and aryl is optionally substituted, and aryl independently is optionally substituted phenyl; wherein said -alkyl-O—, -alkyl-, or -alkyl-O-alkyl-portion respectively of said -alkyl-O-phenyl-, -alkyl-phenyl-, or -alkyl-O-alkyl-phenyl-, and said

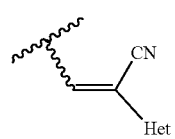

are in 1,3-position with respect to each other on the phenyl ring; i.e., $R^2$ is represented respectively by:

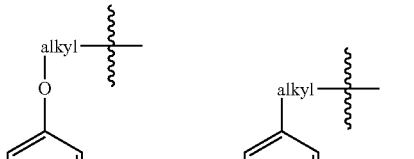

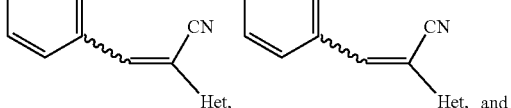

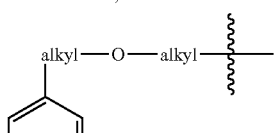

Embodiment 16

The compound and/or pharmaceutically acceptable salt of any of Embodiments 4, 11-12, 13D, and 14-15, wherein X is -alkyl-aryl-, wherein each of said alkyl and aryl is optionally substituted.

Embodiment 16A

The compound and/or pharmaceutically acceptable salt of Embodiment 16, wherein said -alkyl-aryl- is —$(CH_2)_{1-2}$-phenyl-, wherein said phenyl is optionally substituted.

Embodiment 16B

The compound and/or pharmaceutically acceptable salt of Embodiment 16A, wherein said phenyl of said —(CH$_2$)$_{1-2}$-phenyl- group is optionally substituted with one or two substituents selected from cyano, halo, alkyl, hydroxyalkyl, and alkoxyalkyl.

Embodiment 17

The compound and/or pharmaceutically acceptable salt of any of Embodiments 5, 11-12, 13D, and 14-15, wherein X is -alkyl-aryl-, wherein each of said alkyl and aryl is optionally substituted.

Embodiment 17A

The compound and/or pharmaceutically acceptable salt of Embodiment 17, wherein said -alkyl-aryl- is —(CH$_2$)$_{1-2}$-phenyl-.

Embodiment 18

The compound and/or pharmaceutically acceptable salt of any of Embodiments 1-11, 13, 14, and 16, wherein $X^1$ is —C(=O)—.

Embodiment 19

The compound and/or pharmaceutically acceptable salt of any of Embodiments 1-11, 13, 14, and 16-18, wherein $R^6$ is hydrogen, alkyl, or optionally substituted heterocyclyl; and $R^7$ is hydrogen, alkyl, haloalkyl, alkoxyalkyl, optionally substituted aryl or optionally substituted heterocyclyl.

Embodiment 19A

The compound and/or pharmaceutically acceptable salt of Embodiment 19, wherein $R^6$ is hydrogen, alkyl, or optionally substituted heterocyclyl; and $R^7$ is hydrogen, alkyl, haloalkyl, alkoxyalkyl, optionally substituted aryl or optionally substituted heterocyclyl; wherein said aryl is phenyl and said heterocyclyl is a 5-6 membered monocyclic ring.

Embodiment 19B

The compound and/or pharmaceutically acceptable salt of Embodiment 19A, wherein $R^6$ is H, methyl, ethyl, isopropyl or tetrahydropyranyl; and $R^7$ is methyl, ethyl, isopropyl, t-butyl, 2,2,2-trifluoroethyl, —CH$_2$—C(CH$_3$)$_2$—O—CH$_3$, —(CH$_2$)$_2$—O—CH$_3$, —C(CH$_3$)$_2$CH$_2$—O—CH$_3$, phenyl, or tetrahydropyranyl.

Embodiment 20

The compound and/or pharmaceutically acceptable salt of any of Embodiments 1-11, 13, 14, and 16-18, wherein $R^6$ and $R^7$ together with the nitrogen atom to which they are shown attached form a heterocyclyl, which is optionally substituted with 1-2 substituents chosen from halo, hydroxy, alkyl, alkoxy, cyano, haloalkyl, —NH$_2$, —NH(alkyl), —N(alkyl)$_2$, and heterocyclyl.

Embodiment 20A

The compound and/or pharmaceutically acceptable salt of Embodiment 20, wherein said optionally substituted heterocyclyl is morpholinyl, 3,5-dimethylmorpholinyl, 3,3-dimethylmopholinyl, azetidinyl, azetidin-1-yl, piperadinyl, piperazinyl, 4-methylpiperazin-1-yl, -piperazinyl-oxetanyl,

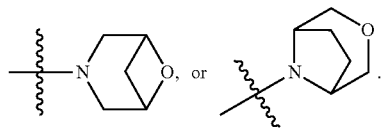 [SMILES: *N1CC2CC(C1)O2 ; *N1C2CCC1COC2]

Embodiment 21

The compound and/or pharmaceutically acceptable salt of any of Embodiments 1-9, 10, 12, 13, 15, and 16-17, wherein said Het is a five to ten membered heteroaryl ring, which is optionally substituted with 1-3 substituents chosen from halo, hydroxy, alkyl, alkoxy, cyano, haloalkyl, —NH$_2$, —NH(alkyl), —N(alkyl)$_2$, and heterocyclyl.

Embodiment 21A

The compound and/or pharmaceutically acceptable salt of Embodiment 21, wherein said five to ten membered heteroaryl ring of said Het is a five- to six-membered monocyclic heteroaryl ring, or a five- to six-membered monocyclic heteroaryl ring which is benzo-fused; wherein each if said heteroaryl ring is optionally substituted with 1-3 substituents chosen from halo, hydroxy, alkyl, alkoxy, cyano, haloalkyl, —NH$_2$, —NH(alkyl), —N(alkyl)$_2$, and heterocyclyl.

Embodiment 21B

The compound and/or pharmaceutically acceptable salt of Embodiment 21A, wherein said heteroaryl is pyridinyl, fluororopyridinyl, methoxypyridinyl, trifluoromethylpyridinyl, pyrazinyl, pyrimidinyl, 1-methyl-6-oxo-1,6-dihydropyrimidin-4-yl, pyradin-N-oxide-2-yl, triazolyl, or benzimidazolyl.

Embodiment 21C

The compound and/or pharmaceutically acceptable salt of Embodiment 21B, wherein said heteroaryl is 2-pyridinyl, 3-fluoropyridin-2-yl, 3-methoxypyridin-2-yl, 5-cyanopydiny-2-yl, 1,2,4-triazol-1-yl, 5-(trifluoromethyl)-pyridin-2-yl, 4-pyrimidinyl, 2-pyrimidinyl, 2-pyrazinyl, 1-methyl-6-oxo-1,6-dihydropyrimidin-4-yl, or 1,2,4-triazol-1-yl.

Embodiment 22

The compound and/or pharmaceutically acceptable salt of any of Embodiments 1-21, and, wherein $R^{b1}$ is optionally substituted aryl or optionally substituted alkyl, wherein said alkyl is optionally substituted with 1-2 substituents chosen from —O-aryl, —O-heteroaryl, —N(R)-aryl, —N(R)— heteroaryl, aryl, heterocyclyl, heterocyclenyl, and a heteroaryl, wherein each instance of said aryl, heteroaryl, heterocyclyl, and heterocyclenyl substituent of said optionally substituted alkyl of $R^{b1}$ is optionally substituted with 1-3 substituents chosen from halo, alkyl, alkoxy, haloalkyl, cyano, —NH$_2$, —NH(alkyl), —N(alkyl)$_2$, and heterocyclyl.

Embodiment 22A

The compound and/or pharmaceutically acceptable salt of Embodiment 22, wherein said optionally substituted alkyl is a substituted alkyl of of the formula —(CH$_2$)$_{1-2}$—R" wherein R" is —O-aryl, —O-heteroaryl, —N(R)-aryl, —N(R)-heteroaryl, aryl, cycloalkyl, cycloalkenyl, heterocyclyl, heterocyclenyl, or a heteroaryl, wherein each of said aryl, heteroaryl, heterocyclyl, and heterocyclenyl substituent of said alkyl of R$^{b1}$ is optionally substituted with 1-3 substituents chosen from halo, alkyl, alkoxy, haloalkyl, cyano, —NH$_2$, —NH(alkyl), —N(alkyl)$_2$, and heterocyclyl.

Embodiment 22B

The compound and/or pharmaceutically acceptable salt of Embodiment 22A, wherein said —O-aryl substituent of R" is —O-phenyl; said aryl substituent of R, is phenyl, wherein said phenyl is optionally substituted with 1-3 substituents chosen from alkyl, halo, haloalkyl, and alkoxy; said heteroaryl substituent of R" is thiophenyl, benzofuranyl or benzimidazolyl; said heterocyclyl substituent of R" is tetrahydropyranyl, dihydrobenzofuranyl, or dihydroindolyl; said —N(R)-aryl substituent of R" is —N(alkyl)phenyl; said cycloalkenyl substituent of R" is cyclopentenyl; and said cycloalkyl substituent of R" is cyclopentyl or cyclohexyl.

Embodiment 22C

The compound and/or pharmaceutically acceptable salt of Embodiment 22, wherein R$^{b1}$ is optionally substituted aryl, wherein said aryl is phenyl which is optionally substituted with 1-3 substituents chosen from halo, alkyl, alkoxy, haloalkyl, cyano, —NH$_2$, —NH(alkyl), —N(alkyl)$_2$, and heterocyclyl.

Embodiment 22D

The compound and/or pharmaceutically acceptable salt of Embodiment 22, wherein R$^{b1}$ is alkyl which is optionally substituted with -aryl, or heteroaryl; wherein said aryl is phenyl and said heteroaryl is 5-6 membered monocyclic heteroaryl ring or a 5-6 membered monocyclic heteroaryl ring which is benzo-fused (i.e., thus forming a bicyclic ring with the benzene ring); wherein each of said aryl and heteroaryl is optionally substituted with 1-3 substituents chosen from halo, alkyl, alkoxy, haloalkyl, cyano, —NH$_2$, —NH(alkyl), —N(alkyl)$_2$, and heterocyclyl.

Embodiment 22E

The compound and/or pharmaceutically acceptable salt of Embodiment 22D, wherein R$^{b1}$ is unsubstituted alkyl, wherein said unsubstituted alkyl is —CH$_2$CH(CH$_3$)$_2$, or —CH$_2$C(CH$_3$)$_3$.

Embodiment 22F

The compound and/or pharmaceutically acceptable salt of Embodiment 22, wherein said R$^{b1}$ is —CH$_2$CH(CH$_3$)$_2$, —CH$_2$C(CH$_3$)$_3$, —CH$_2$-phenyl, —CH$_2$CH$_2$-phenyl, —CH$_2$CH$_2$-phenyl-methyl, —CH$_2$CH$_2$-(dimethylphenyl), —CH$_2$-phenyl-methyl, —CH$_2$-phenyl-ethyl, —CH$_2$-phenyl-Cl, —CH$_2$-thiophenyl, —CH$_2$—CH$_2$-benzofuranyl, —CH$_2$CH$_2$-benzimidazolyl, —CH$_2$CH$_2$-dihydroindolyl, —CH$_2$-benzofuranyl, —CH$_2$-benzimidazolyl, —CH$_2$-dihydroindolyl, —CH$_2$—O-phenyl, or —CH$_2$—N(CH$_3$)-phenyl.

Embodiment 23

The compound and/or pharmaceutically acceptable salt of any of Embodiments 1-22, wherein R$^{b2}$ and R$^{b3}$ are hydrogen, or wherein said cyclic boronic ester formed by R$^{b2}$ and R$^{b3}$ together with the boron atom to which they are shown attached is chosen from:

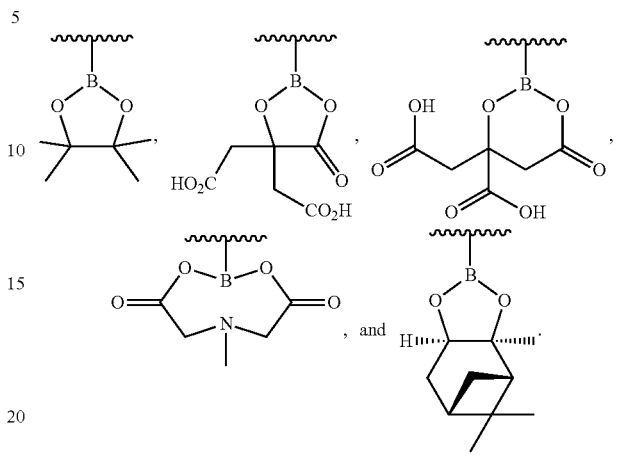

Embodiment 24

The compound and/or pharmaceutically acceptable salt of any of Embodiments 3, 6, 9, and 11-23, wherein the compound is chosen from:
(R)-(1-(3-(3-(3-(tert-butylamino)-2-cyano-3-oxoprop-1-en-1-yl)phenoxy)propanamido)-2-phenylethyl)boronic acid;
(R)-(1-(3-(3-(3-(tert-butylamino)-2-cyano-3-oxoprop-1-en-1-yl)phenyl)propanamido)-2-phenylethyl)boronic acid;
(R)-(1-(3-(3-(2-cyano-3-(dimethylamino)-3-oxoprop-1-en-1-yl)phenoxy)propanamido)-2-phenylethyl)boronic acid;
(R)-(1-(3-(3-(2-cyano-2-(pyridin-2-yl)vinyl)phenoxy)propanamido)-2-phenylethyl)boronic acid;
(R)-(1-(3-(3-(2-cyano-3-(diethylamino)-3-oxoprop-1-en-1-yl)phenoxy)propanamido)-2-phenylethyl)boronic acid;
(R)-(1-(3-(3-(3-(tert-butylamino)-2-cyano-3-oxoprop-1-en-1-yl)phenoxy)propanamido)-2-(3-ethylphenyl)ethyl)boronic acid;
(R)-(1-(3-(3-(2-cyano-3-morpholino-3-oxoprop-1-en-1-yl)phenoxy)propanamido)-2-phenylethyl)boronic acid;
(R)-(1-(3-(3-(2-cyano-3-oxo-3-((tetrahydro-2H-pyran-4-yl)amino)prop-1-en-1-yl)phenoxy)propanamido)-2-phenylethyl)boronic acid;
(R)-(1-(3-(3-(3-(tert-butylamino)-2-cyano-3-oxoprop-1-en-1-yl)phenoxy)propanamido)-3-phenylpropyl)boronic acid;
(R)-(1-(3-(3-(2-cyano-3-(isopropylamino)-3-oxoprop-1-en-1-yl)phenoxy)propanamido)-2-phenylethyl)boronic acid;
(R)-(1-(3-(3-(3-(tert-butylamino)-2-cyano-3-oxoprop-1-en-1-yl)phenoxy)propanamido)-3,3-dimethylbutyl)boronic acid;
(R)-(2-(benzofuran-3-yl)-1-(3-(3-(3-(tert-butylamino)-2-cyano-3-oxoprop-1-en-1-yl)phenoxy)propanamido)ethyl)boronic acid;
(R)-(1-(3-(5-(3-(tert-butylamino)-2-cyano-3-oxoprop-1-en-1-yl)-2-fluorophenoxy)propanamido)-2-phenylethyl)boronic acid;
(R)-(1-(3-(3-(2-cyano-3-(4-methylpiperazin-1-yl)-3-oxoprop-1-en-1-yl)phenoxy)propanamido)-2-phenylethyl)boronic acid;
(R)-(1-(3-(3-(2-cyano-3-(methylamino)-3-oxoprop-1-en-1-yl)phenoxy)propanamido)-2-phenylethyl)boronic acid;

(R)-(1-(3-(3-(2-cyano-2-(pyridin-2-yl)vinyl)phenoxy)propanamido)-3-phenylpropyl)boronic acid;
(R)-(1-(3-(3-(2-cyano-3-(methyl(phenyl)amino)-3-oxoprop-1-en-1-yl)phenoxy)propanamido)-2-phenylethyl)boronic acid;
(R)-(2-(benzofuran-3-yl)-1-(3-(3-(2-cyano-2-(pyridin-2-yl)vinyl)phenoxy)propanamido)ethyl)boronic acid;
(R)-(1-(4-(3-(2-cyano-3-(dimethylamino)-3-oxoprop-1-en-1-yl)phenyl)butanamido)-2-phenylethyl)boronic acid;
(R)-(1-(4-(3-(2-cyano-2-(1H-1,2,4-triazol-1-yl)vinyl)phenyl)butanamido)-2-phenylethyl)boronic acid;
(R)-(1-(3-(5-(2-cyano-3-(dimethylamino)-3-oxoprop-1-en-1-yl)-2-methoxyphenoxy)propanamido)-2-phenylethyl)boronic acid;
(R)-(1-(3-(5-(2-cyano-3-(dimethylamino)-3-oxoprop-1-en-1-yl)-2-fluorophenoxy)propanamido)-2-phenylethyl)boronic acid;
(R)-(1-(3-(5-(2-cyano-2-(pyridin-2-yl)vinyl)-2-fluorophenoxy)propanamido)-2-phenylethyl)boronic acid;
(R)-(1-(3-(5-(2-cyano-2-(pyridin-2-yl)vinyl)-2-methoxyphenoxy)propanamido)-2-phenylethyl)boronic acid;
(R)-(1-(3-(3-(3-(azetidin-1-yl)-2-cyano-3-oxoprop-1-en-1-yl)phenoxy)propanamido)-2-phenylethyl)boronic acid;
(R)-(1-(3-(3-(2-cyano-3-(ethylamino)-3-oxoprop-1-en-1-yl)phenoxy)propanamido)-2-phenylethyl)boronic acid;
(R)-(1-(3-(3-(2-cyano-3-(4-(oxetan-3-yl)piperazin-1-yl)-3-oxoprop-1-en-1-yl)phenoxy)propanamido)-2-phenylethyl)boronic acid;
(R)-(1-(3-(3-(2-cyano-2-(5-(trifluoromethyl)pyridin-2-yl)vinyl)phenoxy)propanamido)-2-phenylethyl)boronic acid;
(R)-(1-(3-(3-(2-cyano-2-(3-fluoropyridin-2-yl)vinyl)phenoxy)propanamido)-2-phenylethyl)boronic acid;
(R)-(1-(3-(3-(2-cyano-3-(dimethylamino)-3-oxoprop-1-en-1-yl)-2-fluorophenoxy)propanamido)-2-phenylethyl)boronic acid;
(R)-(1-(3-(2,6-dichloro-3-(2-cyano-3-(dimethylamino)-3-oxoprop-1-en-1-yl)phenoxy)propanamido)-2-phenylethyl)boronic acid;
(R)-(1-(3-(2,6-dichloro-3-(2-cyano-2-(pyridin-2-yl)vinyl)phenoxy)propanamido)-2-phenylethyl)boronic acid;
(R)-(1-(3-(3-(2-cyano-2-(pyridin-2-yl)vinyl)-2-fluorophenoxy)propanamido)-2-phenylethyl)boronic acid;
(R)-(1-(3-(3-(2-cyano-3-(dimethylamino)-3-oxoprop-1-en-1-yl)-5-fluorophenoxy)propanamido)-2-phenylethyl)boronic acid;
(R)-(1-(3-(3-(2-cyano-3-(dimethylamino)-3-oxoprop-1-en-1-yl)-4-fluorophenoxy)propanamido)-2-phenylethyl)boronic acid;
(R)-(1-(3-(3-(2-cyano-2-(pyridin-2-yl)vinyl)-4-fluorophenoxy)propanamido)-2-phenylethyl)boronic acid;
(R)-(1-(3-(3-(2-cyano-3-(dimethylamino)-3-oxoprop-1-en-1-yl)phenoxy)propanamido)-2-(2,4-dimethylphenyl)ethyl)boronic acid;
(R)-(1-(3-(3-(2-cyano-2-(pyridin-2-yl)vinyl)phenoxy)propanamido)-2-(2,4-dimethylphenyl)ethyl)boronic acid;
(R)-(1-(3-(3-(2-cyano-3-((2-methoxyethyl)amino)-3-oxoprop-1-en-1-yl)phenoxy)propanamido)-2-phenylethyl)boronic acid;
(R)-(1-(3-(3-(2-cyano-3-((1-methoxy-2-methylpropan-2-yl)amino)-3-oxoprop-1-en-1-yl)phenoxy)propanamido)-2-phenylethyl)boronic acid;
(R)-(1-(3-(3-(2-cyano-3-((2-methoxy-2-methylpropyl)amino)-3-oxoprop-1-en-1-yl)phenoxy)propanamido)-2-phenylethyl)boronic acid;
(R)-(1-(2-((3-(2-cyano-3-(dimethylamino)-3-oxoprop-1-en-1-yl)benzyl)oxy)acetamido)-2-phenylethyl)boronic acid;
(R)-(1-(3-(3-(2-cyano-2-(3-methoxypyridin-2-yl)vinyl)phenoxy)propanamido)-2-phenylethyl)boronic acid;
(R)-(1-(2-(7-(2-cyano-2-(pyridin-2-yl)vinyl)-3,4-dihydroisoquinolin-2(1H)-yl)acetamido)-2-phenylethyl)boronic acid;
(R)-(2-(benzofuran-3-yl)-1-(2-(7-(2-cyano-3-(ethyl(tetrahydro-2H-pyran-4-yl)amino)-3-oxoprop-1-en-1-yl)-3,4-dihydroisoquinolin-2(1H)-yl)acetamido)ethyl)boronic acid;
(R)-(1-(2-(7-(2-cyano-3-(diethylamino)-3-oxoprop-1-en-1-yl)-3,4-dihydroisoquinolin-2(1H)-yl)acetamido)-2-(p-tolyl)ethyl)boronic acid; and
(R)-(1-(2-(7-(2-cyano-3-(diethylamino)-3-oxoprop-1-en-1-yl)-3,4-dihydroisoquinolin-2(1H)-yl)acetamido)-2-phenylethyl)boronic acid;
(R)-1-(3-(3-(2-cyano-3-(dimethylamino)-3-oxoprop-1-enyl)phenoxy)propanamido)-2-phenylethylboronic acid;
(R)-1-(3-(3-(2-cyano-3-(diethylamino)-3-oxoprop-1-enyl)phenoxy)propanamido)-2-phenylethylboronic acid;
(R)-1-(3-(3-(2-cyano-3-morpholino-3-oxoprop-1-enyl)phenoxy)propanamido)-2-phenylethylboronic acid;
(R)-1-(3-(3-(2-cyano-3-oxo-3-(tetrahydro-2H-pyran-4-ylamino)prop-1-enyl)phenoxy)propanamido)-2-phenylethylboronic acid;
(R)-1-(3-(3-(3-(tert-butylamino)-2-cyano-3-oxoprop-1-enyl)phenoxy)propanamido)-3-phenylpropylboronic acid;
(R)-1-(3-(3-(2-cyano-3-(isopropylamino)-3-oxoprop-1-enyl)phenoxy)propanamido)-2-phenylethylboronic acid; and
(R)-1-(3-(3-(3-(tert-butylamino)-2-cyano-3-oxoprop-1-enyl)phenoxy)propanamido)-3,3-dimethylbutylboronic acid;
an individual E or Z isomer thereof; and/or
a pharmaceutically acceptable salt of any of the foregoing compounds.

Embodiment 25

The compound and/or pharmaceutically acceptable salt of any of Embodiments 3, 7, 10, 13D, 14, 18, 19, 22A-B, 22D, 22F, and 23, wherein the compound is chosen from:
(R)-1-((S)-4-(3-(3-(tert-butylamino)-2-cyano-3-oxoprop-1-enyl)phenyl)-2-(2,5-dichlorobenzamido)butanamido)-2-phenylethylboronic acid;
((R)-1-((S)-4-(3-(3-(tert-butylamino)-2-cyano-3-oxoprop-1-en-1-yl)phenyl)-2-(pyrazine-2-carboxamido)butanamido)-2-phenylethyl)boronic acid; and
((R)-1-((R)-4-(3-(3-(tert-butylamino)-2-cyano-3-oxoprop-1-en-1-yl)phenyl)-2-(2,5-dichlorobenzamido)butanamido)-2-phenylethyl)boronic acid;
an individual E or Z isomer thereof; and/or
a pharmaceutically acceptable salt of any of the foregoing compounds.

Embodiment 26

The compound and/or pharmaceutically acceptable salt of any of Embodiments 4, 11-12, 13D, 14-18, 19A-19B, 20, 22A-22B, 22D, 22F, and 23, wherein the compound is chosen from:
(R)-(1-((((3-(2-cyano-3-(dimethylamino)-3-oxoprop-1-en-1-yl)benzyl)oxy)carbonyl)amino)-2-phenylethyl)boronic acid;
(R)-(1-((((3-(3-(tert-butylamino)-2-cyano-3-oxoprop-1-en-1-yl)benzyl)oxy)carbonyl)amino)-2-phenylethyl)boronic acid;

(R)-(1-(((3-(2-cyano-3-(dimethylamino)-3-oxoprop-1-en-1-yl)phenethoxy)carbonyl)amino)-2-phenylethyl)boronic acid;
(R)-(2-(benzofuran-3-yl)-1-(((3-(2-cyano-2-(pyridin-2-yl)vinyl)phenethoxy)carbonyl)amino)ethyl)boronic acid;
(R)-(1-(((3-(2-cyano-2-(pyridin-2-yl)vinyl)phenethoxy)carbonyl)amino)-2-phenylethyl)boronic acid;
(R)-(1-(((3-(2-cyano-3-(dimethylamino)-3-oxoprop-1-en-1-yl)phenethoxy)carbonyl)amino)-2-(p-tolyl)ethyl)boronic acid;
(R)-(1-(((3-(2-cyano-3-(diethylamino)-3-oxoprop-1-en-1-yl)phenethoxy)carbonyl)amino)-2-phenylethyl)boronic acid;
(R)-(2-(benzofuran-3-yl)-1-(((3-(2-cyano-3-(dimethylamino)-3-oxoprop-1-en-1-yl)phenethoxy)carbonyl)amino)ethyl)boronic acid;
(R)-(1-(((3-(2-cyano-2-(3-fluoropyridin-2-yl)vinyl)phenethoxy)carbonyl)amino)-2-phenylethyl)boronic acid;
(R)-(1-(((3-(2-cyano-3-(diethylamino)-3-oxoprop-1-en-1-yl)phenethoxy)carbonyl)amino)-2-(p-tolyl)ethyl)boronic acid;
(R)-(1-(((3-(2-cyano-2-(5-(trifluoromethyl)pyridin-2-yl)vinyl)phenethoxy)carbonyl)amino)-2-phenylethyl)boronic acid;
(R)-(1-(((3-(2-cyano-2-(pyridin-2-yl)vinyl)phenethoxy)carbonyl)amino)-2-(p-tolyl)ethyl)boronic acid;
(R)-(2-(benzofuran-3-yl)-1-(((3-(2-cyano-3-(diethylamino)-3-oxoprop-1-en-1-yl)phenethoxy)carbonyl)amino)ethyl)boronic acid;
(R)-(1-(((3-(2-cyano-2-(pyrimidin-4-yl)vinyl)phenethoxy)carbonyl)amino)-2-phenylethyl)boronic acid;
(R)-(1-(((3-(2-cyano-2-(pyrimidin-2-yl)vinyl)phenethoxy)carbonyl)amino)-2-phenylethyl)boronic acid;
(R)-(1-(((3-(2-cyano-2-(pyrazin-2-yl)vinyl)phenethoxy)carbonyl)amino)-2-phenylethyl)boronic acid;
(R)-(1-(((3-(2-cyano-3-(ethyl(isopropyl)amino)-3-oxoprop-1-en-1-yl)phenethoxy)carbonyl)amino)-2-phenylethyl)boronic acid;
((R)-1-(((3-(2-cyano-3-((3R,5R)-3,5-dimethylmorpholino)-3-oxoprop-1-en-1-yl)phenethoxy)carbonyl)amino)-2-phenylethyl)boronic acid;
((1R)-1-(((3-(3-(3-oxa-8-azabicyclo[3.2.1]octan-8-yl)-2-cyano-3-oxoprop-1-en-1-yl)phenethoxy)carbonyl)amino)-2-phenylethyl)boronic acid;
((R)-1-(((3-(2-cyano-3-((3S,5S)-3,5-dimethylmorpholino)-3-oxoprop-1-en-1-yl)phenethoxy)carbonyl)amino)-2-phenylethyl)boronic acid;
(R)-(1-(((3-(3-(tert-butyl(ethyl)amino)-2-cyano-3-oxoprop-1-en-1-yl)phenethoxy)carbonyl)amino)-2-phenylethyl)boronic acid;
(R)-(1-(((3-(2-cyano-3-(ethyl(tetrahydro-2H-pyran-4-yl)amino)-3-oxoprop-1-en-1-yl)phenethoxy)carbonyl)amino)-2-phenylethyl)boronic acid;
(R)-(1-(((3-(3-(tert-butyl(methyl)amino)-2-cyano-3-oxoprop-1-en-1-yl)phenethoxy)carbonyl)amino)-2-phenylethyl)boronic acid;
(R)-(1-(((3-(3-(bis(tetrahydro-2H-pyran-4-yl)amino)-2-cyano-3-oxoprop-1-en-1-yl)phenethoxy)carbonyl)amino)-2-phenylethyl)boronic acid;
(R)-(1-(((3-(2-cyano-3-(diisopropylamino)-3-oxoprop-1-en-1-yl)phenethoxy)carbonyl)amino)-2-phenylethyl)boronic acid;
(R)-(1-(((3-(2-cyano-2-(pyridin-2-yl)vinyl)-5-(hydroxymethyl)phenethoxy)carbonyl)amino)-2-phenylethyl)boronic acid;
(R)-(1-(((3-(2-cyano-2-(5-cyanopyridin-2-yl)vinyl)phenethoxy)carbonyl)amino)-2-phenylethyl)boronic acid;
(R)-(1-(((3-(2-cyano-3-(3,3-dimethylmorpholino)-3-oxoprop-1-en-1-yl)phenethoxy)carbonyl)amino)-2-phenylethyl)boronic acid;
(R)-(1-(((3-(2-cyano-2-(5-(trifluoromethyl)pyridin-2-yl)vinyl)phenethoxy)carbonyl)amino)-2-(p-tolyl)ethyl)boronic acid;
(R)-(1-(((3-(2-cyano-2-(1-methyl-6-oxo-1,6-dihydropyrimidin-4-yl)vinyl)phenethoxy)carbonyl)amino)-2-phenylethyl)boronic acid;
((R)-1-(((3-(2-cyano-3-((3R,5R)-3,5-dimethylmorpholino)-3-oxoprop-1-en-1-yl)phenethoxy)carbonyl)amino)-2-(p-tolyl)ethyl)boronic acid;
(R)-(2-(4-chlorophenyl)-1-(((3-(2-cyano-3-(diethylamino)-3-oxoprop-1-en-1-yl)phenethoxy)carbonyl)amino)ethyl)boronic acid;
(R)-(1-(((3-(2-cyano-2-(pyrimidin-2-yl)vinyl)phenethoxy)carbonyl)amino)-2-(p-tolyl)ethyl)boronic acid;
(R)-(1-(((3-(2-cyano-3-(ethyl(tetrahydro-2H-pyran-4-yl)amino)-3-oxoprop-1-en-1-yl)phenethoxy)carbonyl)amino)-2-(p-tolyl)ethyl)boronic acid;
((1R)-1-(((3-(3-(3-oxa-8-azabicyclo[3.2.1]octan-8-yl)-2-cyano-3-oxoprop-1-en-1-yl)phenethoxy)carbonyl)amino)-2-(p-tolyl)ethyl)boronic acid;
(R)-(1-(((3-(2-cyano-3-(ethyl(methyl)amino)-3-oxoprop-1-en-1-yl)phenethoxy)carbonyl)amino)-2-phenylethyl)boronic acid;
(R)-(1-(((3-(2-cyano-3-(methyl(2,2,2-trifluoroethyl)amino)-3-oxoprop-1-en-1-yl)phenethoxy)carbonyl)amino)-2-phenylethyl)boronic acid;
((R)-1-(((3-(2-cyano-3-((3S,5S)-3,5-dimethylmorpholino)-3-oxoprop-1-en-1-yl)phenethoxy)carbonyl)amino)-2-(p-tolyl)ethyl)boronic acid;
(R)-(2-(benzofuran-3-yl)-1-(((3-(2-cyano-3-(3,3-dimethylmorpholino)-3-oxoprop-1-en-1-yl)phenethoxy)carbonyl)amino)ethyl)boronic acid;
(R)-(2-(benzofuran-3-yl)-1-(((3-(2-cyano-3-(ethyl(tetrahydro-2H-pyran-4-yl)amino)-3-oxoprop-1-en-1-yl)phenethoxy)carbonyl)amino)ethyl)boronic acid;
(R)-(2-(benzofuran-3-yl)-1-(((3-cyano-5-(2-cyano-3-(diethylamino)-3-oxoprop-1-en-1-yl)phenethoxy)carbonyl)amino)ethyl)boronic acid;
((R)-2-(benzofuran-3-yl)-1-(((3-(2-cyano-3-((3R,5R)-3,5-dimethylmorpholino)-3-oxoprop-1-en-1-yl)phenethoxy)carbonyl)amino)ethyl)boronic acid;
(R)-(1-(((3-(2-cyano-2-(1H-1,2,4-triazol-1-yl)vinyl)phenethoxy)carbonyl)amino)-2-phenylethyl)boronic acid;
(R)-(1-(((3-cyano-5-(2-cyano-3-(diethylamino)-3-oxoprop-1-en-1-yl)phenethoxy)carbonyl)amino)-2-(p-tolyl)ethyl)boronic acid;
(R)-(1-(((3-cyano-5-(2-cyano-3-(ethyl(tetrahydro-2H-pyran-4-yl)amino)-3-oxoprop-1-en-1-yl)phenethoxy)carbonyl)amino)-2-phenylethyl)boronic acid;
(R)-(1-(((3-cyano-5-(2-cyano-3-(ethyl(tetrahydro-2H-pyran-4-yl)amino)-3-oxoprop-1-en-1-yl)phenethoxy)carbonyl)amino)-2-(p-tolyl)ethyl)boronic acid;
(R)-(1-(((3-cyano-5-(2-cyano-3-(diethylamino)-3-oxoprop-1-en-1-yl)phenethoxy)carbonyl)amino)-2-phenylethyl)boronic acid; and
(R)-(1-(((3-(2-cyano-2-(1H-1,2,4-triazol-1-yl)vinyl)phenethoxy)carbonyl)amino)-3-phenylpropyl)boronic acid;
an individual E or Z isomer thereof; and/or a pharmaceutically acceptable salt of any of the foregoing compounds.

Embodiment 27

The compound and/or pharmaceutically acceptable salt of any of Embodiments 5, 11-12, 13D, 14-16, 17A, 18-18, 19A-19B, 21, 22A-22B, 22D, 22F, and 23, wherein the compound is chosen from:
(R)-(1-(3-(3-(2-cyano-3-(diethylamino)-3-oxoprop-1-en-1-yl)phenethyl)ureido)-2-phenylethyl)boronic acid;
(R)-(1-(3-(3-(2-cyano-2-(pyridin-2-yl)vinyl)phenethyl)ureido)-2-phenylethyl)boronic acid;
(R)-(1-(3-(3-(2-cyano-2-(5-(trifluoromethyl)pyridin-2-yl)vinyl)phenethyl)ureido)-2-phenylethyl)boronic acid;
(R)-(1-(3-(3-(2-cyano-2-(pyridin-2-yl)vinyl)phenethyl)ureido)-2-(p-tolyl)ethyl)boronic acid;
(R)-(1-(3-(3-(2-cyano-2-(5-(trifluoromethyl)pyridin-2-yl)vinyl)phenethyl)ureido)-2-(p-tolyl)ethyl)boronic acid;
(R)-(1-(3-(3-(2-cyano-3-(diethylamino)-3-oxoprop-1-en-1-yl)phenethyl)ureido)-2-(p-tolyl)ethyl)boronic acid;
(R)-(1-(3-(3-(2-cyano-2-(pyrimidin-2-yl)vinyl)phenethyl)ureido)-2-(p-tolyl)ethyl)boronic acid;
(R)-(2-(benzofuran-3-yl)-1-(3-(3-(2-cyano-2-(pyrimidin-2-yl)vinyl)phenethyl)ureido)ethyl)boronic acid;
(R)-(2-(benzofuran-3-yl)-1-(3-(3-(2-cyano-3-(diethylamino)-3-oxoprop-1-en-1-yl)phenethyl)ureido)ethyl)boronic acid;
(R)-(2-(benzofuran-3-yl)-1-(3-(3-(2-cyano-3-(ethyl(tetrahydro-2H-pyran-4-yl)amino)-3-oxoprop-1-en-1-yl)phenethyl)ureido)ethyl)boronic acid; and
(R)-(1-(3-(3-(2-cyano-2-(1H-1,2,4-triazol-1-yl)vinyl)phenethyl)ureido)-2-(p-tolyl)ethyl)boronic acid;
an individual E or Z isomer thereof; and/or
a pharmaceutically acceptable salt of any of the foregoing compounds.

Embodiment 28

Combinations of certain embodiments are further contemplated herein.

For example, in certain embodiments of Formula (I), wherein Y is —OR$^2$ (Embodiment 4), R$^2$ is a group of Formula (a) (Embodiment 11), X is -alkyl-aryl- (Embodiment 16), wherein said -alkyl-aryl- is —(CH$_2$)$_{1-2}$-phenyl- (Embodiment 17-17A), X$^1$ is —C(=O)— (Embodiment 18), R$^{b1}$ is —(CH$_2$)$_{1-2}$— which is substituted with optionally substituted phenyl (Embodiments 22A-22B), such that the compound of Formula (I) is a compound of Formula I(a)

Formula I(a)

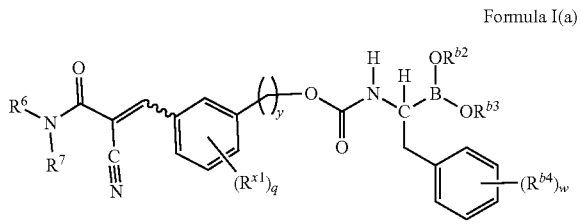

or a pharmaceutically acceptable salt thereof, wherein y is 1 or 2; w is 0, 1, 2, or 3 (Embodiment 22B); R$^{b4}$ is alkyl, halo, haloalkyl, or alkoxy (Embodiment 22B); q is 0 or 1; and R$^{x1}$ is cyano, halo, alkyl, hydroxyalkyl, or alkoxyalkyl (Embodiment 16B).

Embodiment 28A

The compound and/or a pharmaceutically acceptable salt of Embodiment 28, wherein in Formula I(a), R$^{b2}$ and R$^{b3}$ are each hydrogen.

Embodiment 28B

The compound and/or a pharmaceutically acceptable salt of Embodiment 28 or 28A, wherein in Formula I(a), each of R$^6$ and R$^7$ is alkyl.

Embodiment 28C

The compound and/or a pharmaceutically acceptable salt of Embodiment 28B, wherein in Formula I(a), each of said R$^6$ and R$^7$ alkyl is ethyl.

Embodiment 28D

The compound and/or a pharmaceutically acceptable salt of Embodiment 28, wherein in Formula I(a), R$^6$ is alkyl, and R$^7$ is an optionally substituted heterocyclyl.

Embodiment 28E

The compound and/or a pharmaceutically acceptable salt of Embodiment 28D, wherein in Formula I(a), said R$^6$ alkyl is ethyl, and said the optionally substituted heterocyclyl of R$^7$ is morpholinyl.

Embodiment 28F

The compound and/or a pharmaceutically acceptable salt of Embodiment 28, wherein the compound of Formula I(a) is the E-isomer.

Embodiment 28G

The compound and/or a pharmaceutically acceptable salt of Embodiment 28, wherein the compound of Formula I(a) is the Z-isomer.

Embodiment 28H

The compound and/or a pharmaceutically acceptable salt of Embodiment 28, wherein the compound of Formula I(a) is chosen from:
(R)-(1-(((3-(2-cyano-3-(diethylamino)-3-oxoprop-1-en-1-yl)phenethoxy)carbonyl)amino)-2-phenylethyl)boronic acid;
(R)-(1-(((3-(2-cyano-3-(diethylamino)-3-oxoprop-1-en-1-yl)phenethoxy)carbonyl)amino)-2-(p-tolyl)ethyl)boronic acid;
(R)-(2-(benzofuran-3-yl)-1-(((3-(2-cyano-3-(diethylamino)-3-oxoprop-1-en-1-yl)phenethoxy)carbonyl)amino)ethyl)boronic acid;
(R)-(1-(((3-(2-cyano-3-(ethyl(tetrahydro-2H-pyran-4-yl)amino)-3-oxoprop-1-en-1-yl)phenethoxy)carbonyl)amino)-2-phenylethyl)boronic acid;
(R)-(1-(((3-cyano-5-(2-cyano-3-(diethylamino)-3-oxoprop-1-en-1-yl)phenethoxy)carbonyl)amino)-2-(p-tolyl)ethyl)boronic acid;
(R)-(1-(((3-cyano-5-(2-cyano-3-(ethyl(tetrahydro-2H-pyran-4-yl)amino)-3-oxoprop-1-en-1-yl)phenethoxy)carbonyl)amino)-2-phenylethyl)boronic acid;

(R)-(1-(((3-cyano-5-(2-cyano-3-(ethyl(tetrahydro-2H-pyran-4-yl)amino)-3-oxoprop-1-en-1-yl)phenethoxy)carbonyl)amino)-2-(p-tolyl)ethyl)boronic acid;
(R)-(1-(((3-cyano-5-(2-cyano-3-(diethylamino)-3-oxoprop-1-en-1-yl)phenethoxy)carbonyl)amino)-2-phenylethyl)boronic acid;
an individual E or Z isomer thereof; and/or
a pharmaceutically acceptable salt of any of the foregoing compounds.

Embodiment 29

The compound and/or a pharmaceutically acceptable salt of Formula (I), wherein Y is —OR² (Embodiment 4), R² is a group of Formula (b) (Embodiment 12), X is -alkyl-aryl- (Embodiment 16), wherein said -alkyl-aryl- is —(CH$_2$)$_{1-2}$-phenyl- (Embodiment 17-17A), X¹ is —C(=O)— (Embodiment 18), R$^{b1}$ is —(CH$_2$)$_{1-2}$— which is substituted with optionally substituted phenyl (Embodiments 22A-221B), such that the compound of Formula (I) is a compound of Formula I(b):

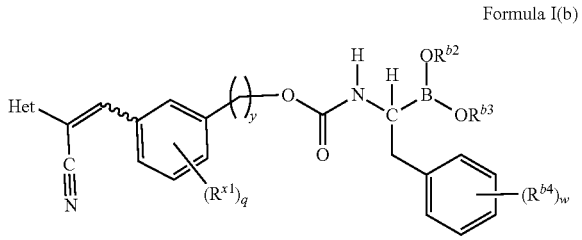

Formula I(b)

wherein in Formula I(b), Het is an aryl or heteroaryl; y is 1 or 2; w is 0, 1, 2, or 3 (Embodiment 22B); R$^{b4}$ is alkyl, halo, haloalkyl, or alkoxy (Embodiment 22B); q is 0 or 1; and R$^{x1}$ is cyano, halo, alkyl, hydroxyalkyl, or alkoxyalkyl (Embodiment 16B).

Embodiment 29A

The compound and/or a pharmaceutically acceptable salt of Embodiment 29, wherein in Formula I(b), R$^{b2}$ and R$^{b3}$ are each hydrogen.

Embodiment 29B

The compound and/or a pharmaceutically acceptable salt of Embodiment 29, wherein in Formula I(b), Het is pyrimidinyl or triazolyl.

Embodiment 29C

The compound and/or a pharmaceutically acceptable salt of Embodiment 29, wherein the compound of Formula I(b) is the E-isomer.

Embodiment 29D

The compound and/or a pharmaceutically acceptable salt of Embodiment 29, wherein the compound of Formula I(b) is the Z-isomer.

Embodiment 29E

The compound and/or a pharmaceutically acceptable salt of Embodiment 29, wherein the compound of Formula I(a) is chosen from:

(R)-(1-(((3-(2-cyano-2-(pyrimidin-2-yl)vinyl)phenethoxy)carbonyl)amino)-2-(p-tolyl)ethyl)boronic acid; and
(R)-(1-(((3-(2-cyano-2-(1H-1,2,4-triazol-1-yl)vinyl)phenethoxy)carbonyl)amino)-2-phenylethyl)boronic acid;
an individual E or Z isomer thereof; and/or
a pharmaceutically acceptable salt of any of the foregoing compounds.
A pharmaceutical composition comprising at least one compound of any of Embodiments 1-29, and/or a pharmaceutical acceptable salt thereof, and a pharmaceutically acceptable excipient.

Embodiment 30

A method of inhibiting Large Multifunctional Protease 2 (LMP2) and/or Large Multifunctional Protease 7 (LMP7) in a subject comprising administering to said subject in need of said inhibition a therapeutically effective amount of a compound of any one of Embodiments 1-29, and/or a pharmaceutically acceptable salt thereof.

Embodiment 31

A method of treating a disease chosen from an autoimmune disorder, an inflammatory disorder, and a hematological disorder in a subject in need of such treatment, comprising administering to the subject a therapeutically effective amount of a compound of any one of Embodiments 1-29, and/or a pharmaceutically acceptable salt thereof.

Embodiment 32

The method of Embodiment 31, wherein the disease is chosen from lupus, rheumatoid arthritis, scleroderma, ankylosing spondylitis, Duchene muscular dystrophy (DMD), Becker muscular dystrophy (BMD), idiopathic inflammatory myopathies (IIMs), polymyositis, sporadic inclusion body myositis, dermatomyositis, immune-mediated necrotizing myopathies (IMNM), psoriasis, multiple sclerosis, inflammatory bowel disease, Behçet's disease, ulcerative colitis, Crohn's disease, Sjogren's Syndrome, bronchitis, conjunctivitis, pancreatitis, cholecystitis, bronchiectasis, aortic valve stenosis, restenosis, fibrosis, infection, ischemia, cardiovascular disease, hepatitis, cirrhosis, steatohepatitis, chronic liver inflammation, Alzheimer's Disease (AD), amyotrophic lateral sclerosis (ALS), Huntington's disease, body myositis, myofibrilar myopathy, GVHD, and multiple myeloma.

The compounds of Formula (I), (I'), (I(a)), and (I(b)) can form salts. Reference to a compound of Formula (I), (I'), (I(a)), and (I(b)) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I), (I'), (I(a)), or (I(b)) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I), (I'), (I(a)), and (I(b)) may be formed, for example, by reacting a compound of Formula (I), ((I'), (I(a)), and (I(b)) respectively with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additional exemplary acids are those generally considered suitable for the formation of pharmaceutically useful salts from basic pharmaceutical compounds, and are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts, and all acid and base salts are considered equivalent to the free forms of the corresponding compounds (for example, a compound of Formula (I) (I), (I'), (I(a)), or (I(b))).

Compounds described herein may contain asymmetric or chiral centers, and, therefore, exist in different stereoisomeric forms. It is intended that all stereoisomeric forms of a compound describe herein (such as a compound of Formula (I) (I'), (I(a)), or (I(b)) as well as mixtures thereof, including racemic mixtures, form part of the described compound. In addition, all geometric and positional isomers are included in a compound described herein. For example, if a compound of Formula (I), (I'), (I(a)), or (I(b)) incorporates a double bond or a fused ring, both the cis- and trans-forms, as well as mixtures, are embraced.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of chiral HPLC column. Also, some of the compounds of Formula (I) (I'), (I(a)), or (I(b)) may be atropisomers (e.g., substituted biaryls) and are considered as part of Formula (I).

It is also possible that compounds described herein (for example, a compound of Formula (I)), (I'), (I(a)), or (I(b))) may exist in different tautomeric forms, and all such forms are embraced. Also, for example, all keto-enol and imine-enamine forms of the compounds described herein are included.

All stereoisomers (for example, geometric isomers, optical isomers and the like) of the compounds described herein (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the compounds described herein, as are positional isomers (such as, for example, 4-pyridyl and 3-pyridyl). (For example, if a compound of Formula (I), (I'), (I(a)), or (I(b)) incorporates a double bond or a fused ring, both the cis- and trans-forms, as well as mixtures) are embraced. Individual stereoisomers of the compounds described herein, for example, may be substantially free of other isomers, or may be admixed, for example, as racemates or with all other, or other selected, stereoisomers. The chiral centers can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the compounds described herein.

Isotopically-labelled compounds of the compounds described herein which are identical to those recited herein, but for the fact that one or more atoms are replaced by an atom having an atomic mass or mass number different from the atomic mass or mass number usually found in nature are also embraced. Examples of isotopes that can be incorporated into compounds described herein include isotopes of hydrogen, carbon, nitrogen, oxygen, phosphorus, fluorine and chlorine and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Certain isotopically-labelled compounds of Formula (I) (I'), (I(a)), or (I(b)) can be useful for medical imaging purposes. for example, those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single Photon Emission Computed Tomography (SPECT). Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^{2}H$) may afford certain therapeutic advantages resulting from greater metabolic stability (e.g., increased in vivo half-life or reduced dosage requirements), and hence, may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half-lives ($t_{1/2}$>1 day), can generally be prepared by following procedures analogous to those disclosed in the Schemes and/or in the Examples herein below, by substituting an appropriate isotopically labeled reagent for a non-isotopically labeled reagent.

Scheme 1 below illustrates a general synthetic procedure for preparing compounds of Formula (I) wherein Y is

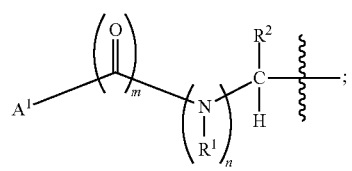

$A^1$, $R^{b1}$, $R^{b2}$, $R^{b3}$, $R^6$, $R^7$, $X^1$ and Het are provided herein, and $R^2$ is a group of Formula (c) where m is 1, n is 1, $R^1$ is H, and X is -alkyl-aryl- (more specifically —(CH$_2$)$_2$-phenyl-). Compound of formula 1, commercially available, undergoes three step sequences to give a compound of formula 4. Amide coupling of a compound of formula 4 with a carboxylic acid of formula 5 and subsequent ester hydrolysis leads to a compound of formula 7. Condensation with a compound of either formula 8 or formula 9 gives compounds with formula 10 or 11. Amide coupling with an aminoborate of formula 12 affords a compound of Formula (I). Deprotection of the boronic ester yields the boronic acid compounds of Formula (I) where $R^{b2}$ and $R^{b3}$ is H.

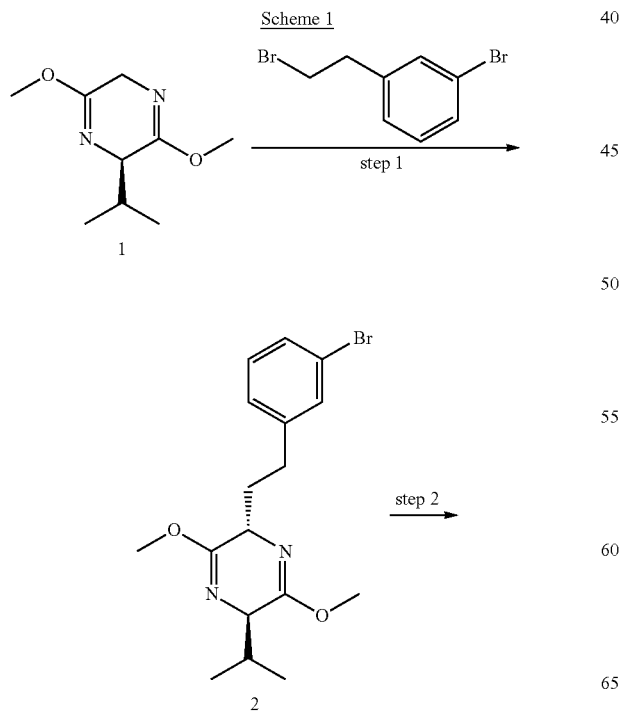

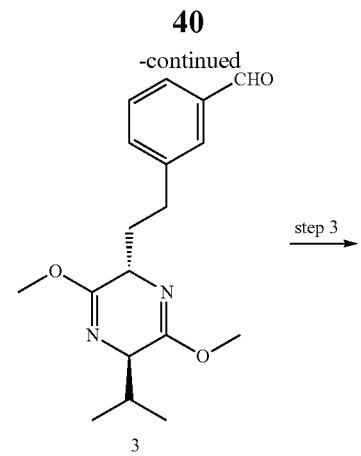

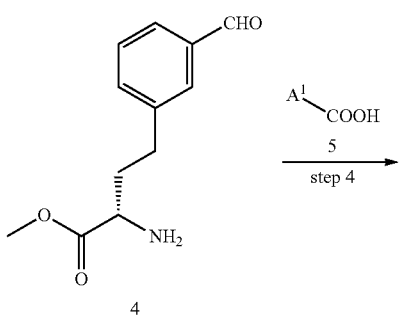

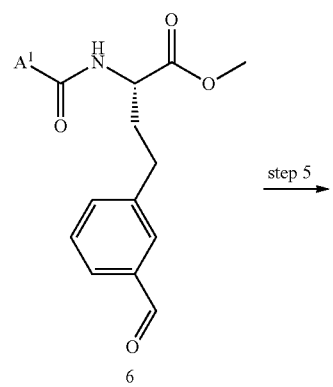

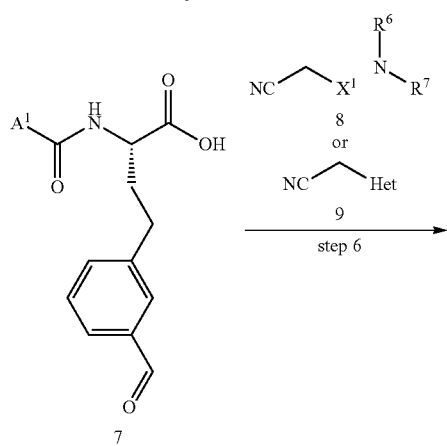

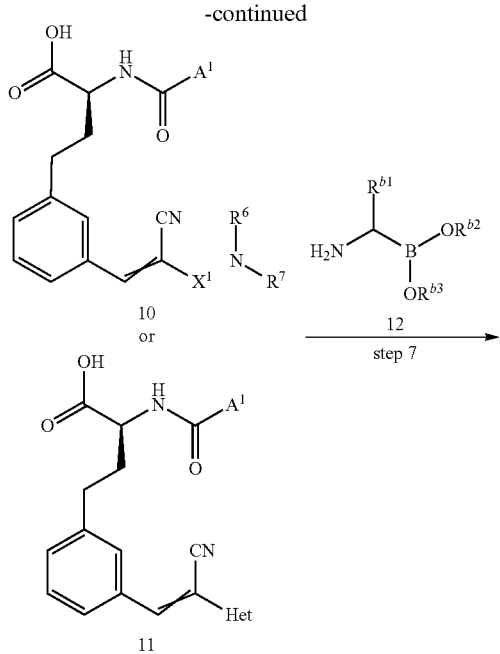

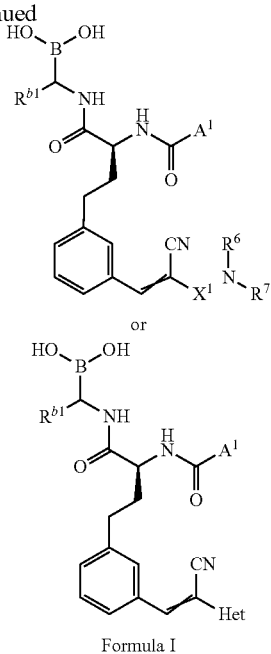

Scheme 2 below illustrates a general synthetic procedure for preparing compounds of Formula (I) wherein Y is

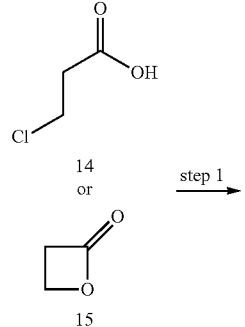

$R^{b1}$, $R^{b2}$, $R^{b3}$, $R^6$, $R^7$, $X^1$ and Het are provided herein, and m is 0, n is 0, $A^1$ is H, and X is -alkyl-O-aryl- (more specifically —$(CH_2)_2$—O-phenyl-). Compound of formula 13, commercially available, reacts with either 3-chloropropanoic acid (14) or oxetan-2-one (15) to give a compound of formula 16. Condensation with a compound of either formula 8 or formula 9 gives compounds with formula 17 or 18. Amide coupling with an aminoborate of formula 12 affords a compound of Formula (I). Deprotection of the boronic ester yields the corresponding boronic acid analogues, where $R^{b2}$ and $R^{b3}$ is H.

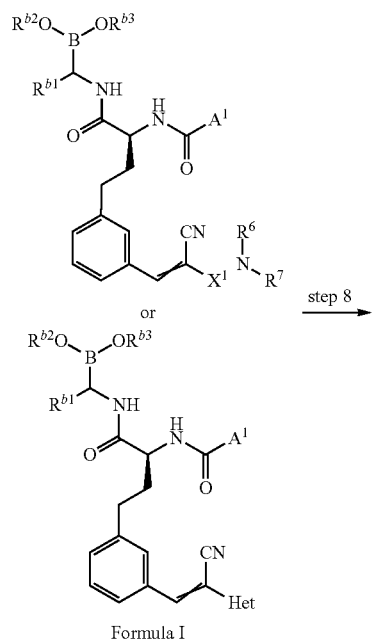

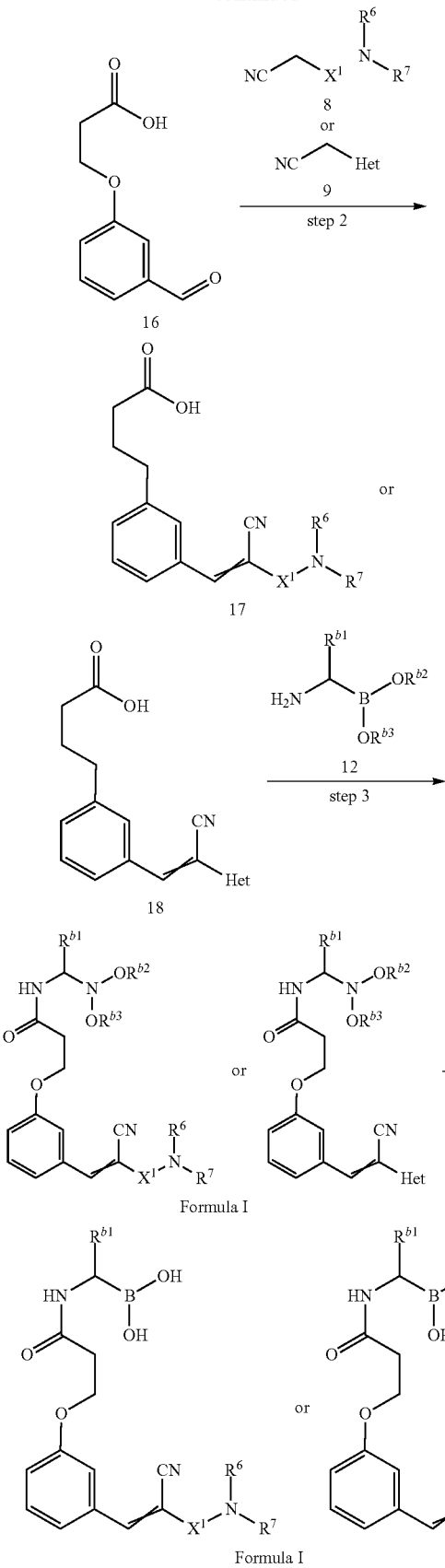

Scheme 3 below illustrates a general synthetic procedure for preparing compounds of Formula (I) wherein Y is $OR^2$; $R^2$, $R^{b1}$, $R^{b2}$, $R^{b3}$, $R^6$, $R^7$, $X^1$ and Het are provided herein, and m is 0, n is 0, $A^1$ is H, and X is -alkyl-aryl- (more specifically —$(CH_2)_2$-phenyl-). Compound of formula 19, undergoes a condensation reaction with a compound of either formula 8 or formula 9 to give compounds with formula 20 or 21. Reaction of the alcohol with a compound of formula 22, such as nitrophenyl chloroformate, carbonyl diimidazole, or disuccinimidyl carbonate, where LG is a leaving group, produces compounds of formula 23 or 24. Displacement of the leaving group (LG) with an aminoborate of formula 12 affords a compound of Formula (I). Deprotection of the boronic ester yields the corresponding boronic acid analogues, where $R^{b2}$ and $R^{b3}$ is H.

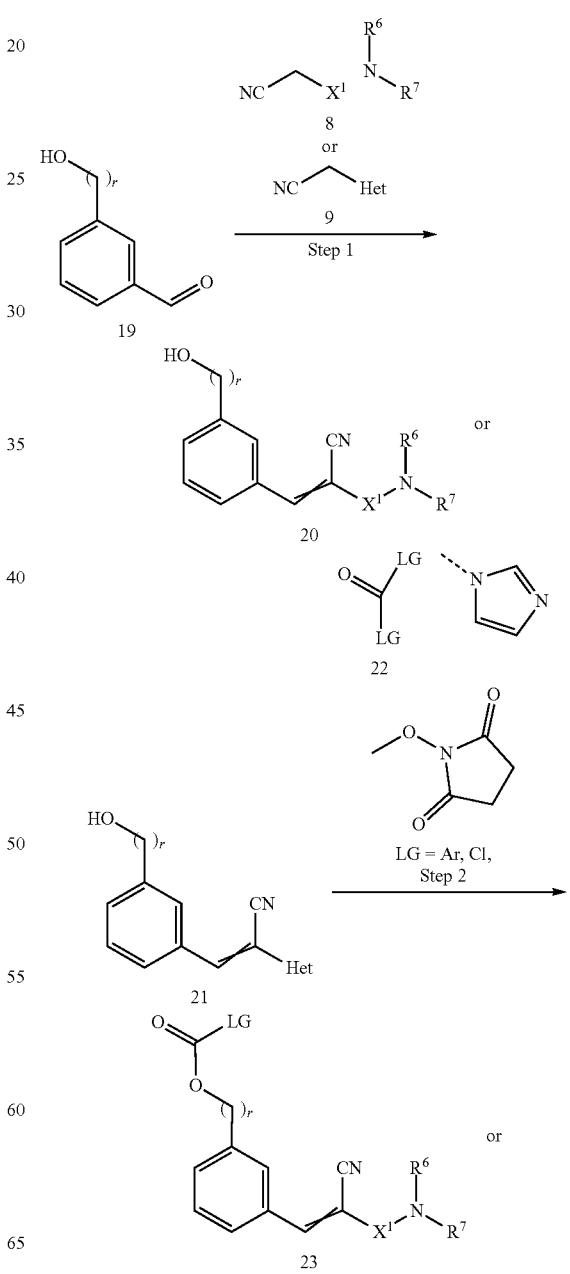

Scheme 3

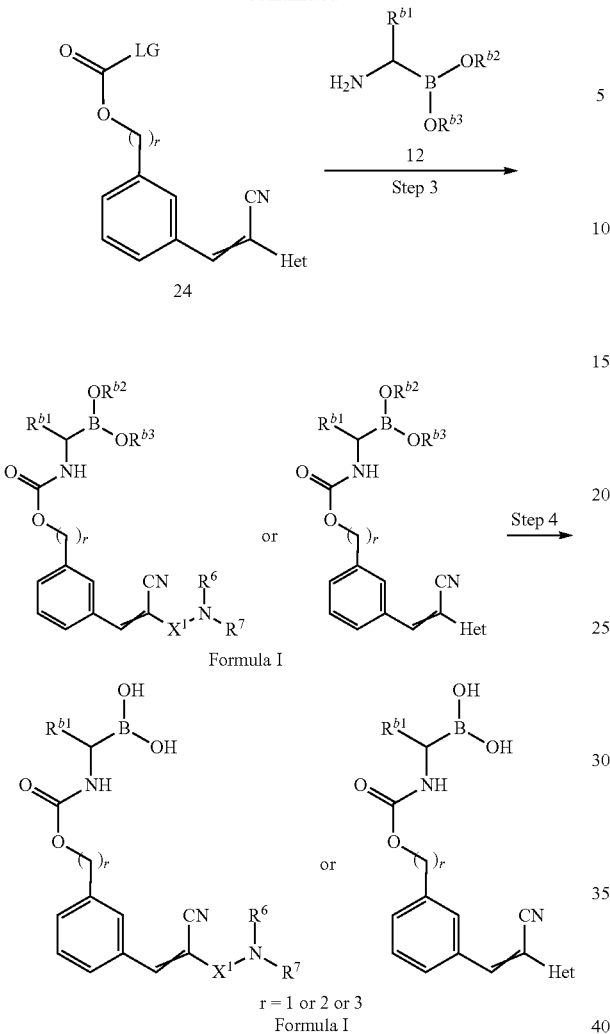
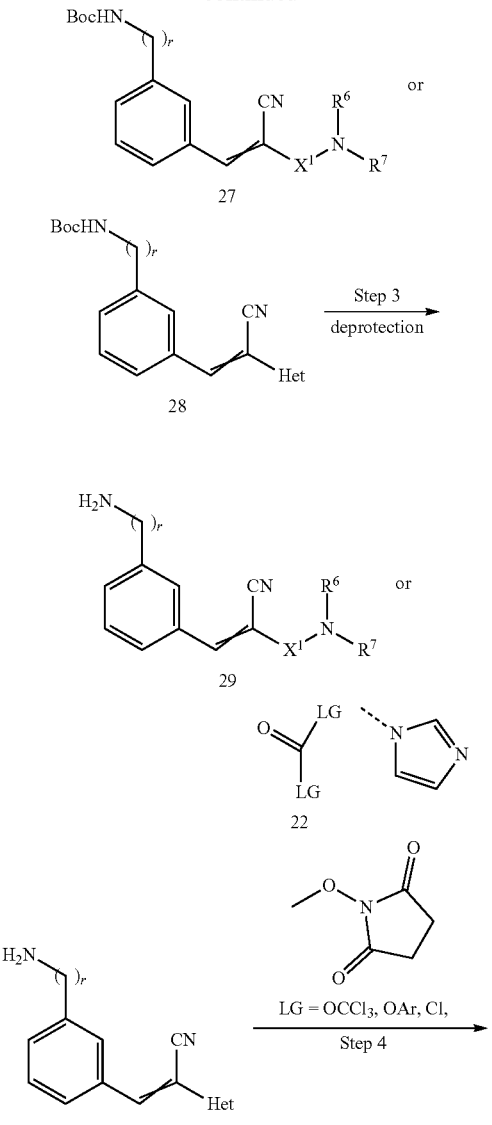
Scheme 4
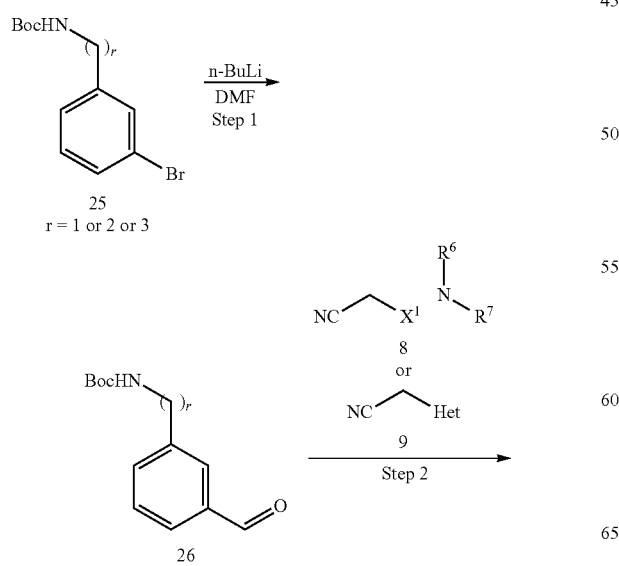

-continued

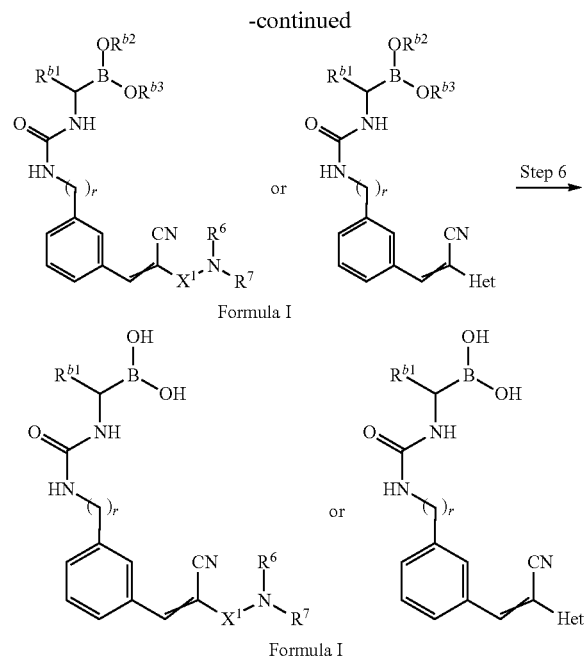

Formula I

Scheme 4 illustrates a general synthetic procedure for preparing compounds of Formula (I) wherein Y is $OR^2$; $R^2$, $R^{b1}$, $R^{b2}$, $R^{b3}$, $R^6$, $R^7$, $X^1$ and Het are as defined in the Summary and m is 0, n is 0, $A^1$ is H, and X is -alkyl-aryl- (more specifically —$(CH_2)_2$-phenyl-). Compound of formula 25, is converted to the corresponding aldehyde of formula 26, then undergoes a condensation reaction with a compound of either formula 8 or formula 9 to give compounds with formula 27 or 28. Deprotection of the Boc group and subsequent reaction with a compound of formula 22, such as triphsogene, produces compounds of formula 31 or 32. Coupling of compound of formula 31 and 32 with aminoborate of formula 12 affords a compound of Formula (I). Deprotection of the boronic ester yields corresponding boronic acid analogues of Formula (I), where $R^{b2}$ and $R^{b3}$ is H.

Utility

Given the evidence that immunoproteasomes (e.g., LMP-2 and/or LMP-7) are important in the regulation of various immune responses and the selective expression of LMP-2 and/or LMP-7 in tissues that contain the immunoproteasome, inhibitors of LMP-2 and/or LMP-7 can be used for the treatment of autoimmune disorders. Autoimmune disorders are characterized by inappropriate reaction of the immune system to the host's healthy organs and tissues. Examples of autoimmune disorders that could be treated with an LMP-2 and/or LMP-7 inhibitors include but are not limited to lupus, rheumatoid arthritis, scleroderma, ankylosing spondylitis, dermatomyositis, psoriasis, multiple sclerosis and inflammatory bowel disease (such as ulcerative colitis and Crohn's disease). Another example of an autoimmune disease is Sjogren's Syndrome (SS), which is characterized by infiltration and focal accumulation of lymphocytes in the exocrine glands. It has been shown that there is a significant up-regulation of LMP7 in the salivary glands of Sjogren's patients (see Egerer et al, 2006. Tissue-specific up-regulation of the proteasome subunit beta5i (LMP7) in Sjögren's syndrome. Arthritis Rheum 54:1501-8). Thus, treatment of SS patients with an immunoproteasome inhibitor can mitigate the symptoms of the disease. In addition to autoimmune diseases, tissue/organ transplant rejection occurs when the immune system attacks therapeutic cells that are introduced to the host's body. Graft versus host disease (GVHD), resulting from allogenic transplantation, arises when the immune cells from the donor tissue attack the host's tissues. Therefore, GVHD is another potential utility of treatment with an immunoproteasome inhibitor.

In addition to autoimmune diseases, immunoproteasome inhibitors can be used in circumstances when chronic or acute inflammation leads to tissue damage or loss of function. Proteasome inhibitors have been shown to have anti-inflammatory activity (see Elliot et al. Proteasome inhibition: a new anti-inflammatory strategy. 2003, J Mol Med. 81:235-245). Examples of inflammatory diseases in which treatment with an immunoproteasome inhibitor may have utility include acute conditions (e.g., bronchitis, conjunctivitis, pancreatitis) and chronic conditions (e.g., chronic cholecystitis, hepatitis, bronchiectasis, aortic valve stenosis, restenosis, Behçet's disease, psoriasis and arthritis), along with conditions associated with inflammation (such as fibrosis, infection and ischemia). Behçet's disease (BD) is a chronic, relapsing, inflammatory multisystem disease of unknown etiology. Oral ulcers, genital ulcers, cutaneous lesions, and ocular and articular involvement are the most frequent features of the disease. Accordingly, immunoproteasome inhibitors may be used to treat one or more of oral ulcers, genital ulcers, cutaneous lesions, and ocular and articular involvement.

Upregulation of the immunoproteasome has been detected in response to cardiovascular inflammation potentially resulting in vascular cell apoptosis (see Zang et al. 2009. Cardiovascular inflammation and lesion cell apoptosis: a novel connection via the interferon-inducible immunoproteasome. Arterioscler Thromb Vase Biol. 29:1213-1219), thus, providing utility in cardiovascular disease. Upregulation of the immunoproteasome has also been detected in liver biopsies of patients with chronic active hepatitis, cirrhosis and steatohepatitis (see French, et al. The immunoproteasome in steatohepatitis: Its role in Mallory-Denk body formation. 2011, Experimental and Molecular Pathology 90: 252-256), thus, providing utility in treating chronic liver inflammation. Another chronic inflammatory condition characterized by tissue damage is Alzheimer's Disease (AD) in which microglia, the resident macrophages in the brain, are stimulated to release various proinflammatory cytokines. Increased expression of the immunoproteasome has been found in brain tissue from AD patients compared to control elderly adults not exhibiting symptoms of dementia (see Mishto et al. Immunoproteasome and LMP2 polymorphism in aged and Alzheimer's disease brains. 2006. Neurobiol Aging 27:54-66). In addition, inclusion body myositis and myofibrilar myopathy are muscle diseases that show protein accumulation and increased immunoproteasome expression (see Ferrer et al. 2004. Proteasomal expression, induction of immunoproteasome subunits and local MHC class I presentation in myofibrillar myopathy and inclusion body myositis. J Neuropathol Exp Neurol. 63:484-498). Therefore, treatment of AD patients or other neurodegenerative conditions (such as amyotrophic lateral sclerosis (ALS), and Huntington's disease resulting from chronic inflammation in response to accumulation of protein aggregates) with an immunoproteasome inhibitor constitute additional potential utilities.

Duchene muscular dystrophy (DMD) is an inherited disease, characterized by progressive muscle degeneration and weakness. The disease is caused by a mutation of the DMD gene which leads to deficiency of dystrophin, a protein found throughout the cyctoplasmic face of the plasma membrane in both skeletal and cardiac muscle. Becker muscular dystrophy (BMD), a much milder allelic form of the disease, is caused by a reduction in the amount, or an alteration in the size, of the dystrophin protein. These diseases may also be treated by the presently disclosed immunoproteasome inhibitors.

Idiopathic inflammatory myopathies (IIMs) are muscle diseases characterized by muscle weakness and specific inflammatory infiltrates in muscle. These diseases can be classified as polymyositis, sporadic inclusion body myositis (sIBM), dermatomyositis (DM) and immune-mediated necrotizing myopathies (IMNM). These diseases may also be treated by the presently disclosed immunoproteasome inhibitors.

Targeted inhibition of immunoproteasome is also a potent strategy against models of multiple myeloma that overcome resistance to conventional drugs and nonspecific proteasome inhibitors. Accordingly multiple myeloma may also be treated by the presently disclosed immunoproteasome inhibitors.

Testing

The immunoproteasome inhibitory activity of the compounds described herein can be tested using the in vitro assays described in Biological Examples below. A determination of the immunoproteasome inhibitory activity by any of those assays is considered to be immunoproteasome inhibitory activity within the scope of this disclosure even if any or all of the other assays do not result in a determination of immunoproteasome inhibitory activity. The residence time of the compound immunoproteasome bound complexes can be tested using the Biological Example 5 and 6 below. The ability of the compounds described herein to form reversible covalent bond with the immunoproteasome can be determined by the assays described in Biological Examples 4-6 below.

Without being bound to any specific mechanistic theory, when a compound described herein forms a reversible covalent bond with a cysteine of the immunoproteasome, it is believed that the cysteine sulfhydryl group and a carbon atom forming part of the carbon-carbon double bond in the Y group of Formula (I) where $R^2$ is a group of Formula (a) or (b) (see Formula (I)) can form a reversible, i.e., labile, covalent bond, defined herein, such as wherein Cys48 of LMP7 attacks an electron deficient carbon atom of the carbon-carbon double bond in the group of Formula (a) or (b) in the compound of Formula (I) to form a thiol adduct (e.g., Michael reaction with cysteine).

Furthermore, all the subunits of an immunoproteasome contain a catalytic threonine residue which can interact with the boronic acid/boronic esters through labile covalent binding (see for example Reem Smoum eta al., "Boron Containing Compounds as Protease Inhibitors", *Chemical Reviews*, 2012, 112, 4156-4220.) In some embodiments, the electron deficient carbon atom of the olefin is distal to the carbon attached to the cyano group and to the electron withdrawing —$X^1NR^6R^7$ or Het, moiety in the compounds described herein. Therefore, the combination of the cyano, a second electron withdrawing group and the olefinic moiety to which they are bonded in a compound described herein (for example, a compound of Formula (I)) can increase the reactivity of the olefin to form a thiol adduct with the active site cysteine residue in LMP7.

The compounds described herein can bind with the immunoproteasome in several different manners. In addition to the labile covalent binding, discussed above (with respect to the cysteine —SH group and the threonine —OH group), they also can form non-covalent binding (e.g., via van der Waals binding, hydrogen binding, hydrophobic binding, hydrophilic binding, and/or electrostatic charge binding) with the immunoproteasome, the non-covalent binding being sufficient to at least partially inhibit the kinase activity of the immunoproteasome As disclosed herein, with regard to LMP7, one of the labile covalent bindings between compound described herein and the immunoproteasome occurs between the olefin mentioned above in the compound and the thiol (sulfydryl) residue of cysteine 48 of LMP7, at or near the site where the compound has the aforementioned non-covalent binding with the LMP7.

Therefore, a compound described herein, which form a reversible covalent with the immunoproteasome, can have both a cysteine-mediated covalent binding (in the case of LMP7) and threonine-mediated covalent binding (for all subunits of immunoproteasome) and a non-covalent binding. This is in contrast with non-covalent reversible inhibitors which inhibit the immunoproteasome only via non-covalent binding and lack the cysteine-mediated and/or the threonine-mediated covalent binding.

The result of the binding of a compound described herein (for example, a compound of Formula (I)) with the immunoproteasome in the several different manners as disclosed herein is a reversible covalent inhibitor having a slow off-rate and a protracted duration of action, in some instances comparable to an irreversible covalent inhibitor without forming permanent irreversible protein adducts. The difference between irreversible and reversible covalent inhibitors, particularly the compounds disclosed herein, can be ascertained utilizing assays disclosed herein.

In general, the binding involved in an inhibitor that forms a reversible covalent bond with the immunoproteasome, i.e., the compounds disclosed herein, is stable when the immunoproteasome/immunoproteasome subunit is in certain configurations and susceptible to being broken when the immunoproteasome/immunoproteasome subunit is in different configurations (in both cases under physiologic conditions), whereas the interaction between an inhibitor that forms an irreversible covalent bond is stable under physiologic conditions even when the immunoproteasome/immunoproteasome subunit is in different configurations.

A reversible covalent bond often imparts unique properties related to the residence time of the compound within the cysteine-containing and/or threonine-containing binding site. In this context, residence time refers to the temporal duration of the compound-target complex under different conditions (see Copeland R A, Pompliano D L, Meek T D. Drug-target residence time and its implications for lead optimization. Nat. Rev. Drug Discov. 5(9), 730-739 (2006)).

The presence of a reversible covalent bond in a reversible covalent inhibitor as disclosed herein can lead to an extended residence time when compared to a compound that does not form a covalent bond with the immunoproteasome/immunoproteasome subunit. In some embodiments disclosed herein, a compound described herein (for example, a compound of Formula (I)) that are reversible covalent inhibitors have a residence time of at least about 1 h, Residence time may be measured using wash-out assay in a biochemical or cellular environment (see Biological Examples 4-6 below.) A determination of the binding reversibility of the covalent bond between the cysteine residue and the olefinic bond (in the case of LMP7) and between the threonine residue and the boronic acid/ester (in the case of all immunoproteasome subunits) of the compounds described herein by any of the Biological Examples 4-6 below is considered to be binding reversibility within the scope of this disclosure even if one or the other method does not result in a determination of binding reversibility.

Administration and Pharmaceutical Composition

In general, the compounds described herein will be administered in a therapeutically effective amount by any of the accepted modes of administration for agents that serve similar utilities. Therapeutically effective amounts of a compound described herein may range from about 0.01 to about 500 mg per kg patient body weight per day, which can be administered in single or multiple doses. A suitable dosage level may be from about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound, i.e., the active ingredient, will depend upon numerous factors such as the severity of the disease to be treated, the age and relative health of the patient, the potency of the compound being utilized, the route and form of administration, and other factors.

In general, compounds described herein will be administered as pharmaceutical compositions by any one of the following routes: oral, systemic (e.g., transdermal, intranasal or by suppository), parenteral (e.g., intramuscular, intravenous or subcutaneous) or topical (e.g., application to skin) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound described herein) in combination with at least one pharmaceutically acceptable excipient. Acceptable excipients are non-toxic, aid administration, and do not adversely affect the therapeutic benefit of the compound. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be chosen from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound described herein in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %) basis, from about 0.01-99.99 wt % of a compound described based on the total formulation, with the balance being one or more suitable pharmaceutical excipients. Preferably, the compound is present at a level of about 1-80 wt %.

A compound described herein may be used in combination with one or more other drugs in the treatment of diseases or conditions for which a compound described herein or the other drugs may have utility, where the combination of the drugs together are safer or more effective than either drug alone. Such other drug(s) may be administered, by a route and in an amount commonly used therefore, contemporaneously or sequentially with a compound described herein. When a compound described herein is used contemporaneously with one or more other drugs, a pharmaceutical composition in unit dosage form containing such other drugs and a compound described herein is preferred. However, the combination therapy may also include therapies in which a compound described herein and one or more other drugs are administered on different overlapping schedules. It is also contemplated that when used in combination with one or more other active ingredients, a compound described herein and the other active ingredients may be used in lower doses than when each is used singly.

Accordingly, a pharmaceutical composition described herein also can include those that contain one or more other active ingredients, in addition to a compound described herein.

SYNTHETIC EXAMPLES
Example 1
((R)-1-((S)-4-(3-(3-(tert-butylamino)-2-cyano-3-oxoprop-1-en-1-yl)phenyl)-2-(pyrazine-2-carboxamido)butanamido)-2-phenylethyl)boronic Acid
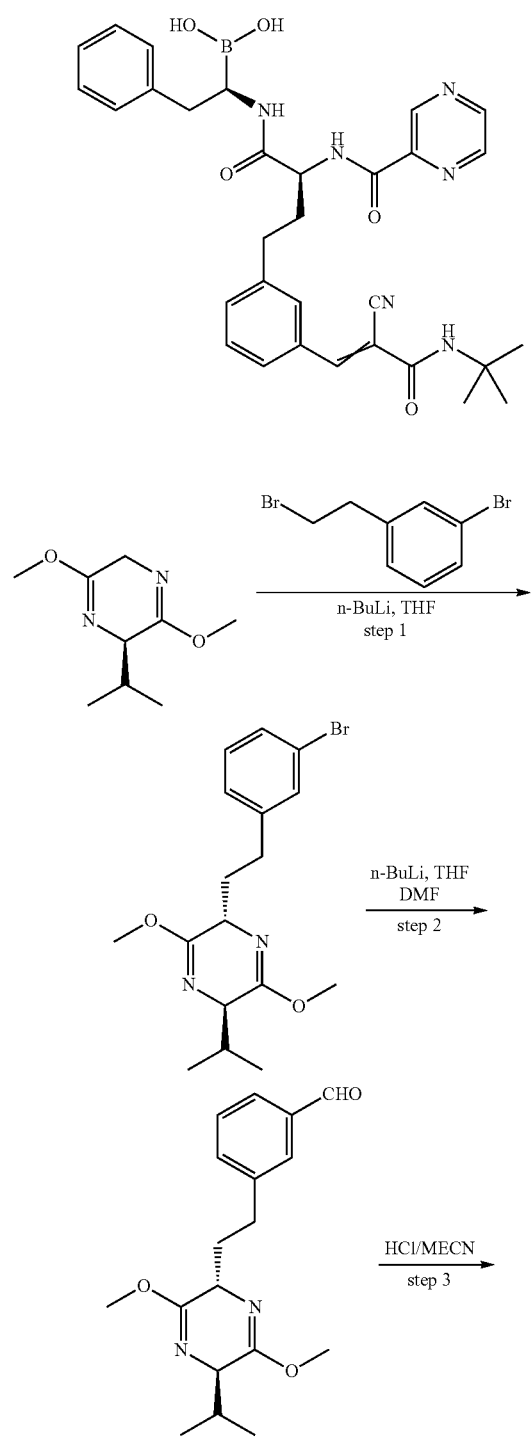
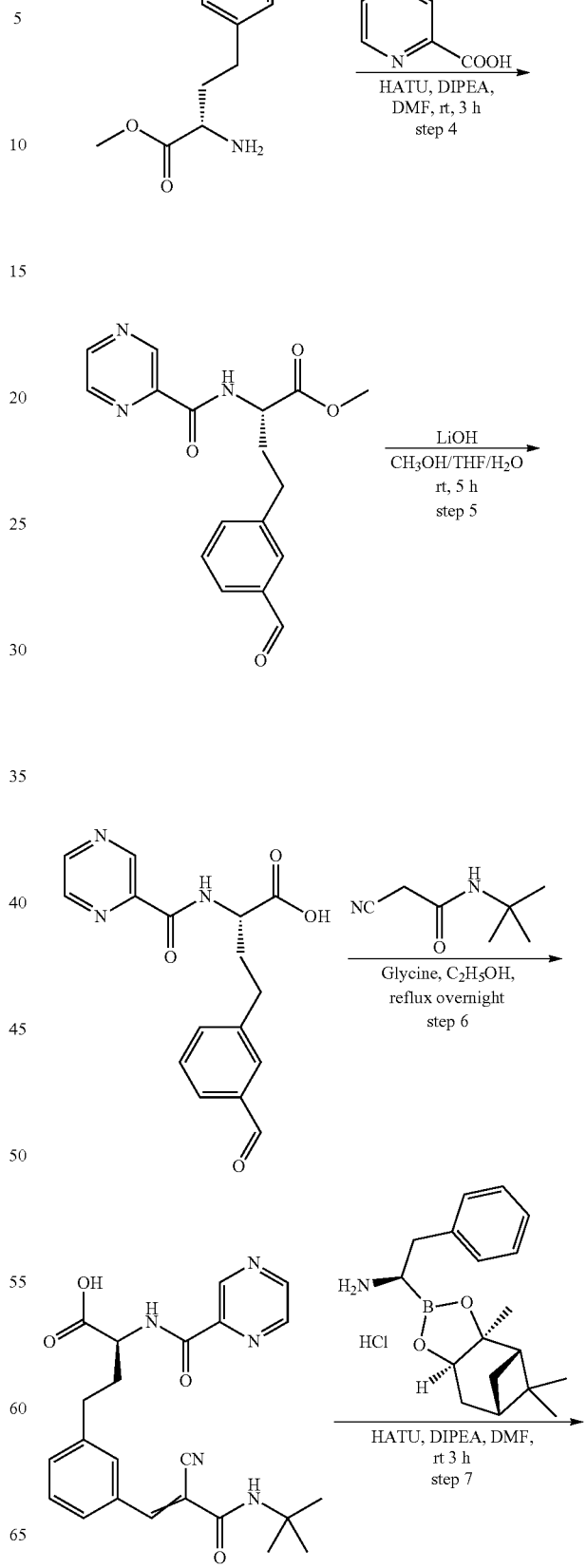

-continued

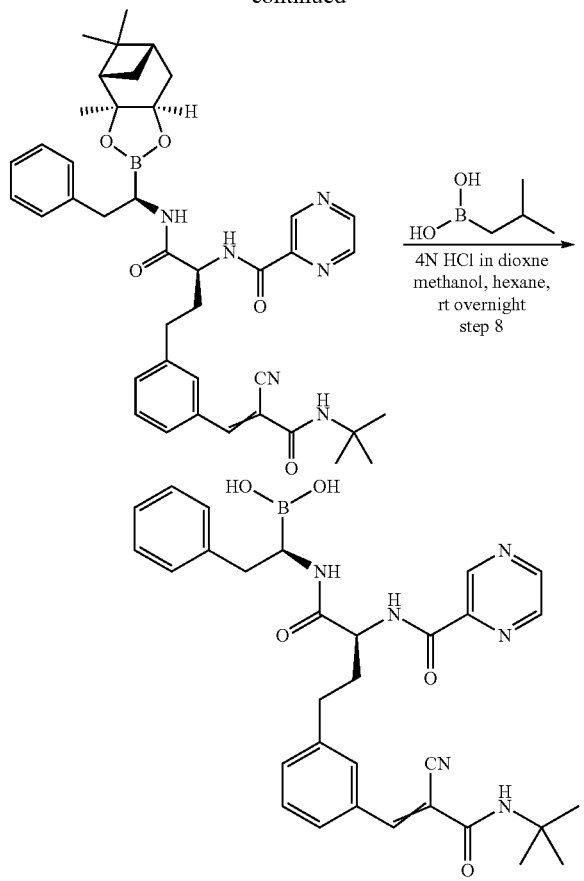

To a 100 mL three neck round bottomed flask under nitrogen atmosphere, (R)-2-isopropyl-3,6-dimethoxy-2,5-dihydropyrazine (4 g, 21.7 mmol) was dissolved in dry THF (28 mL) and cooled to −78° C. To this reaction mixture, 1.6 M solution of n-BuLi in hexanes (16.28 mL, 26 mmol) was added dropwise at −78° C. and stirred at same temperature for 15 minutes. After 15 minutes, 1-bromo-3-(2-bromoethyl) benzene (5.73 g, 21.7 mmol) in dry THF (13 mL) was added dropwise at −78° C. and stirred at −78° C. for 1 h followed by stirring at room temperature (rt) for 3 h. The reaction was monitored by TLC using ethyl acetate:hexanes (0.3:9.7) as a mobile phase. After completion of the reaction, reaction mixture was quenched with saturated ammonium chloride solution (75 mL) and extracted using ethyl acetate (3×100 mL). Combined organic layer was dried over sodium sulphate and concentrated to give crude which was purified by flash column purification with 1-3% ethyl acetate in hexanes to yield 3.3 g of (2S,5R)-2-(3-bromophenethyl)-5-isopropyl-3,6-dimethoxy-2,5-dihydropyrazine (41.38% yield).

To a 100 mL three neck round bottomed flask under nitrogen atmosphere, (2S,5R)-2-(3-bromophenethyl)-5-isopropyl-3,6-dimethoxy-2,5-dihydropyrazine (3.3 g, 8.9 mmol) was dissolved in dry THF (33 mL) and cooled to −78° C. To this reaction mixture, 1.6 M solution of n-BuLi in hexanes (6.8 mL, 10 mmol) was added dropwise at −78° C. and stirred at same temperature for 15 minutes. After 15 minutes, DMF (2.7 mL, 37 mmol) was added dropwise at −78° C. and stirred at −78° C. for 3 h. The reaction was monitored by TLC using ethyl acetate:hexanes (0.3:9.7) as a mobile phase. After completion of the reaction, reaction mixture was quenched with saturated ammonium chloride solution (50 mL) and extracted using ethyl acetate (50 mL×3). Combined organic layer was dried over sodium sulphate and concentrated to give crude which was purified by flash column purification with 5% ethyl acetate in hexanes to yield 1.9 g of 3-(2-((2S,5R)-5-isopropyl-3,6-dimethoxy-2,5-dihydropyrazin-2-yl)ethyl)benzaldehyde (66.83% yield).

To a 50 mL round bottomed flask, 3-(2-((2S,5R)-5-isopropyl-3,6-dimethoxy-2,5-dihydropyrazin-2-yl) ethyl)benzaldehyde (1.7 g, 5.3 mmol) was dissolved in acetonitrile (17 mL). To this, 2 N HC (17 mL) was added and stirred at rt for 16 h. The reaction was monitored by TLC using ethyl acetate: hexanes (2:8) as a mobile phase. After completion of reaction, reaction mixture was evaporated and azeotrope with toluene (50 mL×2) to yield 1.7 g crude of methyl (S)-2-amino-4-(3-formylphenyl)butanoate which was purified using acid base treatment. The crude was dissolved in dilute HCl (50 mL) and washed with ethyl acetate (50 mL×3). The organic layer was discarded and acidic layer was basify using sodium bicarbonate. The aqueous was extracted with ethyl acetate (100 mL×3). Combine organic layer was dried, concentrated and evaporated to get the 0.4 g of methyl (S)-2-amino-4-(3-formylphenyl)butanoate (33.65% yield).

To a solution of (S)-2-amino-4-(3-formylphenyl)butanoate (2 g, 9 mmol), pyrazine-2-carboxylic acid (1.35 g, 10.8 mmol) and HATU (5.1 g, 13.5 mmol) in DMF (25 mL) at rt was slowly added Et₃N (1.8 g, 18 mmol). After 1 h, the reaction was diluted with H₂O (30 mL) and extracted with EtOAc (50 mL). The organic layer was dried over anhydrous sodium sulfate, filtered and concentrated to give a crude residue which was purified by column chromatography with PE:EA (4:1) to afford methyl (S)-4-(3-formylphenyl)-2-(pyrazine-2-carboxamido)butanoate as a light yellow solid (1.9 g, 65%).

To a solution of methyl (S)-4-(3-formylphenyl)-2-(pyrazine-2-carboxamido)butanoate (2.6 g, 8.0 mmol) in THF: water (25:25 mL) was added LiOH (290 mg, 11.9 mmol) was added and stirred at rt for 2 h. The reaction was monitored by TLC using ethyl acetate: hexanes (1:1) as a mobile phase. After completion of reaction, THF was evaporated from the reaction mixture and aqueous layer was washed with ethyl acetate (20 mL) and organic layer was discarded. The aqueous layer was acidify with 1N HCl and extracted using ethyl acetate (20 mL×3). Combined organic layer was dried over sodium sulphate and concentrated under vacuum to give (S)-4-(3-formylphenyl)-2-(pyrazine-2-carboxamido)butanoic acid (2.1 g, 85%).

To a solution of (S)-4-(3-formylphenyl)-2-(pyrazine-2-carboxamido)butanoic acid (240 mg, 0.77 mmol) in C₂H₅OH (10 mL) were added N-(tert-butyl)-2-cyanoacetamide (160 mg, 1.15 mmol), followed by addition of glycine (289 mg, 3.85 mmol) with stirring. The resulting mixture was refluxed for overnight. The mixture was concentrated and the residue was purified by silica gel column chromatography (PE:EtOAc=4:1 to 1:1) to give (R)-4-(3-(3-(tert-butylamino)-2-cyano-3-oxoprop-1-en-1-yl)phenyl)-2-(pyrazine-2-carboxamido)butanoic acid as light yellow solid (200 mg, 60%).

To a solution of (R)-4-(3-(3-(tert-butylamino)-2-cyano-3-oxoprop-1-en-1-yl)phenyl)-2-(pyrazine-2-carboxamido)butanoic acid (200 mg, 0.46 mmol), (R)-2-phenyl-1-((3aS,4S,6S,7aR)-3a,5,5-trimethylhexahydro-4,6-methanobenzo[d][1,3,2]dioxaborol-2-yl)ethan-1-amine (185 mg, 0.55 mmol) and HATU (262 mg, 0.69 mmol) in DMF (5 mL) at rt was slowly added DIPEA (178 mg, 1.38 mmol). After 1 h, the reaction was diluted with H₂O (10 mL) and extracted with EtOAc (20 mL). The organic layer was dried over anhydrous sodium sulfate, filtered and concentrated to give a crude residue which was purified by column chromatography to afford N—((R)-4-(3-(3-(tert-butylamino)-2-cyano-3-oxoprop-1-en-1-yl)phenyl)-1-oxo-1-(((R)-2-phenyl-1-((3aS,4S,6S,7aR)-3a,5,5-trimethylhexahydro-4,6-methanobenzo[d][1,3,2]dioxaborol-2-yl)ethyl)amino)butan-2-yl)pyrazine-2-carboxamide as a light yellow solid (115 mg, 35%).

To a solution of N—((R)-4-(3-(3-(tert-butylamino)-2-cyano-3-oxoprop-1-en-1-yl)phenyl)-1-oxo-1-(((R)-2-phenyl-1-((3aS,4S,6S,7aR)-3a,5,5-trimethylhexahydro-4,6-methanobenzo[d][1,3,2]dioxaborol-2-yl)ethyl)amino)butan-2-yl)pyrazine-2-carboxamide (110 mg, 0.15 mmol) in MeOH (5 mL) were added hexane (5 mL) and 4 mol/L HCl (2 mL), then isobutyl boronic acid (30 mg, 0.30 mol) was added. After stirring at rt for 12 h, the solvent was he solvent was removed. The crude material was purified by Prep-HPLC to afford ((R)-1-((R)-4-(3-(3-(tert-butylamino)-2-cyano-3-oxoprop-1-en-1-yl)phenyl)-2-(pyrazine-2-carboxamido)butanamido)-2-phenylethyl)boronic acid as white solid (8 mg, 10%). LC-MS (ES, m/z): 604.9 [M+23]; 564.9 [M−17].

Example 2

(R)-(1-(3-(3-(3-(tert-butylamino)-2-cyano-3-oxoprop-1-en-1-yl)phenoxy)propanamido)-2-phenylethyl)boronic Acid

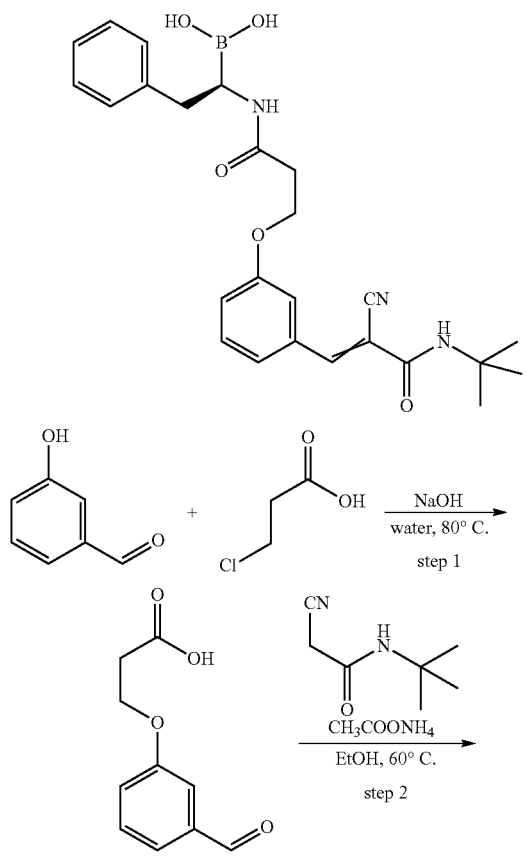

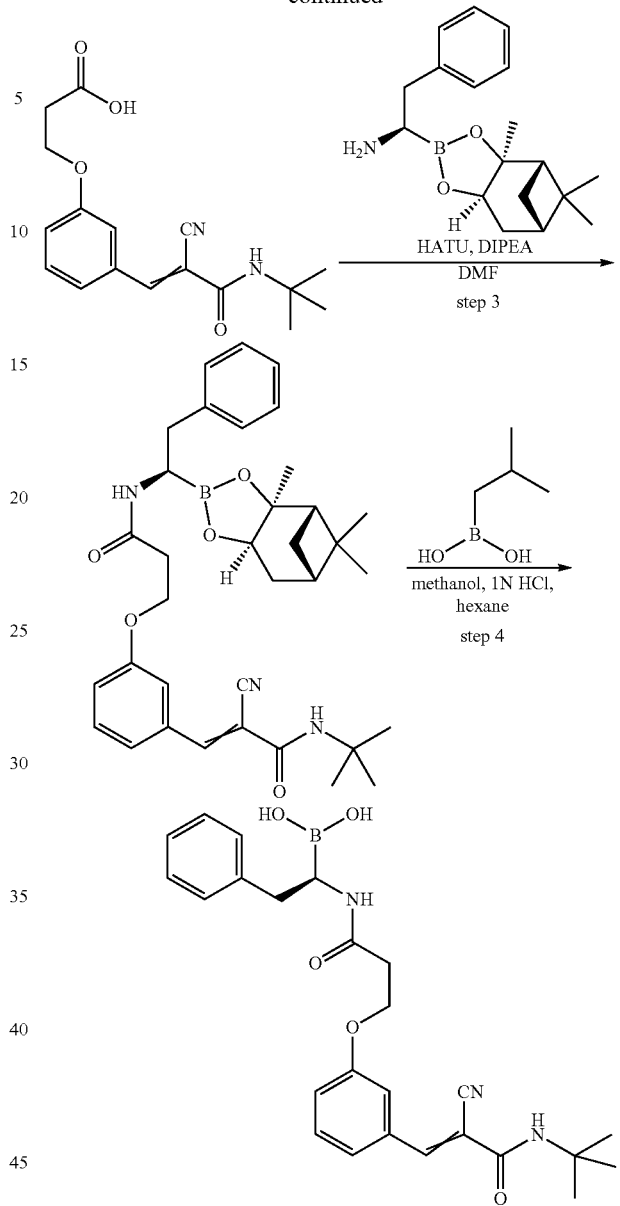

To a solution of 3-hydroxybenzaldehyde (5 g, 41 mmol) and 3-chloropropanoic acid (4.4 g, 41 mmol) in water (100 me) at rt was added NaOH (3.6 g, 90 mmol). The mixture was stirred at 80° C. for 4 h before cooling to rt, and then adjusted to pH=2 with 2N HCl solution and extracted with EtOAc (100 mL×3). Combined organic layer was dried over $Na_2SO_4$ and concentrated. The crude residue was purified by silica gel chromatography (DCM:MeOH:AcOH=20:1:0.02) to afford 3-(3-formylphenoxy)propanoic acid as white solid (1.5 g, 19%).

A mixture of 3-(3-formylphenoxy)propanoic acid (364 mg, 2 mmol), N-(tert-butyl)-2-cyanoacetamide (280 mg, 2 mmol) and ammonium acetate (770 mg, 10 mmol) in methanol (10 mL) was stirred at reflux temperature for 2 h. After cooling to rt, filtered and concentrate in vacuo to give a crude residue, which was diluted with EtOAc (40 mL) and water (10 mL). The organic layer was dried over $Na_2SO_4$ and concentrated to afford 3-(3-(3-(tert-butylamino)-2-cyano-3-oxoprop-1-en-1-yl)phenoxy)propanoic acid as a colorless gum (420 mg, 68%).

DIPEA (312 mg, 2.42 mmol) was added to stirred solution of 3-(3-(3-(tert-butylamino)-2-cyano-3-oxoprop-1-en-1-yl)phenoxy)propanoic acid (350 mg, 1.1 mmol), (R)-2-phenyl-1-((3aS,4S,6S,7aR)-3a,5,5-trimethylhexahydro-4,6-methanobenzo[d][11,3,2]dioxaborol-2-yl)ethan-1-amine (369 mg, 1.1 mmol) and HATU (463 mg, 1.2 mmol) in DMF (5 mL) at rt. The mixture was stirred at rt for 2 h, then quenched with water (10 mL) and filtered to afford N-(tert-butyl)-2-cyano-3-(3-(3-oxo-3-(((R)-2-phenyl-1-((3aS,4S,6S,7aR)-3a,5,5-trimethylhexahydro-4,6-methanobenzo[d][1,3,2]dioxaborol-2-yl)ethyl)amino)propoxy)phenyl)acrylamide as a yellow solid (250 mg, crude) which was used without further purification.

To a solution of N-(tert-butyl)-2-cyano-3-(3-(3-oxo-3-(((R)-2-phenyl-1-((3aS,4S,6S,7aR)-3a,5,5-trimethylhexahydro-4,6-methanobenzo[d][1,3,2]dioxaborol-2-yl)ethyl)amino)propoxy)phenyl)acrylamide (250 mg, crude) in MeOH (10 mL) were added hexane (10 mL) and 1 mol/L HCl (2 mL), followed by isobutyl boronic acid (128 mg, 1.26 mmol). After stirring at rt for 5 h, the solvent was removed. The crude material was purified by Prep-HPLC to afford (R)-1-(3-(3-(3-(tert-butylamino)-2-cyano-3-oxoprop-1-enyl)phenoxy)propanamido)-2-phenylethylboronic acid as white solid (26 mg, 13%). LC-MS m/z: 446.1 [M−17].

Example 3

(R)-(1-(3-(3-(3-(tert-butylamino)-2-cyano-3-oxo-prop-1-en-1-yl)phenyl)propanamido)-2-phenylethyl)boronic Acid

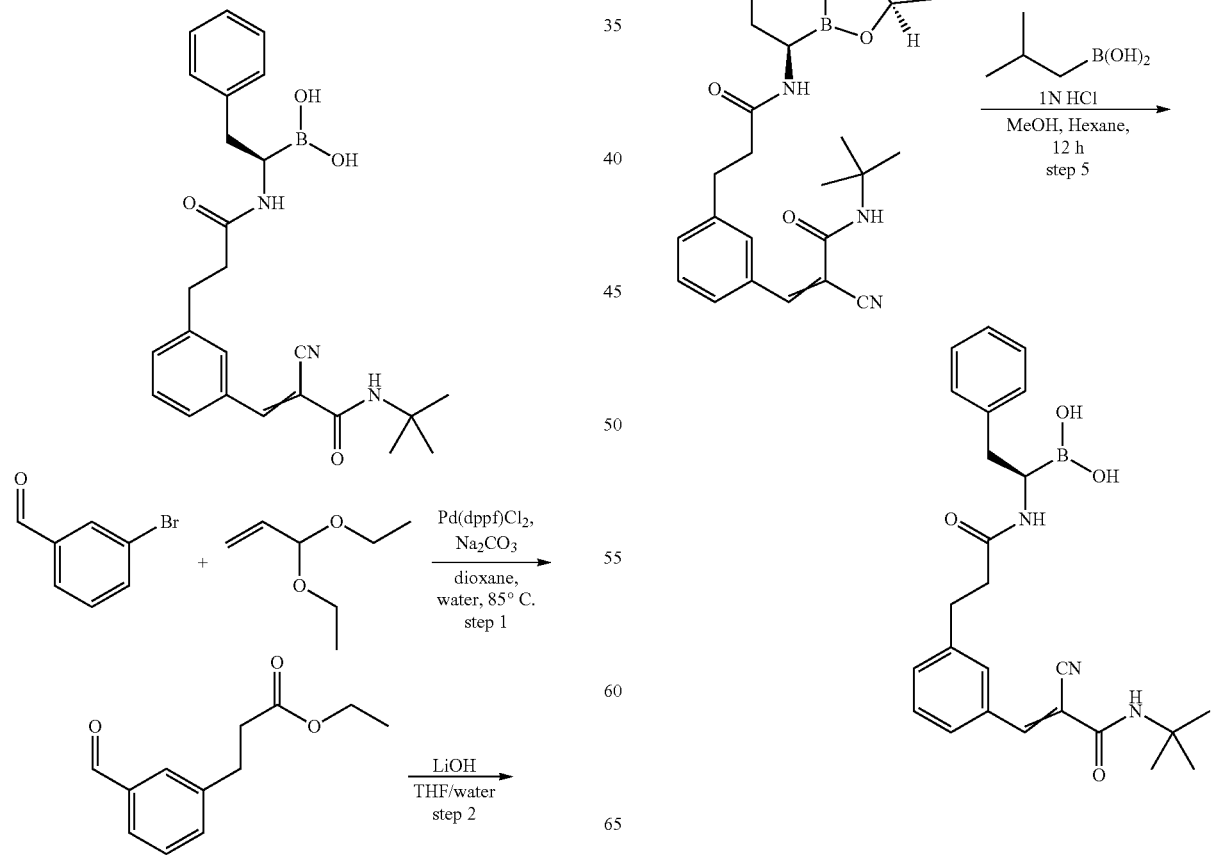

A mixture of 3-bromobenzaldehyde (3.7 g, 20 mmol), 3,3-diethoxyprop-1-ene (7.81 g, 60 mmol), Pd(dppf)Cl$_2$ (0.734 g, 1 mmol) and Na$_2$CO$_3$ (3.24 g, 30 mmol) in dioxane (50 mL) and water (5 mL) was stirred at 85° C. for 4 h under N$_2$ atmosphere before cooling to rt. The reaction was then concentrated, and diluted with EtOAc (100 mL) and water (50 mL). The organics were washed with brine (50 mL), dried and concentrated. The crude residue was purified by silica gel chromatography (PE:EtOAc=10:1) to afford ethyl 3-(3-formylphenyl)propanoate as an oil (0.8 g, 21%).

A mixture of ethyl 3-(3-formylphenyl)propanoate (800 mg, 4.16 mmol) and LiOH (110 mg, 4.56 mmol) in THF (10 mL) and water (2 mL) was stirred at rt for 4 h. Concentrated and diluted with water (10 mL) and Et$_2$O (10 mL). The aqueous layer was adjusted to pH=2 with 2N aq. HCl solution and extracted with EtOAc (100 mL×3). Combined organic layer was dried over Na$_2$SO$_4$ and concentrated to afford 3-(3-formylphenyl)propanoic acid as a gum (410 mg, 55%).

A mixture of 3-(3-formylphenyl)propanoic acid (364 mg, 2 mmol), N-(tert-butyl)-2-cyanoacetamide (280 mg, 2 mmol) and ammonium acetate (770 mg, 10 mmol) in methanol (10 mL) was stirred at reflux temperature for 2 h. After cooling to rt, the reaction was filtered and concentrated in vacuo to give a crude residue, which was diluted with EtOAc (40 mL) and water (10 mL). The organic layer was dried over Na$_2$SO$_4$ and concentrated to afford 3-(3-(3-(tert-butylamino)-2-cyano-3-oxoprop-1-en-1-yl)phenyl)propanoic acid as a colorless gum (420 mg, 68%).

DIPEA (227 mg, 1.76 mmol) was added to stirred solution of 3-(3-(3-(tert-butylamino)-2-cyano-3-oxoprop-1-en-1-yl)phenyl)propanoic acid (240 mg, 0.8 mmol), (R)-2-phenyl-1-((3aS,4S,6S,7aR)-3a,5,5-trimethylhexahydro-4,6-methanobenzo[d][1,3,2]dioxaborol-2-yl)ethan-1-amine (268 mg, 0.8 mmol) and HATU (334 mg, 0.88 mmol) in DMF (5 mL) at rt. The mixture was stirred at rt for 2 h, then quenched with water (10 mL) and filtered to afford the title compound as a yellow solid (230 mg, crude) which was purified with Prep-HPLC to afford N-(tert-butyl)-2-cyano-3-(3-(3-oxo-3-(((R)-2-phenyl-1-((3aS,4S,6S,7aR)-3a,5,5-trimethylhexahydro-4,6-methanobenzo[d][1,3,2]dioxaborol-2-yl)ethyl)amino)propyl)phenyl)acrylamide (100 mg, 22%) as a white solid.

To a solution of N-(tert-butyl)-2-cyano-3-(3-(3-oxo-3-(((R)-2-phenyl-1-((3aS,4S,6S,7aR)-3a,5,5-trimethylhexahydro-4,6-methanobenzo[d][1,3,2]dioxaborol-2-yl)ethyl)amino)propyl)phenyl)acrylamide (100 mg, 0.17 mmol) in MeOH (2.5 mL) were added hexane (2.5 mL) and 1 N HCl (1 mL), followed by isobutyl boronic acid (53 mg, 0.27 mmol). After stirring at rt for 3 h and LCMS suggested the reaction was completed, the hexane layer was discarded, the methanol layer was diluted with water (10 mL) and freeze dried directly to give a crude product, this crude product was further purified with neutral Al$_2$O$_3$ column (Methanol:DCM=0-20% as eluent) to afford (R)-(1-(3-(3-(3-(tert-butylamino)-2-cyano-3-oxoprop-1-en-1-yl)phenyl)propanamido)-2-phenylethyl)boronic acid (10 mg, 13%) as a white solid. LC-MS m/z: 430.1 [M−17].

Example 4

(R)-1-((S)-4-(3-(3-(tert-butylamino)-2-cyano-3-oxoprop-1-enyl)phenyl)-2-(2,5-dichlorobenzamido)butanamido)-2-phenylethylboronic Acid

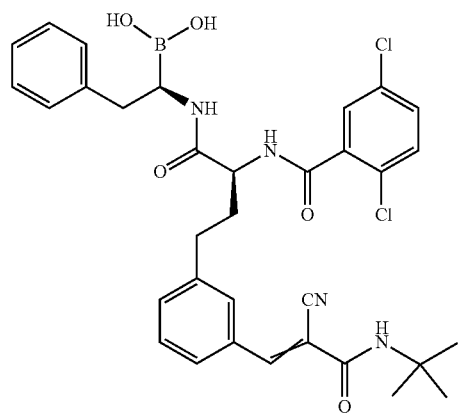 [SMILES: CC(C)(C)NC(=O)C(C#N)=Cc1cccc(CC[C@H](NC(=O)c2cc(Cl)ccc2Cl)C(=O)N[C@@H](Cc2ccccc2)B(O)O)c1]

Using the procedure in Example 1, and starting with 2,5-dichlorobenzoic acid, the title compound was obtained. LC-MS (ES, m/z): 631.2 [M−17].

Example 5

(R)-1-(3-(3-(2-cyano-3-(dimethylamino)-3-oxoprop-1-enyl)phenoxy)propanamido)-2-phenylethylboronic Acid

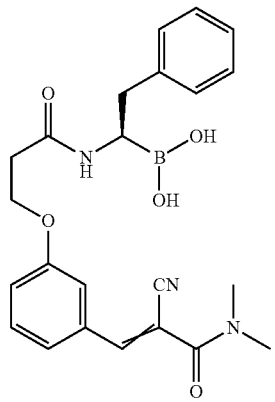 [SMILES: CN(C)C(=O)C(C#N)=Cc1cccc(OCCC(=O)N[C@@H](Cc2ccccc2)B(O)O)c1]

Using the procedure in Example 2, and starting with N,N-dimethylamine-3-oxopropanenitrile, the title compound was obtained. LC-MS (ES, m/z): 418.3 [M−17].

Example 6

(R)-(1-(3-(3-(2-cyano-2-(pyridin-2-yl)vinyl)phenoxy)propanamido)-2-phenylethyl)boronic Acid

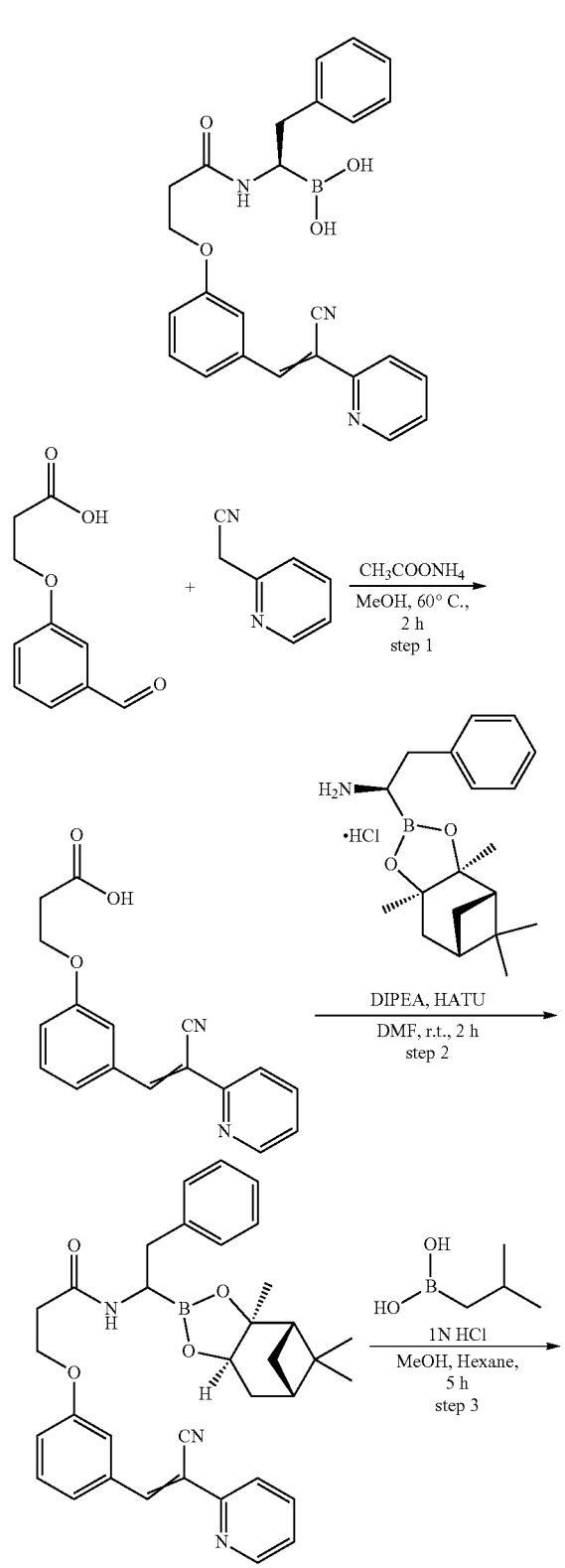

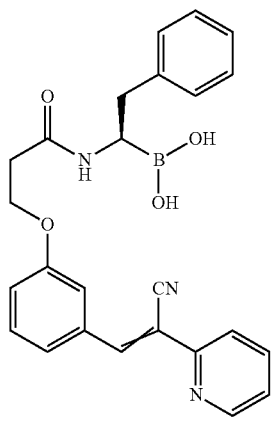 [SMILES: N#CC(=Cc1cccc(OCCC(=O)N[C@@H](Cc2ccccc2)B(O)O)c1)c1ccccn1]

A mixture of 3-(3-formylphenoxy)propanoic acid (500 mg, 2.57 mmol, synthesis described in Example 2), 2-(pyridin-2-yl)acetonitrile (340 mg, 2.57 mmol) and ammonium acetate (990 mg, 12.87 mmol) in methanol (35 mL) was stirred at reflux temperature for 2 h. After cooling to rt, filtered and concentrate in vacuo to give a crude residue, which was diluted with EtOAc (60 mL) and water (20 mL). The organic layer was dried over $Na_2SO_4$ and concentrated to afford 3-(3-(2-cyano-2-(pyridin-2-yl)vinyl)phenoxy)propanoic acid as a yellow solid (620 mg, 82%).

DIPEA (410 mg, 3.3 mmol) was added to stirred solution of 3-(3-(2-cyano-2-(pyridin-2-yl)vinyl)phenoxy)propanoic acid (300 mg, 1 mmol), (R)-2-phenyl-1-((3aS,4S,6S,7aR)-3a,5,5-trimethylhexahydro-4,6-methanobenzo[d][1,3,2]dioxaborol-2-yl)ethan-1-amine (340 mg, 1 mmol) and HATU (420 mg, 1.1 mmol) in DMF (3 mL) at rt. The mixture was stirred at rt for 2 h, then quenched with water (10 mL) and filtered to afford the title compound as a yellow solid (500 mg, crude) which was purified by Prep-HPLC to afford 3-(3-(2-cyano-2-(pyridin-2-yl)vinyl)phenoxy)-N—((R)-2-phenyl-1-((3aS,4S,6S,7aR)-3a,5,5-trimethylhexahydro-4,6-methanobenzo[d][1,3,2]dioxaborol-2-yl)ethyl)propanamide as a white solid (150 mg, 26%)

To a solution of 3-(3-(2-cyano-2-(pyridin-2-yl)vinyl)phenoxy)-N—((R)-2-phenyl-1-((3aS,4S,6S,7aR)-3a,5,5-trimethylhexahydro-4,6-methanobenzo[d][1,3,2]dioxaborol-2-yl)ethyl)propanamide (150 mg, 0.26 mmol) in MeOH (4 mL) were added hexane (4 mL) and 1 N HCl (1.5 mL), followed by isobutyl boric acid (79 mg, 0.77 mmol). After stirring at rt for 3 h and LCMS suggested the reaction was completed, the hexane layer was discarded, the methanol layer was diluted with water (10 mL) and freeze dried directly to give a crude product, this crude product was further purified with neutral $Al_2O_3$ column (Methanol:DCM=0-20% as eluent) to afford (R)-(1-(3-(3-(2-cyano-2-(pyridin-2-yl)vinyl)phenoxy)propanamido)-2-phenylethyl)boronic acid as a white solid (60 mg, 54%). LC-MS (ES, m/z): 424.0 [M−17].

Example 7

(R)-1-(3-(3-(2-cyano-3-(diethylamino)-3-oxoprop-1-enyl)phenoxy)propanamido)-2-phenylethylboronic Acid

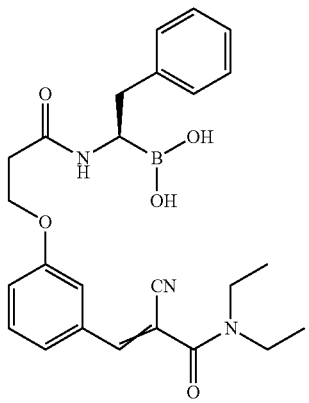 [SMILES: CCN(CC)C(=O)C(C#N)=Cc1cccc(OCCC(=O)N[C@@H](Cc2ccccc2)B(O)O)c1]

Using the procedure in Example 2, and starting with N,N-diethyl amine-3-oxopropanenitrile, the title compound was obtained. LC-MS (ES, m/z): 446.4 [M−17].

Example 8

(R)-(1-(3-(3-(3-(tert-butylamino)-2-cyano-3-oxo-prop-1-en-1-yl)phenoxy)propanamido)-2-(3-ethylphenyl)ethyl)boronic Acid

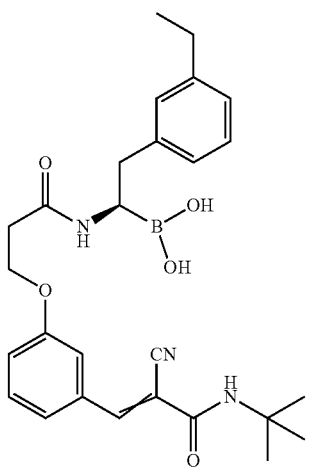 [SMILES: CCc1cccc(C[C@H](NC(=O)CCOc2cccc(C=C(C#N)C(=O)NC(C)(C)C)c2)B(O)O)c1]

Using the procedure in Example 2, and starting with (R)-2-(3-ethylphenyl)-1-((3aS,4S,6S,7aR)-3a,5,5-trimethyl-hexahydro-4,6-methanobenzo[d][1,3,2]dioxaborol-2-yl)ethan-1-amine, the title compound was obtained. LC-MS (ES, m/z): 474.1 [M−17].

Example 9

(R)-1-(3-(3-(2-cyano-3-morpholino-3-oxoprop-1-enyl)phenoxy)propanamido)-2-phenylethylboronic Acid

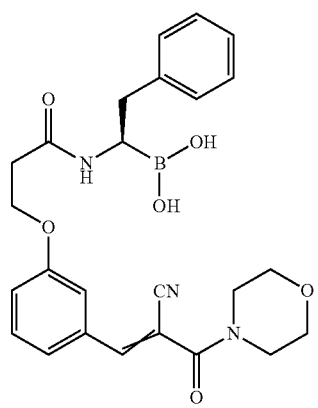 [SMILES: N#CC(=Cc1cccc(OCCC(=O)N[C@@H](Cc2ccccc2)B(O)O)c1)C(=O)N1CCOCC1]

Using the procedure in Example 2, and starting with 3-morpholino-3-oxopropanenitrile, the title compound was obtained. LC-MS (ES, m/z): 460.3 [M−17].

Example 10

(R)-1-(3-(3-(2-cyano-3-oxo-3-(tetrahydro-2H-pyran-4-ylamino)prop-1-enyl)phenoxy)propanamido)-2-phenylethylboronic Acid

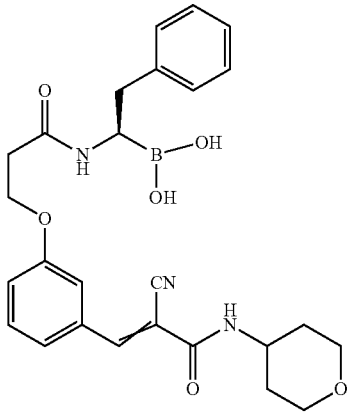 [SMILES: N#CC(=Cc1cccc(OCCC(=O)N[C@@H](Cc2ccccc2)B(O)O)c1)C(=O)NC1CCOCC1]

Using the procedure in Example 2, and starting with 2-cyano-N-(tetrahydro-2H-pyran-4-yl)acetamide, the title compound was obtained. LC-MS (ES, m/z): 474.1 [M−17].

Example 11

(R)-1-(3-(3-(3-(tert-butylamino)-2-cyano-3-oxoprop-1-enyl)phenoxy)propanamido)-3-phenylpropylboronic Acid

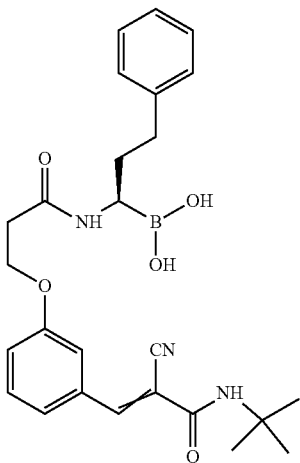 [SMILES: CC(C)(C)NC(=O)C(C#N)=Cc1cccc(OCCC(=O)N[C@@H](CCc2ccccc2)B(O)O)c1]

Using the procedure in Example 2, and starting with (R)-3-phenyl-1-(4,4,5,5-tetramethyl-1,3,2-dioxaborolan-2-yl)propan-1-amine, the title compound was obtained. LC-MS (ES, m/z): 460.1 [M−17].

Example 12

(R)-1-(3-(3-(2-cyano-3-(isopropylamino)-3-oxoprop-1-enyl)phenoxy)propanamido)-2-phenylethylboronic Acid

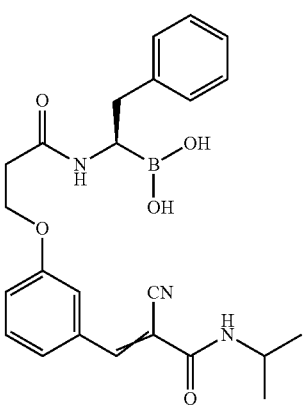 [SMILES: CC(C)NC(=O)C(C#N)=Cc1cccc(OCCC(=O)N[C@@H](Cc2ccccc2)B(O)O)c1]

Using the procedure in Example 2, and starting with 2-cyano-N-isopropylacetamide, the title compound was obtained. LC-MS (ES, m/z): 432.3 [M−17].

Example 13

(R)-1-(3-(3-(3-(tert-butylamino)-2-cyano-3-oxoprop-1-enyl)phenoxy)propanamido)-3,3-dimethylbutylboronic Acid

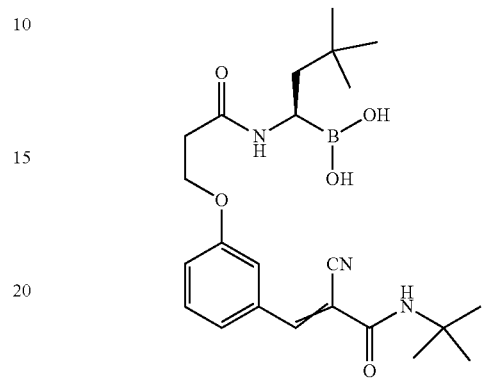

Using the procedure in Example 2, and starting with (R)-3,3-dimethyl-1-(4,4,5,5-tetramethyl-1,3,2-dioxaborolan-2-yl)butan-1-amine, the title compound was obtained. LC-MS (ES, m/z): 426.2 [M−17].

Example 14

(R)-(2-(benzofuran-3-yl)-1-(3-(3-(3-(tert-butylamino)-2-cyano-3-oxoprop-1-en-1-yl)phenoxy)propanamido)ethyl)boronic Acid

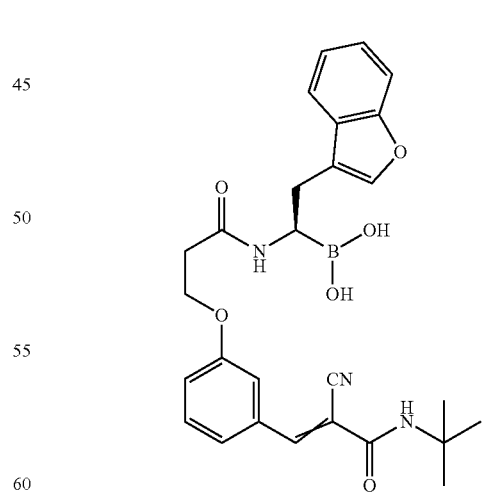

Using the procedure in Example 2, and starting (R)-2-(benzofuran-3-yl)-1-((3aS,4S,6S,7aR)-3a,5,5-trimethylhexahydro-4,6-methanobenzo[d][1,3,2]dioxaborol-2-yl)ethan-1-amine, the title compound was obtained. LC-MS (ES, m/z): 486.1 [M−17].

Example 15

(R)-(1-((((3-(2-cyano-3-(dimethylamino)-3-oxoprop-1-en-1-yl)benzyl)oxy)carbonyl)amino)-2-phenyl-ethyl)boronic Acid

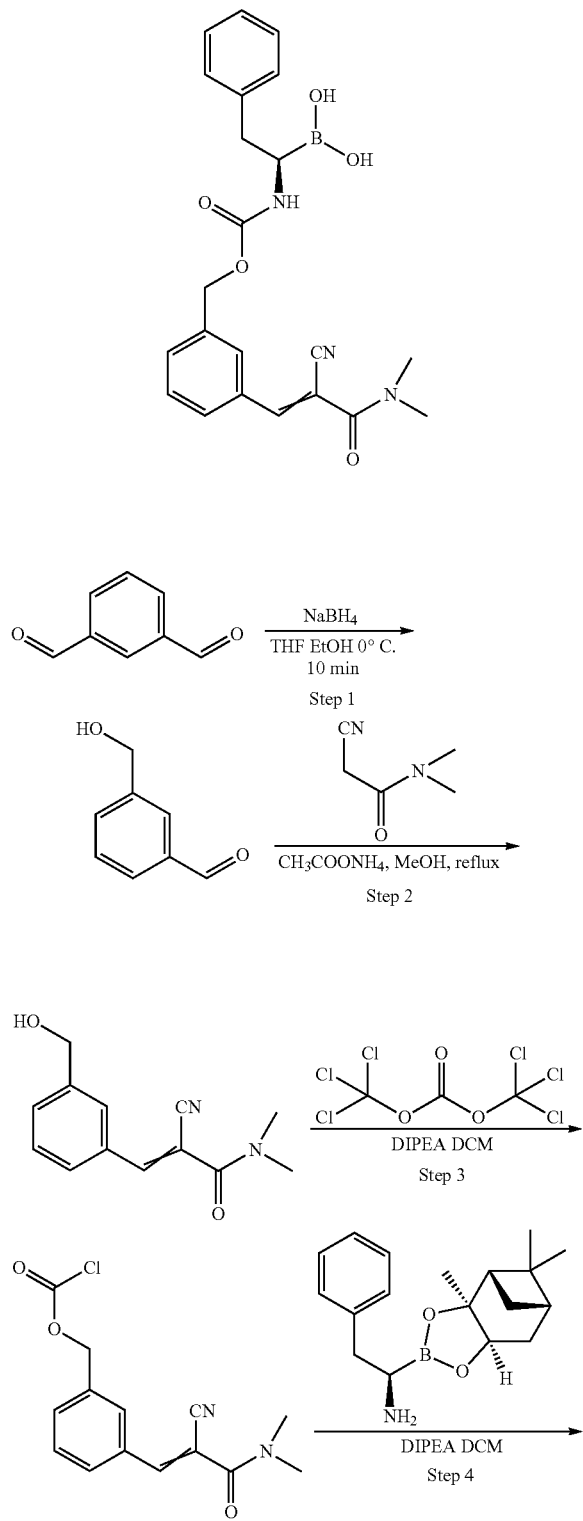

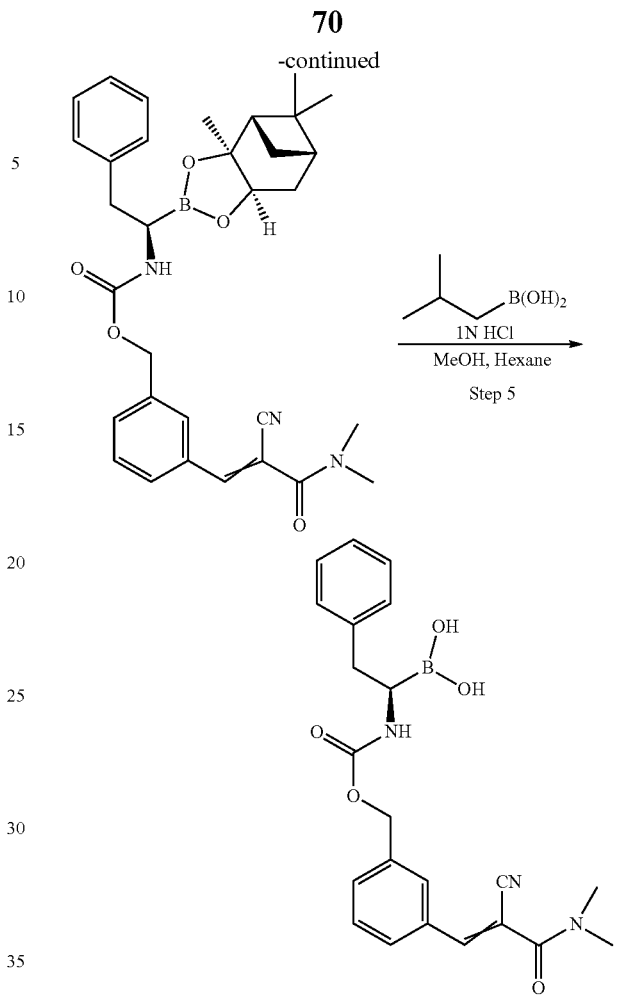

To a solution of isophthalaldehyde (7.0 g, 52.19 mmol) in THF (35 mL) and EtOH (70 mL) at 0° C. was added NaBH₄ (789.75 mg, 20.87 mmol) portion wise, the resulting solution was stirred at 0° C. for 10 min, then 10% HCl (aq. 50 mL) was added, the mixture was extracted with EtOAc (50 mL×3). The combined organic layer was washed with brine (25 mL×2), dried over Na₂SO₄, and concentrated in vacuo. The crude residue was purified via silica chromatography and a gradient of 0%-100% EtOAc in Hexane to afford 3-(hydroxymethyl)benzaldehyde as a yellow oil (2.6 g, 36.57%).

A mixture of 3-(hydroxymethyl)benzaldehyde (400 mg, 2.94 mmol), 2-cyano-N,N-dimethylacetamide (329.44 mg, 2.94 mmol) and ammonium acetate (1.83 g, 23.75 mmol) in ethanol (15 mL) was stirred at reflux temperature for 4 h. After cooling to rt, the mixture was concentrated to dryness. The residue was diluted with EtOAc (30 mL), and washed with water (15 mL) and brine (15 mL). The organic layer was dried over Na₂SO₄ and concentrated in vacuo. The crude residue was purified via silica chromatography and a gradient of 0%-100% EtOAc in hexane to afford 2-cyano-3-(3-(hydroxymethyl)phenyl)-N,N-dimethylacrylamide as a yellow oil (500 mg, 73.97%).

Bis(trichloromethyl) carbonate (338.94 mg, 1.14 mmol) in DCM (5 mL) was added to a stirred solution of 2-cyano-3-(3-(hydroxymethyl)phenyl)-N,N-dimethylacrylamide (500 mg, 2.28 mmol) and DIPEA (885.71 mg, 6.85 mmol) in DCM (10 mL) at 0° C., the resultant reaction was stirred for 2 h at 0° C. before next use.

The reaction solution from previous step was added dropwise into a well-stirred solution of (R)-2-phenyl-1-((3aS,4S,6S,7aR)-3a,5,5-trimethylhexahydro-4,6-methanobenzo[d][1,3,2]dioxaborol-2-yl)ethan-1-amine (688.06 mg, 2.05 mmol) and DIPEA (529.83 mg, 4.10 mmol) in DCM (20 mL) at 0° C. The reaction was stirred at rt for 1 h, then washed with water (20 mL) and brine (20 mL), the organic extracts was dried over Na$_2$SO$_4$ and concentrated in vacuo. The crude material was purified by Prep-HPLC to afford 3-(2-cyano-3-(dimethylamino)-3-oxoprop-1-en-1-yl)benzyl ((R)-2-phenyl-1-((3aS,4S,6S,7aR)-3a,5,5-trimethylhexahydro-4,6-methanobenzo[d][1,3,2]dioxaborol-2-yl)ethyl) carbamate as a white solid (380 mg, 33.33%).

To a solution of 3-(2-cyano-3-(dimethylamino)-3-oxoprop-1-en-1-yl)benzyl((R)-2-phenyl-1-((3aS,4S,6S,7aR)-3a,5,5-trimethylhexahydro-4,6-methanobenzo[d][1,3,2]dioxaborol-2-yl)ethyl)carbamate (380 mg, 0.68 mmol) in MeOH (5 mL) were added hexane (5 mL) and 1 N HCl (1 mL), followed by isobutyl boric acid (209.21 mg, 2.05 mmol). After stirring at rt for 3 h and TLC suggested the reaction was completed, the hexane layer was discarded. The methanol layer was diluted with water (10 mL), then dried over lyophilization to give a crude product which was further purified by neutral Al$_2$O$_3$ column (Methanol: DCM=0-10% as eluent) to afford (R)-(1-((((3-(2-cyano-3-(dimethylamino)-3-oxoprop-1-en-1-yl)benzyl)oxy)carbonyl)amino)-2-phenylethyl)boronic acid as a white solid (50 mg, 18.18%). LC-MS (ES, m/z): 404.0 [M−17].

Example 16

(R)-(1-((((3-(3-(tert-butylamino)-2-cyano-3-oxoprop-1-en-1-yl)benzyl)oxy)carbonyl)amino)-2-phenylethyl)boronic Acid

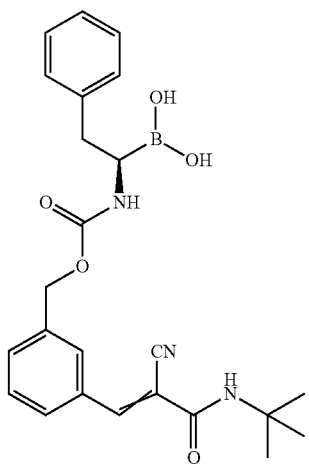 [SMILES: CC(C)(C)NC(=O)C(C#N)=Cc1cccc(COC(=O)N[C@@H](Cc2ccccc2)B(O)O)c1]

Using the procedure in Example 15, and starting with N-(tert-butyl)-2-cyanoacetamide, the title compound was obtained. LC-MS (ES, m/z): 432.1 [M−17].

Example 17

(R)-(1-(((3-(2-cyano-3-(dimethylamino)-3-oxoprop-1-en-1-yl)phenethoxy)carbonyl)amino)-2-phenylethyl)boronic Acid

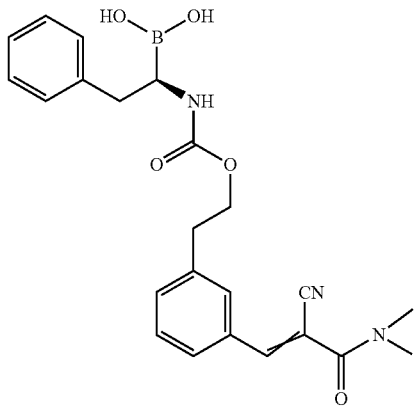 [SMILES: CN(C)C(=O)C(C#N)=Cc1cccc(CCOC(=O)N[C@@H](Cc2ccccc2)B(O)O)c1]

Using the procedure in Example 15, and starting with 3-(2-hydroxyethyl)benzaldehyde (which can be prepared in one step as shown in below procedure), the title compound was obtained. LC-MS (ES, m/z): 417.7 [M−17].

Synthesis of 3-(2-hydroxyethyl)benzaldehyde: A mixture of n-Butyl lithium (2.4 M solution in hexanes, 8.0 mL, 19.6 mmol) in anhydrous THF (20 mL) was cooled to −78° C. To this reaction mixture, 2-(3-bromophenyl)ethan-1-ol (1.0 g, 4.97 mmol) in THF (15 mL) was added dropwise at −78° C. and stirred at same temperature for 20 min. N,N-dimethylformamide (6 mL) was added dropwise at −78° C. and stirred at same temperature for 2 h. The reaction mixture was quenched with a saturated solution of ammonium chloride and the aqueous portion was extracted with ethyl acetate. The combined extracts were washed with brine, dried over magnesium sulfate, filtered and evaporated. The residue was purified by silica gel column chromatography using ethyl acetate:hexanes (2:3) as eluent to provide 3-(2-hydroxyethyl)benzaldehyde as colorless oil (580 mg, 77.75%).

Example 18

(R)-(1-(3-(5-(3-(tert-butylamino)-2-cyano-3-oxoprop-1-en-1-yl)-2-fluorophenoxy)propanamido)-2-phenylethyl)boronic Acid

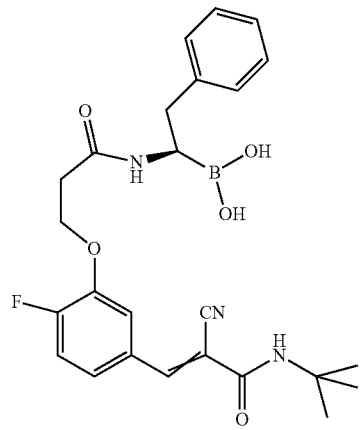

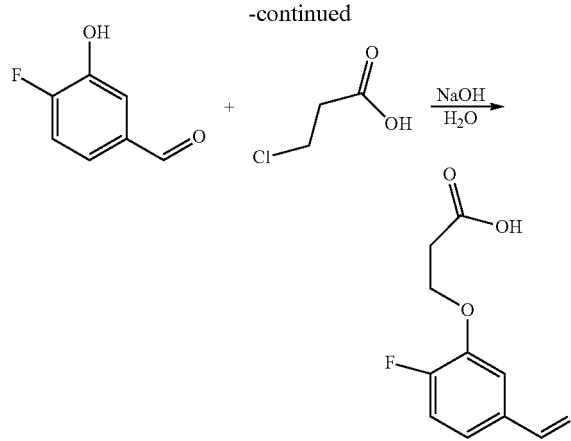

Into an 8-mL sealed tube, was placed 4-fluoro-3-hydroxy-benzaldehyde (20 mg, 0.14 mmol, 1.00 eq.), water (0.4 mL), 3-chloropropanoic acid (15.4 mg, 0.14 mmol, 1.00 eq.), sodium hydroxide (6.3 mg, 0.16 mmol, 2.20 eq.). The resulting solution was stirred for 60 min at 80° C. The reaction mixture was cooled to 25° C. with a water bath. The pH value of the solution was adjusted to 2 with hydrogen chloride (2 mol/L). The resulting solution was extracted with 3×10 mL of ethyl acetate and the organic layers combined. The resulting mixture was washed with 3×10 mL of saturated brine. The mixture was dried over anhydrous sodium sulfate and concentrated under vacuum. The crude product was purified by Flash-Prep-HPLC with the following conditions (IntelFlash-1): mobile phase, $H_2O$/ACN=100:1 increasing to $H_2O$/ACN=1:1 within 60 min; Detector, UV 254 nm. This resulted in 5 mg (17%) of 3-(2-fluoro-5-formylphenoxy)propanoic acid as a yellow solid.

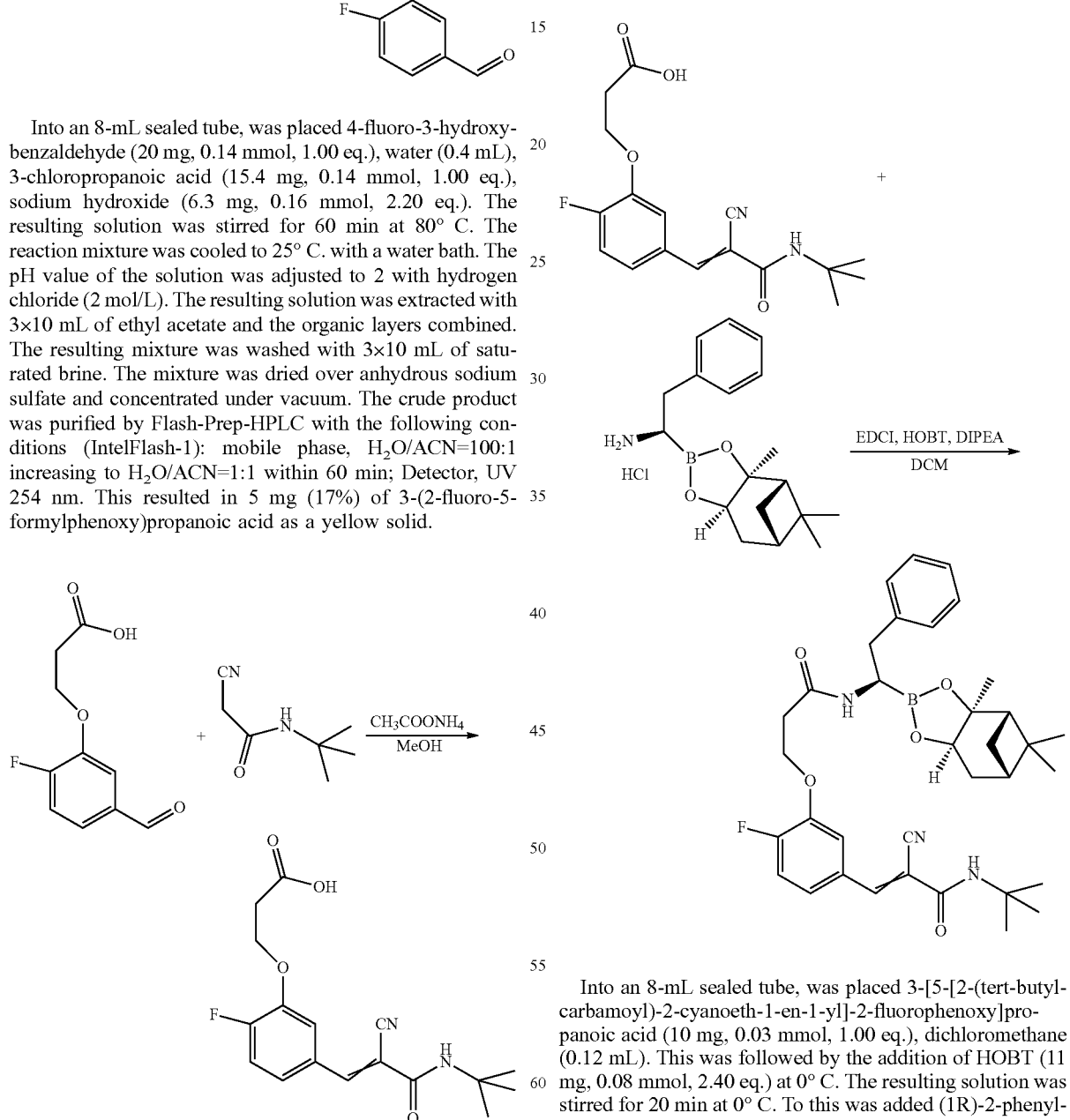

Into a 8-mL sealed tube, was placed 3-(2-fluoro-5-form-ylphenoxy)propanoic acid (20 mg, 0.09 mmol, 1.00 eq.), methanol (0.25 mL), N-tert-butyl-2-cyanoacetamide (13.2 mg, 0.09 mmol, 1.00 eq.), CH3COONH4 (36.3 mg, 0.47 mmol, 5.00 eq.). The resulting solution was stirred for 30 min at 60° C. The reaction was then quenched by the addition of 10 mL of water. The resulting solution was extracted with 3×10 mL of ethyl acetate and the organic layers combined and dried over anhydrous sodium sulfate and concentrated under vacuum. The crude product was purified by Flash-Prep-HPLC with the following conditions (CombiFlash-1): Column, C18 silica gel; mobile phase, $H_2O$:ACN=99:1 increasing to $H_2O$:ACN=1:99 within 100 min; Detector, UV 254 nm. This resulted in 5 mg (16%) of 3-[5-[2-(tert-butylcarbamoyl)-2-cyanoeth-1-en-1-yl]-2-fluorophenoxy]propanoic acid as a white solid.

Into an 8-mL sealed tube, was placed 3-[5-[2-(tert-butylcarbamoyl)-2-cyanoeth-1-en-1-yl]-2-fluorophenoxy]propanoic acid (10 mg, 0.03 mmol, 1.00 eq.), dichloromethane (0.12 mL). This was followed by the addition of HOBT (11 mg, 0.08 mmol, 2.40 eq.) at 0° C. The resulting solution was stirred for 20 min at 0° C. To this was added (1R)-2-phenyl-1-[(1S,2S,6R,8S)-2,9,9-trimethyl-3,5-dioxa-4-boratricyclo[6.1.1.0`[2,6]]decan-4-yl]ethan-1-amine (8.9 mg, 0.03 mmol, 1.00 eq.), EDCI (13.7 mg, 0.07 mmol, 2.40 eq.), DIPEA (8.5 mg, 0.07 mmol, 2.20 eq.) at −15° C. The resulting solution was allowed to react, with stirring, for an additional 60 min at 25° C. The resulting solution was diluted with 10 mL of H2O. The resulting solution was extracted with 3×20 mL of dichloromethane and the organic layers combined and dried over anhydrous sodium sulfate and concentrated under vacuum. The residue was separated by Prep-TLC with ethyl acetate/petroleum ether (2:1). This resulted in 12 mg (65%) of N-tert-butyl-2-cyano-3-[4-fluoro-3-(2-[[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamoyl]ethoxy)phenyl]prop-2-enamide as a yellow solid.

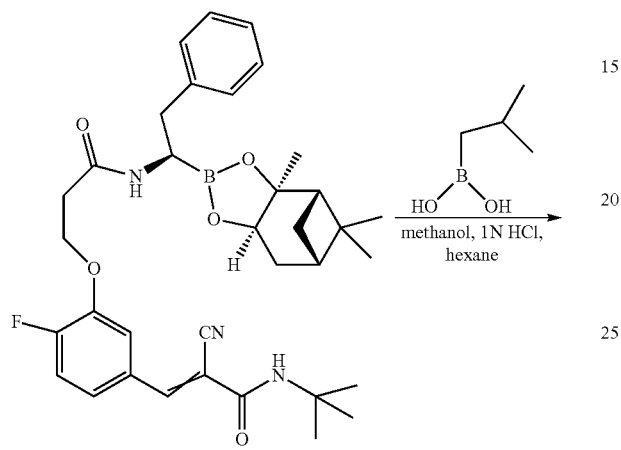

Into an 8-mL sealed tube, was placed N-tert-butyl-2-cyano-3-[4-fluoro-3-(2-[[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamoyl]ethoxy)phenyl]prop-2-enamide (60 mg, 0.10 mmol, 1.00 eq.), (2-methylpropyl)boronic acid (28.8 mg, 0.28 mmol, 2.90 eq.), hexane (1.6 mL), Methanol (0.8 mL), 1N hydrogen chloride (0.26 mL, 2.60 eq.). The resulting solution was stirred for 4 h at 25° C. The resulting solution was extracted with 3×1 mL of hexane and the methanol layers combined and lyophilized. The resulting solid crude product was purified by Prep-HPLC with the following conditions (2#-AnalyseHPLC-SHIMADZU (HPLC-10)): Column, XBridge Prep C18 OBD Column, 19??150 mm 5 um; mobile phase, Water (0.05% NH3H2O) and ACN (hold 39.0% ACN in 7 min); Detector, UV 254/220 nm; Then lyophilization; This resulted in 11.1 mg (24%) of [(1R)-1-(3-[5-[2-(tert-butylcarbamoyl)-2-cyano-eth-1-en-1-yl]-2-fluorophenoxy]propanamido)-2-phenyl-ethyl]boronic acid as a white solid. LC-MS m/z: 464 [M−17].

Example 19

(R)-(1-(3-(3-(2-cyano-3-(4-methylpiperazin-1-yl)-3-oxoprop-1-en-1-yl)phenoxy)propanamido)-2-phenyl-ethyl)boronic Acid

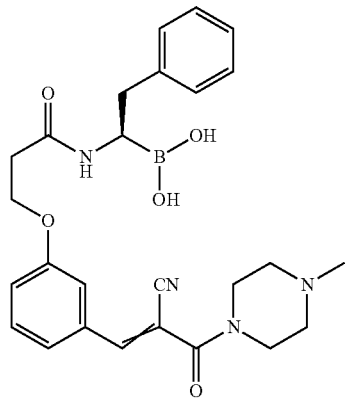 [SMILES: CN1CCN(C(=O)C(C#N)=Cc2cccc(OCCC(=O)N[C@@H](Cc3ccccc3)B(O)O)c2)CC1]

Synthetic Scheme

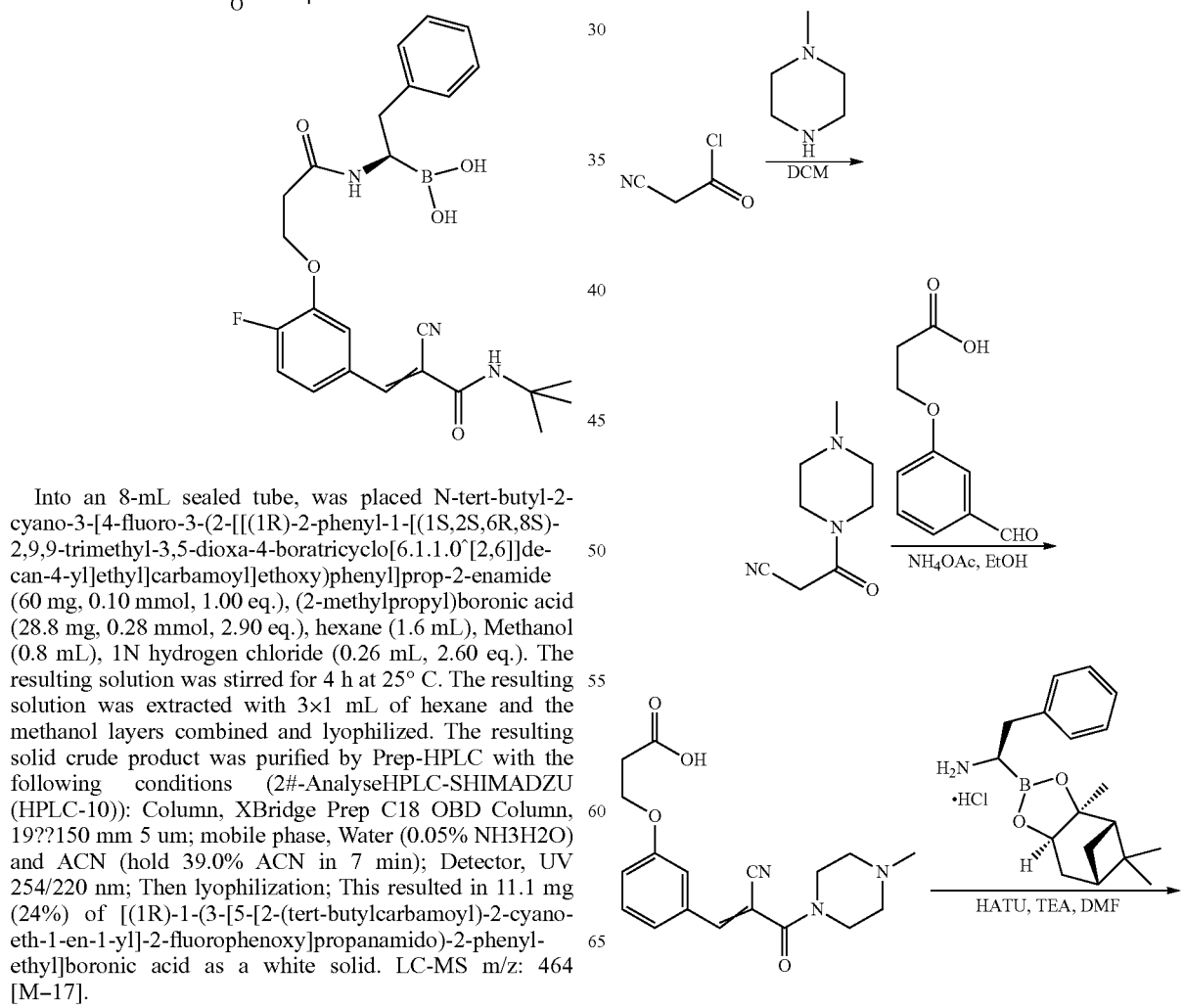

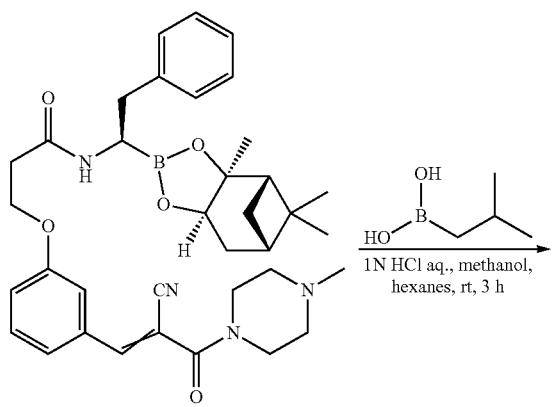

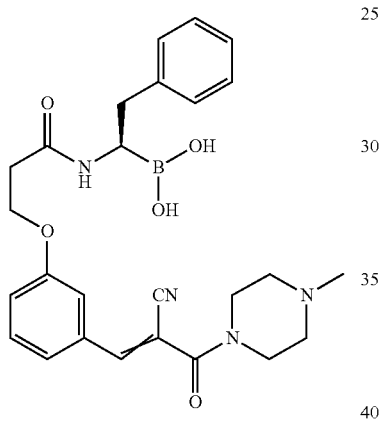

To a solution of 4-methylpiperazin (3.75 g, 37.5 mmol) in anhydrous DCM (30 mL) at 0° C. was added dropwise a solution of 2-cyanoacetyl chloride (12.5 mmol) in DCM (10 mL) which was prepared from 2-cyanoacetic acid (1.06 g, 12.5 mmol), (COCl)$_2$ (1.59 g, 12.5 mmol) and DMF (8 mg) in dichloromethane (10 mL) by stirring at r.t. for 3 h. The resulted mixture was stirred at r.t. for 12 h, then concentrated to dryness. The residue was purified by column chromatography on silica gel (eluent: petroleum ether/ethyl acetate from 1:1 to 1:3) to afford 3-(4-methylpiperazin-1-yl)-3-oxopropanenitrile as a yellow solid (1.1 g, 70%).

A mixture of 3-(4-methylpiperazin-1-yl)-3-oxopropanenitrile (240 mg, 1.44 mmol), 3-(3-formylphenoxy)propanoic acid (280 mg, 1.44 mmol) and ammonium acetate (555 mg, 7.2 mmol) in ethanol (10 mL) was stirred at reflux temperature for 2 h. After cooling to rt, the mixture was filtered and concentrated in vacuo to give a crude residue, which was distributed with EtOAc (100 mL) and water (10 mL). The organic layer was dried over Na$_2$SO$_4$ and concentrated to afford 3-(3-(2-cyano-3-(4-methylpiperazin-1-yl)-3-oxoprop-1-enyl)phenoxy)propanoic acid as light yellow solid (510 mg crude).

Triethylamine (450 mg, 4.44 mmol) was added to a stirred solution of 3-(3-(2-cyano-3-(4-methylpiperazin-1-yl)-3-oxoprop-1-enyl)phenoxy)propanoic acid (510 mg crude, 1.48 mmol), (R)-2-phenyl-1-((3aS,4S,6S,7aR)-3a,5,5-trimethylhexahydro-4,6-methanobenzo[d][1,3,2]dioxaborol-2-yl)ethanamine hydrochloride (500 mg, 1.48 mmol) and HATU (563 mg, 1.48 mmol) in DMF (5 mL) at rt. The mixture was stirred at rt for 2 h, then quenched with water (10 mL) and filtered to afford the title compound (0.55 g crude) which was purified by prep-HPLC to afford 3-(3-(2-cyano-3-(4-methylpiperazin-1-yl)-3-oxoprop-1-en-1-yl)phenoxy)-N—((R)-2-phenyl-1-((3aS,4S,6S,7aR)-3a,5,5-trimethylhexahydro-4,6-methanobenzo[d][1,3,2]dioxaborol-2-yl)ethyl)propanamide (N133-B160075-056-006) as white solid (230 mg, 25%).

To a solution of 3-(3-(2-cyano-3-(4-methylpiperazin-1-yl)-3-oxoprop-1-en-1-yl)phenoxy)-N—((R)-2-phenyl-1-((3aS,4S,6S,7aR)-3a,5,5-trimethylhexahydro-4,6-methanobenzo[d][1,3,2]dioxaborol-2-yl)ethyl)propanamide (230 mg, 0.368 mmol) in MeOH (5 mL) were added hexanes (5 mL) and 1 N HCl (1 mL), followed by isobutyl boric acid (113 mg, 1.1 mmol). After stirring at rt for 3 h and TLC suggested the reaction was completed, the hexanes layer was discarded, the methanol layer was diluted with water (10 mL) and dried over lyophylization to give a crude product which was further purified by neutral Al$_2$O$_3$ column (Methanol/DCM=0-10% as eluent) to afford (R)-1-(3-(3-(2-cyano-3-(4-methylpiperazin-1-yl)-3-oxoprop-1-enyl)phenoxy)propanamido)-2-phenylethylboronic acid as white solid (41.7 mg, 23%). LCMS: 491 [M+1].

Example 20

(R)-(1-(3-(3-(2-cyano-3-(methylamino)-3-oxoprop-1-en-1-yl)phenoxy)propanamido)-2-phenylethyl) boronic Acid

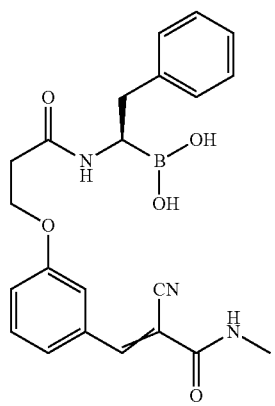 [SMILES: CNC(=O)C(C#N)=Cc1cccc(OCCC(=O)N[C@@H](Cc2ccccc2)B(O)O)c1]

The title compound was prepared as in example 19 by replacing N-methyl piperazine with methylamine. LC-MS m/z: 404 [M−17].

Example 21

(R)-(1-(3-(3-(2-cyano-2-(pyridin-2-yl)vinyl)phenoxy)propanamido)-3-phenylpropyl)boronic Acid

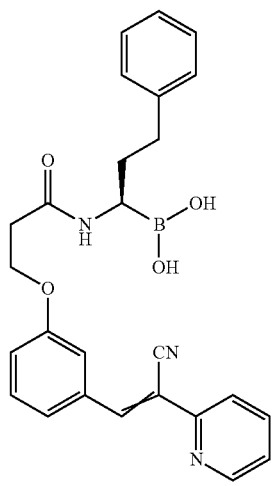 [SMILES: N#CC(=Cc1cccc(OCCC(=O)N[C@@H](CCc2ccccc2)B(O)O)c1)c1ccccn1]

Synthetic Scheme

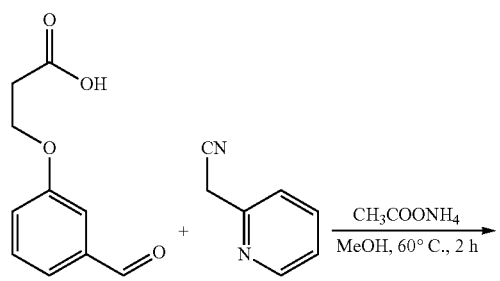

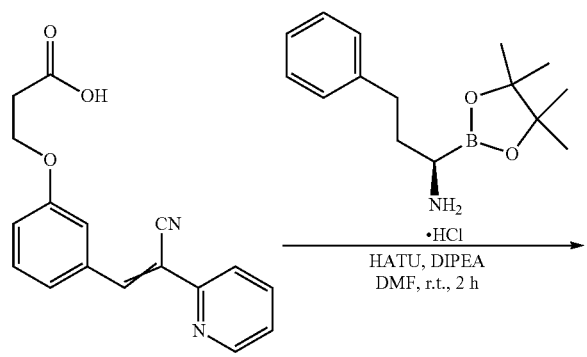

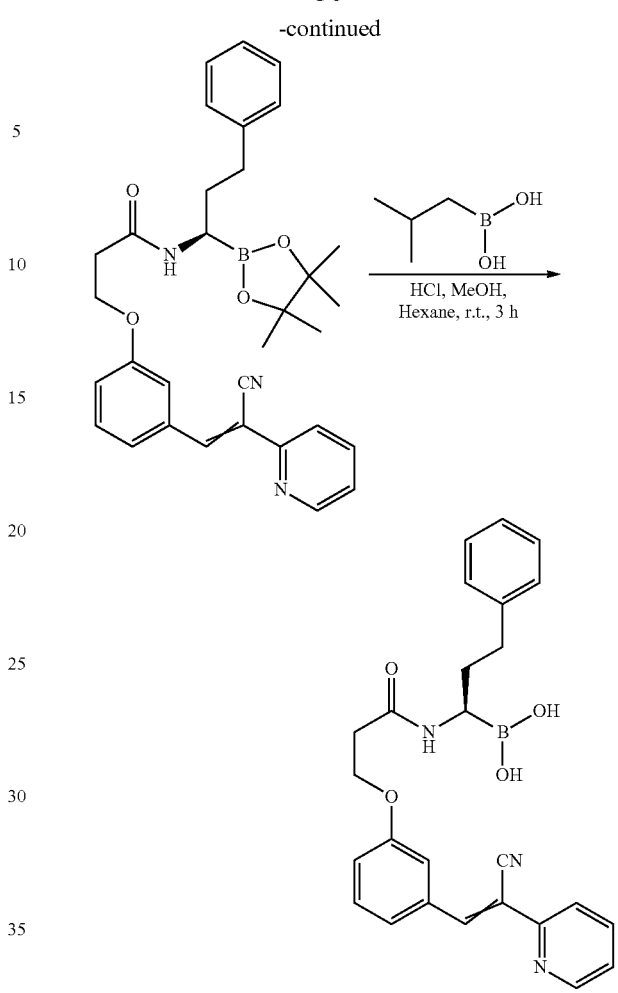

A mixture of 3-(3-formylphenoxy)propanoic acid (500 mg, 2.58 mmol), 2-(pyridin-2-yl)acetonitrile (320 mg, 2.71 mmol) and ammonium acetate (994 g, 12.9 mmol) in ethanol (35 mL) was stirred at reflux temperature for 2 h. After cooling to rt, the mixture was filtered and concentrated in vacuo to give a crude residue, which was diluted with EtOAc (100 mL) and water (10 mL). The organic layer was dried over $Na_2SO_4$ and concentrated to afford 3-(3-(2-cyano-2-(pyridin-2-yl)vinyl)phenoxy)propanoic acid as light yellow solid (680 mg, 90%).

Diisopropylamine (328 mg, 2.54 mmol) was added to stirred solution of 3-(3-(2-cyano-2-(pyridin-2-yl)vinyl)phenoxy)propanoic acid (340 mg, 1.15 mmol), (R)-3-phenyl-1-(4,4,5,5-tetramethyl-1,3,2-dioxaborolan-2-yl)propan-1-amine hydrochloride (343 mg, 1.15 mmol) and HATU (481 mg, 1.27 mmol) in DMF (3 mL) at rt. The mixture was stirred at rt for 2 h, then quenched with water (10 mL) and filtered to afford the title compound which was purified by Prep-HPLC to afford (R)-3-(3-(2-cyano-2-(pyridin-2-yl)vinyl)phenoxy)-N-(3-phenyl-1-(4,4,5,5-tetramethyl-1,3,2-dioxaborolan-2-yl)propyl)propanamide as a white solid (150 mg, 24%).

To a solution of (R)-3-(3-(2-cyano-2-(pyridin-2-yl)vinyl)phenoxy)-N-(3-phenyl-1-(4,4,5,5-tetramethyl-1,3,2-dioxaborolan-2-yl)propyl)propanamide (150 mg, 0.28 mmol) in MeOH (3 mL) were added hexane (3 mL) and 1 N HCl (1.5 mL), followed by isobutyl boric acid (84 mg, 0.84 mmol). After stirring at rt for 3 h and LCMS suggested the reaction was completed, the hexane layer was discarded, the methanol layer was diluted with water (10 mL) and freeze dried directly to give a crude product, this crude product was further purified with neutral Al₂O₃ column (Methanol/DCM=0-20% as eluent) to afford (R)-(1-(3-(3-(2-cyano-2-(pyridin-2-yl)vinyl)phenoxy)propanamido)-3-phenylpropyl)boronic acid as a white solid (45.2 mg, 36%). LCMS: 438 [M−17].

Example 22

(R)-(1-(3-(3-(2-cyano-3-(methyl(phenyl)amino)-3-oxoprop-1-en-1-yl)phenoxy)propanamido)-2-phenylethyl)boronic Acid

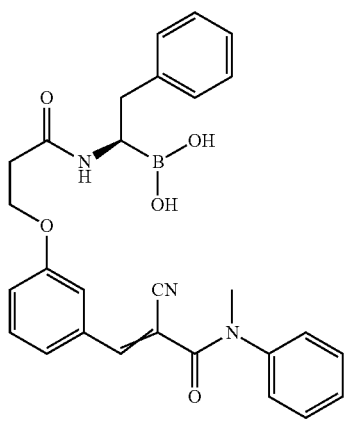 [SMILES: CN(C(=O)C(C#N)=Cc1cccc(OCCC(=O)N[C@@H](Cc2ccccc2)B(O)O)c1)c1ccccc1]

The title compound was prepared as in example 19 by replacing N-methyl piperazine with N-methyl phenylamine. LC-MS m/z: 480 [M−17].

Example 23

(R)-(2-(benzofuran-3-yl)-1-(3-(3-(2-cyano-2-(pyridin-2-yl)vinyl)phenoxy)propanamido)ethyl)boronic Acid

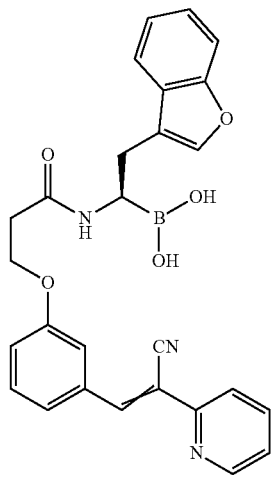 [SMILES: N#CC(=Cc1cccc(OCCC(=O)N[C@@H](Cc2coc3ccccc23)B(O)O)c1)c1ccccn1]

The title compound was prepared as in example 21 by replacing (R)-3-phenyl-1-(4,4,5,5-tetramethyl-1,3,2-dioxaborolan-2-yl)propan-1-amine hydrochloride with 2-(benzofuran-3-yl)-1-(((3aS,4S,6S,7aR)-3a,5,5-trimethylhexahydro-4,6-methanobenzo[d][1,3,2]dioxaborol-2-yl)ethan-1-amine hydrochloride. LC-MS m/z: 464 [M−17].

Example 24

(R)-(1-(4-(3-(2-cyano-3-(dimethylamino)-3-oxoprop-1-en-1-yl)phenyl)butanamido)-2-phenylethyl) boronic Acid

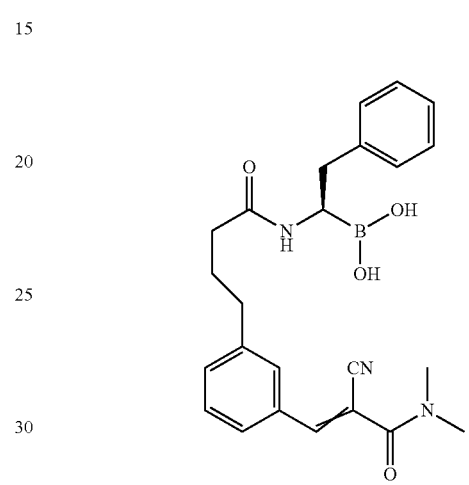

Synthetic Scheme

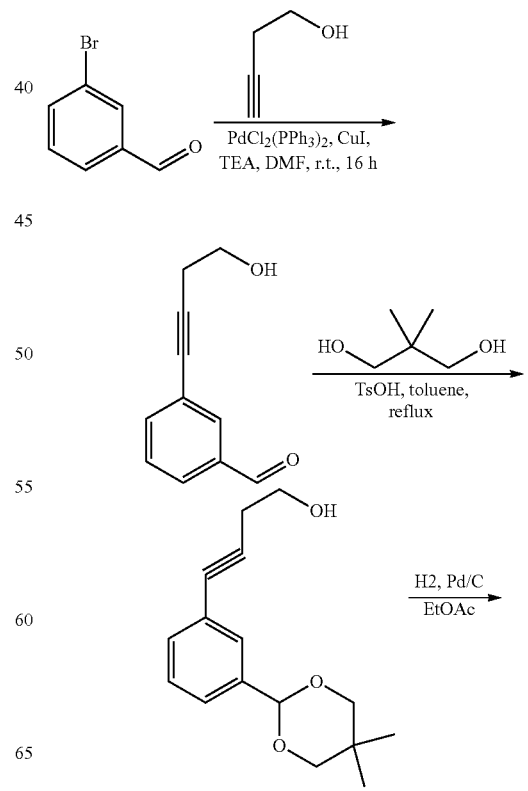

-continued

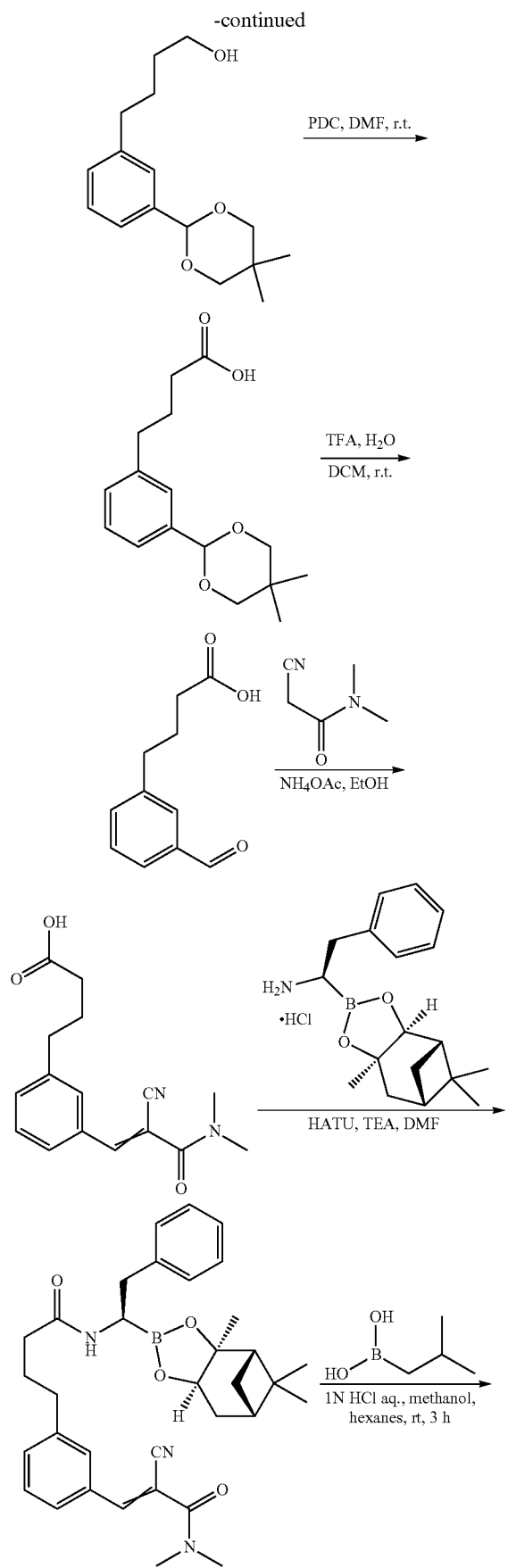

-continued

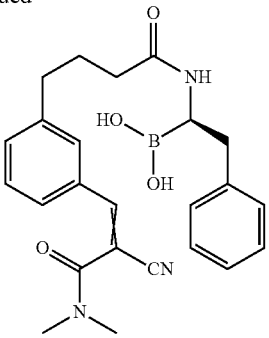

To a suspension of Pd(PPh₃)Cl₂ (331 mg, 0.472 mmol) and CuI (90 mg, 0.472 mmol) in degassed DMF (30 mL) at 20° C. under argon atmosphere were added 3-bromobenzaldehyde (4.37 g, 23.6 mmol), but-3-yn-1-ol (1.82 g, 26 mmol) and TEA (4.82 g, 47.2 mmol). The mixture was stirred at r.t. for 16 h, then poured into water (300 mL) and extracted with DCM (50 mL×3). The combined organic phase was washed with brine (50 mL), dried over Na₂SO₄ and concentrated to dryness. The residue was purified by column chromatography on silica gel (eluent: petroleum ether/ethyl acetate from 3:1 to 1:1) to afford 3-(4-hydroxy-but-1-ynyl)benzaldehyde as light yellow oil (3.2 g, 78%).

A solution of 3-(4-hydroxybut-1-ynyl)benzaldehyde (3.2 g, 18.4 mmol), 2,2-dimethylpropane-1,3-diol (5.73 g, 55.2 mmol) and TsOH (48 mg, 0.275 mmol) in toluene (50 mL) was refluxed for 2 h in a 100 mL flask with Dean-Stark trap. After cooling to r.t., the mixture was concentrated to dryness. The residue was purified by column chromatography on silica gel (eluent: petroleum ether/ethyl acetate from 5:1 to 2:1) to afford 4-(3-(5,5-dimethyl-1,3-dioxan-2-yl)phenyl)but-3-yn-1-ol as light yellow solid (4.5 g, 94%).

A suspension of 4-(3-(5,5-dimethyl-1,3-dioxan-2-yl)phenyl)but-3-yn-1-ol (4.5 g, 17.3 mmol) and Pd/C (450 mg, 10% w.t/w.t) in EtOAc (100 mL) was stirred at r.t. for 2 h, then filtered through a pad of celite. The filtrate was concentrated to dryness to afford 4-(3-(5,5-dimethyl-1,3-dioxan-2-yl)phenyl)butan-1-ol as light yellow solid (4.5 g, 99%).

A suspension of 4-(3-(5,5-dimethyl-1,3-dioxan-2-yl)phenyl)butan-1-ol (4.5 g, 17.2 mmol) and PDC (22.6 g, 60.2 mmol) in DMF (50 mL) was stirred at r.t. for 18 h, then poured into EtOAc (400 mL) slowly with stirring. The sticky black solid was discarded and the clear solution was concentrated to remove DMF. The residue was treated with water (300 mL), then extracted with EtOAc (80 mL×3). The combined organic phase was washed with brine (70 mL), dried over Na₂SO₄ and concentrated to afford 4-(3-(5,5-dimethyl-1,3-dioxan-2-yl)phenyl)butanoic acid as light yellow solid (4.6 g crude) which was used into next step directly.

A solution of 4-(3-(5,5-dimethyl-1,3-dioxan-2-yl)phenyl)butanoic acid (4.6 g crude) in DCM/TFA/H₂O (15 mL/15 mL/3 mL) was stirred at r.t. for 13 h, then concentrated to dryness. The residue was purified by column chromatography on silica gel (eluent: petroleum ether/ethyl acetate from 1:1 to 1:3) to afford 4-(3-formylphenyl)butanoic acid as light yellow sticky solid (1.75 g, 53% over 2 steps).

A mixture of 4-(3-formylphenyl)butanoic acid (288 mg, 1.5 mmol), 2-cyano-N,N-dimethylacetamide (202 mg, 1.8 mmol) and ammonium acetate (578 mg, 7.5 mmol) in ethanol (10 mL) was stirred at reflux temperature for 2 h. After cooling to rt, filtered and concentrated in vacuo to give a crude residue, which was distributed with EtOAc (100 mL) and water (10 mL). The organic layer was dried over $Na_2SO_4$ and concentrated to afford 4-(3-(2-cyano-3-(dimethylamino)-3-oxoprop-1-enyl)phenyl)butanoic acid as light yellow solid (450 mg crude).

TEA (480 mg, 4.71 mmol) was added to a stirred solution of 4-(3-(2-cyano-3-(dimethylamino)-3-oxoprop-1-enyl)phenyl)butanoic acid (450 mg crude, 1.57 mmol), (R)-2-phenyl-1-((3aS,4S,6S,7aR)-3a,5,5-trimethylhexahydro-4,6-methanobenzo[d][1,3,2]dioxaborol-2-yl)ethanamine hydrochloride (527 mg, 1.57 mmol) and HATU (597 mg, 1.57 mmol) in DMF (3.5 mL) at rt. The mixture was stirred at rt for 2 h, then quenched with water (10 mL) and filtered to afford the title compound which was purified by prep-HPLC to afford pinane ester of (R)-1-(4-(3-(2-cyano-3-(dimethylamino)-3-oxoprop-1-enyl)phenyl)butanamido)-2-phenylethylboronic acid as white solid (135 mg, 16% over 2 steps).

To a solution of pinane ester of (R)-1-(4-(3-(2-cyano-3-(dimethylamino)-3-oxoprop-1-enyl)phenyl)butanamido)-2-phenylethylboronic acid (135 mg, 0.238 mmol) in MeOH (3 mL) were added hexanes (3 mL) and 1 N HCl (0.6 mL), followed by isobutyl boric acid (73 mg, 0.714 mmol). After stirring at rt for 3 h and TLC suggested the reaction was completed, the hexanes layer was discarded, the methanol layer was diluted with water (10 mL) and dried over lyophylization to give a crude product which was further purified by neutral $Al_2O_3$ column (Methanol/DCM=0-15% as eluent) to afford (R)-(1-(4-(3-(2-cyano-3-(dimethylamino)-3-oxoprop-1-en-1-yl)phenyl)butanamido)-2-phenylethyl)boronic acid as white solid (33.8 mg, 33%). LCMS: 416 [M−17].

Example 25

(R)-(1-(4-(3-(2-cyano-2-(1H-1,2,4-triazol-1-yl)vinyl)phenyl)butanamido)-2-phenylethyl)boronic Acid

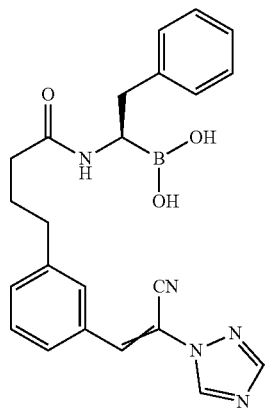 [SMILES: N#CC(=Cc1cccc(CCCC(=O)N[C@@H](Cc2ccccc2)B(O)O)c1)n1cncn1]

Synthetic Scheme

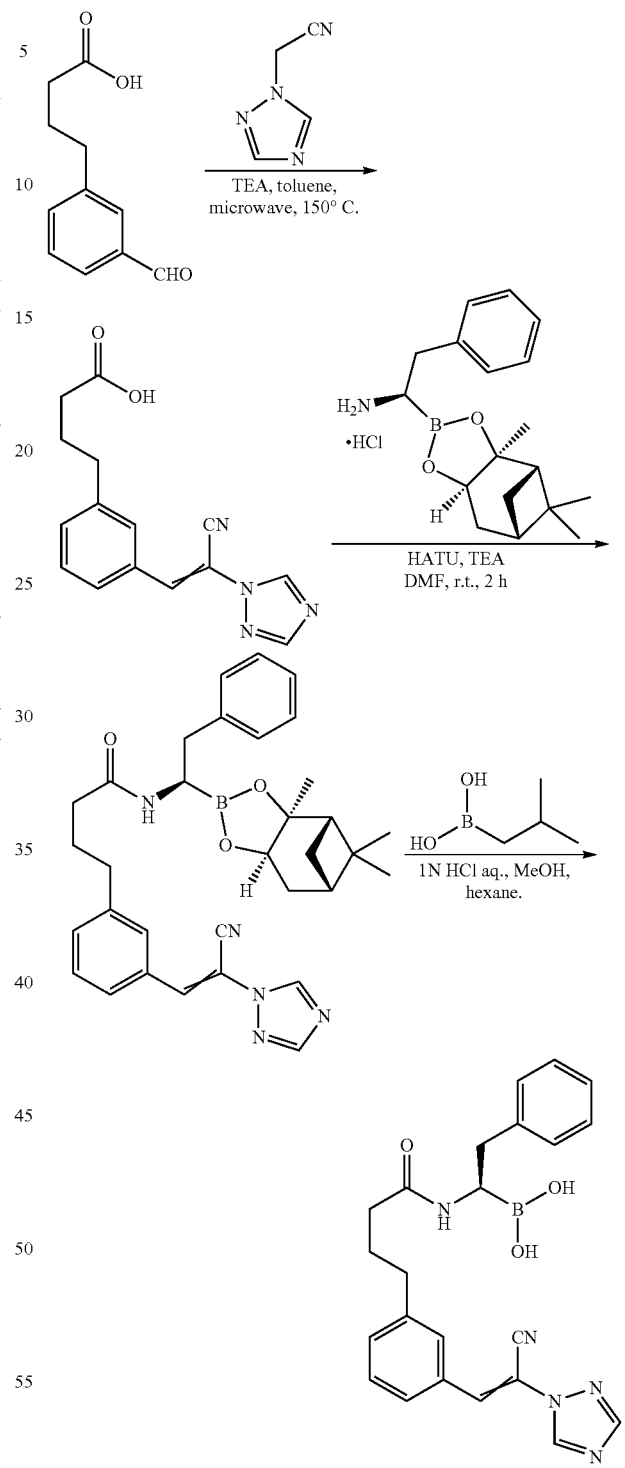

A mixture of 4-(3-formylphenyl)butanoic acid (960 mg, 5 mmol), 2-(1H-1,2,4-triazol-1-yl)acetonitrile (1.08 g, 10 mmol) and TEA (2.52 g, 25 mmol) in toluene (10 mL) was stirred in microwave reactor at 150° C. for 1.5 h. After cooling to rt, the mixture was concentrated to dryness, the residue was purified by column chromatography (ethyl acetate/petroleum ether 0-50% as eluent) to afford 4-(3-(2- cyano-2-(1H-1,2,4-triazol-1-yl)vinyl)phenyl)butanoic acid as a light yellow solid (605 mg, 43% yield).

TEA (303 mg, 3 mmol) was added to a stirred solution of 4-(3-(2-cyano-2-(1H-1,2,4-triazol-1-yl)vinyl)phenyl)butanoic acid (282 mg, 1.0 mmol), (R)-2-phenyl-1-((3aS,4S,6S,7aR)-3a,5,5-trimethylhexahydro-4,6-methanobenzo[d][1,3,2]dioxaborol-2-yl)ethanamine hydrochloride (336 mg, 1.0 mmol) and HATU (380 mg, 1.0 mmol) in DMF (3 mL) at rt. The mixture was stirred at rt for 2 h, then quenched with water (10 mL) and filtered to afford the title compound which was purified by prep-HPLC to afford 4-(3-(2-cyano-2-(1H-1,2,4-triazol-1-yl)vinyl)phenyl)-N—((R)-2-phenyl-1-((3aS,4S,6S,7aR)-3a,5,5-trimethylhexahydro-4,6-methanobenzo[d][1,3,2]dioxaborol-2-yl)ethyl)butanamide as white solid (56 mg, 10% yield).

To a solution of 4-(3-(2-cyano-2-(1H-1,2,4-triazol-1-yl)vinyl)phenyl)-N—((R)-2-phenyl-1-((3aS,4S,6S,7aR)-3a,5,5-trimethylhexahydro-4,6-methanobenzo[d][1,3,2]dioxaborol-2-yl)ethyl)butanamide (56 mg, 0.1 mmol) in MeOH (2 mL) were added hexanes (2 mL) and 1 N HCl (0.4 mL), followed by isobutyl boric acid (30 mg, 0.3 mmol). After stirring at rt for 3 h and TLC suggested the reaction was completed, the hexanes layer was discarded, the methanol layer was diluted with water (10 mL) and dried over lyophilizer to give a crude product which was further purified by neutral Al₂O₃ column (Methanol/DCM=0-15% as eluent) to afford (R)-(1-(4-(3-(2-cyano-2-(1H-1,2,4-triazol-1-yl)vinyl)phenyl)butanamido)-2-phenylethyl)boronic acid as white solid (13.6 mg, 32% yield). LCMS: 416 [M−17].

Example 26

(R)-(1-(3-(5-(2-cyano-3-(dimethylamino)-3-oxoprop-1-en-1-yl)-2-methoxyphenoxy)propanamido)-2-phenylethyl)boronic Acid

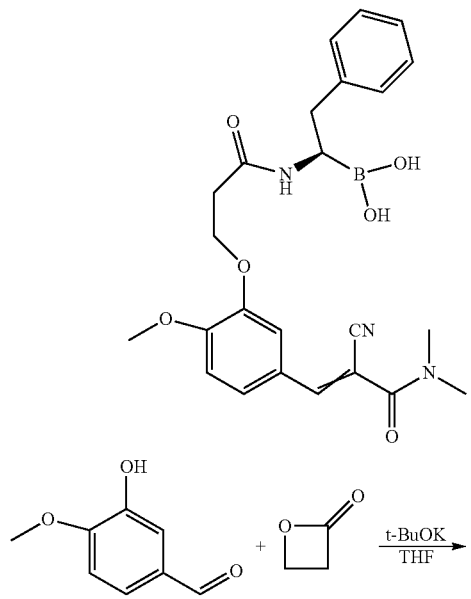

Into a 25-mL round-bottom flask, was placed 3-hydroxy-4-methoxybenzaldehyde (500 mg, 3.29 mmol, 1.00 eq.), oxetan-2-one (260 mg, 3.61 mmol, 1.10 eq.), t-BuOK (370 mg, 3.30 mmol, 1.00 eq.), tetrahydrofuran (6.5 mL). The resulting solution was stirred for 1 overnight at 25° C. The pH value of the solution was adjusted to 2 with 1M hydrogen chloride. The resulting solution was diluted with 100 mL of H2O. The resulting solution was extracted with 3×100 mL of ethyl acetate and the organic layers combined. The resulting mixture was washed with 3×100 mL of saturated brine. The mixture was dried over anhydrous sodium sulfate and concentrated under vacuum. The resulting mixture was washed with 1×100 mL of PE:EA=5:1 and 1×100 mL of Hexane. This resulted in 0.65 g (88%) of 3-(5-formyl-2-methoxyphenoxy)propanoic acid as a yellow solid.

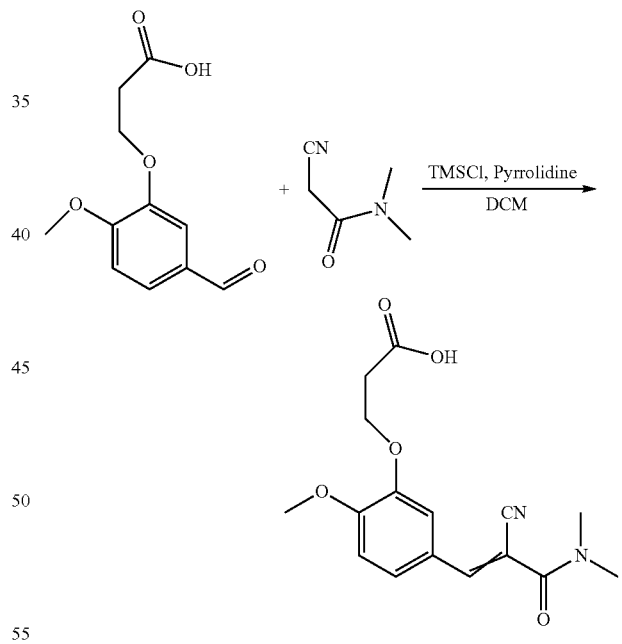

Into an 8-mL sealed tube, was placed 3-(5-formyl-2-methoxyphenoxy)propanoic acid (50 mg, 0.22 mmol, 1.00 eq.), 2-cyano-N,N-dimethylacetamide (25 mg, 0.22 mmol, 1.00 eq.), dichloromethane (0.6 mL). This was followed by the addition of pyrrolidine (63.4 mg, 0.89 mmol, 4.00 eq.) dropwise with stirring at 10° C. The resulting solution was stirred for 10 min at 10° C. To this was added TMSCl (72.3 mg, 0.67 mmol, 3.00 eq.) dropwise with stirring at 10° C. The resulting solution was allowed to react, with stirring, for an additional 2 h at 25° C. The resulting mixture was concentrated under vacuum. The residue was separated by Prep-TLC with EA:AcOH (1:0.1). This resulted in 18 mg (25%) of 3-[5-[2-cyano-2-(dimethylcarbamoyl)eth-1-en-1-yl]-2-methoxyphenoxy]propanoic acid as a solid.

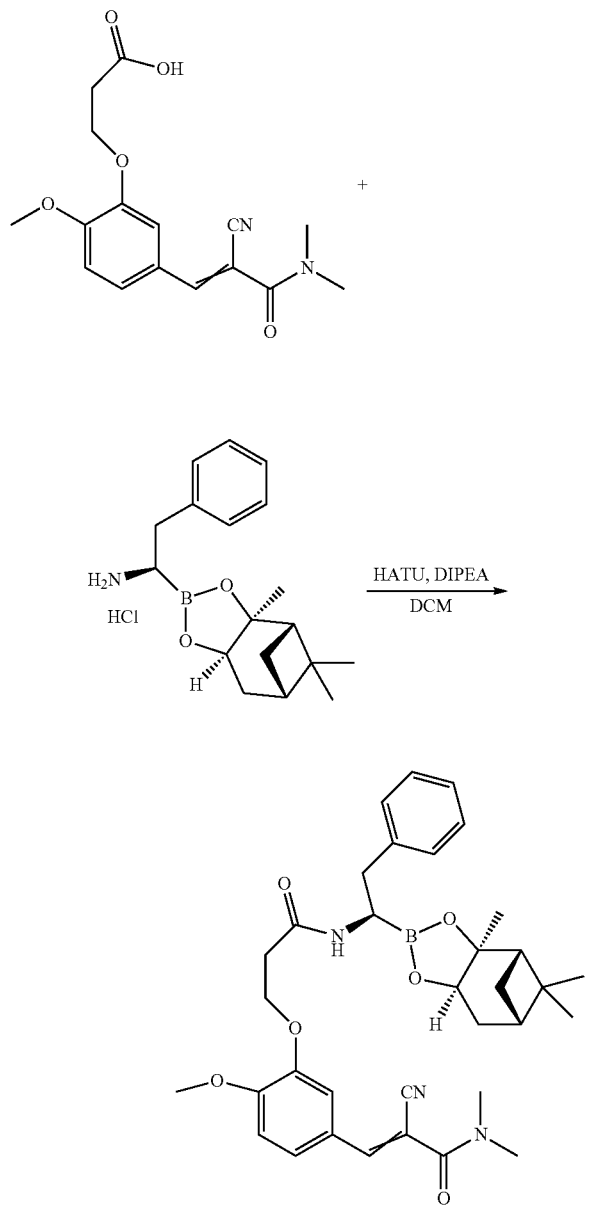

Into a 50-mL round-bottom flask, was placed 3-[5-[2-cyano-2-(dimethylcarbamoyl) eth-1-en-1-yl]-2-methoxyphenoxy]propanoic acid (330 mg, 1.04 mmol, 1.00 eq.), (1R)-2-phenyl-1-[(1S,2S,6R,8S)-2,9,9-trimethyl-3,5-dioxa-4-boratricyclo[6.1.1.0^[2,6]]decan-4-yl]ethan-1-amine (310.3 mg, 1.04 mmol, 1.00 eq.), HATU (591.5 mg, 1.56 mmol, 1.50 eq.), DIPEA (401.6 mg, 3.11 mmol, 3.00 eq.), dichloromethane (10 mL). The resulting solution was stirred for 30 min at 25° C. The resulting solution was diluted with 100 mL of H2O. The resulting solution was extracted with 3×100 mL of dichloromethane and the organic layers combined and dried over anhydrous sodium sulfate and concentrated under vacuum. The residue was separated by PREP-TLC with ethyl acetate/petroleum ether (2:1). The crude product was purified by Prep-HPLC with the following conditions (2#-AnalyseHPLC-SHIMADZU (HPLC-10)): Column, XBridge Prep C18 OBD Column, mobile phase, Water (0.05% NH3H2O) and ACN (57.0% ACN up to 62.0% in 7 min); Detector, UV 254/220 nm. Then lyophilization; This resulted in 209 mg (34%) of 2-cyano-3-[4-methoxy-3-(2-[[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamoyl]ethoxy)phenyl]-N,N-dimethylprop-2-enamide as a yellow solid.

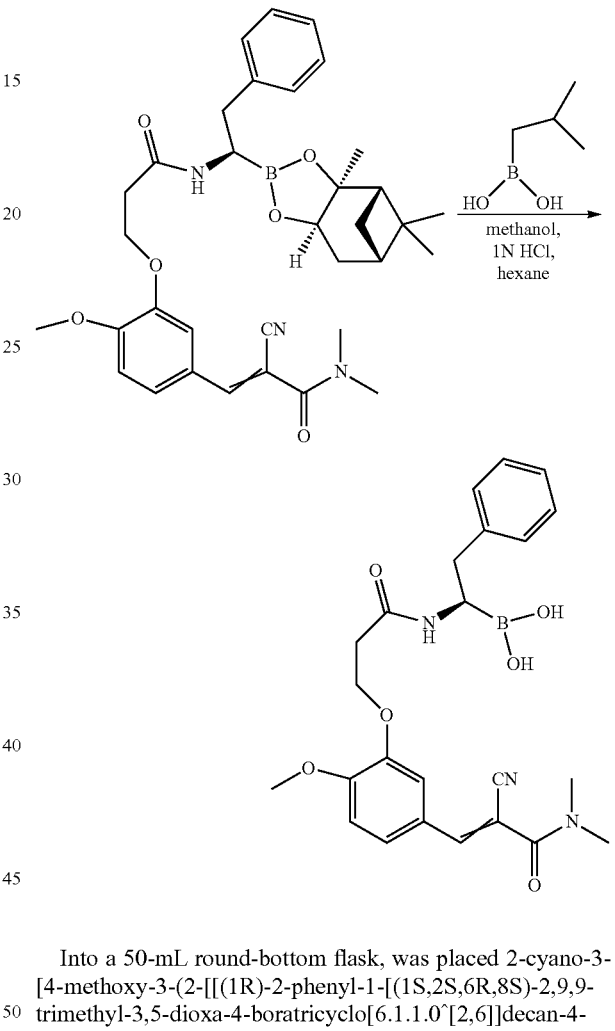

Into a 50-mL round-bottom flask, was placed 2-cyano-3-[4-methoxy-3-(2-[[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamoyl]ethoxy)phenyl]-N,N-dimethylprop-2-enamide (110 mg, 0.18 mmol, 1.00 eq.), (2-methylpropyl) boronic acid (54.3 mg, 0.53 mmol, 2.90 eq.), 1N hydrogen chloride (3.7 mL, 20.00 eq.), Methanol (4.5 mL), hexane (4.5 mL). The resulting solution was stirred for 2 h at 25° C. The methanol layer was lyophilized directly; The crude product solid was purified by Prep-HPLC with the following conditions (2#-AnalyseHPLC-SHIMADZU (HPLC-10)): Column, XBridge Prep C18 OBD Column, 19??150 mm 5 um; mobile phase, Water (10 MMOL/L NH4HCO3+0.1% NH3·H2O) and ACN (25.0% ACN up to 29.0% in 7 min); Detector, UV 254/220 nm; Then lyophilization; This resulted in 21.1 mg (25%) of (R)-(1-(3-(5-(2-cyano-3-(dimethylamino)-3-oxoprop-1-en-1-yl)-2-methoxyphenoxy) propanamido)-2-phenylethyl)boronic acid as a white solid. LC-MS m/z: 448[M−17].

Example 27

(R)-(1-(3-(5-(2-cyano-3-(dimethylamino)-3-oxo-prop-1-en-1-yl)-2-fluorophenoxy)propanamido)-2-phenylethyl)boronic Acid

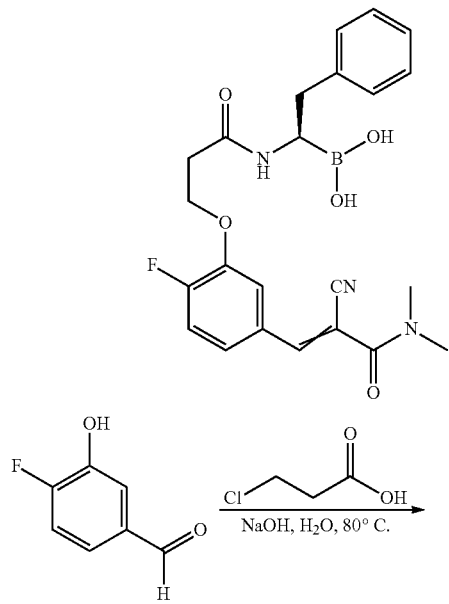

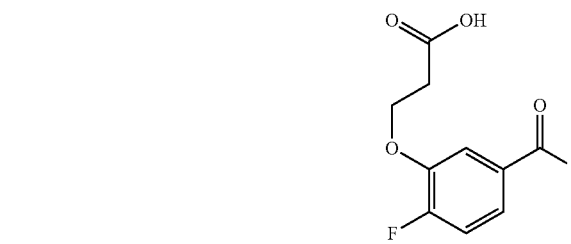

Into a 100-mL round-bottom flask, was placed 4-fluoro-3-hydroxybenzaldehyde (2.5 g, 17.84 mmol, 1.00 eq.), 3-chloropropanoic acid (1.93 g, 17.78 mmol, 1.00 eq.), water (50 mL). Sodium hydroxide (1.57 g, 39.25 mmol, 2.20 eq.) was added at rt and the resulting solution was stirred for 1 h at 80° C. in an oil bath. The pH value of the solution was adjusted to 2 with hydrogen chloride (2N). The resulting solution was extracted with 3×100 mL of ethyl acetate and the organic layers combined and dried over anhydrous sodium sulfate and concentrated under vacuum. This resulted in 3.7 g (crude) of 3-(2-fluoro-5-formylphenoxy)propanoic acid.

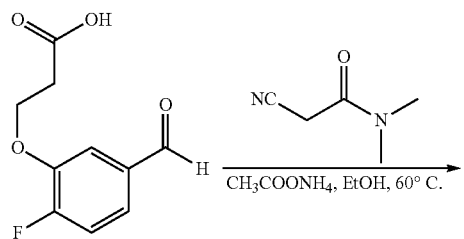

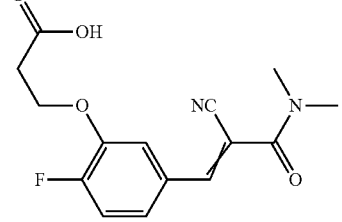

Into a 100-mL round-bottom flask, was placed 3-(2-fluoro-5-formylphenoxy)propanoic acid (3.7 g, 17.44 mmol, 1.00 eq.), 2-isocyano-N,N-dimethylacetamide (1.95 g, 17.39 mmol, 1.00 eq.), NH4OAc (6.72 g, 87.27 mmol, 5.00 eq.), ethanol (50 mL). The resulting solution was heated to reflux for 2 hr. The resulting solution was extracted with 3×100 mL of ethyl acetate and the organic layers combined. The resulting mixture was washed with 1×100 mL of sodium chloride (sat.). The mixture was dried over anhydrous sodium sulfate and concentrated under vacuum. The residue was applied onto a silica gel column with ethyl acetate/petroleum ether (4:1). This resulted in 2.3 g (43%) of 3-[5-[2-cyano-2-(dimethylcarbamoyl)eth-1-en-1-yl]-2-fluorophenoxy]propanoic acid as a yellow solid.

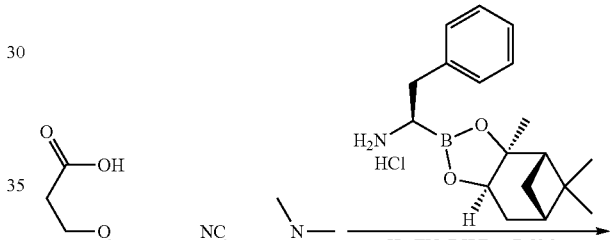

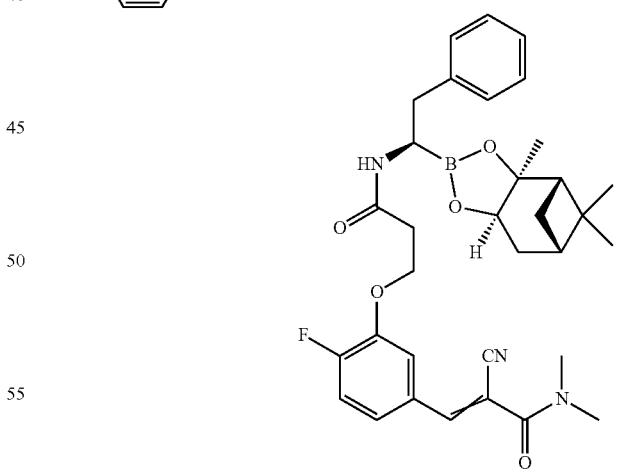

Into a 25-mL round-bottom flask, was placed a solution of 3-[5-[2-cyano-2-(dimethylcarbamoyl)eth-1-en-1-yl]-2-fluorophenoxy]propanoic acid (274 mg, 0.89 mmol, 1.00 eq.) in dichloromethane (6 mL), (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride (300 mg, 0.89 mmol, 1.20 eq.), DIEA (345 mg, 2.67 mmol, 3.00 eq.), HATU (508 mg, 1.34 mmol, 1.50 eq.). The resulting solution was stirred for 1 h at rt. The reaction was then quenched by the addition of 10 mL of water. The resulting solution was extracted with 2×10 mL of dichloromethane and the organic layers combined. The resulting mixture was washed with 1×10 mL of brine. The mixture was dried over anhydrous sodium sulfate and concentrated under vacuum. The crude product (300 mg) was purified by Prep-HPLC with the following conditions (2#-AnalyseHPLC-SHIMADZU (HPLC-10)): Column, XBridge Prep C18 OBD Column, 5 um, 19*150 mm; mobile phase, Water (0.05% NH3H2O) and ACN (50% ACN up to 75% in 7 min); Detector, UV 254/220 nm. This resulted in 52 mg (10%) of 2-cyano-3-[4-fluoro-3-(2-[[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamoyl]ethoxy)phenyl]-N,N-dimethylprop-2-enamide as a yellow solid.

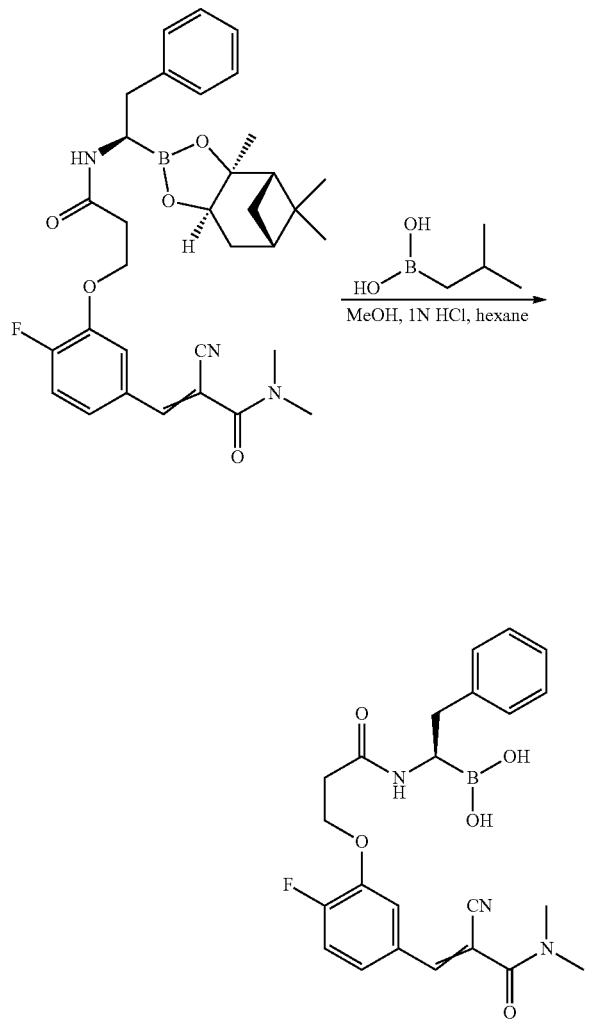

Into a 8-mL round-bottom flask, was placed 2-cyano-3-[4-fluoro-3-(2-[[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamoyl]ethoxy)phenyl]-N,N-dimethylprop-2-enamide (25 mg, 0.04 mmol, 1.00 eq.), methanol/n-hexane (1/1 mL), 1NHCl (0.85 mL, 20.00 eq.), (2-methylpropyl) boronic acid (13 mg, 0.13 mmol, 3.00 eq.). The resulting solution was stirred for 4 h at rt. The hexane layer was discarded. The methanol layer was diluted with water (10 mL), then dried over lyophylization to give a crude product. The crude product (25 mg) was purified by Prep-HPLC with the following conditions (2#-AnalyseHPLC-SHIMADZU (HPLC-10)): Column, XBridge Prep C18 OBD Column, 19??150 mm 5 um; mobile phase, Water (0.05% NH3H2O) and ACN (25.0% ACN up to 26.0% in 10 min); Detector, UV 254/220 nm. This resulted in 4.7 mg (23%) of (R)-(1-(3-(5-(2-cyano-3-(dimethylamino)-3-oxoprop-1-en-1-yl)-2-fluorophenoxy)propanamido)-2-phenylethyl)boronic acid as a white solid. LC-MS m/z: 436 [M−17].

Example 28

(R)-(1-(3-(5-(2-cyano-2-(pyridin-2-yl)vinyl)-2-fluorophenoxy)propanamido)-2-phenylethyl)boronic Acid

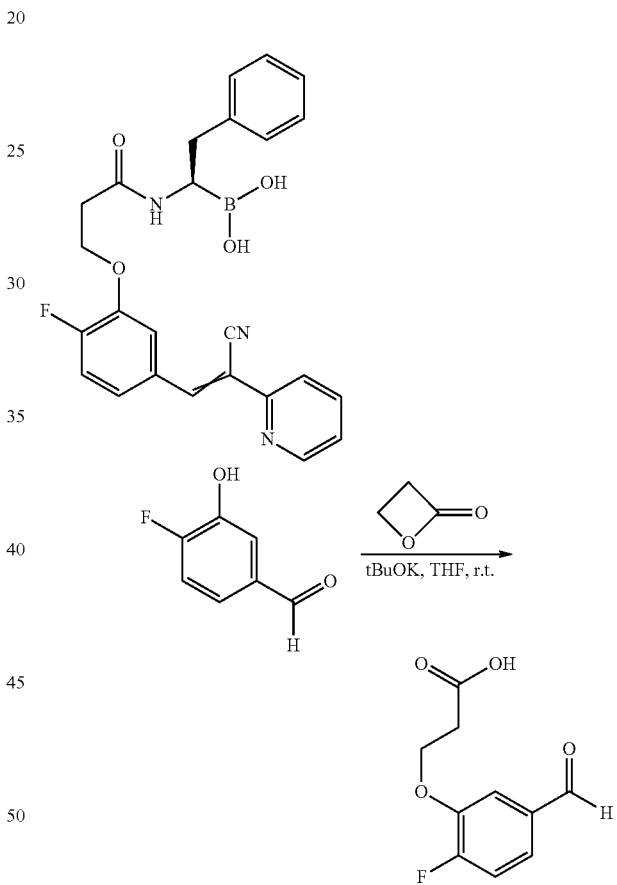

Into a 100-mL 3-necked round-bottom flask purged and maintained with an inert atmosphere of nitrogen, was placed 4-fluoro-3-hydroxybenzaldehyde (2.5 g, 17.84 mmol, 1.00 eq.) and tBuOK (1.60 g, 14.29 mmol, 0.80 eq.) in tetrahydrofuran (50 mL). Oxetan-2-one (1.41 g, 19.57 mmol, 1.10 eq.) was added at 0° C. and the resulting solution was stirred overnight at rt. The reaction was then quenched by the addition of hydrogen chloride (10%). The resulting solution was extracted with 3×100 mL of ethyl acetate and the organic layers combined and dried over anhydrous sodium sulfate and concentrated under vacuum. This resulted in 3.4 g (crude) of 3-(2-fluoro-5-formylphenoxy)propanoic acid as a yellow solid.

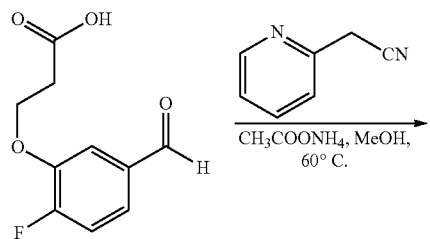

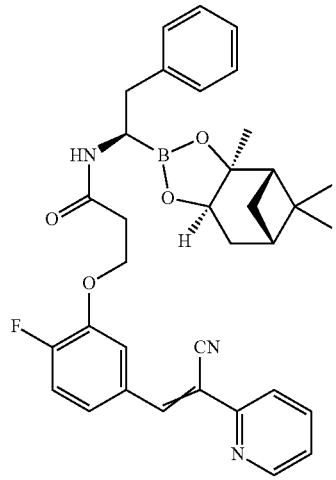

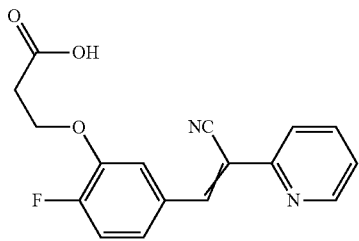

Into a 100-mL round-bottom flask, was placed 3-(2-fluoro-5-formylphenoxy)propanoic acid (3.4 g, 16.02 mmol, 1.00 eq.), 2-(pyridin-2-yl)acetonitrile (1.89 g, 16.00 mmol, 1.00 eq.), NH$_4$OAc (6.17 g, 80.13 mmol, 5.00 eq.), methanol (50 mL). The resulting solution was heated to reflux for 2 hr. The resulting solution was extracted with 3×100 mL of ethyl acetate and the organic layers combined. The resulting mixture was washed with 1×100 mL of sodium chloride (sat.). The mixture was dried over anhydrous sodium sulfate and concentrated under vacuum. The residue was applied onto a silica gel column with ethyl acetate/petroleum ether (4:1). This resulted in 3.7 g (74%) of 3-[5-[2-cyano-2-(pyridin-2-yl)eth-1-en-1-yl]-2-fluorophenoxy]propanoic acid as an off-white solid.

Into a 25-mL round-bottom flask, was placed a solution of 3-[5-[2-cyano-2-(pyridin-2-yl)eth-1-en-1-yl]-2-fluorophenoxy]propanoic acid (278 mg, 0.89 mmol, 1.00 eq.) in dichloromethane (6 mL), (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride (300 mg, 0.89 mmol, 1.00 eq.), DIEA (345 mg, 2.67 mmol, 1.20 eq.), HATU (508 mg, 1.34 mmol, 1.50 eq.). The resulting solution was stirred for 1 h at rt. The reaction was then quenched by the addition of 10 mL of water. The resulting solution was extracted with 2×10 mL of dichloromethane and the organic layers combined. The resulting mixture was washed with 1×10 mL of sodium chloride. The mixture was dried over anhydrous sodium sulfate and concentrated under vacuum. The crude product (300 mg) was purified by Prep-HPLC with the following conditions (2#-AnalyseHPLC-SHIMADZU (HPLC-10)): Column, XBridge Prep C18 OBD Column, 19,Ã150 mm 5 um; mobile phase, Water (0.05% NH3H2O) and ACN (70% ACN up to 79% in 7 min); Detector, UV 254/220 nm. This resulted in 200 mg (34%) of 3-[5-[2-cyano-2-(pyridin-2-yl)eth-1-en-1-yl]-2-fluorophenoxy]-N-[(1R)-2-phenyl-1-[(1S,2S,6R,8S)-2,9,9-trimethyl-3,5-dioxa-4-boratricyclo[6.1.1.0^[2,6]]decan-4-yl]ethyl]propanamide as a white solid.

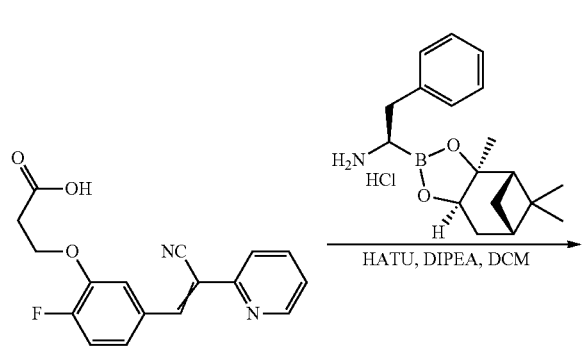

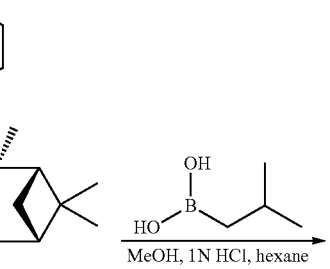

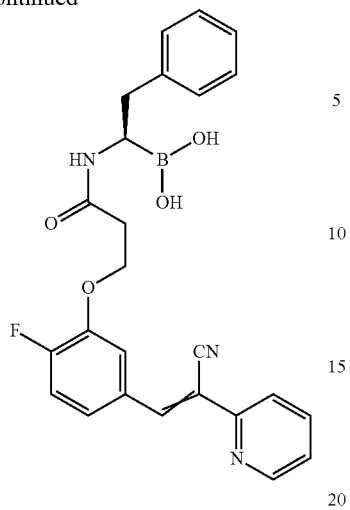

Into a 8-mL round-bottom flask, was placed 3-[5-[2-cyano-2-(pyridin-2-yl)eth-1-en-1-yl]-2-fluorophenoxy]-N-[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]propanamide (50 mg, 0.08 mmol, 1.00 eq.), methanol/n-hexane (1/1 mL), 1NHCl (1.75 mL, 20.00 eq.), (2-methylpropyl)boronic acid (26 mg, 0.26 mmol, 3.00 eq.). The resulting solution was stirred for 4 h at rt. Combined with PH-PBF-028-052-0-2 to purify. The hexane layer was discarded. The methanol layer was diluted with water (10 mL), then dried over lyophylization to give a crude product. The crude product (100 mg) was purified by Prep-HPLC with the following conditions (2#-AnalyseHPLC-SHI-MADZU (HPLC-10)): Column, XBridge Prep C18 OBD Column, 19*150 mm 5 um; mobile phase, Water (10 MMOL/L NH4HCO3+0.1% NH3·H2O) and ACN (33.0% ACN up to 45.0% in 7 min); Detector, UV 254/220 nm. This resulted in 20.7 mg of (R)-(1-(3-(5-(2-cyano-2-(pyridin-2-yl)vinyl)-2-fluorophenoxy)propanamido)-2-phenylethyl)boronic acid as a white solid. LC-MS m/z: 442 [M−17].

Example 29

(R)-(1-(3-(5-(2-cyano-2-(pyridin-2-yl)vinyl)-2-methoxyphenoxy)propanamido)-2-phenylethyl)boronic Acid

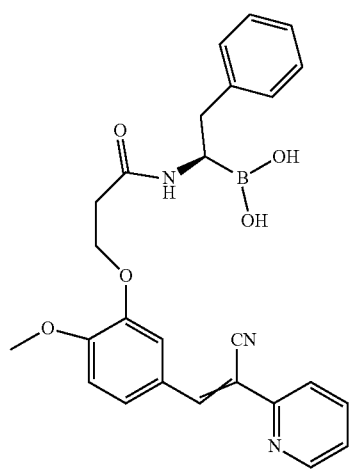 [SMILES: COc1ccc(C=C(C#N)c2ccccn2)cc1OCCC(=O)N[C@@H](Cc1ccccc1)B(O)O]

The title compound was prepared as in example 28 by replacing 4-fluoro-3-hydroxybenzaldehyde with 3-hydroxy-4-methoxybenzaldehyde. LC-MS m/z: 454 [M−17].

Example 30

(R)-(1-(3-(3-(3-(azetidin-1-yl)-2-cyano-3-oxoprop-1-en-1-yl)phenoxy)propanamido)-2-phenylethyl)boronic Acid

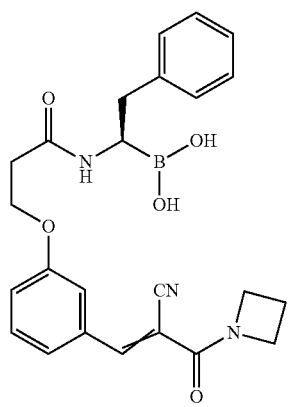 [SMILES: N#CC(=Cc1cccc(OCCC(=O)N[C@@H](Cc2ccccc2)B(O)O)c1)C(=O)N1CCC1]

The title compound was prepared as in example 19 by replacing N-methyl piperazine with N-methyl phenylamine. LC-MS m/z: 480 [M−17].

Example 31

(R)-(1-(3-(3-(2-cyano-3-(ethylamino)-3-oxoprop-1-en-1-yl)phenoxy)propanamido)-2-phenylethyl)boronic Acid

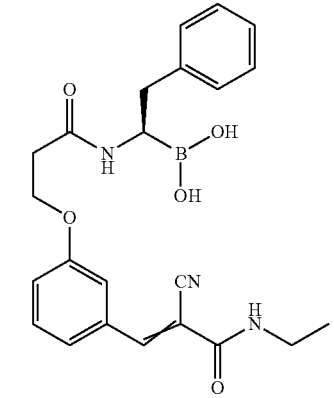 [SMILES: CCNC(=O)C(C#N)=Cc1cccc(OCCC(=O)N[C@@H](Cc2ccccc2)B(O)O)c1]

The title compound was prepared as in example 19 by replacing N-methyl piperazine with ethylamine. LC-MS m/z: 418 [M−17].

Example 32

(R)-(1-(3-(3-(2-cyano-3-(4-(oxetan-3-yl)piperazin-1-yl)-3-oxoprop-1-en-1-yl)phenoxy)propanamido)-2-phenylethyl)boronic Acid

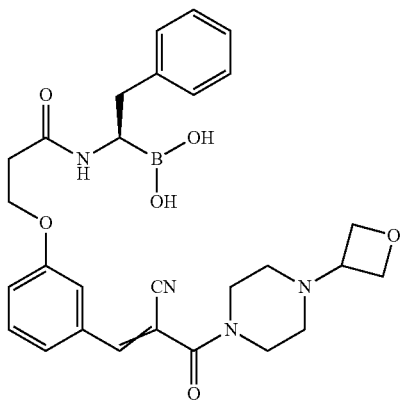 [SMILES: N#CC(=Cc1cccc(OCCC(=O)N[C@@H](Cc2ccccc2)B(O)O)c1)C(=O)N1CCN(C2COC2)CC1]

The title compound was prepared as in example 19 by replacing N-methyl piperazine with 1-(oxetan-3-yl)piperazine. LC-MS m/z: 515 [M−17].

Example 33

(R)-(1-(3-(3-(2-cyano-2-(5-(trifluoromethyl)pyridin-2-yl)vinyl)phenoxy)propanamido)-2-phenylethyl) boronic Acid

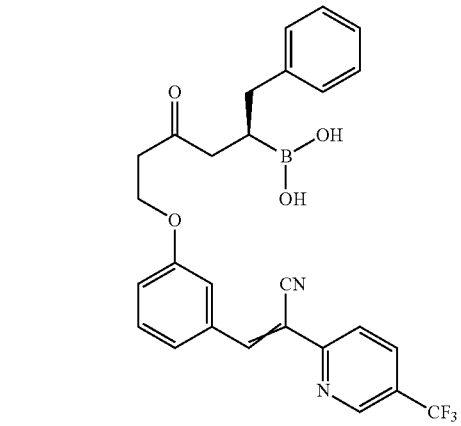 [SMILES: N#CC(=Cc1cccc(OCCC(=O)N[C@@H](Cc2ccccc2)B(O)O)c1)c1ccc(C(F)(F)F)cn1]

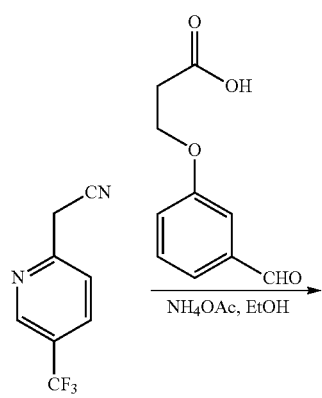

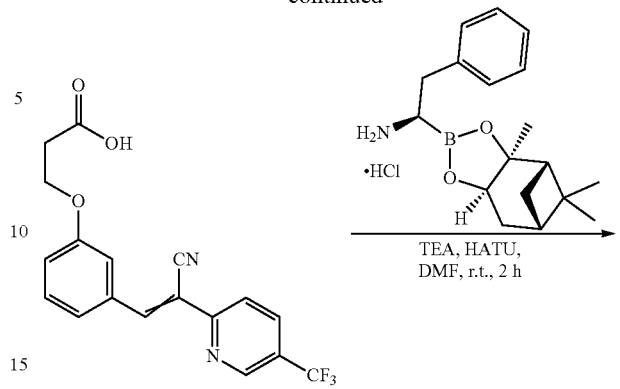

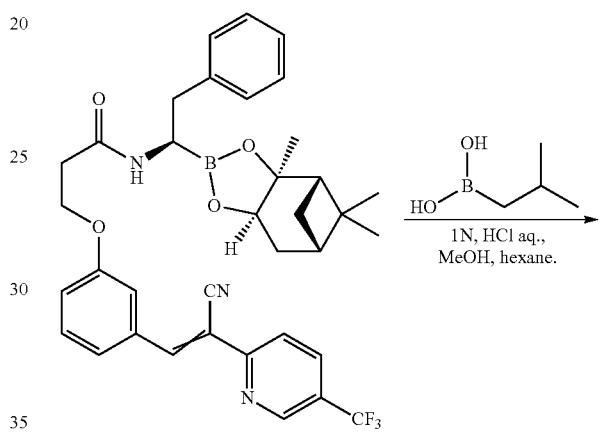

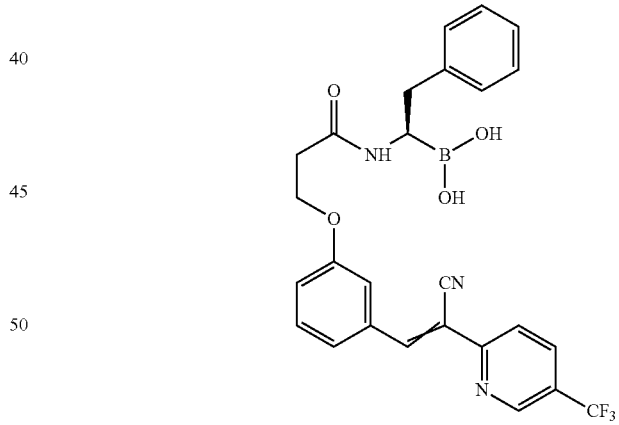

A mixture of 2-(5-(trifluoromethyl)pyridin-2-yl)acetonitrile (281 mg, 1.51 mmol), 3-(3-formylphenoxy)propanoic acid (280 mg, 1.44 mmol) and ammonium acetate (555 mg, 7.2 mmol) in ethanol (10 mL) was stirred at reflux temperature for 2 h. After cooling to rt, the reaction was filtered and concentrated in vacuo to give a crude residue, which was distributed between EtOAc (100 mL) and water (10 mL). The organic layer was dried over $Na_2SO_4$ and concentrated to dryness. The residue was purified by column flash to afford 3-(3-(2-cyano-2-(5-(trifluoromethyl)pyridin-2-yl)vinyl)phenoxy)propanoic acid as light yellow solid (362 mg, 69%).

TEA (303 mg, 3.0 mmol) was added to a stirred solution of 3-(3-(2-cyano-2-(5-(trifluoromethyl)pyridin-2-yl)vinyl)phenoxy)propanoic acid (362 mg, 1.0 mmol), (R)-2-phenyl-1-((3aS,4S,6S,7aR)-3a,5,5-trimethylhexahydro-4,6-methanobenzo[d][1,3,2]dioxaborol-2-yl)ethanamine hydrochloride (336 mg, 1.01 mmol) and HATU (390 mg, 1.0 mmol) in DMF (1.5 mL) at rt. The mixture was stirred at rt for 2 h, then quenched with water (10 mL) and filtered to afford the title compound (0.55 g crude) which was further purified by prep-HPLC to afford 3-(3-(2-cyano-2-(5-(trifluoromethyl)pyridin-2-yl)vinyl)phenoxy)-N—((R)-2-phenyl-1-((3aS,4S,6S,7aR)-3a,5,5-trimethylhexahydro-4,6-methanobenzo[d][1,3,2]dioxaborol-2-yl)ethyl)propanamide as a white solid (173 mg, 27%).

To a solution of 3-(3-(2-cyano-2-(5-(trifluoromethyl)pyridin-2-yl)vinyl)phenoxy)-N—((R)-2-phenyl-1-((3aS,4S,6S,7aR)-3a,5,5-trimethylhexahydro-4,6-methanobenzo[d][1,3,2]dioxaborol-2-yl)ethyl)propanamide (173 mg, 0.269 mmol) in MeOH (4 mL) were added hexanes (4 mL) and 1 N HCl (0.8 mL), followed by isobutyl boric acid (82 mg, 0.806 mmol). After stirring at rt for 3 h and TLC suggested the reaction was completed, the hexanes layer was discarded, the methanol layer was diluted with water (10 mL) and dried over lyophilizer to give a crude product which was further purified by neutral $Al_2O_3$ column (Methanol/DCM=0-15% as eluent) to afford (R)-(1-(3-(3-(2-cyano-2-(5-(trifluoromethyl)pyridin-2-yl)vinyl)phenoxy)propanamido)-2-phenylethyl)boronic acid as a white solid (75.1 mg, 55%). LCMS: 532 [M+23].

Example 34

(R)-(1-(3-(3-(2-cyano-2-(3-fluoropyridin-2-yl)vinyl)phenoxy)propanamido)-2-phenylethyl)boronic Acid

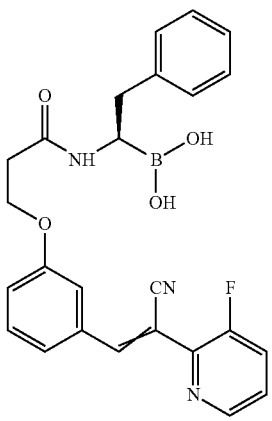 [SMILES: N#CC(=Cc1cccc(OCCC(=O)N[C@@H](Cc2ccccc2)B(O)O)c1)c1ncccc1F]

The title compound was prepared as in example 33 by replacing 2-(5-(trifluoromethyl)pyridin-2-yl)acetonitrile with 2-(3-fluoropyridin-2-yl)acetonitrile. LC-MS m/z: 482 [M+23].

Example 35

(R)-(2-(benzofuran-3-yl)-1-(((3-(2-cyano-2-(pyridin-2-yl)vinyl)phenethoxy)carbonyl)amino)ethyl)boronic Acid

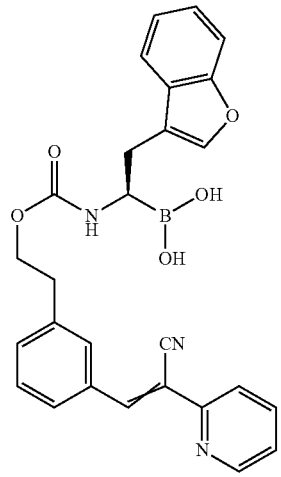 [SMILES: N#CC(=Cc1cccc(CCOC(=O)N[C@@H](Cc2coc3ccccc23)B(O)O)c1)c1ccccn1]

Synthetic Scheme

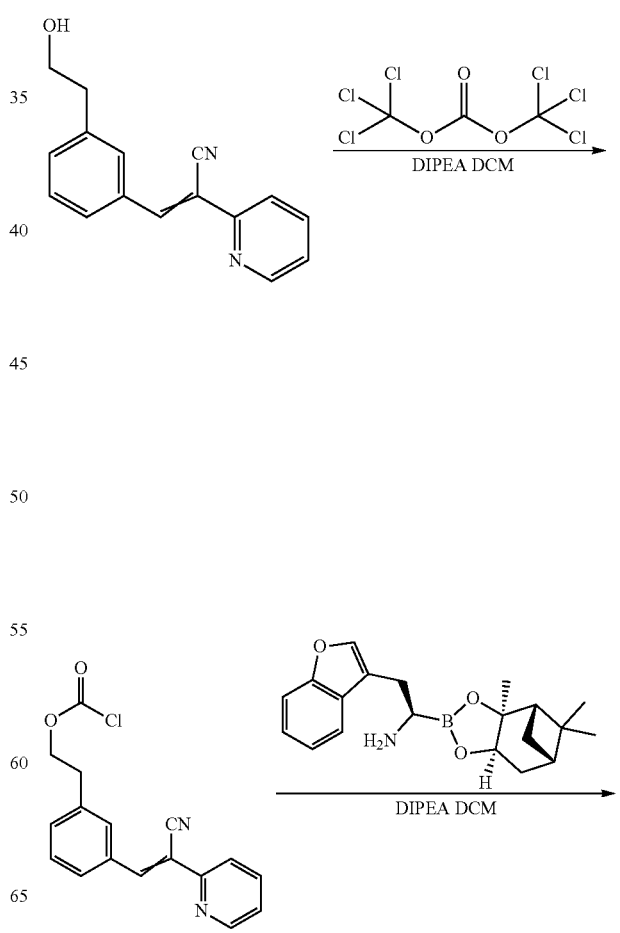

-continued

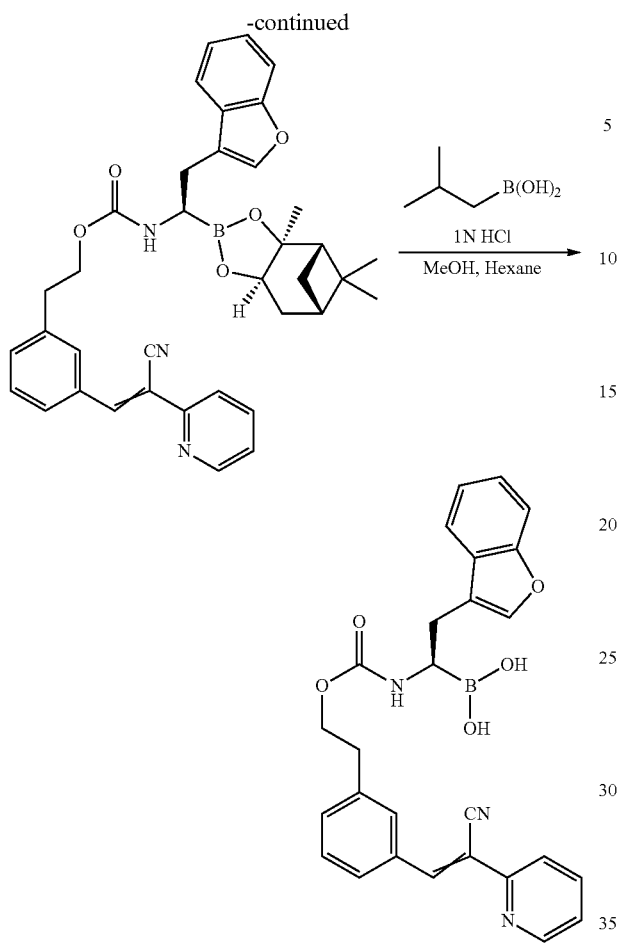

Bis(trichloromethyl) carbonate (118.56 mg, 0.40 mmol) in DCM (5 mL) was added to a stirred solution of 3-(3-(2-hydroxyethyl)phenyl)-2-(pyridin-2-yl)acrylonitrile (200 mg, 0.80 mmol) and DIPEA (309.82 mg, 2.40 mmol) in DCM (10 mL) at 0° C., the resultant reaction was stirred for 2 h at 0° C. before next use.

The above reaction solution of (3-(2-cyano-2-(pyridin-2-yl)vinyl)phenethyl carbonochloridate) was added dropwise into a well-stirred solution of (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine hydrochloride (300.32 mg, 0.8 mmol) and DIPEA (309.82 mg, 2.40 mmol) in DCM (20 mL) at 0° C. The reaction was stirred at rt for 1 h, then washed with water (20 mL) and brine (20 mL), the organic extracts was dried over Na2SO4 and concentrated in vacuo. The crude material was purified by Prep-HPLC to afford 3-(2-cyano-2-(pyridin-2-yl)vinyl)phenethyl ((1R)-2-(benzofuran-3-yl)-1-((4S,6S,7aR)-5,5-dimethylhexahydro-4,6-methanobenzo[d][1,3,2]dioxaborol-2-yl)ethyl)carbamate as light yellow solid (110 mg, 22.45%).

To a solution of 3-(2-cyano-2-(pyridin-2-yl)vinyl)phenethyl ((1R)-2-(benzofuran-3-yl)-1-((4S,6S,7aR)-5,5-dimethylhexahydro-4,6-methanobenzo[d][1,3,2]dioxaborol-2-yl)ethyl)carbamate (110 mg, 0.18 mmol) in MeOH (5 mL) were added hexane (5 mL) and 1 N HCl (1 mL), followed by isobutyl boric acid (54.65 mg, 0.54 mmol). After stirring at rt for 3 h and TLC suggested the reaction was completed, the hexane layer was discarded. The methanol layer was diluted with water (10 mL), then dried over lyophilizer to give a crude product which was further purified by neutral Al₂O₃ column (Methanol/DCM=0-10% as eluent) to afford (R)-(2-(benzofuran-3-yl)-1-(((3-(2-cyano-2-(pyridin-2-yl)vinyl)phenethoxy)carbonyl)amino)ethyl)boronic acid as a light yellow solid (42 mg, 48.8%). LC-MS m/z: 504 [M+23].

Example 36

(R)-(1-(((3-(2-cyano-2-(pyridin-2-yl)vinyl)phenethoxy)carbonyl)amino)-2-phenylethyl)boronic Acid

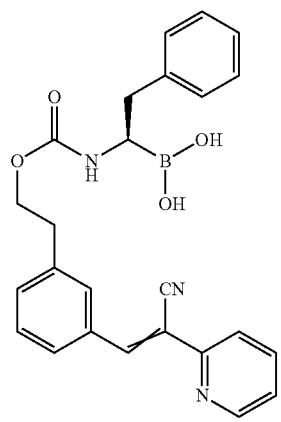 [SMILES: N#CC(=Cc1cccc(CCOC(=O)N[C@@H](Cc2ccccc2)B(O)O)c1)c1ccccn1]

The title compound was prepared as in example 35 by replacing (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine with ((R)-2-phenyl-1-((3aS,4S,6S,7aR)-3a,5,5-trimethylhexahydro-4,6-methanobenzo[d][1,3,2]dioxaborol-2-yl)ethyl)carbamate. LC-MS m/z: 464 [M+23].

Example 37

(R)-(1-(3-(3-(2-cyano-3-(dimethylamino)-3-oxo-prop-1-en-1-yl)-2-fluorophenoxy)propanamido)-2-phenylethyl)boronic Acid

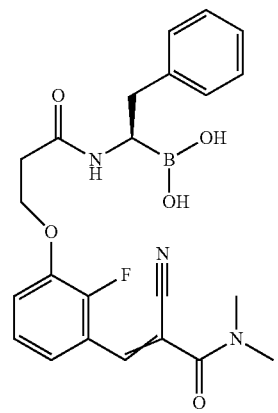 [SMILES: CN(C)C(=O)C(C#N)=Cc1cccc(OCCC(=O)N[C@@H](Cc2ccccc2)B(O)O)c1F]

The title compound was prepared as in example 38 by replacing 2,4-dichloro-3-hydroxybenzaldehyde with 2-fluoro-3-hydroxybenzaldehyde. LC-MS m/z: 436 [M−17].

Example 38

(R)-(1-(3-(2,6-dichloro-3-(2-cyano-3-(dimethyl-amino)-3-oxoprop-1-en-1-yl)phenoxy)propana-mido)-2-phenylethyl)boronic Acid

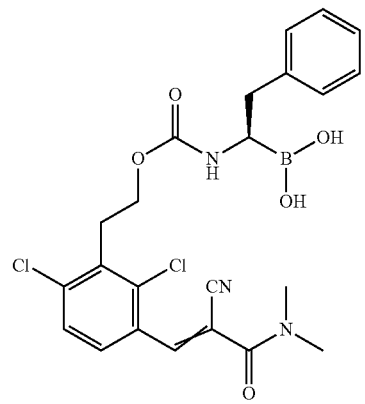

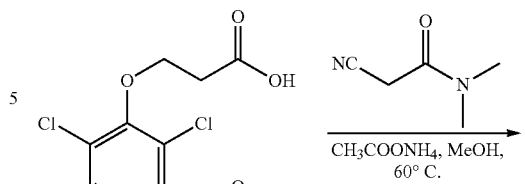

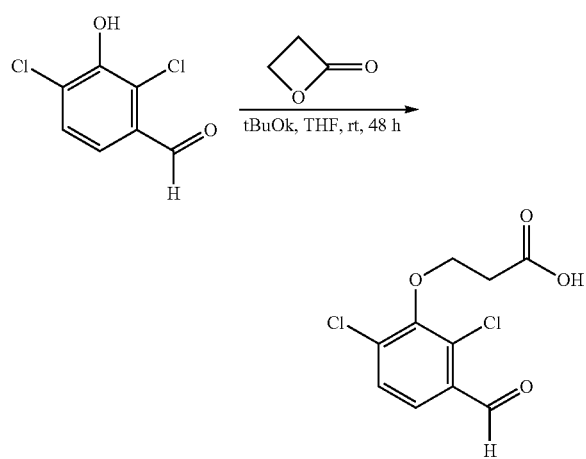

Into a 250-mL 3-necked round-bottom flask, was placed a solution of 2,4-dichloro-3-hydroxybenzaldehyde (5 g, 26.18 mmol, 1.00 eq.) in tetrahydrofuran (100 mL). This was followed by the addition of t-BuOK (2.94 g, 26.20 mmol, 1.00 eq.) in several batches at 0° C. To this was added oxetan-2-one (2.08 g, 28.86 mmol, 1.10 eq.) dropwise with stirring at 0° C. The resulting solution was stirred for 1 overnight at rt. The reaction was then quenched by the addition of 100 mL of water. The resulting solution was extracted with 10×50 mL of ethyl acetate and the water layers combined. The pH value of the solution was adjusted to 0-2 with hydrogen chloride (1 mol/L). The resulting solution was extracted with 2×50 mL of ethyl acetate and the organic layers combined. The resulting mixture was washed with 1×20 mL of water and 1×20 mL of brine. The mixture was dried over anhydrous sodium sulfate and concentrated under vacuum. The residue was applied onto a silica gel column with ethyl acetate/petroleum ether (1:10). This resulted in 690 mg (10%) of 3-(2,6-dichloro-3-formylphenoxy)propanoic acid as a white solid.

Into a 25-mL round-bottom flask, was placed a solution of 3-(2,6-dichloro-3-formylphenoxy)propanoic acid (240 mg, 0.91 mmol, 1.00 eq.) in methanol (5 mL), 2-cyano-N,N-dimethylacetamide (103 mg, 0.92 mmol, 1.00 eq.), $CH_3COONH_4$ (355 mg, 4.61 mmol, 5.00 eq.). The resulting solution was stirred for 1 overnight at 70° C. The resulting mixture was concentrated under vacuum. The residue was dissolved in 50 mL of EA. The resulting mixture was washed with 1×20 mL of $H_2O$. The resulting mixture was washed with 1×20 mL of brine. The mixture was dried over sodium sulfate and concentrated under vacuum. The residue was applied onto a silica gel column with PE:EA (70:30). This resulted in 180 mg (55%) of 3-[2,6-dichloro-3-[2-cyano-2-(dimethylcarbamoyl)eth-1-en-1-yl]phenoxy]propanoic acid as light yellow oil.

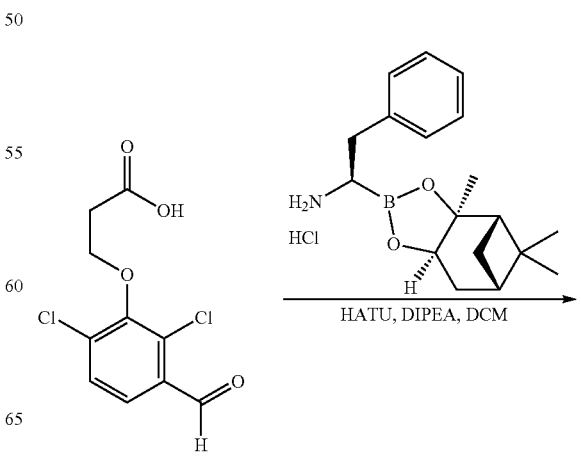

-continued

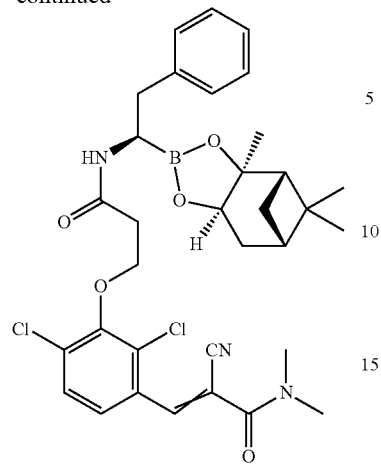

Into a 25-mL round-bottom flask, was placed a solution of 3-[2,6-dichloro-3-[2-cyano-2-(dimethylcarbamoyl)eth-1-en-1-yl]phenoxy]propanoic acid (160 mg, 0.45 mmol, 1.00 eq.) in dichloromethane (4 mL), HATU (256 mg, 0.67 mmol, 1.50 eq.), DIEA (174 mg, 1.35 mmol, 3.04 eq.), (1R)-2-phenyl-1-[(1S,2S,6R,8S)-2,9,9-trimethyl-3,5-dioxa-4-boratricyclo[6.1.1.0ˆ2,6]decan-4-yl]ethan-1-amine hydrochloride (151 mg, 0.45 mmol, 1.00 eq.). The resulting solution was stirred for 1 h at rt. The reaction was then quenched by the addition of 10 mL of water. The resulting mixture was washed with 1×20 mL of brine. The mixture was dried over anhydrous sodium sulfate and concentrated under vacuum. The crude product (160 mg) was purified by Prep-HPLC with the following conditions (2#-AnalyseHPLC-SHIMADZU (HPLC-10)): Column, XBridge Prep C18 OBD Column, 19,Á150 mm 5 um; mobile phase, Water (10 MMOL/L NH$_4$HCO$_3$+0.1% NH$_3$·H$_2$O) and ACN (66% ACN up to 67% in 7 min); Detector, UV 254/220 nm. This resulted in 140 mg (49%) of 2-cyano-3-[2,4-dichloro-3-(2-[[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamoyl]ethoxy)phenyl]-N,N-dimethylprop-2-enamide as a white solid.

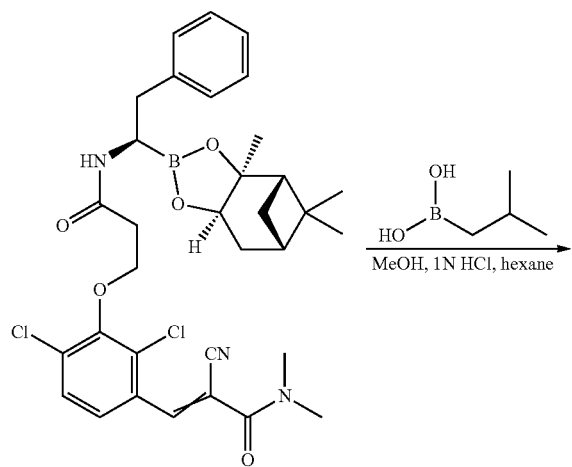

-continued

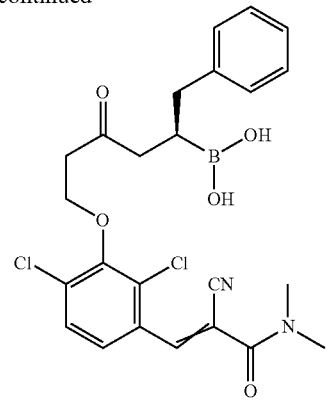

Into a 8-mL vial, was placed a solution of 2-cyano-3-[2,4-dichloro-3-(2-[[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamoyl]ethoxy)phenyl]-N,N-dimethylprop-2-enamide (70 mg, 0.11 mmol, 1.00 eq.) in methanol/Hexane (1.5/1.5 mL), 1N HCl (2.2 mL, 20.00 eq.), (2-methylpropyl) boronic acid (34 mg, 0.33 mmol, 3.00 eq.). The resulting solution was stirred for 4 h at rt. The hexane layer was discarded, the methanol layer was diluted with water and freeze dried directly to give a crude product. The crude product was purified by Prep-HPLC. This resulted in 28.5 mg (51%) of (R)-(1-(3-(2,6-dichloro-3-(2-cyano-3-(dimethylamino)-3-oxoprop-1-en-1-yl)phenoxy)propanamido)-2-phenylethyl)boronic acid as a white solid. LC-MS m/z: 486 [M−17].

Example 39

(R)-(1-(3-(2,6-dichloro-3-(2-cyano-2-(pyridin-2-yl)vinyl)phenoxy)propanamido)-2-phenylethyl)boronic Acid

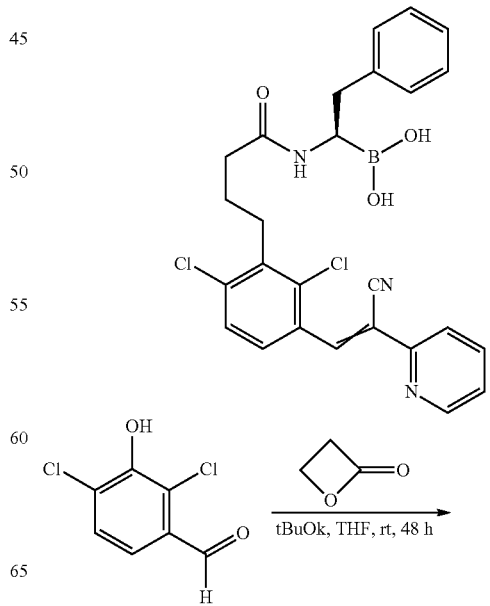

-continued

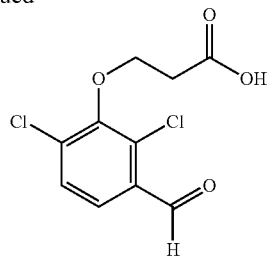

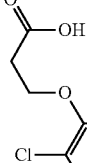

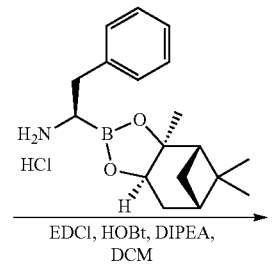

Into a 250-mL 3-necked round-bottom flask, was placed a solution of 2,4-dichloro-3-hydroxybenzaldehyde (5 g, 26.18 mmol, 1.00 eq.) in tetrahydrofuran (100 mL). This was followed by the addition of t-BuOK (2.94 g, 26.20 mmol, 1.00 eq.) in several batches at 0° C. To this was added oxetan-2-one (2.08 g, 28.86 mmol, 1.10 eq.) dropwise with stirring at 0° C. The resulting solution was stirred for 1 overnight at rt. The reaction was then quenched by the addition of 100 mL of water. The resulting solution was extracted with 10×50 mL of ethyl acetate and the water layers combined. The pH value of the solution was adjusted to 0-2 with hydrogen chloride (1 mol/L). The resulting solution was extracted with 2×50 mL of ethyl acetate and the organic layers combined. The resulting mixture was washed with 1×20 mL of water and 1×20 mL of brine. The mixture was dried over anhydrous sodium sulfate and concentrated under vacuum. The residue was applied onto a silica gel column with ethyl acetate:petroleum ether (1:10). This resulted in 690 mg (10%) of 3-(2,6-dichloro-3-formylphenoxy)propanoic acid as a white solid.

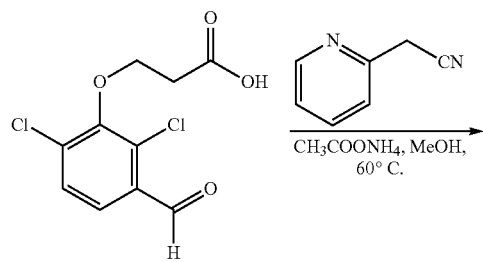

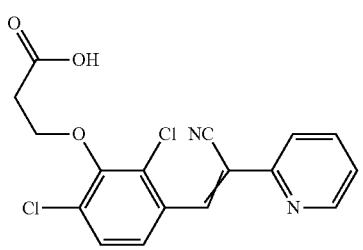

Into a 50-mL round-bottom flask, was placed a solution of 3-(2,6-dichloro-3-formylphenoxy)propanoic acid (300 mg, 1.14 mmol, 1.00 eq.) in ethanol (5 mL), CH₃COONH₄ (441 mg, 5.72 mmol, 5.00 eq.), 2-(pyridin-2-yl)acetonitrile (135 mg, 1.14 mmol, 1.00 eq.). The resulting solution was stirred for 0.5 h at 85° C. After cooling to rt, the solids were collected by filtration. This resulted in 220 mg (53%) of 3-[2,6-dichloro-3-[2-cyano-2-(pyridin-2-yl)eth-1-en-1-yl] phenoxy]propanoic acid as a white solid.

Into a 25-mL round-bottom flask, was placed a solution of 3-[2,6-dichloro-3-[2-cyano-2-(pyridin-2-yl)eth-1-en-1-yl] phenoxy]propanoic acid (210 mg, 0.58 mmol, 1.00 eq.) in dichloromethane (10 mL), HATU (32331 mg, 85.03 mmol, 1.50 eq.), DIEA (225 mg, 1.74 mmol, 3.00 eq.), (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride (195 mg, 0.58 mmol, 1.00 eq.). The resulting solution was stirred for 1 h at rt. The reaction was then quenched by the addition of 5 mL of water. The resulting mixture was washed with 1×10 mL of brine. The mixture was dried over anhydrous sodium sulfate and concentrated under vacuum. The crude product (210 mg) was purified by Prep-HPLC with the following conditions (2#-AnalyseHPLC-SHI-MADZU (HPLC-10)): Column, XBridge Prep C18 OBD Column, 19,Á150 mm 5 um; mobile phase, Water (10 MMOL/L NH4HCO3+0.1% NH₃·H₂O) and ACN (73% ACN up to 85% in 7 min); Detector, UV 254/220 nm. This resulted in 220 mg (59%) of 3-[2,6-dichloro-3-[2-cyano-2-(pyridin-2-yl)eth-1-en-1-yl]phenoxy]-N-[(1R)-2-phenyl-1-[(1S,2S,6R,8S)-2,9,9-trimethyl-3,5-dioxa-4-boratricyclo[6.1.1.0^[2,6]]decan-4-yl]ethyl]propanamide as a white solid.

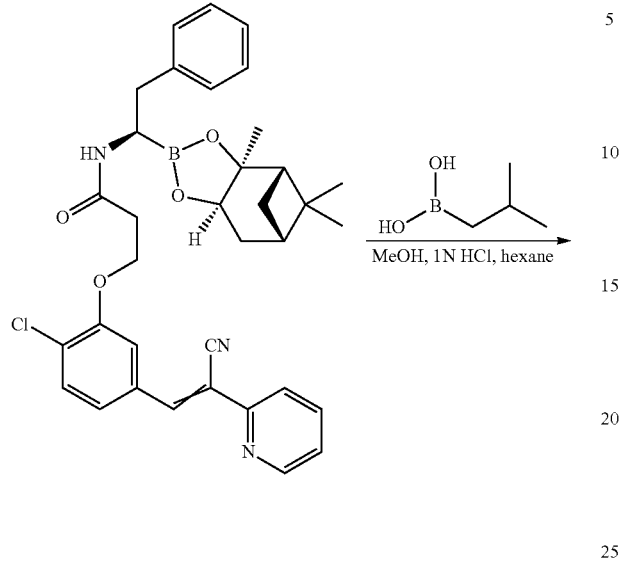

Example 40

(R)-(1-(3-(3-(2-cyano-2-(pyridin-2-yl)vinyl)-2-fluorophenoxy)propanamido)-2-phenylethyl)boronic Acid

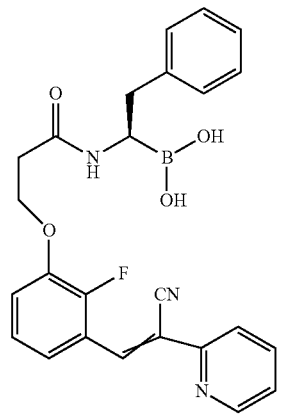 [SMILES: N#CC(=Cc1cccc(OCCC(=O)N[C@@H](Cc2ccccc2)B(O)O)c1F)c1ccccn1]

The title compound was prepared as in example 39 by replacing 2,4-dichloro-3-hydroxybenzaldehyde with 2-fluoro-3-hydroxybenzaldehyde. LC-MS m/z: 442 [M−17].

Example 41

(R)-(1-(3-(3-(2-cyano-3-(dimethylamino)-3-oxoprop-1-en-1-yl)-5-fluorophenoxy)propanamido)-2-phenylethyl)boronic Acid

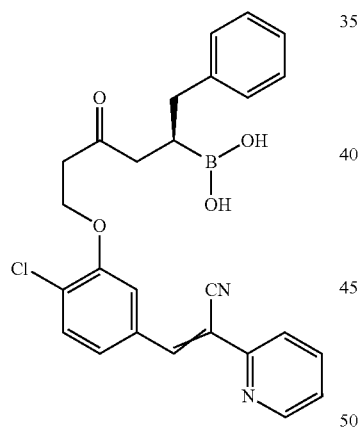

Into a 8-mL vial, was placed a solution of 3-[2,6-dichloro-3-[2-cyano-2-(pyridin-2-yl)eth-1-en-1-yl]phenoxy]-N-[(1R)-2-phenyl-1-[(1S,2S,6R,8S)-2,9,9-trimethyl-3,5-dioxa-4-boratricyclo[6.1.1.0^[2,6]]decan-4-yl]ethyl]propanamide (100 mg, 0.16 mmol, 1.00 eq.) in methanol/Hexane (1.5/1.5 mL), 1N HCl (3 mL, 20.00 eq.), (2-methylpropyl)boronic acid (48 mg, 0.47 mmol, 3.00 eq.). The resulting solution was stirred for 4 h at rt. The hexane layer was discarded, the methanol layer was diluted with water and freeze dried directly to give a crude product. The crude product was purified by Prep-HPLC. This resulted in 45.1 mg (56%) of (R)-(1-(3-(2,6-dichloro-3-(2-cyano-2-(pyridin-2-yl)vinyl)phenoxy)propanamido)-2-phenylethyl)boronic acid as a white solid. LC-MS m/z: 492 [M−17].

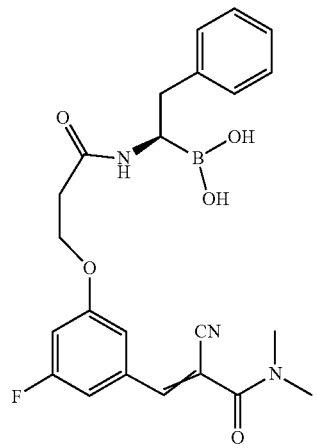 [SMILES: CN(C)C(=O)C(C#N)=Cc1cc(F)cc(OCCC(=O)N[C@@H](Cc2ccccc2)B(O)O)c1]

The title compound was prepared as in example 38 by replacing 2,4-dichloro-3-hydroxybenzaldehyde with 3-fluoro-5-hydroxybenzaldehyde. LC-MS m/z: 436 [M−17].

Example 42

(R)-(1-(3-(3-(2-cyano-3-(dimethylamino)-3-oxo-prop-1-en-1-yl)-4-fluorophenoxy)propanamido)-2-phenylethyl)boronic Acid

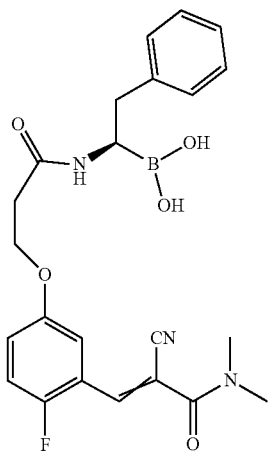 [SMILES: CN(C)C(=O)C(C#N)=Cc1cc(OCCC(=O)N[C@@H](Cc2ccccc2)B(O)O)ccc1F]

The title compound was prepared as in example 38 by replacing 2,4-dichloro-3-hydroxybenzaldehyde with 2-fluoro-5-hydroxybenzaldehyde. LC-MS m/z: 436 [M−17].

Example 43

(R)-(1-(3-(3-(2-cyano-2-(pyridin-2-yl)vinyl)-4-fluorophenoxy)propanamido)-2-phenylethyl)boronic Acid

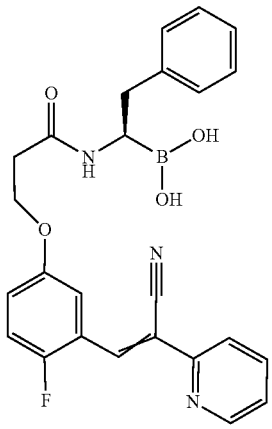 [SMILES: N#CC(=Cc1cc(OCCC(=O)N[C@@H](Cc2ccccc2)B(O)O)ccc1F)c1ccccn1]

The title compound was prepared as in example 39 by replacing 2,4-dichloro-3-hydroxybenzaldehyde with 2-fluoro-5-hydroxybenzaldehyde. LC-MS m/z: 442 [M−17].

Example 44

(R)-(1-(3-(3-(2-cyano-3-(dimethylamino)-3-oxo-prop-1-en-1-yl)phenoxy)propanamido)-2-(2,4-dimethylphenyl)ethyl)boronic Acid

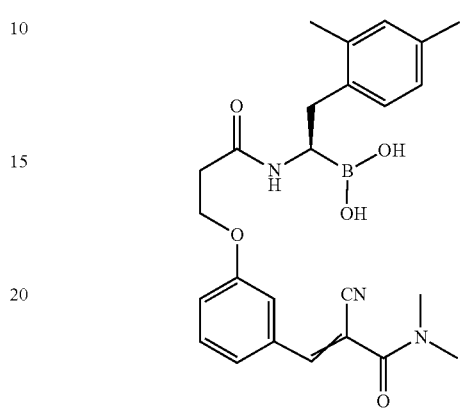

The title compound was prepared as in example 5 by replacing (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride with (R)-2-(2,4-dimethylphenyl)-1-((3aS,4S,6S,7aR)-3a,5,5-trimethylhexahydro-4,6-methanobenzo[d][1,3,2]dioxaborol-2-yl)ethan-1-amine hydrochloride. LC-MS m/z: 446 [M−17].

Example 45

(R)-1-(3-(3-(2-cyano-2-(pyridin-2-yl)vinyl)phenoxy)propanamido)-2-(2,4-dimethylphenyl)ethylboronic Acid

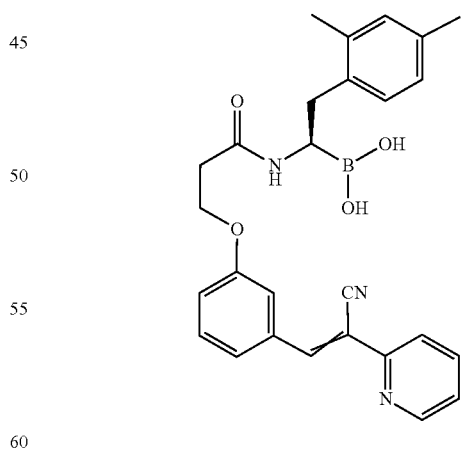

The title compound was prepared as in example 21 by replacing (R)-3-phenyl-1-(4,4,5,5-tetramethyl-1,3,2-dioxaborolan-2-yl)propan-1-amine hydrochloride with (R)-2-(2,4-dimethylphenyl)-1-((3aS,4S,6S,7aR)-3a,5,5-trimethylhexahydro-4,6-methanobenzo[d][1,3,2]dioxaborol-2-yl)ethan-1-amine hydrochloride. LC-MS m/z: 452 [M−17].

Example 46

(R)-(1-(3-(3-(2-cyano-3-((2-methoxyethyl)amino)-3-oxoprop-1-en-1-yl)phenoxy)propanamido)-2-phenylethyl)boronic Acid

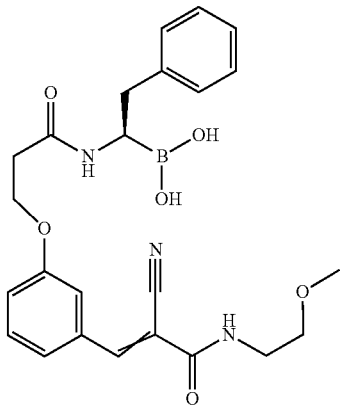 [SMILES: COCCNC(=O)C(C#N)=Cc1cccc(OCCC(=O)N[C@@H](Cc2ccccc2)B(O)O)c1]

The title compound was prepared as in example 19 by replacing N-methyl piperazine with 2-methoxyethanamine. LC-MS m/z: 448 [M−17].

Example 47

(R)-(1-(3-(3-(2-cyano-3-((1-methoxy-2-methylpropan-2-yl)amino)-3-oxoprop-1-en-1-yl)phenoxy)propanamido)-2-phenylethyl)boronic Acid

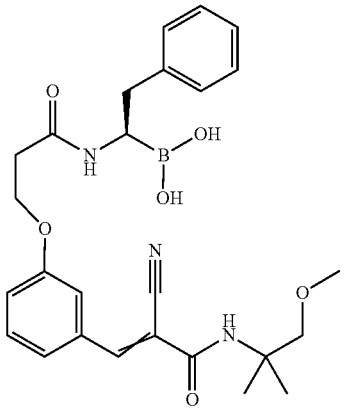 [SMILES: COCC(C)(C)NC(=O)C(C#N)=Cc1cccc(OCCC(=O)N[C@@H](Cc2ccccc2)B(O)O)c1]

The title compound was prepared as in example 19 by replacing N-methyl piperazine with 1-methoxy-2-methylpropan-2-amine. LC-MS m/z: 476 [M−17].

Example 48

(R)-(1-(3-(3-(2-cyano-3-((2-methoxy-2-methylpropyl)amino)-3-oxoprop-1-en-1-yl)phenoxy)propanamido)-2-phenylethyl)boronic Acid

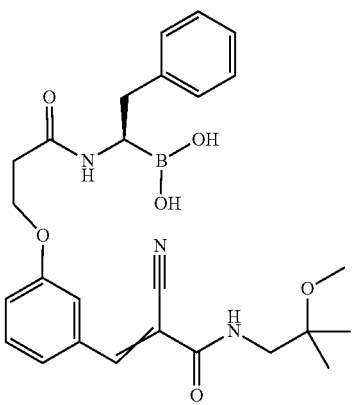 [SMILES: COC(C)(C)CNC(=O)C(C#N)=Cc1cccc(OCCC(=O)N[C@@H](Cc2ccccc2)B(O)O)c1]

The title compound was prepared as in example 19 by replacing N-methyl piperazine with 1-methoxy-2-methylpropan-2-amine. LC-MS m/z: 476 [M−17].

Example 49

(R)-(1-(2-((3-(2-cyano-3-(dimethylamino)-3-oxoprop-1-en-1-yl)benzyl)oxy)acetamido)-2-phenylethyl)boronic Acid

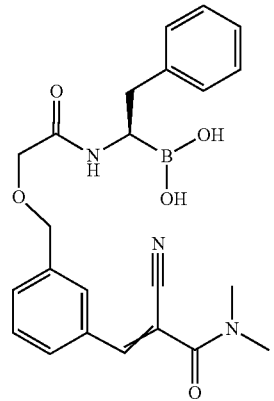 [SMILES: CN(C)C(=O)C(C#N)=Cc1cccc(COCC(=O)N[C@@H](Cc2ccccc2)B(O)O)c1]

Synthetic Scheme

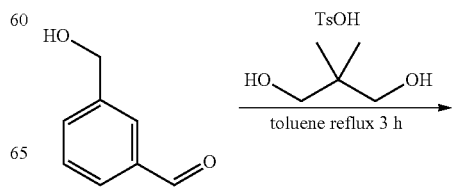

-continued

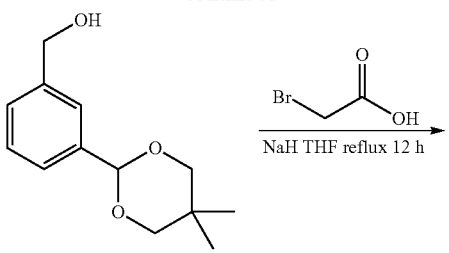

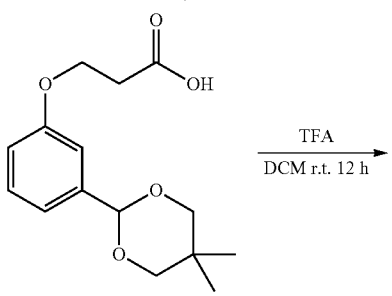

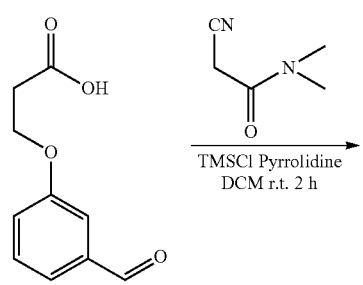

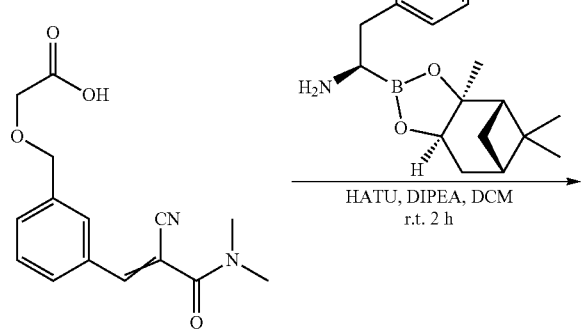

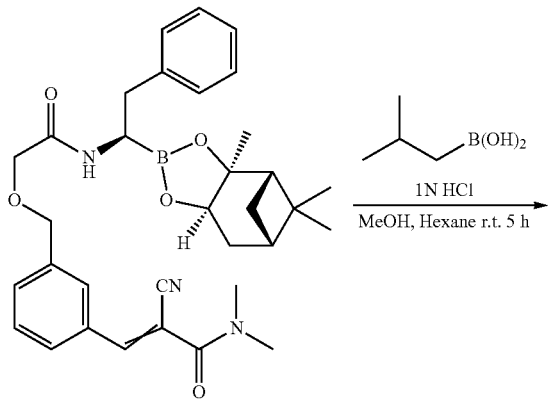

-continued

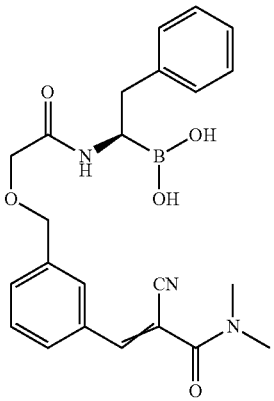

A solution of 3-(hydroxymethyl)benzaldehyde (2.3 g, 16.89 mmol), 2,2-dimethylpropane-1,3-diol (5.25 g, 50.68 mmol) and TsOH (290.91 mg, 1.69 mmol) in toluene (60 Mo) was refluxed for 2 h in a 100 mL flask with Dean-Stark trap. After cooling to rt, the mixture was concentrated to dryness. The residue was purified by column chromatography on silica gel (eluent: petroleum ether/ethyl acetate from 5:1 to 1:1) to afford (3-(5,5-dimethyl-1,3-dioxan-2-yl)phenyl)methanol as an oil (3 g, 80%).

To a suspension of NaH (3.42 g, 60% dispersion in mineral oil, 85.48 mmol) in dry THf (50 mL) under Ar at 0° C. was added a solution of (3-(5,5-dimethyl-1,3-dioxan-2-yl)phenyl)methanol (1.90 g, 8.55 mmol) in THF (20 mL). After the mixture was stirred for 1 h, a solution of 2-bromoacetic acid (1.19 g, 8.55 mmol) in THF (20 mL) was added and the mixture was refluxed overnight. The mixture was concentrated under reduced pressure, then, the resultant white solid residue was dissolved in ice cold water. The PH of the mixture was adjusted to 4 with HCl (1 N) before extracting with ethyl acetate. The combined ethyl acetate extracts were dried filtered, and concentrated to give 3.3 g of crude product as oil.

A solution of 2-((3-(5,5-dimethyl-1,3-dioxan-2-yl)benzyl)oxy)acetic acid (3.3 g, 11.77 mmol) in DCM/TFA/H$_2$O (18 mL/20 mL/6 mL) was stirred at rt for 13 h, then concentrated to dryness. The residue was purified by column chromatography on silica gel (eluent: DCM:MeOH from 100:1 to 1:10) to afford 2-((3-formylbenzyl)oxy)acetic acid as a yellow oil (1.1 g, 68.75% over 2 steps).

To a solution of 2-((3-formylbenzyl)oxy)acetic acid (1 g, 5.15 mmol), 2-cyano-N,N-dimethylacetamide (2.31 g, 20.60 mmol) and pyrrolidine (3.66 g, 51.50 mmol) in CH$_2$Cl$_2$ (30 mL) at rt was slowly added chloro(trimethyl)silane (4.48 g, 41.20 mmol). After 1 h, the reaction was diluted with DCM (40 mL) and washed with water (20 mL). The organic layer was dried over anhydrous sodium sulfate, filtered and concentrated to give a crude residue which was purified by column chromatography on silica gel (eluent: DCM/MeOH from 100:1 to 1:10) to afford 2-((3-(2-cyano-3-(dimethylamino)-3-oxoprop-1-en-1-yl)benzyl)oxy)acetic acid as a brown oil (800 mg, 54.05%).

DIPEA (537.96 mg, 4.16 mmol) was added to stirred solution of 2-((3-(2-cyano-3-(dimethylamino)-3-oxoprop-1-en-1-yl)benzyl)oxy)acetic acid (400 mg, 1.39 mmol), (R)-2-phenyl-1-((3aS,4S,6S,7aR)-3a,5,5-trimethylhexahydro-4,6-methanobenzo[d][1,3,2]dioxaborol-2-yl)ethanamine hydrochloride (465.74 mg, 1.39 mmol) and HATU (1.06 g, 2.77 mmol) in DMF (10 mL) at rt. The mixture was stirred at rt for 2 h, then quenched with water (10 mL) and extracted with ethyl acetate. The combined extracts were washed with brine, dried over magnesium sulfate, filtered and evaporated. The crude residue was purified by prep-HPLC to afford the title compound as brown oil (50 mg, 6.3%).

To a solution of 2-cyano-N,N-dimethyl-3-(3-((2-oxo-2-(((R)-2-phenyl-1-((3aS,4S,6S,7aR)-3a,5,5-trimethylhexahydro-4,6-methanobenzo[d][1,3,2]dioxaborol-2-yl)ethyl)amino)ethoxy)methyl)phenyl)acrylamide (50 mg, 0.089 mmol) in MeOH (3 mL) were added hexane (3 mL) and 1 N HCl (1.5 mL), followed by isobutyl boric acid (26.85 mg, 0.026 mmol). After stirring at rt for 3 h and LCMS suggested the reaction was completed, the hexane layer was discarded, the methanol layer was diluted with water (10 mL) and freeze dried directly to give a crude product, this crude product was further purified with neutral Al$_2$O$_3$ column (Methanol/DCM=0-20% as eluent) to afford (R)-(1-(2-((3-(2-cyano-3-(dimethylamino)-3-oxoprop-1-en-1-yl)benzyl)oxy)acetamido)-2-phenylethyl)boronic acid as white solid (18 mg, 47.37%). LCMS: 418 [M−17].

Example 50

(R)-(1-(((3-(2-cyano-3-(dimethylamino)-3-oxoprop-1-en-1-yl)phenethoxy)carbonyl)amino)-2-(p-tolyl)ethyl)boronic Acid

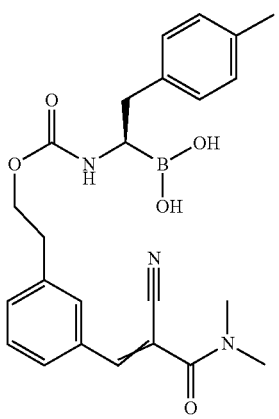 [SMILES: Cc1ccc(C[C@H](NC(=O)OCCc2cccc(C=C(C#N)C(=O)N(C)C)c2)B(O)O)cc1]

The title compound was prepared as in example 17 by replacing (R)-2-phenyl-1-((3aS,4S,6S,7aR)-3a,5,5-trimethylhexahydro-4,6-methanobenzo[d][1,3,2]dioxaborol-2-yl)ethanamine hydrochloride with (R)-1-(4,4,5,5-tetramethyl-1,3,2-dioxaborolan-2-yl)-2-(p-tolyl)ethanamine hydrochloride. LC-MS m/z: 432 [M−17].

Example 51

(R)-(1-(3-(3-(2-cyano-2-(3-methoxypyridin-2-yl)vinyl)phenoxy)propanamido)-2-phenylethyl)boronic Acid

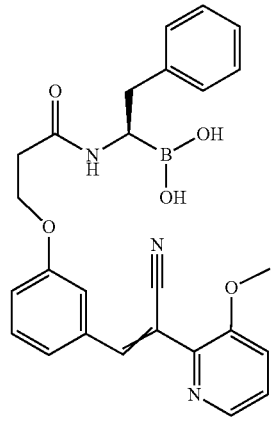 [SMILES: COc1cccnc1C(C#N)=Cc1cccc(OCCC(=O)N[C@@H](Cc2ccccc2)B(O)O)c1]

The title compound was prepared as in example 33 by replacing 2-(5-(trifluoromethyl)pyridin-2-yl)acetonitrile with 2-(3-methoxypyridin-2-yl)acetonitrile. LC-MS m/z: 454 [M−17]. 2-(3-methoxypyridin-2-yl)acetonitrile was made according to below procedure: to a mixture of dry CH$_3$CN (0.6 mL, 11.66 mmol) in anhydrous THF (20 mL) at −78° C. under N$_2$ was added dropwise n-butyl lithium (2.4 M solution in hexanes, 4.52 mL, 10.85 mmol), followed by a solution of 2-bromo-3-methoxypyridine (510.0 mg, 2.71 mmol) in dry THF (15 mL). The mixture was stirred at −78° C. for 1 h, then warmed to 0° C. and stirred for additional 3.5 h. After LCMS suggested the reaction was completed, the reaction was quenched with water and extracted with ethyl acetate. The combined extracts were washed with brine, dried over magnesium sulfate, filtered and evaporated. The residue was purified by silica gel column chromatography using ethyl hexanes-acetate (0-70%) as eluent to afford 2-(3-methoxypyridin-2-yl)acetonitrile as oil (230 mg, 57.36%).

Example 52

(R)-(1-(((3-(2-cyano-3-(diethylamino)-3-oxoprop-1-en-1-yl)phenethoxy)carbonyl)amino)-2-phenylethyl)boronic Acid

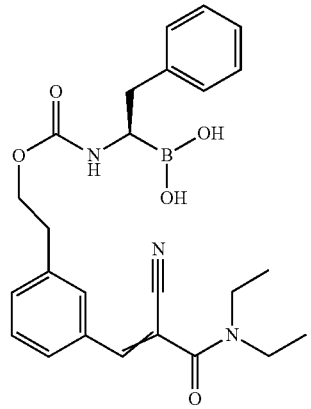 [SMILES: CCN(CC)C(=O)C(C#N)=Cc1cccc(CCOC(=O)N[C@@H](Cc2ccccc2)B(O)O)c1]

The title compound was prepared as in example 17 by replacing dimethylamine with diethylamine. LC-MS m/z: 486 [M+23].

Example 53

(R)-2-(benzofuran-3-yl)-1-(((3-(2-cyano-3-(dimethylamino)-3-oxoprop-1-en-1-yl)phenethoxy)carbonyl)amino)ethyl)boronic Acid

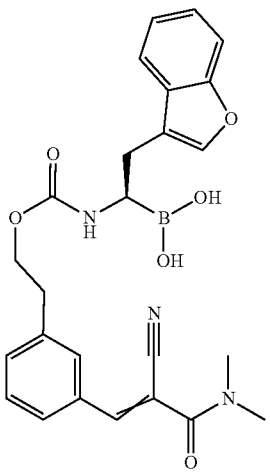 [SMILES: CN(C)C(=O)C(C#N)=Cc1cccc(CCOC(=O)N[C@@H](Cc2coc3ccccc23)B(O)O)c1]

The title compound was prepared as in example 17 by replacing (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride with (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine hydrochloride. LC-MS m/z: 458 [M−17].

Example 54

(R)-(1-(((3-(2-cyano-2-(3-fluoropyridin-2-yl)vinyl)phenethoxy)carbonyl)amino)-2-phenylethyl)boronic Acid

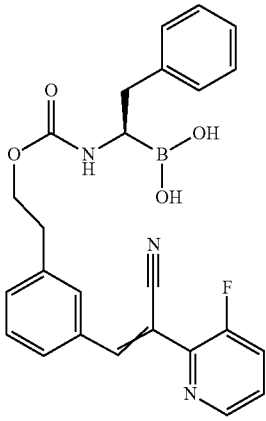 [SMILES: N#CC(=Cc1cccc(CCOC(=O)N[C@@H](Cc2ccccc2)B(O)O)c1)c1ncccc1F]

The title compound was prepared as in example 36 by replacing 2-(pyridin-2-yl)acetonitrile with 2-(3-fluoropyridin-2-yl)acetonitrile. LC-MS m/z: 482 [M+23].

Example 55

(R)-(1-(((3-(2-cyano-3-(diethylamino)-3-oxoprop-1-en-1-yl)phenethoxy)carbonyl)amino)-2-(p-tolyl)ethyl)boronic Acid

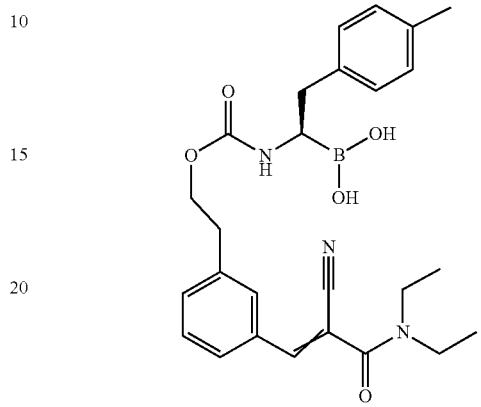

The title compound was prepared as in example 52 by replacing (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride with (R)-1-(4,4,5,5-tetramethyl-1,3,2-dioxaborolan-2-yl)-2-(p-tolyl)ethanamine hydrochloride. LC-MS m/z: 500 [M+23].

Example 56

(R)-(1-(((3-(2-cyano-2-(5-(trifluoromethyl)pyridin-2-yl)vinyl)phenethoxy)carbonyl)amino)-2-phenylethyl)boronic Acid

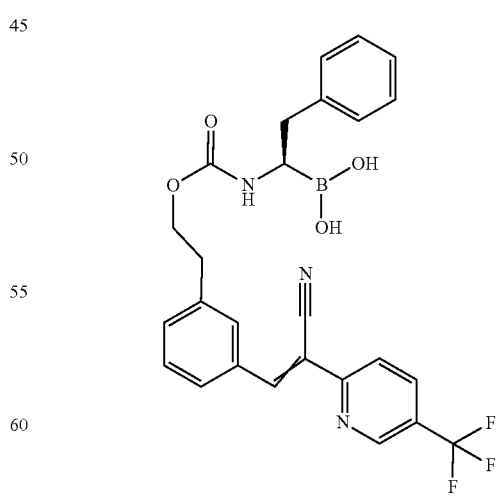

The title compound was prepared as in example 36 by replacing 2-(pyridin-2-yl)acetonitrile with 2-(5-(trifluoromethyl)pyridin-2-yl)acetonitrile. LC-MS m/z: 532 [M+23].

Example 57

(R)-(1-(((3-(2-cyano-2-(pyridin-2-yl)vinyl)
phenethoxy)carbonyl)amino)-2-(p-tolyl)ethyl)boronic Acid

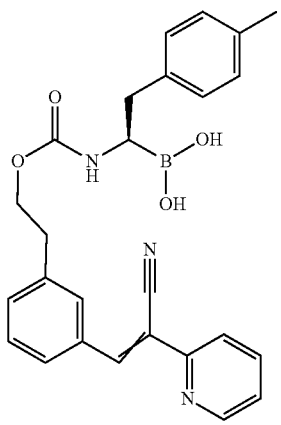 [SMILES: Cc1ccc(C[C@H](NC(=O)OCCc2cccc(C=C(C#N)c3ccccn3)c2)B(O)O)cc1]

The title compound was prepared as in example 35 by replacing (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine with (R)-1-(4,4,5,5-tetramethyl-1,3,2-dioxaborolan-2-yl)-2-(p-tolyl)ethanamine hydrochloride. LC-MS m/z: 478 [M+23].

Example 58

(R)-2-(benzofuran-3-yl)-1-(((3-(2-cyano-3-(diethylamino)-3-oxoprop-1-en-1-yl)phenethoxy)carbonyl)amino)ethyl)boronic Acid

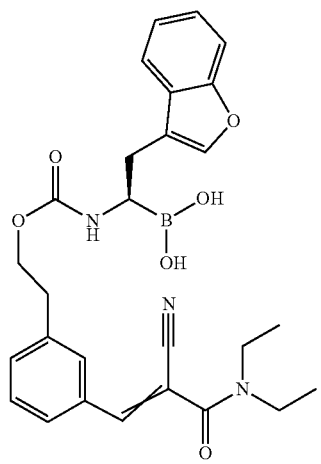 [SMILES: CCN(CC)C(=O)C(C#N)=Cc1cccc(CCOC(=O)N[C@@H](Cc2coc3ccccc23)B(O)O)c1]

The title compound was prepared as in example 52 by replacing (1R)-2-phenyl-1-[(1S,2S,6R,8S)-2,9,9-trimethyl-3,5-dioxa-4-boratricyclo[6.1.1.0ˆ2,6]decan-4-yl]ethan-1-amine hydrochloride with (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine hydrochloride. LC-MS m/z: 526 [M+23].

Example 59

(R)-(1-(((3-(2-cyano-2-(pyrimidin-4-yl)vinyl)
phenethoxy)carbonyl)amino)-2-phenylethyl)boronic Acid

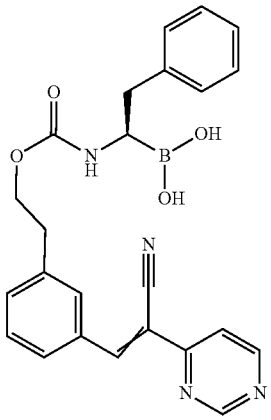 [SMILES: N#CC(=Cc1cccc(CCOC(=O)N[C@@H](Cc2ccccc2)B(O)O)c1)c1ccncn1]

The title compound was prepared as in example 36 by replacing 2-(pyridin-2-yl)acetonitrile with 2-(pyrimidin-4-yl)acetonitrile. LC-MS m/z: 465 [M+23].

Example 60

(R)-(1-(((3-(2-cyano-2-(pyrimidin-2-yl)vinyl)
phenethoxy)carbonyl)amino)-2-phenylethyl)boronic Acid

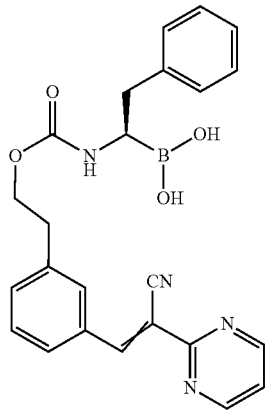 [SMILES: N#CC(=Cc1cccc(CCOC(=O)N[C@@H](Cc2ccccc2)B(O)O)c1)c1ncccn1]

The title compound was prepared as in example 36 by replacing 2-(pyridin-2-yl)acetonitrile with 2-(pyrimidin-2-yl)acetonitrile. LC-MS m/z: 465 [M+23].

Example 61

(R)-(1-(3-(3-(2-cyano-3-(diethylamino)-3-oxoprop-1-en-1-yl)phenethyl)ureido)-2-phenylethyl)boronic Acid

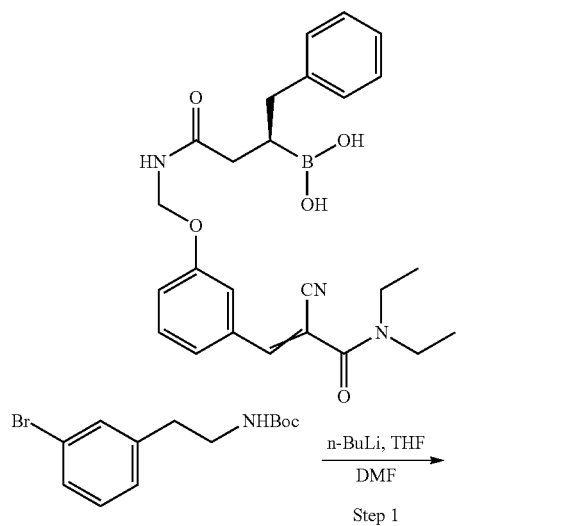

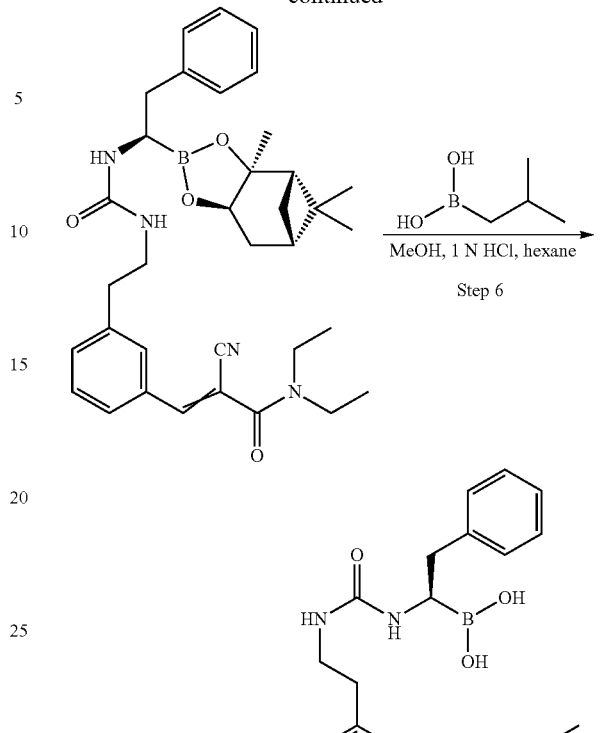

Into a 500-mL 3-necked round-bottom flask, was placed tetrahydrofuran (50 mL). This was followed by the addition of n-BuLi (20 mL, 3 eq.) dropwise with stirring at −78° C. To this was added a solution of tert-butyl N-[2-(3-bromophenyl)ethyl]carbamate (5 g, 16.66 mmol, 1 eq.) in tetrahydrofuran (75 mL) dropwise with stirring at −78° C. The resulting solution was stirred for 20 min at −78° C. To the mixture was added N,N-dimethylformamide (20 mL) dropwise with stirring at −78° C. The resulting solution was allowed to react, with stirring, for an additional 2 h at rt. The reaction was quenched by $NH_4Cl$ (aq. 250 mL), then extracted by ethyl acetate (100 mL×3). The organic phase was dried by anhydrous $Na_2SO_4$ and concentrated under vacuum. The residue was applied onto a silica gel column with petroleum ether: ethyl acetate (4:1). Tert-butyl N-[2-(3-formylphenyl)ethyl]carbamate was obtained in 2.35 g (57%) as a yellow oil.

Into a 50-mL round-bottom flask, was placed tert-butyl N-[2-(3-formylphenyl)ethyl]carbamate (1 g, 4.01 mmol, 1 eq.), ethanol (40 mL), $CH_3COONH_4$ (1.55 g, 20.11 mmol, 5 eq.) and 2-cyano-N,N-diethylacetamide (563 mg, 4.02 mmol, 1 eq.). The resulting solution was stirred for 4 h at 85° C. The resulting mixture was concentrated under vacuum. The residue was dissolved ethyl acetate (100 mL). The resulting mixture was washed with water (50 mL) and sodium chloride (50 mL). The mixture was dried over anhydrous sodium sulfate and concentrated under vacuum. The residue was applied onto a silica gel column with ethyl acetate:petroleum ether (1:2). This resulted in 1.2 g (81%) of tert-butyl N-(2-[3-[2-cyano-2-(diethylcarbamoyl)eth-1-en-1-yl]phenyl]ethyl)carbamate as a yellow oil.

Into a 100-mL round-bottom flask, was placed tert-butyl N-(2-[3-[2-cyano-2-(diethylcarbamoyl)eth-1-en-1-yl]phenyl]ethyl)carbamate (500 mg, 1.35 mmol, 1 eq.), dichloromethane (5 mL), acetic acid (2.5 mL). The resulting solution was stirred for 1 h at rt. The resulting mixture was concentrated under vacuum. The pH value of the solution was adjusted to 9 with sodium bicarbonate (saturated solution). The resulting solution was extracted with dichloromethane (50 mL×3). The organic layers combined, dried over anhydrous sodium sulfate and concentrated under vacuum. This resulted in 340 mg (93%) of 3-[3-(2-aminoethyl)phenyl]-2-cyano-N,N-diethylprop-2-enamide as a yellow oil.

Into a 50-mL 3-necked round-bottom flask, was placed a solution of 3-[3-(2-aminoethyl)phenyl]-2-cyano-N,N-diethylprop-2-enamide (340 mg, 1.25 mmol, 1 eq.) in dichloromethane (5 mL) and DIEA (324 mg, 2.51 mmol, 2 eq.). This was followed by the addition of ditrichloromethyl carbonate (371 mg, 1.25 mmol, 1 eq.) in several batches at 0-5° C. The resulting solution was stirred for 3 h at rt. The resulting mixture was concentrated under vacuum. This resulted in 372 mg (crude) of 2-cyano-N,N-diethyl-3-[3-(2-isocyanatoethyl)phenyl]prop-2-enamide as a yellow oil.

Into a 50-mL round-bottom flask, was placed a solution of 2-cyano-N,N-diethyl-3-[3-(2-isocyanatoethyl)phenyl]prop-2-enamide (372 mg, 1.25 mmol, 1.00 eq.) in dichloromethane (5 mL), DIEA (324 mg, 2.51 mmol, 2.00 eq.) and (1R)-2-phenyl-1-[(1S,2S,6R,8S)-2,9,9-trimethyl-3,5-dioxa-4-boratricyclo[6.1.1.0ˆ2,6]decan-4-yl]ethan-1-amine hydrochloride (421 mg, 1.25 mmol, 1.00 eq.). The resulting solution was stirred for approximate 16 h at rt. The reaction was then quenched by the addition of water (20 mL). The resulting solution was extracted with dichloromethane (20 mL×2). The organic layers combined, dried over anhydrous sodium sulfate and concentrated under vacuum. The crude product was purified by Prep-HPLC. This resulted in 120 mg (16%) of 2-cyano-N,N-diethyl-3-[3-[2-([[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamoyl]amino)ethyl]phenyl]prop-2-enamide as a white solid after the lyophilization.

Into a 100-mL round-bottom flask, was placed a solution of 2-cyano-N,N-diethyl-3-[3-[2-([[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamoyl]amino)ethyl]phenyl]prop-2-enamide (120 mg, 0.20 mmol, 1 eq.) in methanol:Hexane (3:3 mL), 1NHCl (4 mL, 20 eq.) and (2-methylpropyl)boronic acid (62 mg, 0.61 mmol, 3 eq.). The resulting solution was stirred for 3 h at rt. The hexane layer was discarded. The methanol layer was diluted with water (20 mL), then dried over lyophylization. The crude product was purified by Prep-HPLC. This resulted in 45.7 mg (46%) of (R)-(1-(3-(3-(2-cyano-3-(diethylamino)-3-oxoprop-1-en-1-yl)phenethyl)ureido)-2-phenylethyl)boronic acid as a white solid after lyophilization. LC-MS m/z: 445.

Example 62

(R)-(1-(3-(3-(2-cyano-2-(pyridin-2-yl)vinyl)phenethyl)ureido)-2-phenylethyl)boronic Acid

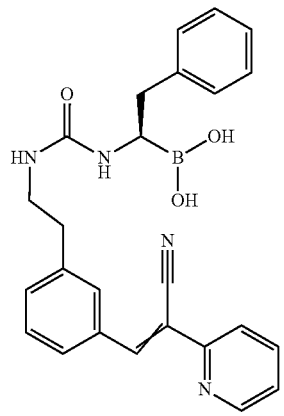 [SMILES: N#CC(=Cc1cccc(CCNC(=O)N[C@@H](Cc2ccccc2)B(O)O)c1)c1ccccn1]

The title compound was prepared as in example 61 by replacing 2-cyano-N,N-diethylacetamide with 2-(pyridin-2-yl)acetonitrile. LC-MS m/z: 423 [M−17].

Example 63

(R)-(1-(((3-(2-cyano-2-(pyrazin-2-yl)vinyl)phenethoxy)carbonyl)amino)-2-phenylethyl)boronic Acid

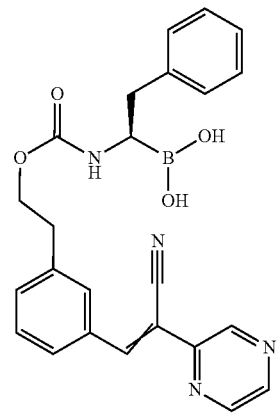 [SMILES: N#CC(=Cc1cccc(CCOC(=O)N[C@@H](Cc2ccccc2)B(O)O)c1)c1cnccn1]

The title compound was prepared as in example 36 by replacing 2-(pyridin-2-yl)acetonitrile with 2-(pyrazin-2-yl)acetonitrile. LC-MS m/z: 465 [M+23].

Example 64

(R)-(1-(((3-(2-cyano-3-(ethyl(isopropyl)amino)-3-oxoprop-1-en-1-yl)phenethoxy)carbonyl)amino)-2-phenylethyl)boronic Acid

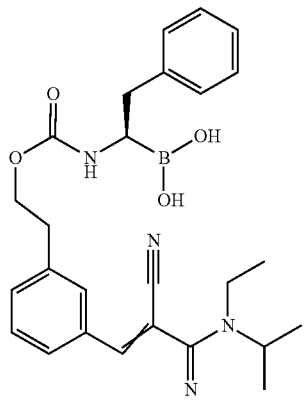 [SMILES: CCN(C(=N)C(C#N)=Cc1cccc(CCOC(=O)N[C@@H](Cc2ccccc2)B(O)O)c1)C(C)C]

The title compound was prepared as in example 17 by replacing dimethylamine with N-ethylpropan-2-amine. LC-MS m/z: 500 [M+23].

Example 65

((R)-1-(((3-(2-cyano-3-((3R,5R)-3,5-dimethylmorpholino)-3-oxoprop-1-en-1-yl)phenethoxy)carbonyl)amino)-2-phenylethyl)boronic Acid

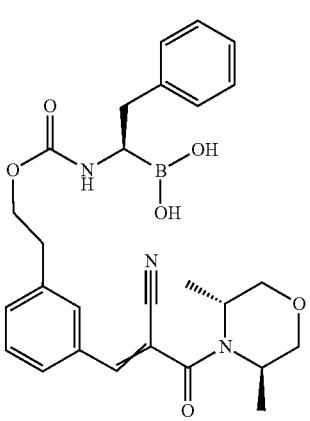 [SMILES: C[C@@H]1COC[C@@H](C)N1C(=O)C(C#N)=Cc1cccc(CCOC(=O)N[C@@H](Cc2ccccc2)B(O)O)c1]

The title compound was prepared as in example 17 by replacing dimethylamine with (3R,5R)-3,5-dimethylmorpholine. LC-MS m/z: 528 [M+23].

Example 66

(R)-(1-(2-(7-(2-cyano-2-(pyridin-2-yl)vinyl)-3,4-dihydroisoquinolin-2(1H)-yl)acetamido)-2-phenylethyl)boronic Acid

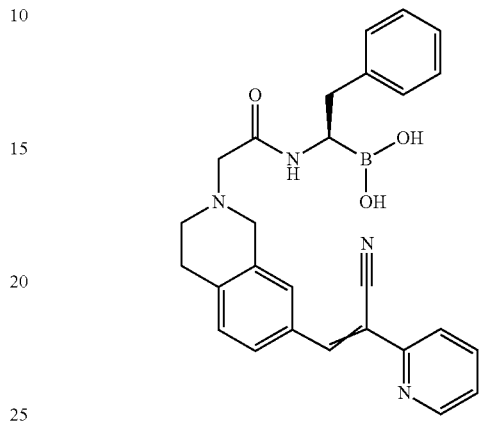

Synthetic Scheme

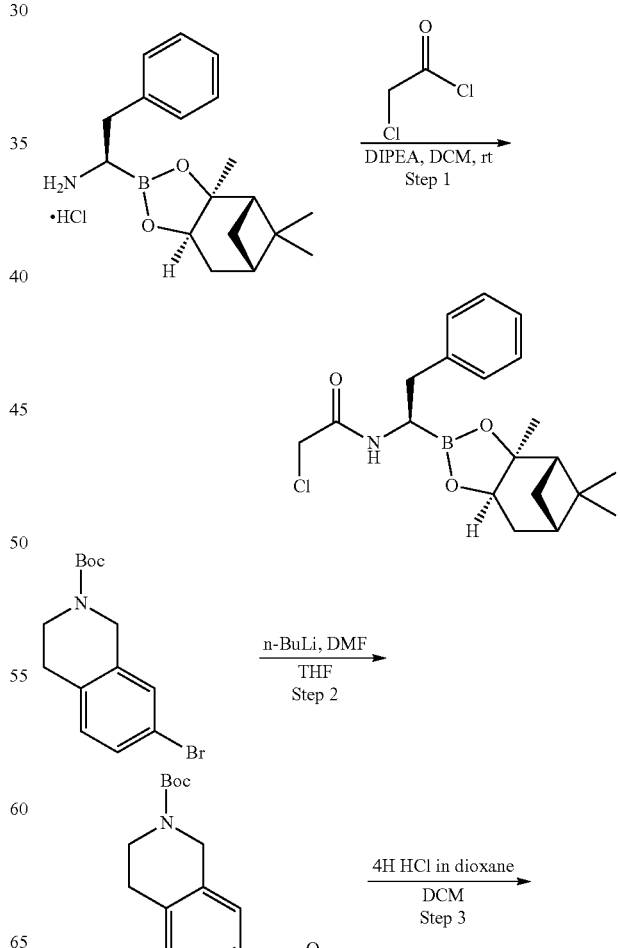

-continued

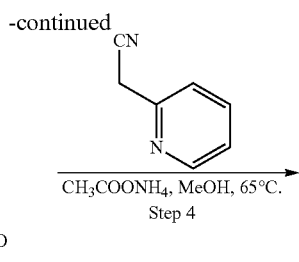

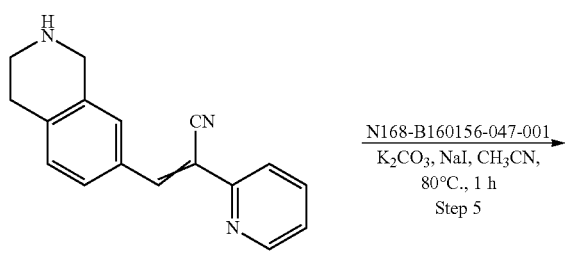

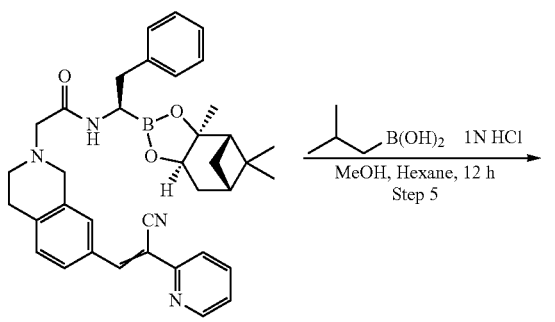

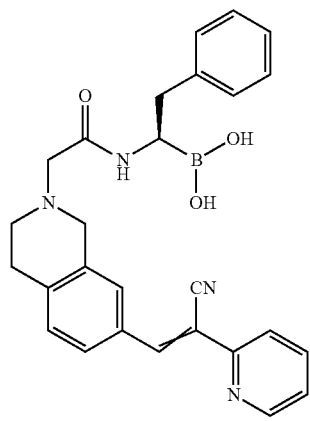 [SMILES: N#CC(=Cc1ccc2c(c1)CN(CC(=O)N[C@@H](Cc1ccccc1)B(O)O)CC2)c1ccccn1]

To a solution of (R)-2-phenyl-1-((3aS,4S,6S,7aR)-3a,5,5-trimethylhexahydro-4,6-methanobenzo[d][1,3,2]dioxaborol-2-yl)ethan-1-amine hydrochloride (500 mg, 1.5 mmol) and DIPEA (387 mg, 3 mmol) in DCM (5 mL) was added dropwise 2-chloroacetyl chloride (169 mg, 1.5 mmol) at 0° C. The resultant reaction was stirred for 2 h at rt, then quenched with water (5 mL), the organic layer was dried over $Na_2SO_4$ and concentrated in vacuo. The crude material was purified by silica gel chromatography to afford the title compound as a drown gum (300 mg, 53%).

To a solution of tert-butyl 7-bromo-3,4-dihydroisoquinoline-2(1H)-carboxylate (2 g, 6.4 mmol) in anhydrous THF (80 mL) at −78° C. under an inert atmosphere of nitrogen was added dropwise n-Butyl lithium (2.4 M solution in hexanes, 5.6 mL, 13.4 mmol). The reaction was stirred at same temperature for 20 min. N,N-dimethylformamide (0.98 g, 12.8 mmol) was added dropwise at −78° C. and stirred at same temperature for 2 h. The reaction mixture was quenched with a saturated solution of ammonium chloride and the aqueous portion was extracted with ethyl acetate. The combined extracts were washed with brine, dried over $Na_2SO_4$, filtered and evaporated. The residue was purified by silica gel chromatography to afford the title compound as colorless oil (1.2 g, 71%).

A solution of tert-butyl 7-formyl-3,4-dihydroisoquinoline-2(1H)-carboxylate (1.2 g, 4.6 mmol) and HCl (2 mL, 4 M in dioxane) in DCM (2 mL) was stirred at rt for 2 h, then concentrated in vacuo. The residue was adjusted to pH=8 with aqueous sodium bicarbonate solution and extracted with EtOAc (20 mL×3). Combined organic layers were dried over $Na_2SO_4$ and concentrated to afford the title compound as a yellow solid (400 mg, 54%).

To a mixture of 1,2,3,4-tetrahydroisoquinoline-7-carbaldehyde (300 mg, 1.86 mmol), 2-(pyridin-2-yl)acetonitrile (219 mg, 1.86 mmol) and ammonium acetate (716 mg, 9.3 mmol) in methanol (10 mL) was stirred at refluxing temperature for 2 h. After cooling to rt, the mixture was concentrated to dryness. The residue was diluted with EtOAc (30 mL), washed with water (15 mL), followed by brine (15 mL). The organic layer was dried over $Na_2SO_4$ and concentrated to afford the title compound as a yellow solid (150 mg, 31%) which was used into next step directly.

A mixture of 2-(pyridin-2-yl)-3-(1,2,3,4-tetrahydroisoquinolin-7-yl)acrylonitrile (100 mg, 0.38 mmol), 2-chloro-N—((R)-2-phenyl-1-((3aS,4S,6S,7aR)-3a,5,5-trimethylhexahydro-4,6-methanobenzo[d][1,3,2]dioxaborol-2-yl)ethyl)acetamide (129 mg, 0.38 mmol), $K_2CO_3$ (105 mg, 0.76 mmol) and NaI (57 mg, 0.38 mmol) in $CH_3CN$ (10 mL) was stirred at 80° C. for 2 h. Cooled and concentrated. To the residue was added water (10 mL) and EtOAc (10 mL), the organic layer was dried over $Na_2SO_4$, filtered and evaporated. The residue was purified by Prep-HPLC to afford the title compound as yellow solid (160 mg, 70%).

To a solution of 2-(7-(2-cyano-2-(pyridin-2-yl)vinyl)-3,4-dihydroisoquinolin-2(1H)-yl)-N—((R)-2-phenyl-1-((3aS, 4S,6S,7aR)-3a,5,5-trimethylhexahydro-4,6-methanobenzo [d][1,3,2]dioxaborol-2-yl)ethyl)acetamide (160 mg, 0.27 mmol) in MeOH (5 mL) were added hexane (5 mL) and 1 N HCl (1.5 mL), followed by isobutyl boronic acid (81 mg, 0.8 mmol). After stirring at rt for 3 h and LCMS suggested the reaction was completed, the hexane layer was discarded, the methanol layer was diluted with water (10 mL) and freeze dried directly to give a crude product, this crude product was further purified with neutral $Al_2O_3$ column (Methanol/DCM=0-20% as eluent) to afford the title compound as a yellow solid (23 mg, 19%). LCMS: 467 [M+1].

Example 67

((1R)-1-(((3-(3-(3-oxa-8-azabicyclo[3.2.1]octan-8-yl)-2-cyano-3-oxoprop-1-en-1-yl)phenethoxy)carbonyl)amino)-2-phenylethyl)boronic Acid

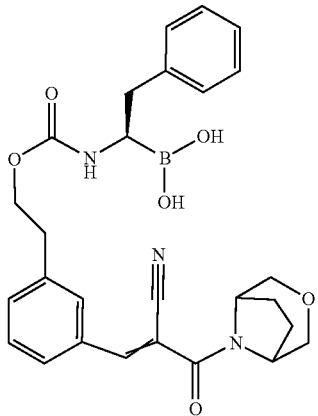 [SMILES: N#CC(=Cc1cccc(CCOC(=O)N[C@@H](Cc2ccccc2)B(O)O)c1)C(=O)N1C2CCC1COC2]

The title compound was prepared as in example 17 by replacing dimethylamine with 3-oxa-8-azabicyclo[3.2.1]octane hydrochloride. LC-MS m/z: 526 [M+23].

Example 68

((R)-1-(((3-(2-cyano-3-((3S,5S)-3,5-dimethylmorpholino)-3-oxoprop-1-en-1-yl)phenethoxy)carbonyl)amino)-2-phenylethyl)boronic Acid

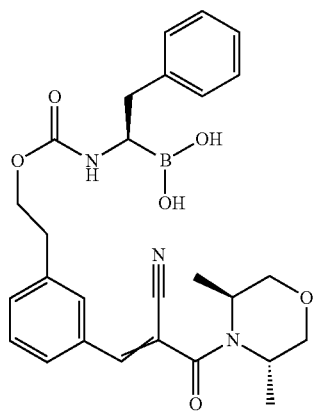 [SMILES: C[C@H]1COC[C@H](C)N1C(=O)C(C#N)=Cc1cccc(CCOC(=O)N[C@@H](Cc2ccccc2)B(O)O)c1]

The title compound was prepared as in example 17 by replacing dimethylamine with (3S,5S)-3,5-dimethylmorpholine. LC-MS m/z: 528 [M+23].

Example 69

(R)-(1-(((3-(3-(tert-butyl(ethyl)amino)-2-cyano-3-oxoprop-1-en-1-yl)phenethoxy)carbonyl)amino)-2-phenylethyl)boronic Acid

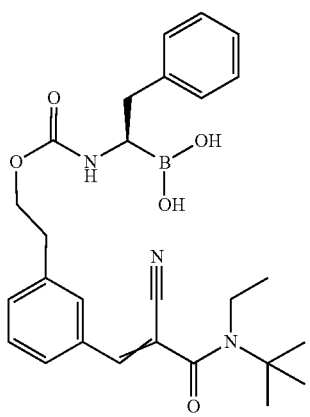 [SMILES: CCN(C(=O)C(C#N)=Cc1cccc(CCOC(=O)N[C@@H](Cc2ccccc2)B(O)O)c1)C(C)(C)C]

The title compound was prepared as in example 17 by replacing dimethylamine with N-ethyl-2-methylpropan-2-amine. LC-MS m/z: 514 [M+23].

Example 70

(R)-(1-(((3-(2-cyano-3-(ethyl(tetrahydro-2H-pyran-4-yl)amino)-3-oxoprop-1-en-1-yl)phenethoxy)carbonyl)amino)-2-phenylethyl)boronic Acid

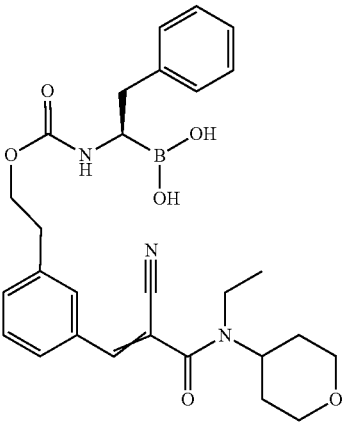 [SMILES: CCN(C(=O)C(C#N)=Cc1cccc(CCOC(=O)N[C@@H](Cc2ccccc2)B(O)O)c1)C1CCOCC1]

The title compound was prepared as in example 17 by replacing dimethylamine with N-ethyl-tetrahydro-2H-pyran-4-amine. LC-MS m/z: 502 [M−17].

Example 71

(R)-(1-(((3-(3-(tert-butyl(methyl)amino)-2-cyano-3-oxoprop-1-en-1-yl)phenethoxy)carbonyl)amino)-2-phenylethyl)boronic Acid

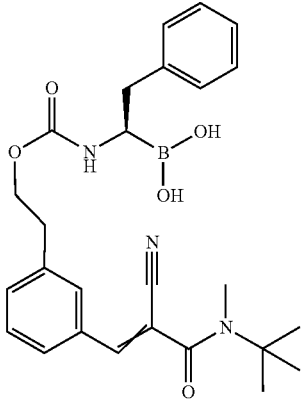 [SMILES: CN(C(=O)C(C#N)=Cc1cccc(CCOC(=O)N[C@@H](Cc2ccccc2)B(O)O)c1)C(C)(C)C]

The title compound was prepared as in example 17 by replacing dimethylamine with N-ethyl-2-methylpropan-2-amine. LC-MS m/z: 500 [M+23].

Example 72

(R)-(1-(((3-(3-(bis(tetrahydro-2H-pyran-4-yl)amino)-2-cyano-3-oxoprop-1-en-1-yl)phenethoxy)carbonyl)amino)-2-phenylethyl)boronic Acid

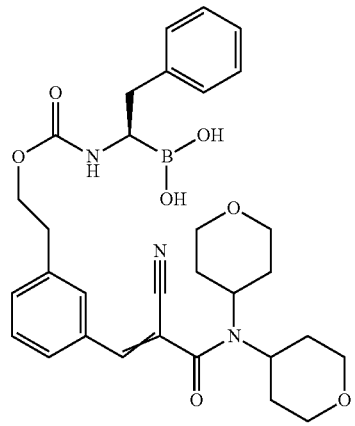 [SMILES: N#CC(=Cc1cccc(CCOC(=O)N[C@@H](Cc2ccccc2)B(O)O)c1)C(=O)N(C1CCOCC1)C1CCOCC1]

The title compound was prepared as in example 17 by replacing dimethylamine with bis(tetrahydro-2H-pyran-4-yl)amine. LC-MS m/z: 598 [M+23].

Example 73

(R)-(1-(3-(3-(2-cyano-2-(5-(trifluoromethyl)pyridin-2-yl)vinyl)phenethyl)ureido)-2-phenylethyl)boronic Acid

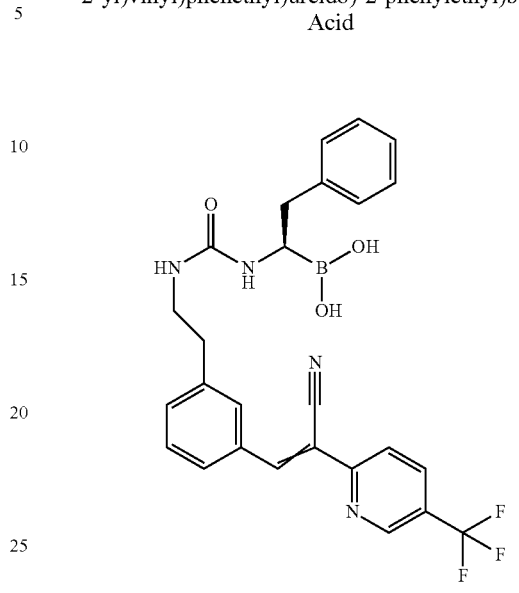

Synthetic Scheme

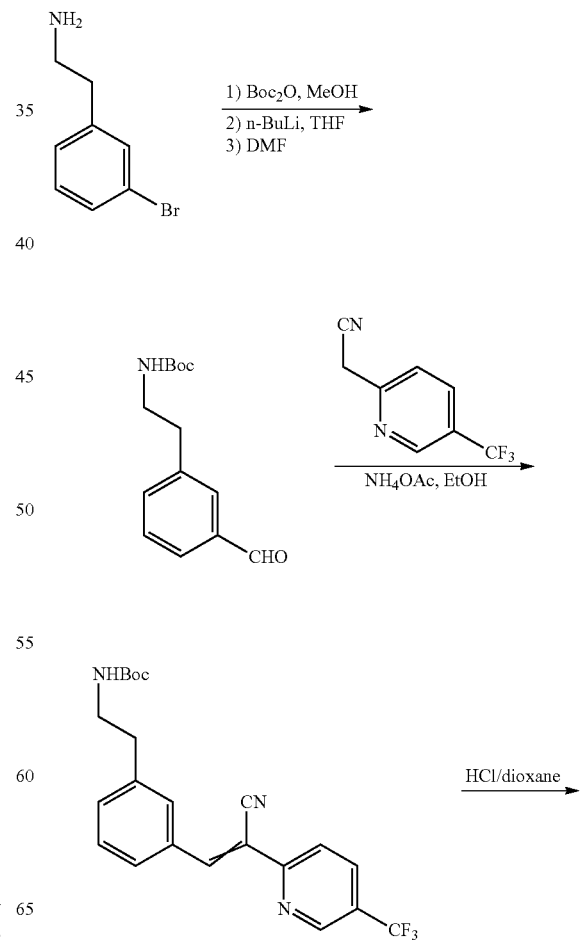

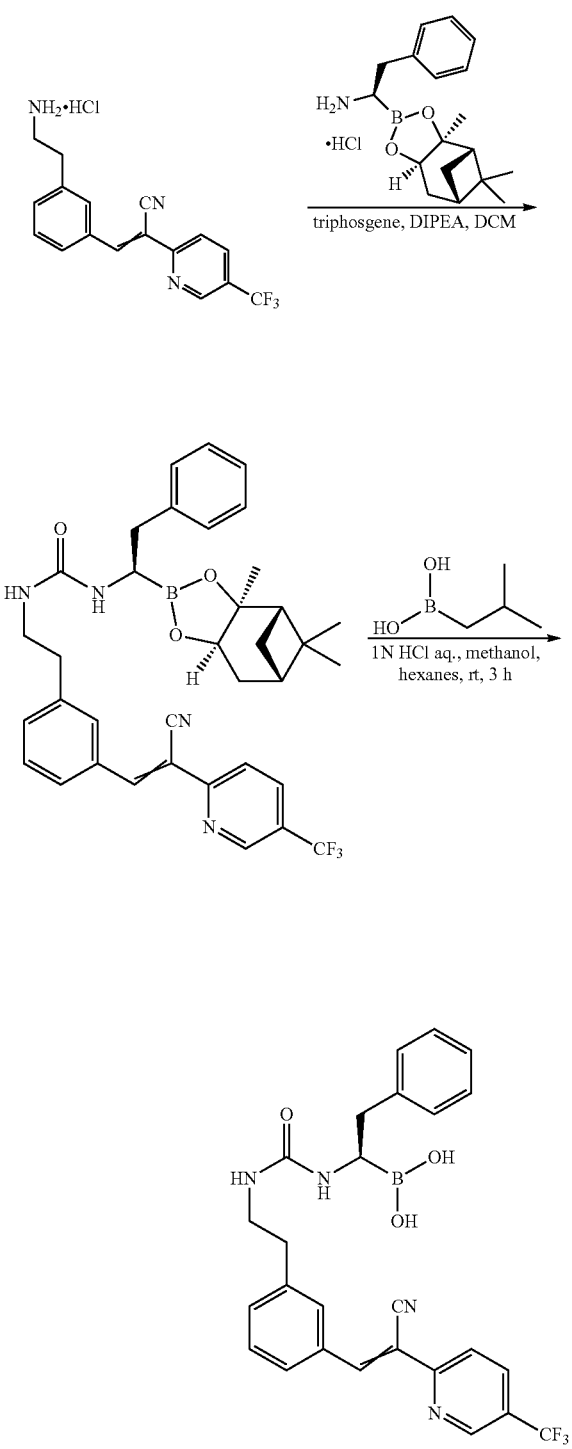

To a solution of 2-(3-bromophenyl)ethanamine (6 g, 30 mmol) in methanol (50 mL) was added (Boc)₂O (6.62 g, 30.6 mmol) slowly at rt. The mixture was stirred at rt for 2 h, then concentrated to dryness. The residue was dissolved in anhydrous THF (30 mL), then added dropwise into a solution of n-BuLi (31.5 mL, 2.4 M in hexanes, 75 mmol) in THF (120 mL) at −78° C. After the reaction was stirred at the low temperature for 1 h, anhydrous DMF (21.9 g, 300 mmol) was added dropwise into the mixture at −78° C. The resulted mixture was stirred at the low temperature for 1.5 h, then quenched with NH₄Cl aqueous (240 mL). THF layer was separated. The aqueous was extracted with EtOAc (80 mL×2). The combined organic layers were washed with brine, dried over Na₂SO₄ and concentrated to dryness. The residue was purified by silica chromatography on silica gel using gradient of 5%-10% EtOAc in Hexanes as eluent to give the title compound as light yellow oil (5.7 g, 76%).

A mixture of tert-butyl 3-formylphenethylcarbamate (1 g, 4 mmol), 2-(5-(trifluoromethyl)pyridin-2-yl)acetonitrile (0.7 g, 3.76 mmol) and ammonium acetate (1.54 g, 20 mmol) in ethanol (30 mL) was stirred at reflux temperature for 2 h. After cooling to rt, the mixture was concentrated to dryness. The residue was diluted with EtOAc (50 mL), and washed with water (20 mL) and brine (15 mL). The organic layers were dried over Na₂SO₄ and concentrated in vacuo. The crude residue was purified via silica chromatography and a gradient of 10%-60% EtOAc in Hexanes to afford tert-butyl 3-(2-cyano-2-(5-(trifluoromethyl)pyridin-2-yl)vinyl)phenethylcarbamate as a yellow solid (0.6 g, 36%).

To a mixture of tert-butyl 3-(2-cyano-2-(5-(trifluoromethyl)pyridin-2-yl)vinyl)phenethylcarbamate (0.42 g, 1 mmol) in HCl/dioxane (4 M, 5 mL) was added MeOH (2 mL). The mixture was stirred at rt for 1 h, then concentrated to dryness over high vacuum to afford 3-(3-(2-aminoethyl)phenyl)-2-(5-(trifluoromethyl)pyridin-2-yl)acrylonitrile hydrochloride (455 mg, 100%).

Bis(trichloromethyl) carbonate (356 mg, 1.2 mmol) in DCM (2 mL) was added dropwise to a stirring solution of (R)-2-phenyl-1-((3aS,4S,6S,7aR)-3a,5,5-trimethylhexahydro-4,6-methanobenzo[d][1,3,2]dioxaborol-2-yl)ethan-1-amine hydrochloride (671 mg, 2 mmol) and DIPEA (1.04 g, 8.0 mmol) in DCM (6 mL) at 0° C. The mixture was stirred for 2 h at 0° C. This resulted solution was added dropwise into a well-stirred solution of 3-(3-(2-aminoethyl)phenyl)-2-(5-(trifluoromethyl)pyridin-2-yl)acrylonitrile hydrochloride (455 mg, 1 mmol) and DIPEA (1.04 g, 8.0 mmol) in DCM (4 mL) at 0° C. The reaction was stirred at rt for 1 h, then diluted with DCM (25 mL), washed with water (10 mL) and brine (10 mL), dried over Na₂SO₄, concentrated in vacuo. The crude material was purified by prep-HPLC to give the title compound as white solid (240 mg, 37%).

To a solution of 1-(3-(2-cyano-2-(5-(trifluoromethyl)pyridin-2-yl)vinyl)phenethyl)-3-((R)-2-phenyl-1-((3aS,4S,6S,7aR)-3a,5,5-trimethylhexahydro-4,6-methanobenzo[d][1,3,2]dioxaborol-2-yl)ethyl)urea (240 mg, 0.374 mmol) in MeOH (6 mL) were added hexanes (6 mL) and 1 N HCl (1.2 mL), followed by isobutyl boric acid (114 mg, 1.12 mmol). After stirred at rt for 3 h and TLC suggested the reaction was completed, the hexanes layer was discarded. The methanol layer was diluted with water (20 mL), then dried over lyophilization to give a crude product which was further purified by neutral Al₂O₃ column (Methanol/DCM=0-10% as eluent) to afford (R)-(1-(3-(3-(2-cyano-2-(5-(trifluoromethyl)pyridin-2-yl)vinyl)phenethyl)ureido)-2-phenylethyl) boronic acid as an off-white solid (100.2 mg, 53%). LCMS: 491 [M−17].

Examples 74 and 75

(R)-(1-(((3-(2-cyano-3-(diisopropylamino)-3-oxo-prop-1-en-1-yl)phenethoxy)carbonyl)amino)-2-phenylethyl)boronic Acid

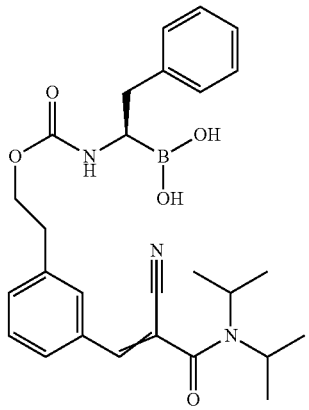 [SMILES: CC(C)N(C(=O)C(C#N)=Cc1cccc(CCOC(=O)N[C@@H](Cc2ccccc2)B(O)O)c1)C(C)C]

The title compounds as likely regio-isomers (E and Z; not assigned) were prepared as in example 17 by replacing dimethylamine with diisopropylamine. LC-MS m/z: 514 [M+23].

Example 76

(R)-(1-(((3-(2-cyano-2-(pyridin-2-yl)vinyl)-5-(hydroxymethyl)phenethoxy)carbonyl)amino)-2-phenylethyl)boronic Acid

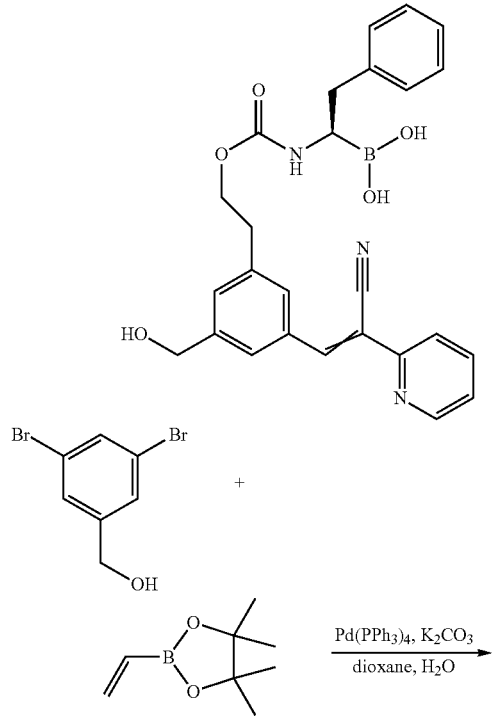

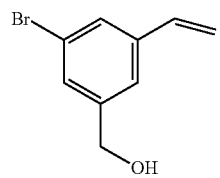

Into a 100-mL round-bottom flask, was placed (3,5-dibromophenyl)methanol (2 g, 7.52 mmol, 1.00 eq.), dioxane (40 mL), water (4 mL), 2-ethenyl-4,4,5,5-tetramethyl-1,3,2-dioxaborolane (1.2 g, 7.79 mmol, 1.00 eq.), Pd(PPh3)4 (900 mg, 0.78 mmol, 0.10 eq.), potassium carbonate (3.1 g, 22.43 mmol, 3.00 eq.). The resulting solution was stirred for 1 overnight at 100° C. The solids were filtered out. The resulting mixture was concentrated under vacuum. The resulting solution was diluted with 100 mL of H₂O. The resulting solution was extracted with 3×100 mL of ethyl acetate and the organic layers combined and dried over anhydrous sodium sulfate and concentrated under vacuum. The residue was applied onto a silica gel column with dichloromethane. This resulted in 1.1 g (69%) of (3-bromo-5-ethenylphenyl)methanol as yellow oil.

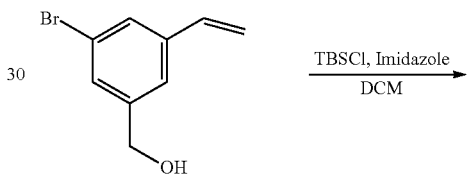

Into a 100-mL round-bottom flask, was placed (3-bromo-5-ethenylphenyl)methanol (1.4 g, 6.57 mmol, 1.00 eq.), dichloromethane (30 mL), TBSCl (2 g, 13.33 mmol, 2.00 eq.), Imidazole (1.8 g, 26.47 mmol, 4.00 eq.). The resulting solution was stirred for 2 h at 25° C. The resulting solution was diluted with 100 mL of DCM. The resulting mixture was washed with 1×100 mL of saturated solution sodium bicarbonate. The resulting mixture was washed with 1×100 mL of saturated brine. The mixture was dried over anhydrous sodium sulfate and concentrated under vacuum. The residue was separated by PREP-TLC with PE. This resulted in 1.3 g (60%) of [(3-bromo-5-ethenylphenyl)methoxy](tert-butyl)dimethylsilane as yellow oil.

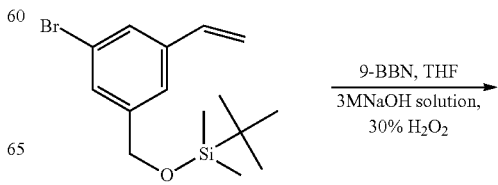

-continued

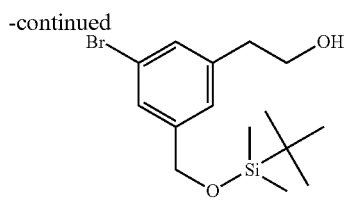

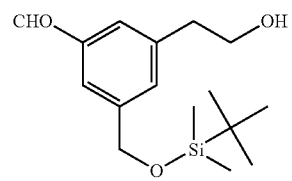

Into a 500-mL 3-necked round-bottom flask, was placed [(3-bromo-5-ethenylphenyl) methoxy](tert-butyl)dimethylsilane (1.3 g, 3.97 mmol, 1.00 eq.), tetrahydrofuran (40 mL). This was followed by the addition of 0.5M 9-BBN (47.6 mL, 6.00 eq.) dropwise with stirring at 0° C. The resulting solution was stirred for 4 h at 25° C. To this was added 1N sodium hydroxide (55.5 mL, 14.00 eq.) dropwise with stirring at 0° C. To the mixture was added $H_2O_2$ (30%) (13.8 mL, 40.00 eq.) dropwise with stirring at 0° C. The resulting solution was stirred for 2 h at 25° C. This was followed by the addition of saturated solution $Na_2S_2O_3$ (156 mL) dropwise with stirring at 0° C. The resulting solution was stirred overnight at 25° C. The resulting solution was extracted with 3×200 mL of ethyl acetate and the organic layers combined. The resulting mixture was washed with 3×200 mL of saturated brine. The mixture was dried over anhydrous sodium sulfate and concentrated under vacuum. The crude product was purified by Flash-Prep-HPLC with the following conditions (CombiFlash): Column, C18 silica gel; mobile phase, CH3CN; Detector, UV 220 nm. This resulted in 0.96 g (70%) of 2-(3-bromo-5-[[(tert-butyldimethylsilyl)oxy]methyl]phenyl)ethan-1-ol as colorless oil.

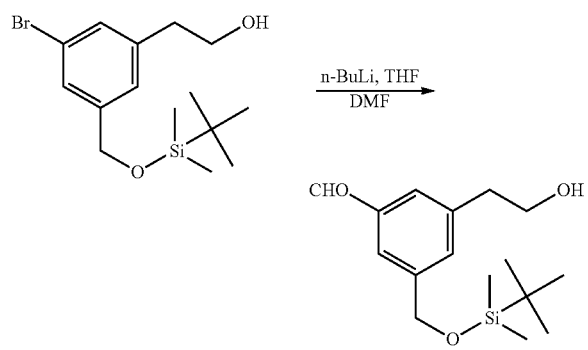

Into a 100-mL 3-necked round-bottom flask, was placed tetrahydrofuran (20 mL), n-BuLi (2.2 mL, 2.00 eq.). This was followed by the addition of 2-(3-bromo-5-[[(tert-butyldimethylsilyl)oxy]methyl]phenyl)ethan-1-ol (960 mg, 2.78 mmol, 1.00 eq.) stirring at −78° C. The resulting solution was stirred for 20 min. at −78° C. To this was added N,N-dimethylformamide (3.3 mL) dropwise with stirring at −78° C. The resulting solution was stirred for 2 h at −78° C. The reaction was then quenched by the addition of 100 mL of saturated solution $NH_4Cl$. The resulting solution was extracted with 3×100 mL of ethyl acetate and the organic layers combined. The resulting mixture was washed with 3×100 mL of saturated brine. The mixture was dried over anhydrous sodium sulfate and concentrated under vacuum. The residue was separated by PREP-TLC with ethyl acetate/ petroleum ether (1:1). This resulted in 270 mg (33%) of 3-[[(tert-butyldimethylsilyl)oxy]methyl]-5-(2-hydroxyethyl)benzaldehyde as yellow oil.

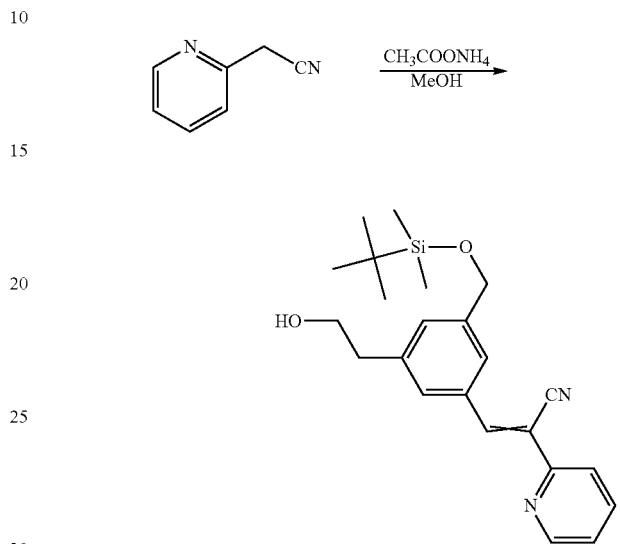

Into a 50-mL round-bottom flask, was placed 3-[[(tert-butyldimethylsilyl)oxy]methyl]-5-(2-hydroxyethyl)benzaldehyde (270 mg, 0.92 mmol, 1.00 eq.), 2-(pyridin-2-yl)acetonitrile (108.4 mg, 0.92 mmol, 1.00 eq.), $CH_3COONH_4$ (353.6 mg, 4.59 mmol, 5.00 eq.), methanol (4 mL). The resulting solution was stirred for 30 min at 60° C. The resulting mixture was concentrated under vacuum. The resulting solution was diluted with 100 mL of $H_2O$. The resulting solution was extracted with 3×100 mL of ethyl acetate and the organic layers combined and dried over anhydrous sodium sulfate and concentrated under vacuum. The residue was separated by PREP-TLC with ethyl acetate/ petroleum ether (1:1). This resulted in 240 mg (66%) of 3-(3-[[(tert-butyldimethylsilyl)oxy]methyl]-5-(2-hydroxyethyl)phenyl)-2-(pyridin-2-yl)prop-2-enenitrile as yellow oil.

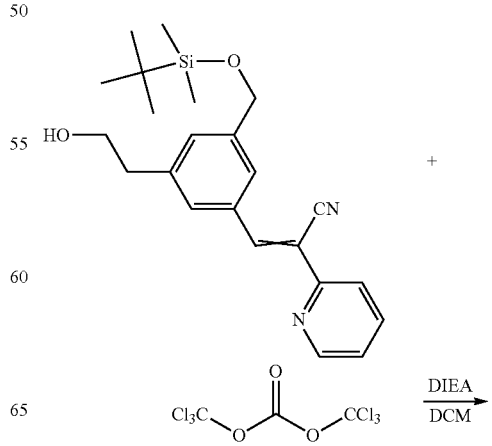

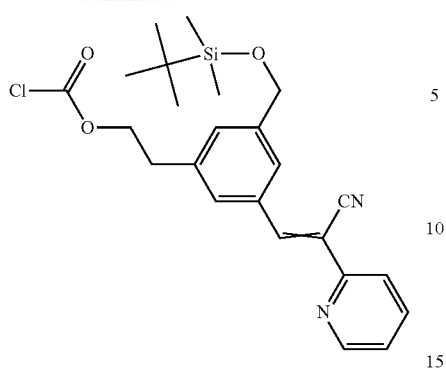

Into a 50-mL 3-necked round-bottom flask purged and maintained with an inert atmosphere of nitrogen, was placed 3-(3-[[(tert-butyldimethylsilyl)oxy]methyl]-5-(2-hydroxyethyl)phenyl)-2-(pyridin-2-yl)prop-2-enenitrile (220 mg, 0.56 mmol, 1.00 eq.), dichloromethane (3 mL), DIPEA (216.1 mg, 1.68 mmol, 3.00 eq.). This was followed by the addition of a solution of ditrichloromethyl carbonate in DCM (82.1 mg, 0.28 mmol, 0.50 eq.) dropwise with stirring at 0° C. The resulting solution was stirred for 3 h at 0° C. The resulting mixture was concentrated under vacuum. This resulted in 254.6 mg (100%) of 2-(3-[[(tert-butyldimethylsilyl)oxy]methyl]-5-[2-cyano-2-(pyridin-2-yl)eth-1-en-1-yl]phenyl)ethyl chloroformate as yellow oil. The crude product was used directly to the next step.

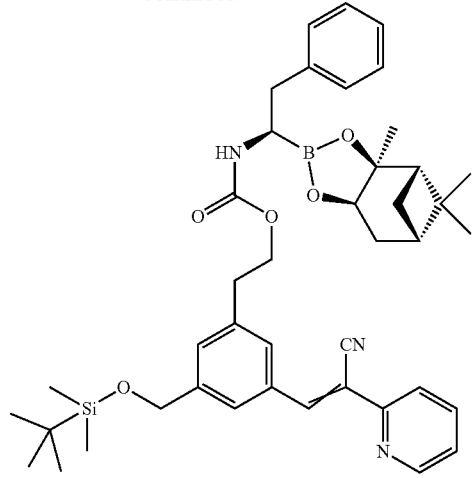

Into a 50-mL 3-necked round-bottom flask purged and maintained with an inert atmosphere of nitrogen, was placed (1R)-2-phenyl-1-[(1S,2S,6R,8S)-2,9,9-trimethyl-3,5-dioxa-4-boratricyclo[6.1.1.0ˆ[2,6]]decan-4-yl]ethan-1-amine hydrochloride (168.4 mg, 0.50 mmol, 0.90 eq.), DIPEA (129.7 mg, 1.01 mmol, 1.80 eq.), dichloromethane (3 mL). This was followed by the addition of 2-(3-[[(tert-butyldimethylsilyl)oxy]methyl]-5-[2-cyano-2-(pyridin-2-yl)eth-1-en-1-yl]phenyl)ethyl chloroformate (254.6 mg, 0.56 mmol, 1.00 eq.) stirring at 0° C. The resulting solution was stirred for 1.5 h at 25° C. The resulting solution was diluted with 100 mL of DCM. The resulting mixture was washed with 3×100 mL of saturated brine. The mixture was dried over anhydrous sodium sulfate and concentrated under vacuum. The residue was separated by PREP-TLC with ethyl acetate/petroleum ether (1:1). This resulted in 220 mg (55%) of 2-(3-[[(tert-butyldimethylsilyl)oxy]methyl]-5-[2-cyano-2-(pyridin-2-yl)eth-1-en-1-yl]phenyl)ethylN-[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamate as yellow oil.

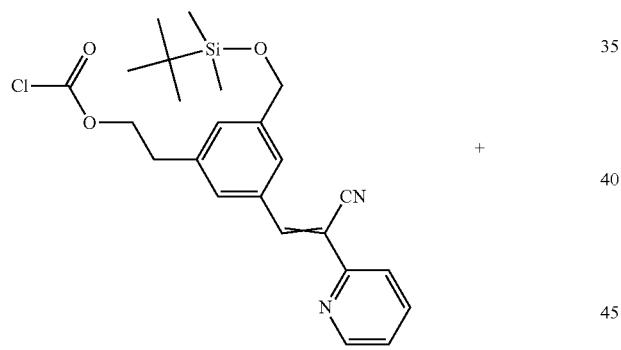

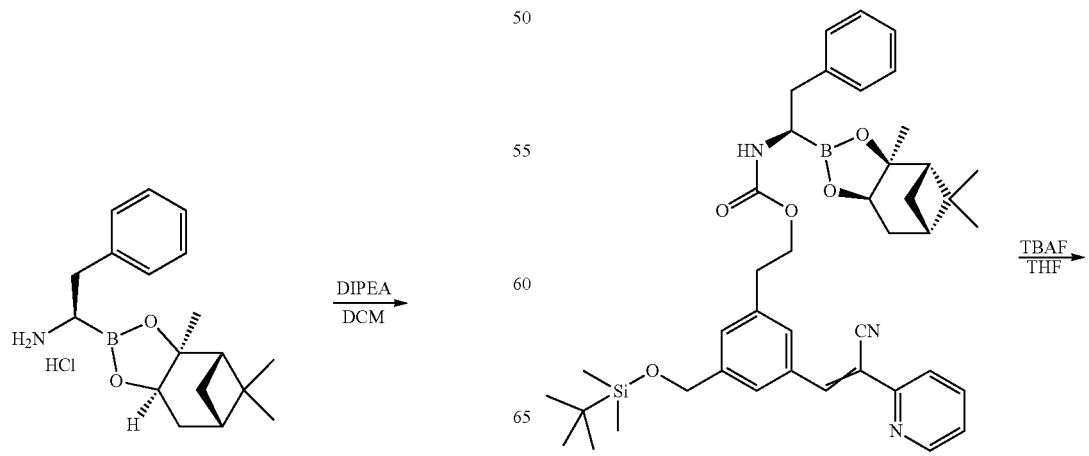

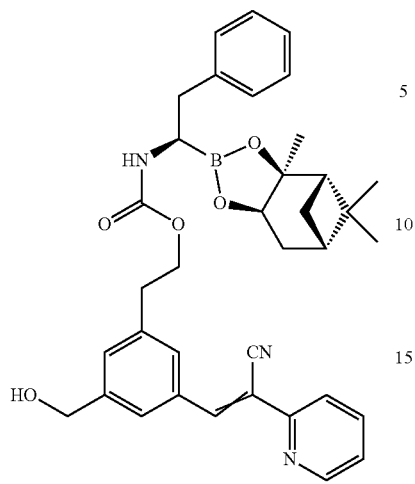

Into a 25-mL round-bottom flask, was placed 2-(3-[[(tert-butyldimethylsilyl) oxy]methyl]-5-[2-cyano-2-(pyridin-2-yl)eth-1-en-1-yl]phenyl)ethylN-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate (220 mg, 0.31 mmol, 1.00 eq.), 1M TBAF (6.4 mL). The resulting solution was stirred for 60 min. at 25° C. The resulting solution was diluted with 100 mL of H$_2$O. The resulting solution was extracted with 3×100 mL of ethyl acetate and the organic layers combined. The resulting mixture was washed with 1×100 mL of saturated solution NH$_4$Cl. The resulting mixture was washed with 1×100 mL of saturated brine. The mixture was dried over anhydrous sodium sulfate and concentrated under vacuum. The crude product was purified by Prep-HPLC with the following conditions: Column, XBridge Prep C18 OBD Column, 19*150 mm, 5 um; mobile phase, Water (10 MMOL/L NH$_4$HCO$_3$+0.1% NH$_3$·H$_2$O) and ACN (56.0% ACN up to 87.0% in 7 min); Detector, UV 254/220 nm. This resulted in 110 mg (59%) of 2-[3-[2-cyano-2-(pyridin-2-yl)eth-1-en-1-yl]-5-(hydroxymethyl)phenyl]ethylN-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate as a white solid after the lyophilization.

Into a 50-mL round-bottom flask purged and maintained with an inert atmosphere of nitrogen, was placed 2-[3-[2-cyano-2-(pyridin-2-yl)eth-en-1-yl]-5-(hydroxymethyl) phenyl]ethylN-[(1R)-2-phenyl-1-[(1S,2S,6R,8S)-2,9,9-trimethyl-3,5-dioxa-4-boratricyclo[6.1.1.0^[2,6]]decan-4-yl] ethyl]carbamate (90 mg, 0.15 mmol, 1.00 eq.), (2-methylpropyl)boronic acid (44 mg, 0.43 mmol, 2.90 eq.), hexane (3.9 mL), methanol (3.9 mL), 1N hydrogen chloride (2.98 mL, 20.00 eq.). The resulting solution was stirred for 2 h at 25° C. The resulting mixture was washed with 3×10 mL of hexane. The methanol layer was diluted with 100 mL of water, then dried over lyophylization to give a crude product which was further purified by Prep-HPLC with the following conditions: Column, XBridge Prep C18 OBD Column, 19*150 mm, 5 um; mobile phase, Water (10 MMOL/L NH$_4$HCO$_3$+0.1% NH$_3$·H$_2$O) and ACN (30.0% ACN up to 47.0% in 7 min); Detector, UV 254/220 nm. This resulted in 47 mg (67%) of (R)-(1-(((3-(2-cyano-2-(pyridin-2-yl)vinyl)-5-(hydroxymethyl)phenethoxy)carbonyl)amino)-2-phenylethyl)boronic acid as a white solid after the lyophilization. LC-MS m/z: 454 [M−17].

Example 77

(R)-(1-(3-(3-(2-cyano-2-(pyridin-2-yl)vinyl)phenethyl)ureido)-2-(p-tolyl)ethyl)boronic Acid

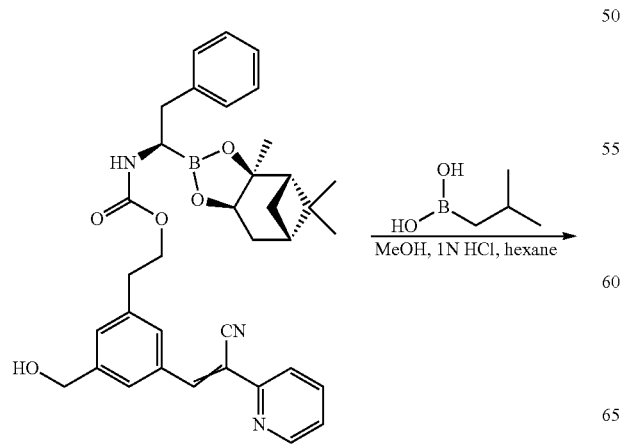

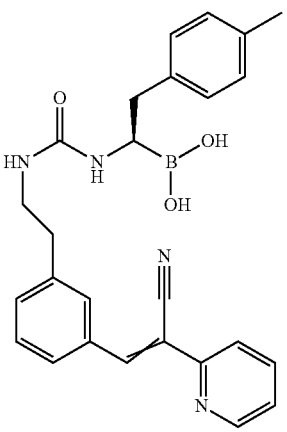 [SMILES: Cc1ccc(C[C@H](NC(=O)NCCc2cccc(C=C(C#N)c3ccccn3)c2)B(O)O)cc1]

The title compound was prepared as in example 61 by replacing (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine with (R)-1-(4,4,5,5-tetramethyl-1,3,2-dioxaborolan-2-yl)-2-(p-tolyl)ethanamine hydrochloride. LC-MS m/z: 437 [M−17].

Example 78

(R)-(1-(((3-(2-cyano-2-(5-cyanopyridin-2-yl)vinyl)phenethoxy)carbonyl)amino)-2-phenylethyl)boronic Acid

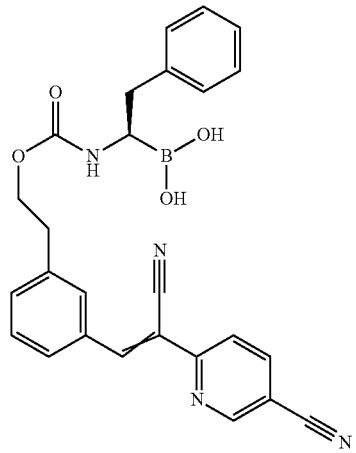 [SMILES: N#CC(=Cc1cccc(CCOC(=O)N[C@@H](Cc2ccccc2)B(O)O)c1)c1ccc(C#N)cn1]

The title compound was prepared as in example 36 by replacing 2-(pyridin-2-yl)acetonitrile with 2-(pyrazin-2-yl)acetonitrile. LC-MS m/z: 489 [M+23]. 2-(pyridin-2-yl)acetonitrile with 2-(pyrazin-2-yl)acetonitrile can be made in two steps with below procedure: 1. To a suspension of NaH (850 mg, 21.25 mmol, 60% oil dispersion) in dry DMSO (40 mL) was added t-butyl cyanoacetate (3 g, 21.25 mmol) at rt for 2 hour. 6-bromonicotinonitrile (2 g, 10.63 mmol) was added to the resulting mixture, the mixture was stirred at 120° C. for 3 h. After cooling, the mixture was poured into saturated ammonium chloride solution, the resulting precipitates were collected by filtration, washed with water to give the title compounds as brown solid (2.6 g, crude); 2. To a solution of tert-butyl 2-cyano-2-(5-cyanopyridin-2-yl)acetate (2.6 g, 10.69 mmol) in toluene (50 mL) was added TsOH (920.25 mg, 5.34 mmol). The resulting solution was stirred under reflux for 6 h. After cooling, the solvent was removed. The residue was purified via silica chromatography and a gradient of 0-10% MeOH in DCM to afford the title compound as a yellow solid (1.2 g, 80%).

Example 79

(R)-(1-(((3-(2-cyano-3-(3,3-dimethylmorpholino)-3-oxoprop-1-en-1-yl)phenethoxy)carbonyl)amino)-2-phenylethyl)boronic Acid

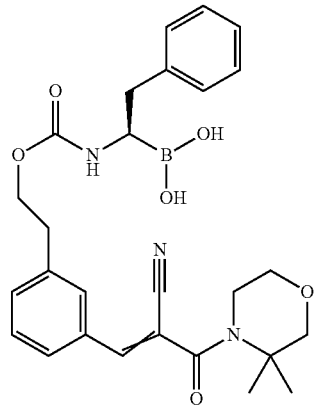 [SMILES: CC1(C)COCCN1C(=O)C(C#N)=Cc1cccc(CCOC(=O)N[C@@H](Cc2ccccc2)B(O)O)c1]

The title compound was prepared as in example 17 by replacing dimethylamine with 3,3-dimethylmorpholine. LC-MS m/z: 528 [M+23].

Example 80

(R)-(1-(3-(3-(2-cyano-2-(5-(trifluoromethyl)pyridin-2-yl)vinyl)phenethyl)ureido)-2-(p-tolyl)ethyl)boronic Acid

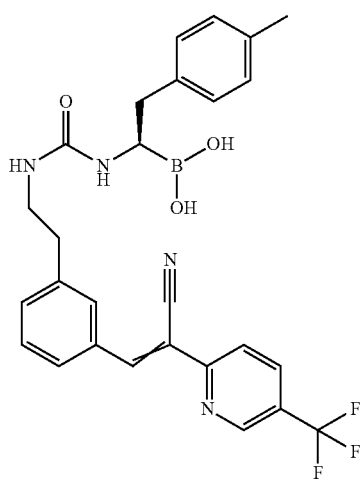 [SMILES: Cc1ccc(C[C@H](NC(=O)NCCc2cccc(C=C(C#N)c3ccc(C(F)(F)F)cn3)c2)B(O)O)cc1]

The title compound was prepared as in example 73 by replacing (1R)-2-phenyl-1-[(1S,2S,6R,8S)-2,9,9-trimethyl-3,5-dioxa-4-boratricyclo[6.1.1.0ˆ[2,6]]decan-4-yl]ethan-1-amine hydrochloride with (R)-1-(4,4,5,5-tetramethyl-1,3,2-dioxaborolan-2-yl)-2-(p-tolyl)ethanamine hydrochloride. LC-MS m/z: 505 [M−17].

Example 81

(R)-(1-(((3-(2-cyano-2-(5-(trifluoromethyl)pyridin-2-yl)vinyl)phenethoxy)carbonyl)amino)-2-(p-tolyl)ethyl)boronic Acid

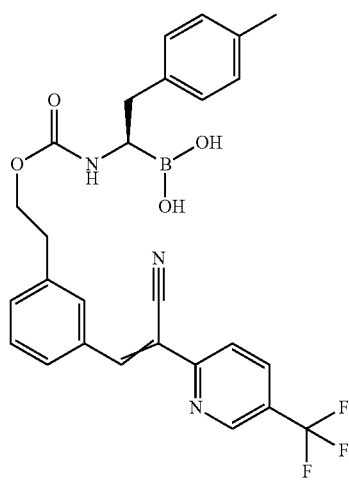 [SMILES: Cc1ccc(C[C@H](NC(=O)OCCc2cccc(C=C(C#N)c3ccc(C(F)(F)F)cn3)c2)B(O)O)cc1]

The title compound was prepared as in example 56 by replacing (1R)-2-phenyl-1-[(1S,2S,6R,8S)-2,9,9-trimethyl-3,5-dioxa-4-boratricyclo[6.1.1.0´[2,6]]decan-4-yl]ethan-1-amine hydrochloride with (R)-1-(4,4,5,5-tetramethyl-1,3,2-dioxaborolan-2-yl)-2-(p-tolyl)ethanamine hydrochloride. LC-MS m/z: 546 [M+23].

Example 82

(R)-(1-(3-(3-(2-cyano-3-(diethylamino)-3-oxoprop-1-en-1-yl)phenethyl)ureido)-2-(p-tolyl)ethyl)boronic Acid

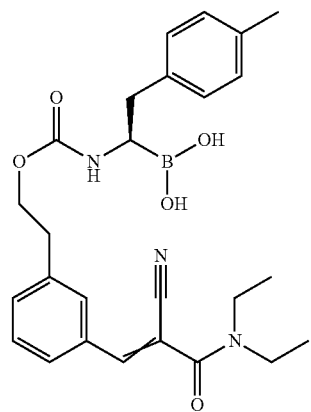 [SMILES: CCN(CC)C(=O)C(C#N)=Cc1cccc(CCOC(=O)N[C@@H](Cc2ccc(C)cc2)B(O)O)c1]

The title compound was prepared as in example 61 by replacing (1R)-2-phenyl-1-[(1S,2S,6R,8S)-2,9,9-trimethyl-3,5-dioxa-4-boratricyclo[6.1.1.0´[2,6]]decan-4-yl]ethan-1-amine hydrochloride with (R)-1-(4,4,5,5-tetramethyl-1,3,2-dioxaborolan-2-yl)-2-(p-tolyl)ethanamine hydrochloride. LC-MS m/z: 459 [M−17].

Example 83

(R)-(1-(3-(3-(2-cyano-2-(pyrimidin-2-yl)vinyl)phenethyl)ureido)-2-(p-tolyl)ethyl)boronic Acid

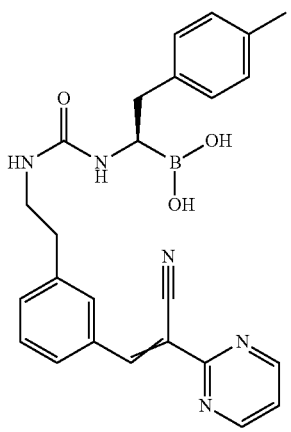 [SMILES: Cc1ccc(C[C@H](NC(=O)NCCc2cccc(C=C(C#N)c3ncccn3)c2)B(O)O)cc1]

The title compound was prepared as in example 77 by replacing 2-(pyridin-2-yl)acetonitrile with 2-(pyrimidin-2-yl)acetonitrile. LC-MS m/z: 438 [M−17].

Example 84

(R)-(1-(((3-(2-cyano-2-(1-methyl-6-oxo-1,6-dihydropyrimidin-4-yl)vinyl)phenethoxy)carbonyl)amino)-2-phenylethyl)boronic Acid

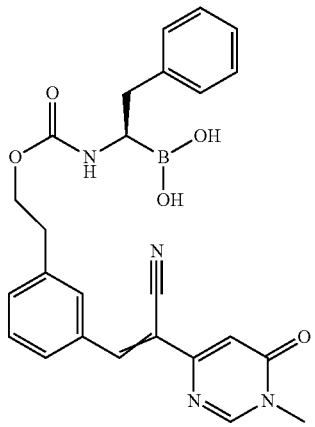 [SMILES: Cn1cnc(C(C#N)=Cc2cccc(CCOC(=O)N[C@@H](Cc3ccccc3)B(O)O)c2)cc1=O]

The title compound was prepared as in example 36 by replacing 2-(pyridin-2-yl)acetonitrile with 2-(1-methyl-6-oxo-1,6-dihydropyrimidin-4-yl)acetonitrile. LC-MS m/z: 455 [M−17].

2-(1-methyl-6-oxo-1,6-dihydropyrimidin-4-yl)acetonitrile can be made in two steps with below procedure: 1. To a suspension of NaH (387 mg, 9.68 mmol, 60% oil dispersion) in dry DMSO (20 mL) at rt was added t-butyl cyanoacetate (1.37 g, 9.68 mmol), after stirring for 2 h, 6-chloro-3-methylpyrimidin-4(3H)-one (700 mg, 4.84 mmol) was added to the resulting mixture, the mixture was stirred at 120° C. for 3 h. After cooling, the mixture was poured into saturated ammonium chloride solution, the resulting precipitates were collected by filtration, washed with water to give the title compounds as brown solid (650 mg, 54%); 2. To a solution of tert-butyl 2-cyano-2-(1-methyl-6-oxo-1,6-dihydropyrimidin-4-yl)acetate (650 mg, 2.61 mmol) in toluene (20 mL) was added TsOH (225 mg, 1.30 mmol). The resulting solution was stirred under reflux 6 h. After cooling, the solvent was removed. The residue was purified via silica chromatography and a gradient of 0-10% MeOH in DCM to afford the title compound as a yellow solid (200 mg, 51%).

Example 85

((R)-1-(((3-(2-cyano-3-((3R,5R)-3,5-dimethylmorpholino)-3-oxoprop-1-en-1-yl)phenethoxy)carbonyl)amino)-2-(p-tolyl)ethyl)boronic Acid

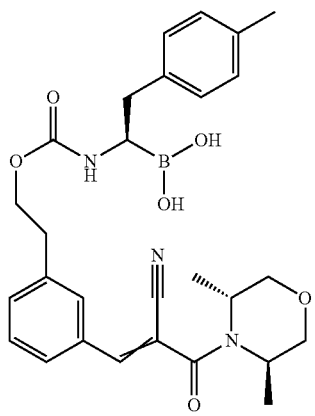 [SMILES: Cc1ccc(C[C@H](NC(=O)OCCc2cccc(C=C(C#N)C(=O)N3[C@H](C)COC[C@H]3C)c2)B(O)O)cc1]

The title compound was prepared as in example 65 by replacing (1R)-2-phenyl-1-[(1S,2S,6R,8S)-2,9,9-trimethyl-3,5-dioxa-4-boratricyclo[6.1.1.0^[2,6]]decan-4-yl]ethan-1-amine hydrochloride with (R)-1-(4,4,5,5-tetramethyl-1,3,2-dioxaborolan-2-yl)-2-(p-tolyl)ethanamine hydrochloride. LC-MS m/z: 542 [M+23].

Example 86

(R)-(2-(4-chlorophenyl)-1-(((3-(2-cyano-3-(diethylamino)-3-oxoprop-1-en-1-yl)phenethoxy)carbonyl)amino)ethyl)boronic Acid

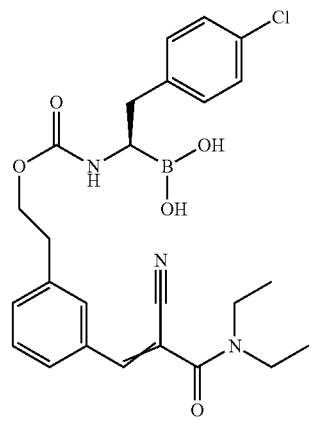 [SMILES: CCN(CC)C(=O)C(C#N)=Cc1cccc(CCOC(=O)N[C@@H](Cc2ccc(Cl)cc2)B(O)O)c1]

The title compound was prepared as in example 52 by replacing (1R)-2-phenyl-1-[(1S,2S,6R,8S)-2,9,9-trimethyl-3,5-dioxa-4-boratricyclo[6.1.1.0^[2,6]]decan-4-yl]ethan-1-amine hydrochloride with (R)-2-(4-chlorophenyl)-1-(4,4,5,5-tetramethyl-1,3,2-dioxaborolan-2-yl)ethanamine hydrochloride. LC-MS m/z: 520 [M+23].

Example 87

(R)-(1-(((3-(2-cyano-2-(pyrimidin-2-yl)vinyl)phenethoxy)carbonyl)amino)-2-(p-tolyl)ethyl)boronic Acid

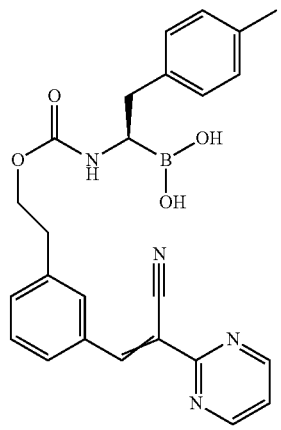 [SMILES: Cc1ccc(C[C@H](NC(=O)OCCc2cccc(C=C(C#N)c3ncccn3)c2)B(O)O)cc1]

The title compound was prepared as in example 60 by replacing (1R)-2-phenyl-1-[(1S,2S,6R,8S)-2,9,9-trimethyl-3,5-dioxa-4-boratricyclo[6.1.1.0^[2,6]]decan-4-yl]ethan-1-amine hydrochloride with (R)-1-(4,4,5,5-tetramethyl-1,3,2-dioxaborolan-2-yl)-2-(p-tolyl)ethanamine hydrochloride. LC-MS m/z: 479 [M+23].

Example 88

(R)-(1-(((3-(2-cyano-3-(ethyl(tetrahydro-2H-pyran-4-yl)amino)-3-oxoprop-1-en-1-yl)phenethoxy)carbonyl)amino)-2-(p-tolyl)ethyl)boronic Acid

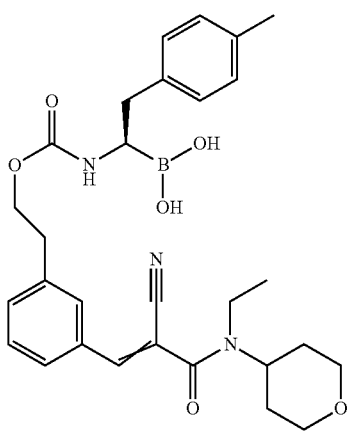 [SMILES: CCN(C(=O)C(C#N)=Cc1cccc(CCOC(=O)N[C@@H](Cc2ccc(C)cc2)B(O)O)c1)C1CCOCC1]

The title compound was prepared as in example 70 by replacing (1R)-2-phenyl-1-[(1S,2S,6R,8S)-2,9,9-trimethyl- 3,5-dioxa-4-boratricyclo[6.1.1.0^[2,6]]decan-4-yl]ethan-1-amine hydrochloride with (R)-1-(4,4,5,5-tetramethyl-1,3,2-dioxaborolan-2-yl)-2-(p-tolyl)ethanamine hydrochloride. LC-MS m/z: 556 [M+23].

Example 89

((1R)-1-(((3-(3-(3-oxa-8-azabicyclo[3.2.1]octan-8-yl)-2-cyano-3-oxoprop-1-en-1-yl)phenethoxy)carbonyl)amino)-2-(p-tolyl)ethyl)boronic Acid

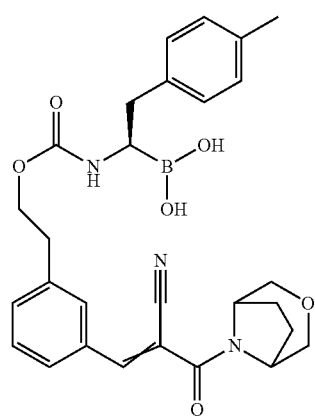 [SMILES: Cc1ccc(C[C@H](NC(=O)OCCc2cccc(C=C(C#N)C(=O)N3C4CCC3COC4)c2)B(O)O)cc1]

The title compound was prepared as in example 67 by replacing (1R)-2-phenyl-1-[(1S,2S,6R,8S)-2,9,9-trimethyl-3,5-dioxa-4-boratricyclo[6.1.1.0^[2,6]]decan-4-yl]ethan-1-amine hydrochloride with (R)-1-(4,4,5,5-tetramethyl-1,3,2-dioxaborolan-2-yl)-2-(p-tolyl)ethanamine hydrochloride. LC-MS m/z: 500 [M−17].

Example 90

(R)-(1-(((3-(2-cyano-3-(ethyl(methyl)amino)-3-oxoprop-1-en-1-yl)phenethoxy)carbonyl)amino)-2-phenylethyl)boronic Acid

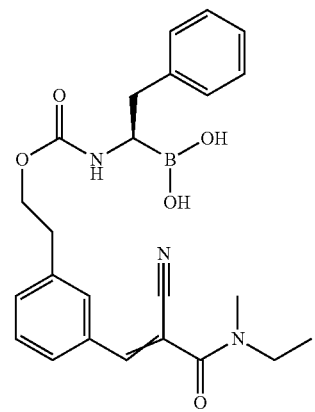 [SMILES: CCN(C)C(=O)C(C#N)=Cc1cccc(CCOC(=O)N[C@@H](Cc2ccccc2)B(O)O)c1]

The title compound was prepared as in example 17 by replacing dimethylamine with N-methylethanamine. LC-MS m/z: 472 [M+23].

Example 91

(R)-(1-(((3-(2-cyano-3-(methyl(2,2,2-trifluoroethyl)amino)-3-oxoprop-1-en-1-yl)phenethoxy)carbonyl)amino)-2-phenylethyl)boronic Acid

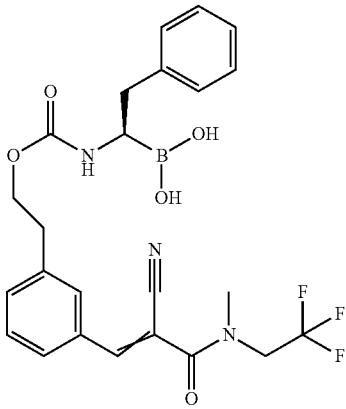 [SMILES: CN(CC(F)(F)F)C(=O)C(C#N)=Cc1cccc(CCOC(=O)N[C@@H](Cc2ccccc2)B(O)O)c1]

The title compound was prepared as in example 17 by replacing dimethylamine with N-methylethanamine. LC-MS m/z: 486 [M−17].

Example 92

((R)-1-(((3-(2-cyano-3-((3S,5S)-3,5-dimethylmorpholino)-3-oxoprop-1-en-1-yl)phenethoxy)carbonyl)amino)-2-(p-tolyl)ethyl)boronic Acid

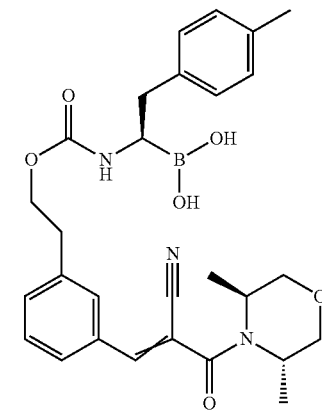

The title compound was prepared as in example 68 by replacing (1R)-2-phenyl-1-[(1S,2S,6R,8S)-2,9,9-trimethyl-3,5-dioxa-4-boratricyclo[6.1.1.0^[2,6]]decan-4-yl]ethan-1-amine hydrochloride with (R)-1-(4,4,5,5-tetramethyl-1,3,2-dioxaborolan-2-yl)-2-(p-tolyl)ethanamine hydrochloride. LC-MS m/z: 542 [M+23].

Example 93

(R)-(2-(benzofuran-3-yl)-1-(((3-(2-cyano-3-(3,3-dimethylmorpholino)-3-oxoprop-1-en-1-yl)phenethoxy)carbonyl)amino)ethyl)boronic Acid

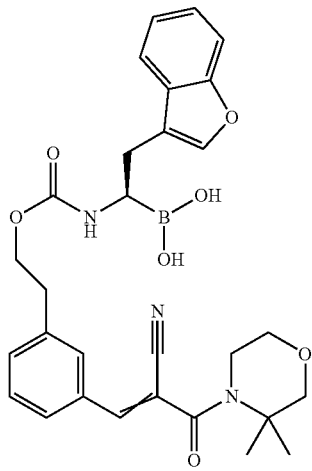 [SMILES: CC1(C)COCCN1C(=O)C(C#N)=Cc1cccc(CCOC(=O)N[C@@H](Cc2coc3ccccc23)B(O)O)c1]

The title compound was prepared as in example 79 by replacing (R)-1-(4,4,5,5-tetramethyl-1,3,2-dioxaborolan-2-yl)-2-(p-tolyl)ethanamine hydrochloride with (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine hydrochloride. LC-MS m/z: 568 [M+23].

Example 94

(R)-(2-(benzofuran-3-yl)-1-(3-(3-(2-cyano-2-(pyrimidin-2-yl)vinyl)phenethyl)ureido)ethyl)boronic Acid

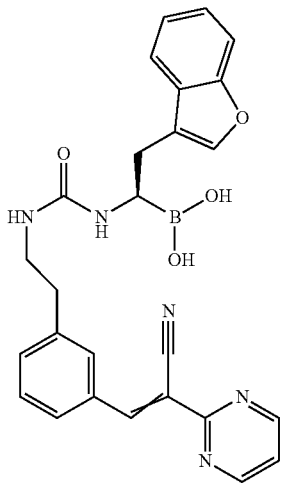 [SMILES: N#CC(=Cc1cccc(CCNC(=O)N[C@@H](Cc2coc3ccccc23)B(O)O)c1)c1ncccn1]

The title compound was prepared as in example 83 by replacing (R)-1-(4,4,5,5-tetramethyl-1,3,2-dioxaborolan-2-yl)-2-(p-tolyl)ethanamine hydrochloride with (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine hydrochloride. LC-MS m/z: 489 [M+23].

Example 95

(R)-(2-(benzofuran-3-yl)-1-(((3-(2-cyano-3-(ethyl(tetrahydro-2H-pyran-4-yl)amino)-3-oxoprop-1-en-1-yl)phenethoxy)carbonyl)amino)ethyl)boronic Acid

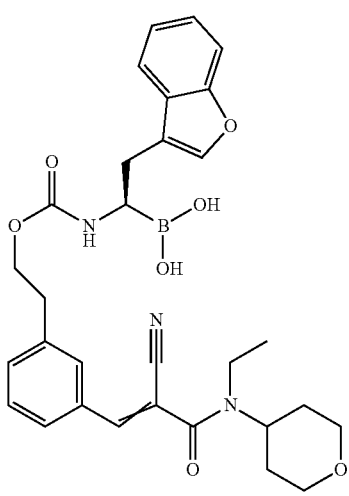 [SMILES: CCN(C(=O)C(C#N)=Cc1cccc(CCOC(=O)N[C@@H](Cc2coc3ccccc23)B(O)O)c1)C1CCOCC1]

The title compound was prepared as in example 88 by replacing (R)-1-(4,4,5,5-tetramethyl-1,3,2-dioxaborolan-2-yl)-2-(p-tolyl)ethanamine hydrochloride with (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine hydrochloride. LC-MS m/z: 556 [M+23].

Example 96

(R)-(2-(benzofuran-3-yl)-1-(3-(3-(2-cyano-3-(diethylamino)-3-oxoprop-1-en-1-yl)phenethyl)ureido)ethyl)boronic Acid

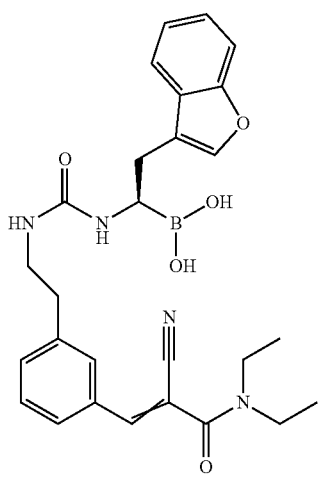 [SMILES: CCN(CC)C(=O)C(C#N)=Cc1cccc(CCNC(=O)N[C@@H](Cc2coc3ccccc23)B(O)O)c1]

The title compound was prepared as in example 61 by replacing (R)-1-(4,4,5,5-tetramethyl-1,3,2-dioxaborolan-2- yl)-2-(p-tolyl)ethanamine hydrochloride with (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine hydrochloride. LC-MS m/z: 459 [M−17].

Example 97

(R)-(2-(benzofuran-3-yl)-1-(((3-cyano-5-(2-cyano-3-(diethylamino)-3-oxoprop-1-en-1-yl)phenethoxy)carbonyl)amino)ethyl)boronic Acid

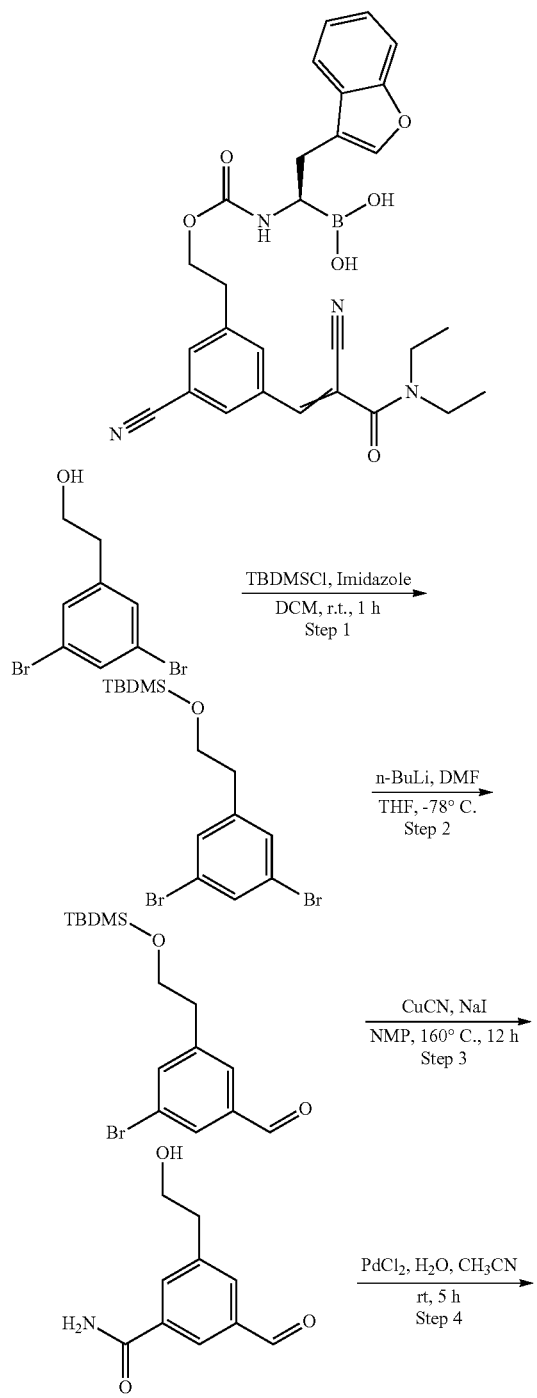

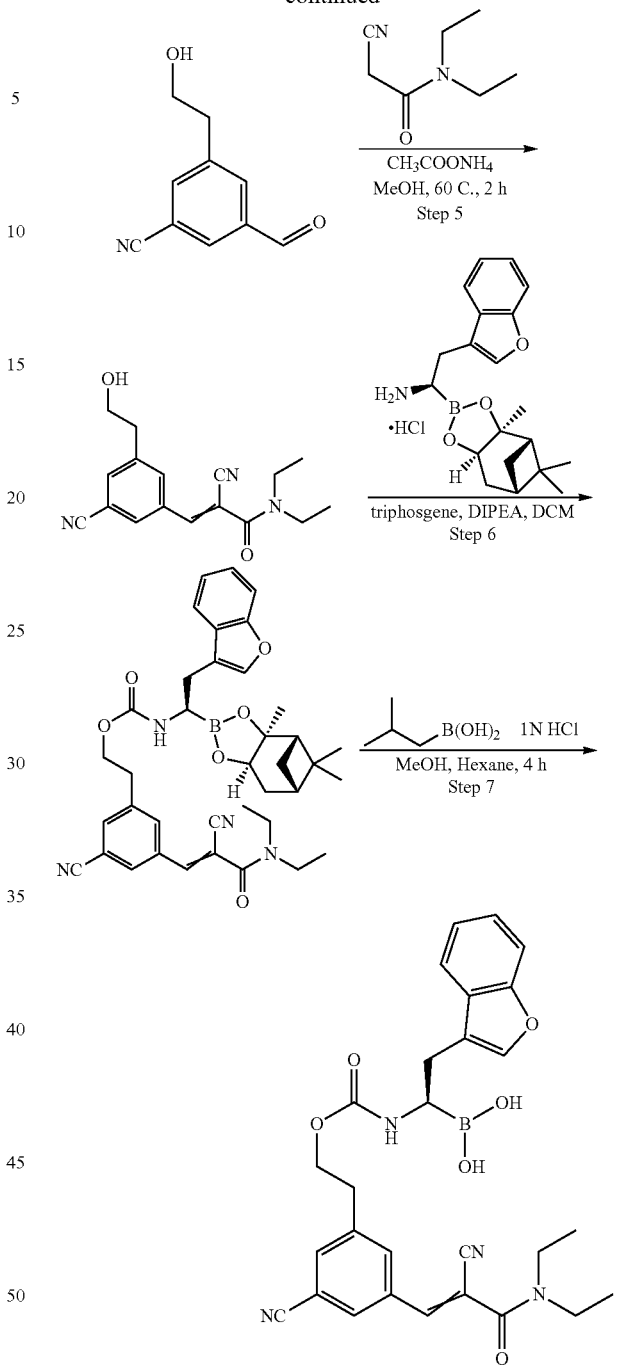

To a solution of 2-(3,5-dibromophenyl)ethan-1-ol (5 g, 17.9 mmol) and imidazole (1.46 g, 21.4 mmol) in DCM (50 mL), was added dropwise TBSCl (3.2 g, 21.4 mmol) in DCM (50 mL) at rt. The reaction was stirred at rt for 1 h. Then quenched with water (50 mL) and the organic layer was dried over Na2SO4, filtered and concentrated to afford the title compound as a colorless oil (6 g, 85%).

A mixture of tert-butyl(3,5-dibromophenethoxy)dimethylsilane (3 g, 7.61 mmol) in THF (30 mL), was added dropwise n-BuLi (3.17 mL, 7.61 mmol) at −78° C. The reaction was stirred at −78° C. for 30 min. The DMF (0.56 g, 7.61 mmol) was added and stirred at −78° C. for 2 h. Then quenched with a saturated solution of ammonium chloride and the aqueous portion was extracted with EtOAc (50 mL). The combined extracts was washed with brine (20 mL), dried over Na$_2$SO$_4$, filtered and concentrated in vacuo. The crude residue was purified by silica gel chromatography (EtOAc/PE=2/3 as eluent) to afford the title compound as a colorless oil (1.5 g, 58%).

A mixture of 3-bromo-5-(2-((tert-butyldimethylsilyl)oxy) ethyl)benzaldehyde (2 g, 5.83 mmol), CuCN (2.61 g, 29 mmol) and NaI (44 mg, 0.29 mmol) in NMP (20 mL), was stirred at 160° C. for 24 h. Concentrated in vacuo. The crude residue was purified by silica gel chromatography (Methanol/DCM=0-10% as eluent) to afford the title compound as a yellow gum (420 mg, 37%).

A mixture of 3-formyl-5-(2-hydroxyethyl)benzamide (420 mg, 2.17 mmol) and PdCl$_2$ (19 mg, 0.108 mmol) in acetonitrile (2 mL) and water (2 mL), was stirred at rt for 12 h. Concentrated. The crude residue was purified by silica gel chromatography (EtOAc:PE=5:1 as eluent) to afford the title compound as a yellow gum (250 mg, 66%).

A mixture of 3-formyl-5-(2-hydroxyethyl)benzonitrile (315 mg, 1.8 mmol), 2-cyano-N,N-diethylacetamide (252 mg, 1.8 mmol) and ammonium acetate (693 mg, 9 mmol) in methanol (10 mL) was stirred at reflux temperature for 4 h. Cooled and concentrated. The residue was diluted with EtOAc (50 mL), and washed with water (50 mL) and brine (50 mL). The organic layers were dried over Na2SO4 and concentrated. The crude residue was purified by silica gel chromatography to afford the title compound as a yellow gum (210 mg, 49%).

Bis(trichloromethyl) carbonate (209 mg, 0.706 mmol) in DCM (4 mL) was added to a stirred solution of 2-cyano-3-(3-cyano-5-(2-hydroxyethyl)phenyl)-N,N-diethylacrylamide 210 mg, 0.706 mmol) and DIPEA (546 mg, 0.424 mmol) in DCM (10 mL) at 0° C., the resultant reaction was stirred for 1 h at 0° C. before next step use.

The reaction solution was added dropwise into a well-stirred solution of (R)-2-(benzofuran-3-yl)-1-((3aS,4S,6S,7aR)-3a,5,5-trimethylhexahydro-4,6-methanobenzo[d][1,3,2]dioxaborol-2-yl)ethan-1-amine hydrochloride (265 mg, 0.706 mmol) and DIPEA (182 mg, 1.41 mmol) in DCM (10 mL) at 0° C. The reaction was stirred at rt for 1 h, then washed with water (20 mL) and brine (20 mL), the organic extracts were dried over Na2SO4 and concentrated in vacuo. The crude material was purified by prep-HPLC to afford the title compound as a white solid (70 mg, 15%).

To a solution of 3-(2-cyano-3-(ethyl(tetrahydro-2H-pyran-4-yl)amino)-3-oxoprop-1-en-1-yl)phenethyl ((R)-2-(benzofuran-3-yl)-1-((3aS,4S,6S,7aR)-3a,5,5,7a-tetramethylhexahydro-4,6-methanobenzo[d][1,3,2]dioxaborol-2-yl) ethyl)carbamate (70 mg, 0.106 mmol) in MeOH (2 mL) were added hexane (2 mL) and 1 N HCl (1 mL), followed by isobutyl boric acid (32 mg, 0.317 mmol). After stirring at rt for 3 h and TLC suggested the reaction was completed, the hexane layer was discarded. The methanol layer was diluted with water (10 mL), then dried over lyophilizer to give a crude product which was further purified by neutral Al2O3 column (Methanol/DCM=0-10% as eluent) to afford (R)-(2-(benzofuran-3-yl)-1-(((3-cyano-5-(2-cyano-3-(diethylamino)-3-oxoprop-1-en-1-yl)phenethoxy)carbonyl)amino) ethyl)boronic acid as a white solid (33 mg, 57%). LC-MS m/z: 511 [M−17].

Example 98

((R)-2-(benzofuran-3-yl)-1-(((3-(2-cyano-3-((3R, 5R)-3,5-dimethylmorpholino)-3-oxoprop-1-en-1-yl) phenethoxy)carbonyl)amino)ethyl)boronic Acid

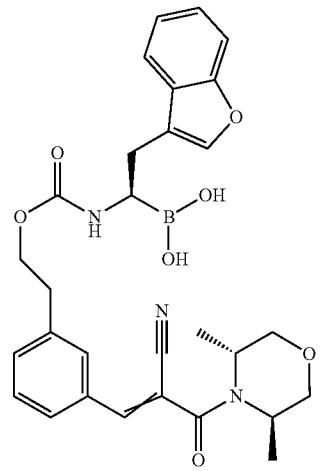 [SMILES: C[C@@H]1COC[C@@H](C)N1C(=O)C(C#N)=Cc1cccc(CCOC(=O)N[C@@H](Cc2coc3ccccc23)B(O)O)c1]

The title compound was prepared as in example 85 by replacing (R)-1-(4,4,5,5-tetramethyl-1,3,2-dioxaborolan-2-yl)-2-(p-tolyl)ethanamine hydrochloride with (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine hydrochloride. LC-MS m/z: 568 [M+23].

Example 99

(R)-(1-(((3-(2-cyano-2-(1H-1,2,4-triazol-1-yl)vinyl) phenethoxy)carbonyl)amino)-2-phenylethyl)boronic Acid

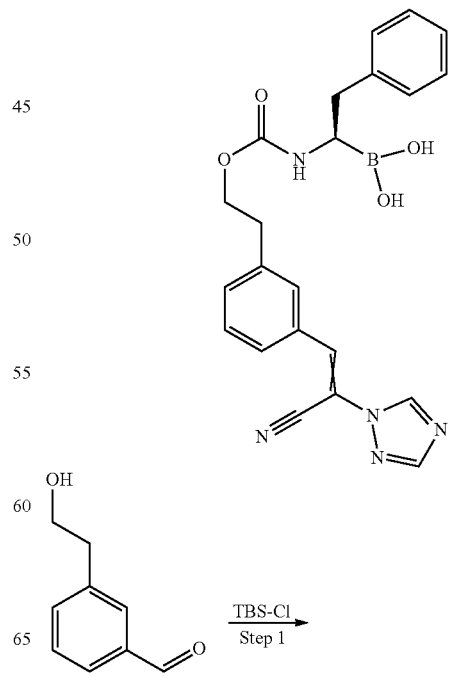

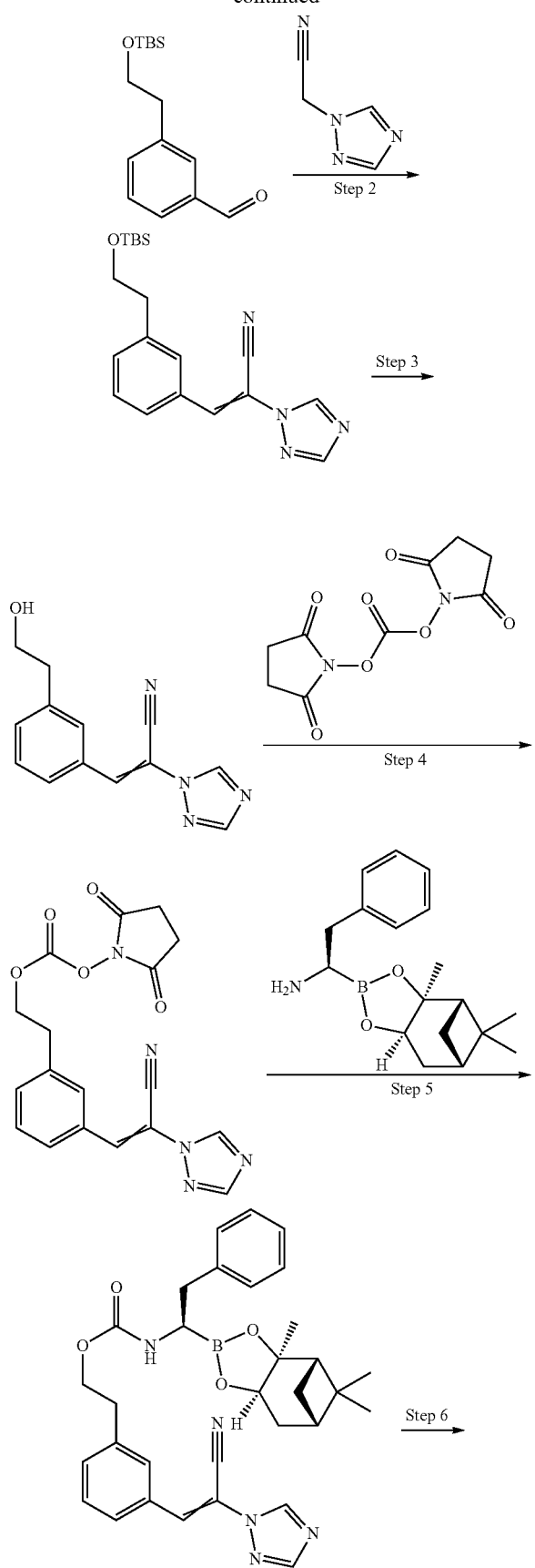

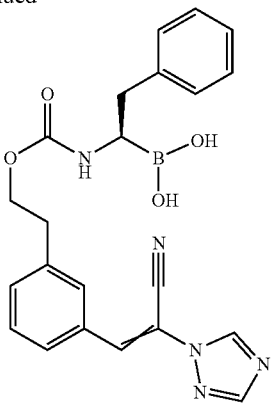

To the solution of 3-(2-hydroxyethyl)benzaldehyde (2000.00 mg, 13.32 mmol), DCM (50 mL), Imidazole (1088.05 mg, 15.98 mmol) was added tert-butyldimethylsilyl chloride (3010.99 mg, 19.98 mmol). The result was stirred at rt for 2 h. The reaction mixture was worked up with water (50 mL) and DCM (50 mL) then dried with MgSO4. The concentrated crude was purified by silica gel chromatography (0-10% EtOAc/Hex, 400 mL) to obtain 3-[2-[tert-butyl(dimethyl)silyl]oxyethyl]benzaldehyde (2379 mg, 8.99 mmol) with, 67.5% yield as clear oil. LC-MS m/z: 280 [M+16].

To the solution of 3-[2-[tert-butyl(dimethyl)silyl]oxyethyl]benzaldehyde (1223.00 mg, 4.62 mmol), Toluene (2.5 mL), Triethylamine (1.95 mL, 13.87 mmol) was added 2-(1H-1,2,4-Triazol-1-yl)acetonitrile (874.91 mg, 8.09 mmol). The resulted mixture was microwaved at 150 degrees for 3 h. LCMS was shown some product and still had some remained starting material. The reaction mixture was worked up with water (50 mL) and DCM (50 mL×2). The organic layer was brined and dried with MgSO4. The concentrated crude was purified by prep HPLC Shimadzu to obtain 3-[3-[2-[tert-butyl(dimethyl)silyl]oxyethyl]phenyl]-2-(1,2,4-triazol-1-yl)prop-2-enenitrile (120.00 mg) with 7.3% yield. LC-MS m/z: 355[M+1].

To the solution of 3-[3-[2-[tert-butyl(dimethyl)silyl]oxyethyl]phenyl]-2-(1,2,4-triazol-1-yl)prop-2-enenitrile (108.0 mg, 0.30 mmol), THF (2.5 mL) was added Tetra-n-butylammonium fluoride 1M in THF (0.53 mL, 0.53 mmol). The result was stirred at rt for 3 h. The reaction mixture was worked up with water (30 mL) and DCM (30 mL×2). The organic layer was brined and dried with MgSO4. The concentrated crude was purified by prep TLC with 10% MeOH/DCM to obtain 3-[3-(2-hydroxyethyl)phenyl]-2-(1,2,4-triazol-1-yl)prop-2-enenitrile (63 mg) with 86.1% yield. LC-MS m/z: 241 [M+1].

To the solution of 3-[3-(2-hydroxyethyl)phenyl]-2-(1,2,4-triazol-1-yl)prop-2-enenitrile (63.0 mg, 0.260 mol), Triethylamine (26.53 mg, 0.26 mmol), THF (1 mL) was added bis(2,5-dioxopyrrolidin-1-yl) carbonate (0.34 mL, 0.34 mmol). The result was stirred at rt for 30 minutes. The reaction was completed by checking TLC and LCMS. The reaction mixture was worked up with water (2 mL) and DCM (5 mL) and organic layer was dried with MgSO4. The concentrated crude was purified prep-TLC (EtOAc) and collected 2-[3-[2-cyano-2-(1,2,4-triazol-1-yl)vinyl]phenyl]ethyl (2,5-dioxopyrrolidin-1-yl) carbonate (63.0 mg) with 63.0% yield as foam after hi-vac. LC-MS m/z: 382[M+1].

To the solution of 2-[3-[2-cyano-2-(1,2,4-triazol-1-yl)vinyl]phenyl]ethyl (2,5-dioxopyrrolidin-1-yl) carbonate (42.0 mg, 0.11 mmol), Triethylamine (0.03 mL, 0.22 mmol), DCM (1 mL) was added (1R)-2-phenyl-1-[(1S,2S,6R,8S)-2,9,9-trimethyl-3,5-dioxa-4-boratricyclo[6.1.1.0ˆ[2,6]]decan-4-yl]ethan-1-amine hydrochloride (0.14 mL, 0.1400 mmol). The result was stirred at rt for 5 minutes. the mixture was concentrated and prepped TLC (30% EtOAc/Hex) to obtain 2-[3-[2-cyano-2-(1,2,4-triazol-1-yl)vinyl]phenyl] ethyl N-[(1R)-2-phenyl-1-[(26S,27S,28R,33S)-32,32,33-trimethyl-40,41-dioxa-1-boratricyclo[6.1.1.0ˆ[2,6]]]decan-1-yl]ethyl]carbamate (22.0 mg) with 35.3% yield. LC-MS m/z: 564 [M−1].

To the solution of 2-[3-[2-cyano-2-(1,2,4-triazol-1-yl)vinyl]phenyl]ethyl N-[(1R)-2-phenyl-1-[(26S,27S,28R,33S)-32,32,33-trimethyl-40,41-dioxa-1-boratricyclo[6.1.1.0ˆ[2,6]]]decan-1-yl]ethyl]carbamate (22.0 mg, 0.04 mmol), 1N HCl (0.5 mL), Methanol (0.5 mL), Hexane (0.5 mL) was added isobutylboronic acid (5.16 mg, 0.05 mmol). The result was stirred at rt for 30 minutes. The mixture was concentrated and prepped by Aluminum Oxide (12% MeOH/DCM). The prep fraction was collected and lyophilized to obtain (R)-(1-(((3-(2-cyano-2-(1H-1,2,4-triazol-1-yl)vinyl) phenethoxy)carbonyl)amino)-2-phenylethyl)boronic acid (7.0 mg) with 41.7% yield. LC-MS m/z: 414 [M−17].

Example 100

(R)-(2-(benzofuran-3-yl)-1-(3-(3-(2-cyano-3-(ethyl (tetrahydro-2H-pyran-4-yl)amino)-3-oxoprop-1-en-1-yl)phenethyl)ureido)ethyl)boronic Acid

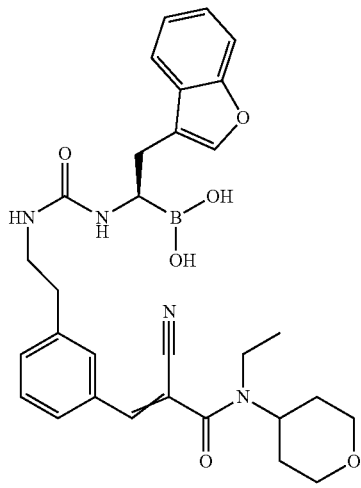 [SMILES: CCN(C(=O)C(C#N)=Cc1cccc(CCNC(=O)N[C@@H](Cc2coc3ccccc23)B(O)O)c1)C1CCOCC1]

The title compound was prepared as in example 96 by replacing diethylamine with N-ethyl-tetrahydro-2H-pyran-4-amine. LC-MS m/z: 541 [M−17].

Example 101

(R)-(1-(((3-cyano-5-(2-cyano-3-(diethylamino)-3-oxoprop-1-en-1-yl)phenethoxy)carbonyl)amino)-2-(p-tolyl)ethyl)boronic Acid

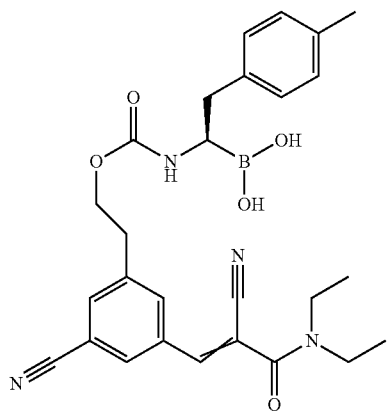 [SMILES: CCN(CC)C(=O)C(C#N)=Cc1cc(C#N)cc(CCOC(=O)N[C@@H](Cc2ccc(C)cc2)B(O)O)c1]

The title compound was prepared as in example 97 by replacing (R)-2-(benzofuran-3-yl)-1-((3aS,4S,6S,7aR)-3a,5,5-trimethylhexahydro-4,6-methanobenzo[d][1,3,2]dioxaborol-2-yl)ethan-1-amine hydrochloride with (R)-1-(4,4,5,5-tetramethyl-1,3,2-dioxaborolan-2-yl)-2-(p-tolyl) ethanamine hydrochloride. LC-MS m/z: 485 [M−17].

Example 102

(R)-(1-(((3-cyano-5-(2-cyano-3-(ethyl(tetrahydro-2H-pyran-4-yl)amino)-3-oxoprop-1-en-1-yl) phenethoxy)carbonyl)amino)-2-phenylethyl)boronic Acid

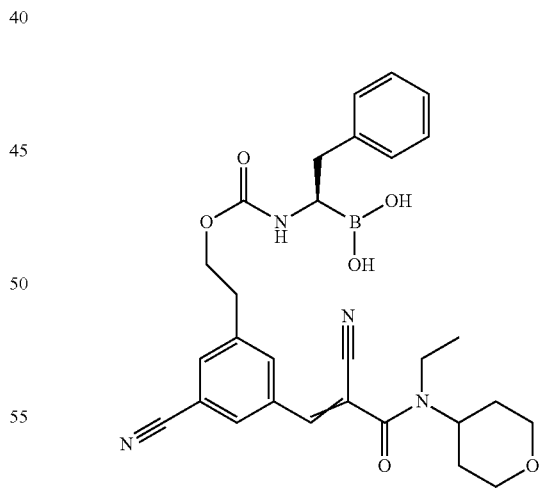

The title compound was prepared as in example 97 by replacing diethylamine with N-ethyl-tetrahydro-2H-pyran-4-amine and (R)-2-(benzofuran-3-yl)-1-((3aS,4S,6S,7aR)-3a,5,5-trimethylhexahydro-4,6-methanobenzo[d][1,3,2]dioxaborol-2-yl)ethan-1-amine hydrochloride with (1R)-2-phenyl-1-[(1S,2S,6R,8S)-2,9,9-trimethyl-3,5-dioxa-4-boratricyclo[6.1.1.0ˆ[2,6]]decan-4-yl]ethan-1-amine hydrochloride. LC-MS m/z: 527 [M−17].

Example 103

(R)-(1-(((3-cyano-5-(2-cyano-3-(ethyl(tetrahydro-2H-pyran-4-yl)amino)-3-oxoprop-1-en-1-yl)phenethoxy)carbonyl)amino)-2-(p-tolyl)ethyl)boronic Acid

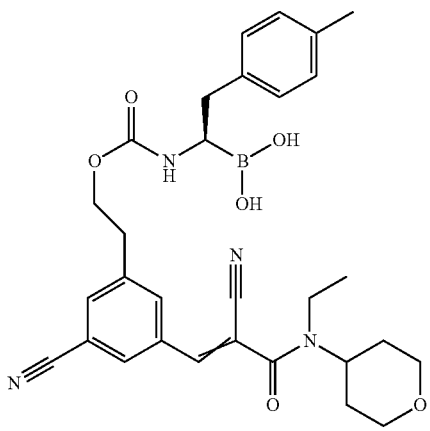 [SMILES: CCN(C(=O)C(C#N)=Cc1cc(C#N)cc(CCOC(=O)N[C@@H](Cc2ccc(C)cc2)B(O)O)c1)C1CCOCC1]

The title compound was prepared as in example 97 by replacing diethylamine with N-ethyl-tetrahydro-2H-pyran-4-amine and (R)-2-(benzofuran-3-yl)-1-((3aS,4S,6S,7aR)-3a,5,5-trimethylhexahydro-4,6-methanobenzo[d][1,3,2]dioxaborol-2-yl)ethan-1-amine hydrochloride with (R)-1-(4,4,5,5-tetramethyl-1,3,2-dioxaborolan-2-yl)-2-(p-tolyl)ethanamine hydrochloride. LC-MS m/z: 541 [M−17].

Example 104

(R)-(1-(((3-cyano-5-(2-cyano-3-(diethylamino)-3-oxoprop-1-en-1-yl)phenethoxy)carbonyl)amino)-2-phenylethyl)boronic Acid

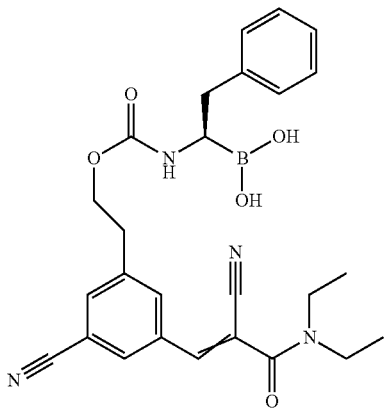 [SMILES: CCN(CC)C(=O)C(C#N)=Cc1cc(C#N)cc(CCOC(=O)N[C@@H](Cc2ccccc2)B(O)O)c1]

The title compound was prepared as in example 97 by replacing (R)-2-(benzofuran-3-yl)-1-((3aS,4S,6S,7aR)-3a,5,5-trimethylhexahydro-4,6-methanobenzo[d][1,3,2]dioxaborol-2-yl)ethan-1-amine hydrochloride with (1R)-2-phenyl-1-[(1S,2S,6R,8S)-2,9,9-trimethyl-3,5-dioxa-4-boratricyclo[6.1.1.0ˆ[2,6]]decan-4-yl]ethan-1-amine hydrochloride. LC-MS m/z: 541 [M−17].

Example 105

(R)-(2-(benzofuran-3-yl)-1-(2-(7-(2-cyano-3-(ethyl(tetrahydro-2H-pyran-4-yl)amino)-3-oxoprop-1-en-1-yl)-3,4-dihydroisoquinolin-2(1H)-yl)acetamido)ethyl)boronic Acid

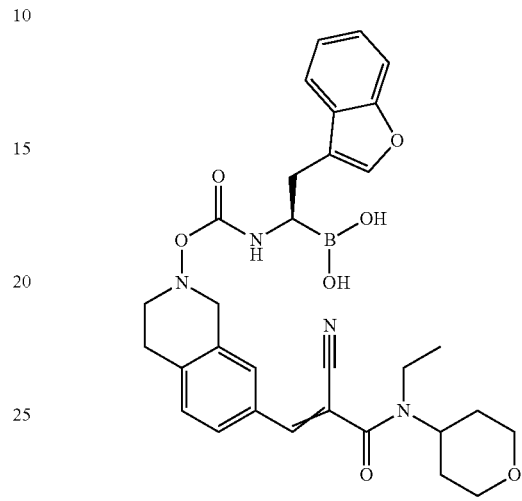

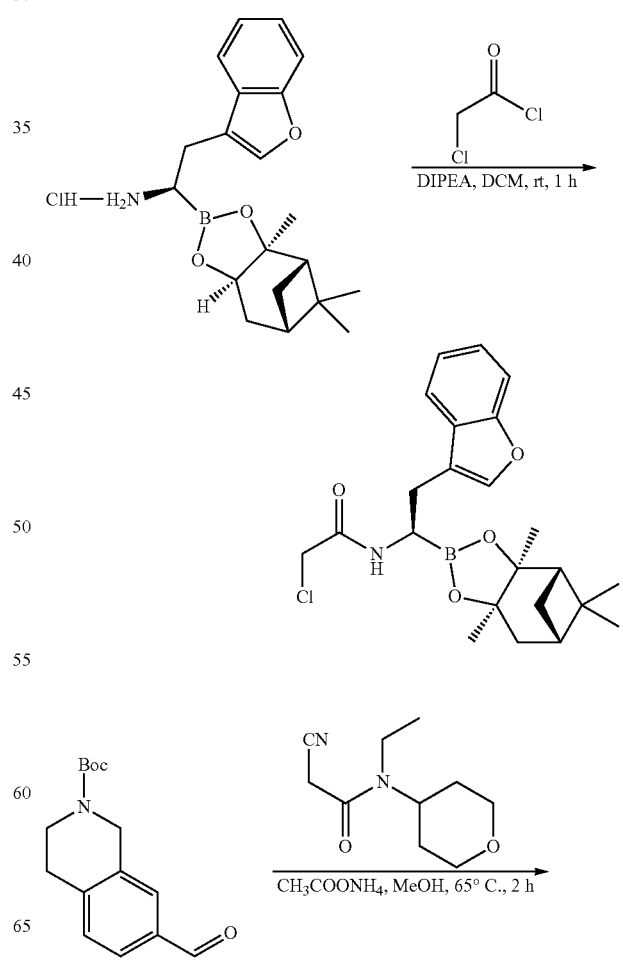

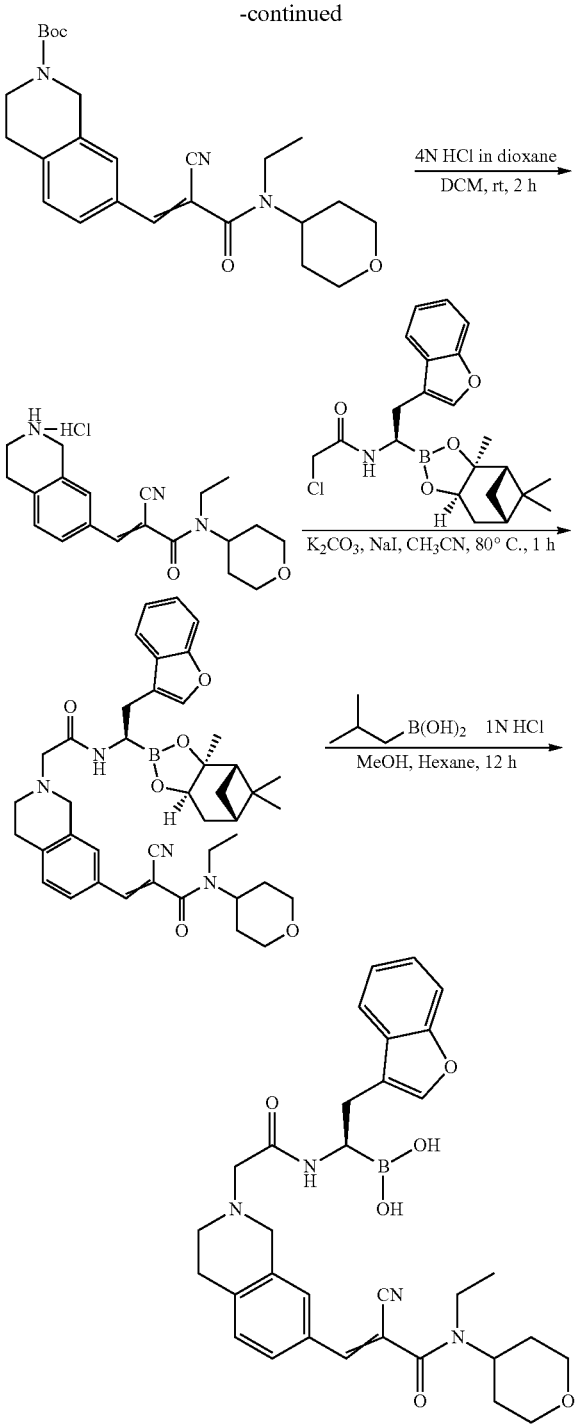

To a solution of ((R)-2-(benzofuran-3-yl)-1-((3aS,4S,6S,7aR)-3a,5,5-trimethylhexahydro-4,6-methanobenzo[d][1,3,2]dioxaborol-2-yl)ethan-1-amine hydrochloride (500 mg, 1.33 mmol) and DIPEA (343 mg, 2.66 mmol) in DCM (10 mL), was added dropwise 2-chloroacetyl chloride (150 mg, 1.33 mmol) at 0° C. The resultant reaction was stirred for 2 h at rt, then quenched with water (5 mL), the organic layer was dried over $Na_2SO_4$ and concentrated in vacuo. The crude material was purified by silica gel chromatography to afford 310 mg of N—((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)-2-chloroacetamide as a brown gum.

To a mixture of tert-butyl 7-formyl-3,4-dihydroisoquinoline-2(1H)-carboxylate (220 mg, 0.842 mmol), 2-cyano-N-ethyl-N-(tetrahydro-2H-pyran-4-yl)acetamide (165 mg, 0.842 mmol) and ammonium acetate (325 mg, 4.21 mmol) in methanol (5 mL) was stirred at reflux for 2 h. After cooling to rt, the mixture was concentrated to dryness. The residue was diluted with EtOAc (10 mL), washed with water (5 mL), followed by brine (5 mL). The organic layer was dried over $Na_2SO_4$ and concentrated to afford 320 mg of tert-butyl 7-(2-cyano-3-(ethyl(tetrahydro-2H-pyran-4-yl)amino)-3-oxoprop-1-en-1-yl)-3,4-dihydroisoquinoline-2(1H)-carboxylate as a yellow solid which was used in the next step directly.

A solution of tert-butyl 7-(2-cyano-3-(ethyl(tetrahydro-2H-pyran-4-yl)amino)-3-oxoprop-1-en-1-yl)-3,4-dihydroisoquinoline-2(1H)-carboxylate (320 mg, 0.728 mmol) and HCl (2 mL, 4 M in dioxane) in DCM (2 mL) was stirred at rt for 2 h, then concentrated to afford 260 mg of 2-cyano-N-ethyl-N-(tetrahydro-2H-pyran-4-yl)-3-(1,2,3,4-tetrahydroisoquinolin-7-yl)acrylamide hydrochloride as a colorless solid which was used directly in the next step.

A mixture of 2-cyano-N-ethyl-N-(tetrahydro-2H-pyran-4-yl)-3-(1,2,3,4-tetrahydroisoquinolin-7-yl)acrylamide hydrochloride (100 mg, 0.266 mmol), N—((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)-2-chloroacetamide (110 mg, 0.266 mmol), $K_2CO_3$ (74 mg, 0.532 mmol) and NaI (40 mg, 0.266 mmol) in CH3CN (5 mL) was stirred at 80° C. for 2 h. The mixture was cooled and concentrated in vacuo. To the residue was added water (10 mL) and EtOAc (10 mL). The organic layer was dried over $Na_2SO_4$, filtered and evaporated. The residue was purified by Prep-HPLC to afford 90 mg of 3-(2-(2-(((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)amino)-2-oxoethyl)-1,2,3,4-tetrahydroisoquinolin-7-yl)-2-cyano-N-ethyl-N-(tetrahydro-2H-pyran-4-yl)acrylamide as a yellow solid.

To a solution of 3-(2-(2-(((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)amino)-2-oxoethyl)-1,2,3,4-tetrahydroisoquinolin-7-yl)-2-cyano-N-ethyl-N-(tetrahydro-2H-pyran-4-yl)acrylamide (90 mg, 0.125 mmol) in MeOH (2 mL) were added hexane (2 mL) and 1 N HCl (1 mL), followed by isobutyl boronic acid (38 mg, 0.376 mmol). After stirring at rt for 3 h, the hexane layer was discarded, the methanol layer was diluted with water (10 mL) and freeze dried directly to give a crude product, that was purified with neutral $Al_2O_3$ column (Methanol/DCM=0-20% as eluent) to afford 23 mg of (R)-(2-(benzofuran-3-yl)-1-(2-(7-(2-cyano-3-(ethyl(tetrahydro-2H-pyran-4-yl)amino)-3-oxoprop-1-en-1-yl)-3,4-dihydroisoquinolin-2(1H)-yl)acetamido)ethyl)boronic acid as a yellow solid. LC-MS m/z: 585 [M+1].

Example 106

(R)-(1-(((3-(2-cyano-2-(1H-1,2,4-triazol-1-yl)vinyl)phenethoxy)carbonyl)amino)-3-phenylpropyl)boronic Acid

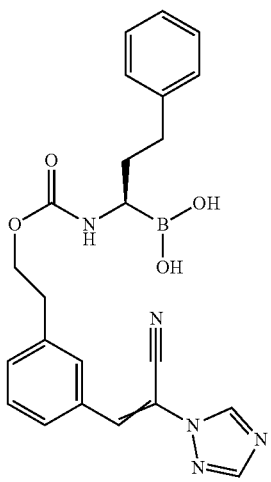

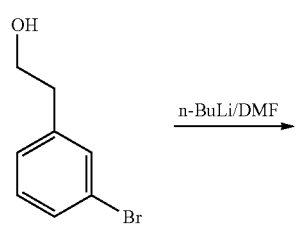

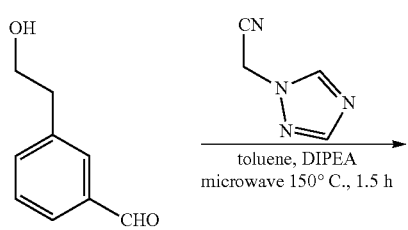

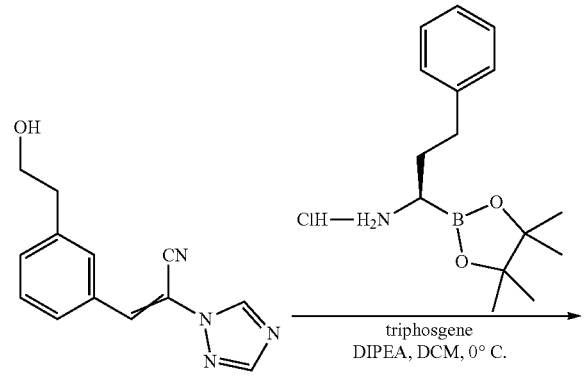

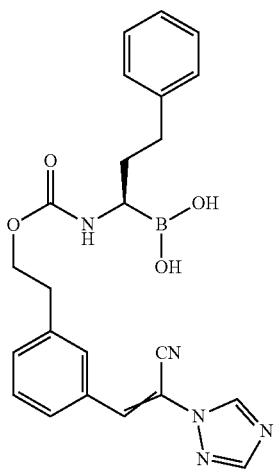

A mixture of n-butyl lithium (2.4 M solution in hexanes, 8.0 mL, 19.6 mmol) in anhydrous THF (20 mL) was cooled to −78° C. To this reaction mixture, N123-B160033-070-1 (1.0 g, 4.97 mmol) in THF (15 mL) was added dropwise at −78° C. and stirred at same temperature for 20 min. N,N-dimethylformamide (6 mL) was added dropwise at −78° C. and stirred at same temperature for 2 h. The reaction mixture was quenched with a saturated solution of ammonium chloride and the aqueous portion was extracted with ethyl acetate. The combined extracts were washed with brine, dried over magnesium sulfate, filtered and evaporated. The residue was purified by silica gel column chromatography using ethyl acetate:hexanes 2:3 as eluent to provide the desired compound. Colorless oil (580 mg, 78%).

To a 50 mL microwave vial with 3-(2-hydroxyethyl)benzaldehyde (620 mg, 4.13 mmol), 2-(1H-1,2,4-triazol-1-yl)acetonitrile (892.60 mg, 8.26 mmol) in toluene (8 mL). DIPEA (2.67 g, 20.64 mmol) was added and stirred at 150° C. in microwave. The crude residue was purified by flash column chromatography with DCM/MeOH to afford the title compound as oil (500 mg, 50%).

Bis(trichloromethyl) carbonate (284.08 mg, 0.96 mmol) in DCM (2 mL) was added to a stirred solution of 3-(3-(2-hydroxyethyl)phenyl)-2-(1H-1,2,4-triazol-1-yl)acrylonitrile (230 mg, 0.96 mmol) and DIPEA (618.62 mg, 4.79 mmol) in DCM (10 mL) at 0° C., the resultant reaction was stirred for 1 h at 0° C. before next step use.

The reaction solution was added dropwise into a well-stirred solution of (R)-3-phenyl-1-(4,4,5,5-tetramethyl-1,3,2-dioxaborolan-2-yl)propan-1-amine hydrochloride (284.14 mg, 0.96 mmol) and DIPEA (370.16 mg, 2.86 mmol) in DCM (5 mL) at 0° C. The reaction was stirred at rt for 1 h, then washed with water (10 mL) and brine (10 mL), the organic extracts were dried over $Na_2SO_4$ and concentrated in vacuo. The crude material was purified by prep-HPLC to afford the title compound as a white solid (18 mg, 4%). LC-MS m/z: 428 [M−17].

Example 107

(R)-(1-(3-(3-(2-cyano-2-(1H-1,2,4-triazol-1-yl)vinyl)phenethyl)ureido)-2-(p-tolyl)ethyl)boronic Acid

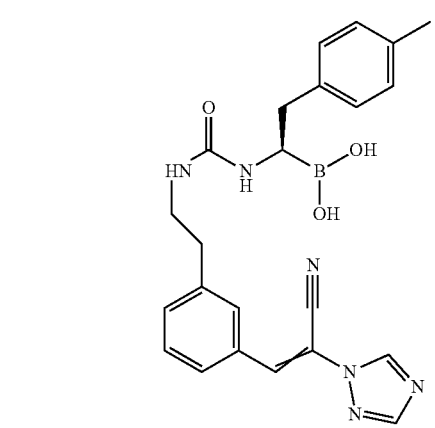

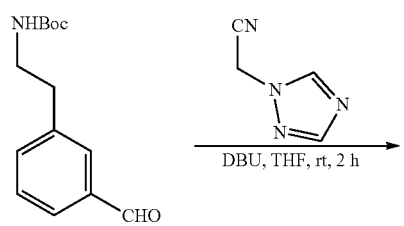

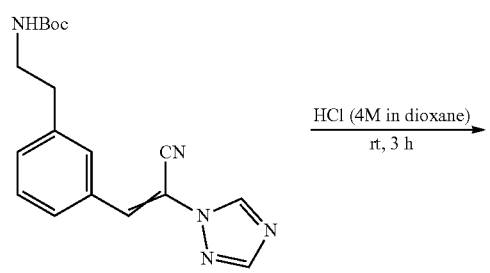

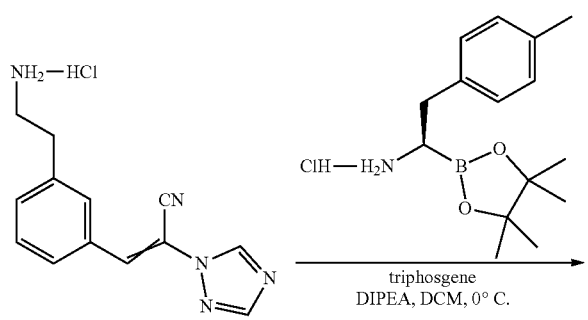

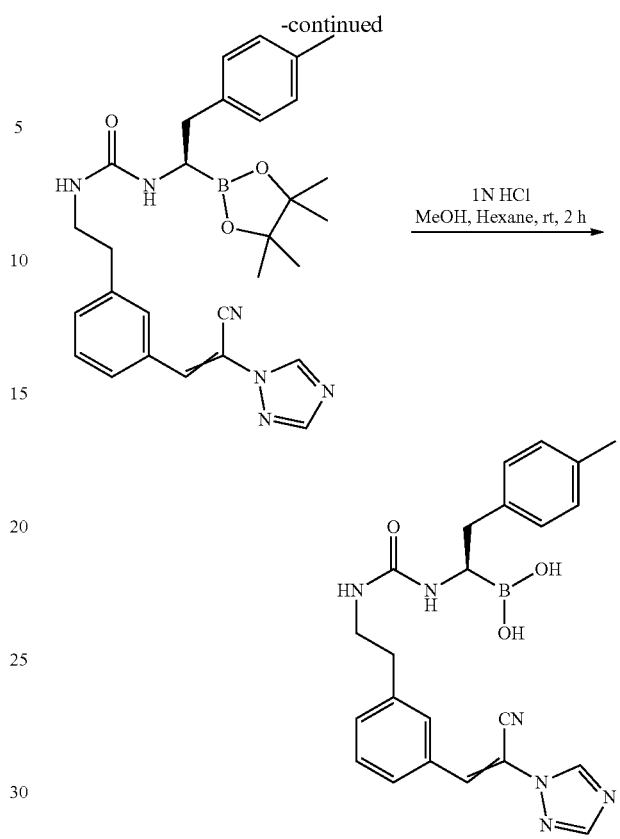

A mixture of tert-butyl 3-formylphenethylcarbamate (1 g, 4 mmol), 2-(1H-1,2,4-triazol-1-yl)acetonitrile (434 mg, 4 mmol) and DBU (610 mg, 4 mmol) in anhydrous THF (10 mL) was stirred at rt for 4 h. The mixture was concentrated to dryness. The residue was purified via silica chromatography and a gradient of 10%-60% EtOAc in Hexanes to afford the title compound as yellow oil (500 mg, 36%).

A mixture of tert-butyl (3-(2-cyano-2-(1H-1,2,4-triazol-1-yl)vinyl)phenethyl)carbamate (500 mg, 1.47 mmol) and HCl/dioxane (4 M, 4 mL) in DCM (4 mL) was stirred at rt for 2 h, then concentrated to dryness over high vacuum to afford the title compound (388 mg, 96%).

A solution of Bis(trichloromethyl) carbonate (154 mg, 0.518 mmol) in DCM (0.6 mL) was added dropwise into a stirring solution of (R)-1-(4,4,5,5-tetramethyl-1,3,2-dioxaborolan-2-yl)-2-(p-tolyl)ethan-1-amine hydrochloride (220 mg, 0.74 mmol) and DIPEA (573 mg, 4.44 mmol) in DCM (6 mL) at 0° C. The mixture was stirred for 1 h at 0° C. This resulted solution was added dropwise into a well-stirred solution of 3-(3-(2-aminoethyl)phenyl)-2-(1H-1,2,4-triazol-1-yl)acrylonitrile hydrochloride (204 mg, 0.74 mmol) and DIPEA (573 mg, 4.44 mmol) in DCM (6 mL) at 0° C. The reaction was stirred at rt for 1 h, then poured into water (20 mL) and brine (20 mL), the organic extracts was dried over Na2SO4, and concentrated in vacuo. The crude residue was purified by Prep-HPLC to afford the title compound as a white solid (110 mg, 29%).

To a solution of (R)-1-(3-(2-cyano-2-(1H-1,2,4-triazol-1-yl)vinyl)phenethyl)-3-(2-(4-methylcyclohexa-1,3-dien-1-yl)-1-(4,4,5,5-tetramethyl-1,3,2-dioxaborolan-2-yl)ethyl)urea (110 mg, 0.209 mmol) in MeOH (2 mL) were added hexanes (2 mL) and 1N HCl (1 mL). After stirred at rt for 3 h and LCMS suggested the reaction was completed, the hexanes layer was discarded. The methanol layer was diluted with water (10 mL), then dried over lyophilization to give a crude product which was purified by neutral Al₂O₃ column (Methanol/DCM=0-20% as eluent) to afford the title compound as a white solid (28 mg, 30%). LC-MS m/z: 428 [M−17].

Example 108

(R)-(1-(2-(7-(2-cyano-3-(diethylamino)-3-oxoprop-1-en-1-yl)-3,4-dihydroisoquinolin-2(1H)-yl)acetamido)-2-(p-tolyl)ethyl)boronic Acid

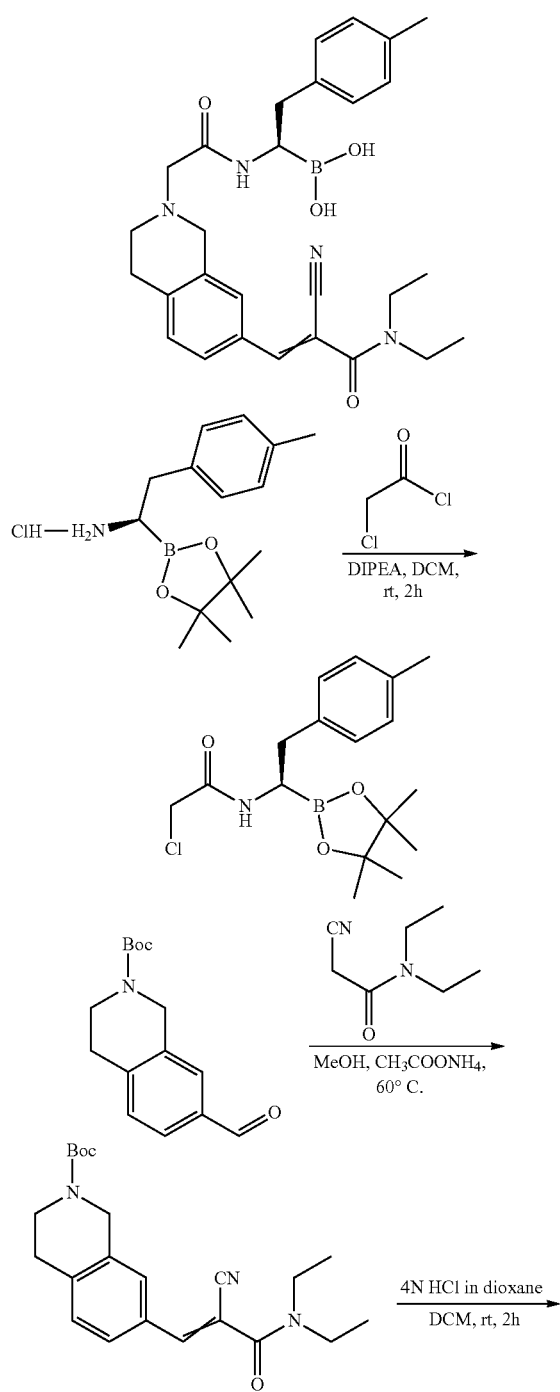

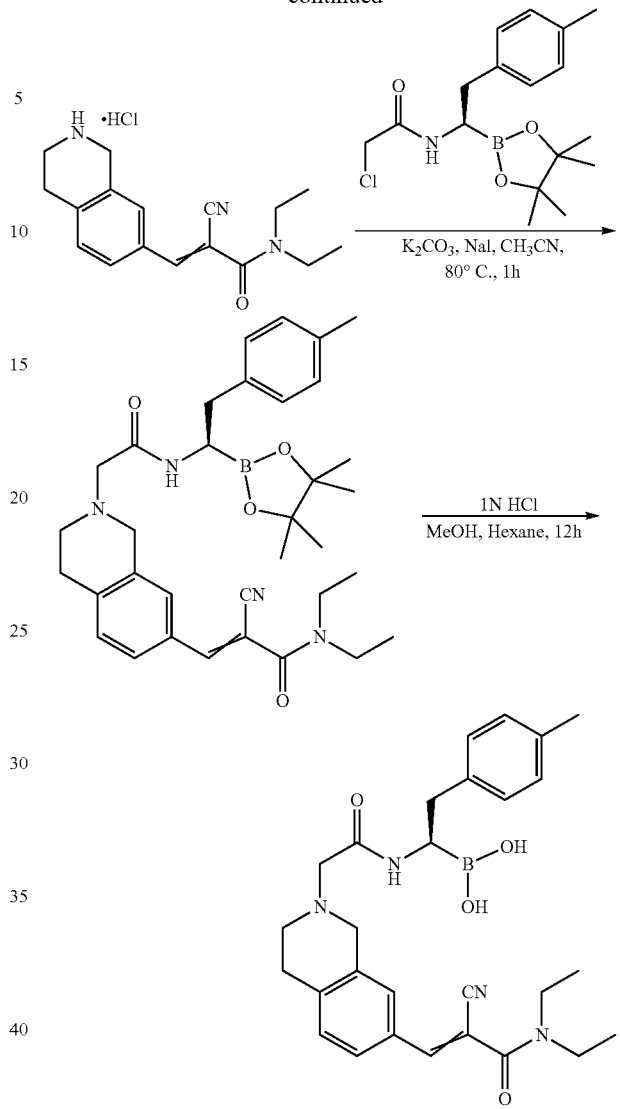

To a solution of (R)-1-(4,4,5,5-tetramethyl-1,3,2-dioxaborolan-2-yl)-2-(p-tolyl)ethan-1-amine hydrochloride (650 mg, 2.18 mmol) and DIPEA (564 mg, 4.37 mmol) in DCM (10 mL), was added dropwise 2-chloroacetyl chloride (247 mg, 2.18 mmol) at 0° C. The resultant reaction was stirred for 2 h at rt, then quenched with water (5 mL), the organic layer was dried over Na₂SO₄ and concentrated in vacuo. The crude material was purified by silica gel chromatography to afford 180 mg of (R)-2-chloro-N-(1-(4,4,5,5-tetramethyl-1,3,2-dioxaborolan-2-yl)-2-(p-tolyl)ethyl)acetamide as a brown gum.

To a mixture of tert-butyl 7-formyl-3,4-dihydroisoquinoline-2(1H)-carboxylate (1 g, 3.83 mmol), 2-cyano-N,N-diethylacetamide (536 mg, 3.83 mmol) and ammonium acetate (1.47 g, 19.13 mmol) in methanol (10 mL) was stirred at reflux for 2 h. After cooling to rt, the mixture was concentrated to dryness. The residue was diluted with EtOAc (40 mL), washed with water (40 mL), followed by brine (40 mL). The organic layer was dried over Na₂SO₄ and concentrated. The crude residue was purified by silica gel chromatography to afford 800 mg of tert-butyl 7-(2-cyano-3-(diethylamino)-3-oxoprop-1-en-1-yl)-3,4-dihydroisoquinoline-2(1H)-carboxylate as a yellow gum.

A solution of tert-butyl 7-(2-cyano-3-(diethylamino)-3-oxoprop-1-en-1-yl)-3,4-dihydroisoquinoline-2(1H)-carboxylate (800 mg, 2.09 mmol) and HCl (5 mL, 4 M in dioxane) in DCM (5 mL) was stirred at rt for 2 h, then concentrated to afford 600 mg of 2-cyano-N, N-diethyl-3-(1,2,3,4-tetrahydroisoquinolin-7-yl)acrylamide hydrochloride as a colorless solid which was used directly in the next step.

A mixture of 2-cyano-N, N-diethyl-3-(1,2,3,4-tetrahydroisoquinolin-7-yl)acrylamide hydrochloride (300 mg, 0.938 mmol), (R)-2-chloro-N-(1-(4,4,5,5-tetramethyl-1,3,2-dioxaborolan-2-yl)-2-(p-tolyl)ethyl)acetamide (317 mg, 0.938 mmol), $K_2CO_3$ (259 mg, 1.88 mmol) and NaI (141 mg, 0.938 mmol) in $CH_3CN$ (5 mL) was stirred at 80° C. for 2 h. Cooled, concentrated. The residue was added water (5 mL) and EtOAc (10 mL). The organic layer was dried over $Na_2SO_4$, filtered and evaporated. The residue was purified with neutral $Al_2O_3$ column (Methanol/DCM=0-20% as eluent) to afford 80 mg of (R)-2-cyano-N,N-diethyl-3-(2-(2-oxo-2-((1-(4,4,5,5-tetramethyl-1,3,2-dioxaborolan-2-yl)-2-(p-tolyl)ethyl)amino)ethyl)-1,2,3,4-tetrahydroisoquinolin-7-yl)acrylamide as a yellow solid.

To a solution of (R)-2-cyano-N,N-diethyl-3-(2-(2-oxo-2-((1-(4,4,5,5-tetramethyl-1,3,2-dioxaborolan-2-yl)-2-(p-tolyl)ethyl)amino)ethyl)-1,2,3,4-tetrahydroisoquinolin-7-yl)acrylamide (80 mg, 0.137 mmol) in MeOH (2 mL) were added hexane (2 mL) and 1 N HCl (1 mL). After stirring at rt for 3 h, the hexane layer was discarded and the methanol layer was diluted with water (20 mL) and freeze dried directly. This crude product was purified by silica gel column (Methanol as eluent) to afford 7 mg of (R)-(1-(2-(7-(2-cyano-3-(diethylamino)-3-oxoprop-1-en-1-yl)-3,4-dihydroisoquinolin-2(1H)-yl)acetamido)-2-(p-tolyl)ethyl)boronic acid as a yellow solid. LC-MS m/z: 503.3 [M+1].

Example 109

(R)-(1-(2-(7-(2-cyano-3-(diethylamino)-3-oxoprop-1-en-1-yl)-3,4-dihydroisoquinolin-2(1H)-yl)acetamido)-2-phenylethyl)boronic Acid

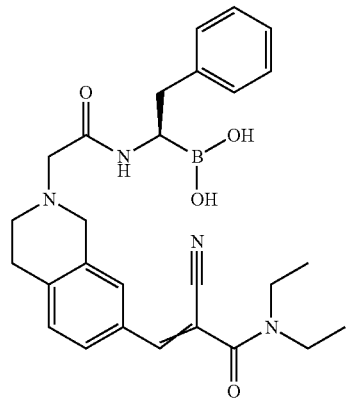 [SMILES: CCN(CC)C(=O)C(C#N)=Cc1ccc2c(c1)CN(CC(=O)N[C@@H](Cc1ccccc1)B(O)O)CC2]

The title compound was prepared as in example 108 by replacing (R)-1-(4,4,5,5-tetramethyl-1,3,2-dioxaborolan-2-yl)-2-(p-tolyl)ethan-1-amine hydrochloride with (R)-2-phenyl-1-((3aS,4S,6S,7aR)-3a,5,5-trimethylhexahydro-4,6-methanobenzo[d][1,3,2]dioxaborol-2-yl)ethan-1-amine hydrochloride. LC-MS m/z: 489.3 [M+1].

A list of the compounds that can be useful as proteasome inhibitors is provided in Table 1 below:

Biological Examples

Example 1

Immunoproteasome and Constitutive Proteasome Enzymatic Activity Assays

A Caliper-based proteasome assay (Caliper Life Sciences, Hopkinton, MA) was used to measure inhibition of the immunoproteasome LMP7/B5i subunit, the immunoproteasome LPM2/βli subunit, and the constitutive proteasome 05c unit for a compound of Formula (I). For LMP7 and 05c, serial dilutions of test compounds were incubated with either human recombinant immunoproteasome or constitutive proteasome (0.3 nM enzyme) and a carboxyfluorescein (FAM)-labeled peptide substrate FAM-TYETFKSIMKKSPF-$NH_2$ (1 μM) at rt for 3 h. The reaction was then terminated with a buffer containing the known proteasome inhibitor carfilzomib at a concentration of 5 uM. For LMP2, serial dilutions of test compounds were incubated with human recombinant immunoproteasome (0.3 nM enzyme) and a carboxyfluorescein (FAM)-labeled peptide substrate FAM-GLTNIKTEEISEVNLDAEFRK-$NH_2$ (1 μM) at rt for 2 h. The reaction was then terminated with a buffer containing the known proteasome inhibitor ixazomib at a concentration of 6.7 uM. The reaction buffer was 20 mM Hepes pH 7.4, 0.01% bovine serum albumin, 0.015% SDS, 0.5 mM EDTA, 1% DMSO. The peptide cleavage reaction product was quantified on a Caliper LabChip 3000. Percent inhibition was calculated for each compound dilution and the concentration that produced 50% inhibition was calculated. This value is presented as the $IC_{50}$. The $IC_{50}$ values for a representative no. of compounds are provided below.

| Synthetic Ex # | LMP7 subunit $IC_{50}$ (nM) | β5c subunit $IC_{50}$ (nM) | LMP2 subunit $IC_{50}$ (nM) |
|---|---|---|---|
| 1 | 6 | 32 | nd |
| 2 | 3 | 66 | 160 |
| 3 | 10 | 120 | nd |
| 4 | 1 | 7 | 16 |
| 5 | 3 | 95 | 140 |
| 6 | 8 | 89 | 84 |
| 7 | 5 | 60 | 500 |
| 8 | 16 | 420 | nd |
| 9 | 8 | 100 | 820 |
| 10 | 5 | 74 | 970 |
| 11 | 2 | 310 | >5000 |
| 12 | 4 | 100 | nd |
| 13 | 149 | 3930 | nd |
| 14 | 0.2 | 4 | 3240 |
| 15 | 8 | 3240 | 2920 |
| 16 | 33 | 3680 | 3570 |
| 17 | 8 | 1310 | >5000 |
| 18 | 15 | 85 | nd |
| 19 | 11 | 43 | 170 |
| 20 | 3 | 32 | 120 |
| 21 | 27 | 260 | >5000 |
| 22 | 3 | 27 | 100 |
| 23 | 0.8 | 8 | >5000 |
| 24 | 12 | 1930 | 1890 |
| 25 | 8 | 4150 | 3000 |
| 26 | 4 | 34 | 310 |
| 27 | 3 | 25 | 160 |
| 28 | 2 | 34 | 49 |
| 29 | 6 | 36 | 17 |
| 30 | 4 | 120 | 150 |
| 31 | 4 | 120 | 270 |
| 32 | 4 | 60 | 180 |

| Synthetic Ex # | LMP7 subunit IC$_{50}$ (nM) | β5c subunit IC$_{50}$ (nM) | LMP2 subunit IC$_{50}$ (nM) |
|---|---|---|---|
| 33 | 5 | 95 | 100 |
| 34 | 8 | 80 | 120 |
| 35 | 2 | 66 | >5000 |
| 36 | 8 | 320 | 3540 |
| 37 | 16.8 | 494.6 | 223.2 |
| 38 | 7.3 | 161.6 | 223.1 |
| 39 | 14.0 | 136.3 | 324.8 |
| 40 | 8.5 | 70.0 | 73.9 |
| 41 | 4.1 | 176.3 | 320.2 |
| 42 | 6.0 | 191.8 | 393.3 |
| 43 | 2.9 | 39.4 | 122.1 |
| 44 | 2.1 | 387.7 | 3133.1 |
| 45 | 4.3 | 92.7 | 1249.5 |
| 46 | 4.6 | 141.0 | 369.9 |
| 47 | 5.3 | 72.2 | 438.4 |
| 48 | 5.1 | 90.4 | 414.7 |
| 49 | 4.9 | 1126.2 | 2896.8 |
| 50 | 1.5 | 1086.6 | >5000 |
| 51 | 20.2 | 122.2 | 306.4 |
| 52 | 10.3 | >5000 | >5000 |
| 53 | 1.0 | 212.1 | >5000 |
| 54 | 3.3 | 610.1 | >5000 |
| 55 | 2.0 | 1180.5 | >5000 |
| 56 | 3.8 | 438.6 | 1767.1 |
| 57 | 1.8 | 187.9 | >5000 |
| 58 | 1.7 | 254.9 | >5000 |
| 59 | 0.9 | 354.1 | 544.1 |
| 60 | 1.1 | 167.2 | 1020.0 |
| 61 | 43.2 | >5000 | >5000 |
| 62 | 185.7 | >5000 | >5000 |
| 63 | 1.4 | 556.1 | 1508.4 |
| 64 | 2.5 | 1919.3 | 4539.2 |
| 65 | 0.6 | 1186.8 | 3556.2 |
| 66 | 4.6 | 33.3 | 74.4 |
| 67 | 0.4 | >5000 | 2319 |
| 68 | 0.7 | >5000 | >5000 |
| 69 | 2.2 | 3022.8 | 3190.5 |
| 70 | 0.6 | >5000 | 4245.8 |
| 71 | 0.9 | 2424 | 2013.5 |
| 72 | 1.4 | >5000 | >5000 |
| 73 | 66.4 | 1901.7 | 2001.2 |
| 74 | 27.1 | >5000 | 2751.4 |
| 75 | 1.4 | 3016.6 | 2519.6 |
| 76 | 3.2 | 3414.1 | >5000 |
| 77 | 42 | 2151 | >5000 |
| 78 | 1.6 | 390 | 690 |
| 79 | 0.9 | 998 | 1597 |
| 80 | 43 | 2573 | >5000 |
| 81 | 5.2 | 438 | 2830 |
| 82 | 24 | >5000 | >5000 |
| 83 | 37 | 1975 | >5000 |
| 84 | 1.9 | 240 | 2015 |
| 85 | 1.1 | 1171 | >5000 |
| 86 | 0.9 | 779 | >5000 |
| 87 | 1.6 | 197 | >5000 |
| 88 | 1.2 | 802 | >5000 |
| 89 | 0.5 | 869 | >5000 |
| 90 | 4.6 | >5000 | >5000 |
| 91 | 2.3 | 3841 | >5000 |
| 92 | 0.6 | 532 | >5000 |
| 93 | 1.1 | 45 | >5000 |
| 94 | 2.2 | 15 | >5000 |
| 95 | 1.2 | 87 | nd |
| 96 | 2.1 | 328 | nd |
| 97 | 0.7 | 43 | Nd |
| 98 | 0.5 | 71 | Nd |
| 99 | 1.5 | 1740 | nd |
| 100 | 5.2 | 1430 | nd |
| 101 | 0.6 | 440 | >5000 |
| 102 | 2.2 | 1550 | nd |
| 103 | 1.4 | 460 | nd |
| 104 | 3.3 | 2870 | nd |
| 105 | 1.6 | 21 | nd |
| 106 | 4.8 | >5000 | nd |
| 107 | 23 | >5000 | nd |
| 108 | 35 | >5000 | nd |
| 109 | 7.5 | 77 | nd | nd = not determined

Example 2

Inhibition of Proteasome Activity Cells

The cell-based effects of a compound described herein on the immunoproteasome were determined by measuring inhibition of proteasome activity in cells using the Proteasome-Glo™ Cell-Based Reagent (Promega, Madison WI). The Proteasome-Glo™ assay contains a specific luminogenic proteasome substrate in a buffer optimized for cell permeabilization, proteasome activity, and luciferase activity. For the chymotrypsin-like activity (LMP7 and 05c), the peptide substrate is Suc-LLVY-aminoluciferin (Succinyl-leucine-leucine-valine-tyrosine-aminoluciferin). Cleavage of the substrate by proteasome results in luminescent signal which is proportional to the proteasome activity. The cell line THP-1 (a monocytic leukemia cell line enriched in immunoproteasome), the cell line HT-29 (a colorectal adenocarcinoma cell line enriched in constitutive proteasome), and primary human peripheral blood mononuclear cells (PBMC) were used to assess proteasome activity. Cells were seeded in a 96-well plate at 10,000 cells per well in RPMI 1640 high glucose medium with 10% fetal bovine serum (FBS). Compound dilutions were added to cells starting at a concentration of 5 uM and decreasing in tripling dilutions. The final DMSO concentration was 1%. The concentration range was adjusted as needed for compounds of different potencies. The cells treated with compounds were incubated for 2 h at 37° C. in 5% CO$_2$. At the end of the 2 hour incubation period, cells were transferred to white 384 well assay plates. 20 uL of Proteasome-Glo™ Reagent was added to each well and incubated for 10 minutes at rt. The plate was read in the Analyst HT instrument (Molecular Devices, Sunnyvale, CA) using luminescence mode. The percent inhibition of activity was plotted as a function of log compound concentration. The IC$_{50}$ was then calculated for each compound using Prism software from GraphPad Software Inc. (San Diego, CA).

| Synthetic Ex# | PBMC/LMP7 IC$_{50}$ (nM) | HT29/β5c IC$_{50}$ (nM) | PBMC/LMP2 IC$_{50}$ (nM) |
|---|---|---|---|
| 2 | 5 | 73 | 3820 |
| 6 | 7 | nd | >5000 |
| 11 | 3 | nd | >5000 |
| 14 | 2 | nd | 510 |
| 15 | 18 | nd | >5000 |
| 17 | 9 | nd | >5000 |
| 19 | 67 | nd | >5000 |
| 20 | 34 | nd | >5000 |
| 21 | 8 | nd | nd |
| 35 | 3 | nd | nd |
| 50 | 4 | nd | nd |
| 52 | 44 | nd | nd |
| 54 | 4 | nd | nd |
| 55 | 4 | nd | nd |
| 58 | 12 | nd | nd |
| 60 | 2 | nd | nd |

-continued

| Synthetic Ex# | PBMC/LMP7 $IC_{50}$ (nM) | HT29/β5c $IC_{50}$ (nM) | PBMC/LMP2 $IC_{50}$ (nM) |
|---|---|---|---|
| 67 | 2 | nd | nd |
| 70 | 2 | nd | nd | nd = not determined

Example 3

IL-2 Production in Anti-CD3 and Anti-CD28 Stimulated Human PBMCs

Peripheral blood mononuclear cells (PBMCs) isolated from human whole blood were preincubated with or without the test compounds in RPMI 1640+10% fetal bovine serum at 37° C. for 30 min. PBMCs were stimulated with 2.5 ug/mL plate bound anti-CD3 and 1 ug/mL soluble anti-CD28 overnight and supernatant was collected for AlphaLISA IL2 assay. The IL-2 production was measured as AlphaLISA (Perkin Elmer) signal counts using Envision plate reader. Human Blood was obtained from healthy volunteer through Stanford Blood Center. Blood was collected by venipuncture into sodium heparin tubes. Blood was layered over Ficoll-Histopaque in 50 mL conical tube and centrifuged at 2000 rpm for 20 minutes at rt. Mononuclear cells were collected into 50 mL conical tubes, pooled and diluted with 1×PBS to make up final volume to 50 mL in each tube. Cells were pelleted at 1500 rpm for 5 minutes and cells are washed two times. The cells were counted in Vi-Cell using trypan blue to determine cell number and viability. PBMCs were then resuspended in RPMI 1640 with 10% fetal bovine serum at a concentration 1×106 cells/mL.

A 96-well polystyrene plate was coated with 2.5 μg/mL anti-CD3 in PBS overnight at 4° C. The wells in column one were coated with PBS only for unstimulated controls. Test compounds were dissolved at 10 mM in 100% DMSO and 1:3 serial dilutions of compounds were prepared in DMSO. The compounds were further diluted in RPMI with 10% fetal bovine serum medium to make final DMSO 0.2% in 96-well polypropylene plate. To treat PBMC with compounds, 100 uL of 1×105 cells were cultured in 96-well polypropylene plate. Then 8 uL of each diluted compound was added in the corresponding wells in duplicate and 8 uL of medium with 2.5% DMSO was added to control wells. The plates were incubated at 37° C. incubator for 30 min. The anti-CD3 coated plates were washed with PBS twice. 92 uL of media containing 1 ug/mL anti-CD28 were added to all wells except unstimulated controls. In unstimulated wells, 92 uL medium was added. Plates were incubated overnight at 37° C., 5% $CO_2$ incubator.

The next day, 150 uL of supernatant was removed from each well for AlphaLISA IL2 assay. According to manufacturer's protocol (Perkin Elmer), 1X buffer, IL2 standards (10 conc.), 2.5X acceptor plus biotinylated beads mixture, 2X streptavidin donor beads were prepared. To each well, 2.5 uL standards or samples were added and then 10 uL of 2.5X beads were added to each well. The plate was sealed with aluminum plate sealer and incubated at room temp on shaker for 1 hr. 12.5 uL of streptavidin donor beads were added to each well in dark room. The plate was sealed with aluminum plate sealer and incubated at room temp on shaker for 30 min. The plate was read in an Envision plate reader.

The $IC_{50}$ for each compound was determined from a ten-point dose response curve for all compounds, each dose being tested in duplicate wells. The $IC_{50}$ represents the concentration of a compound that shows 50% inhibition of IL-2 production in response to anti-CD3+anti-CD28 stimulated PBMCs with compound to 50% of that in control wells without compounds, and was calculated using curve fitting software (Graphpad Prism, San Diego, CA).

Example 4

Recovery of Enzymatic Activity Upon Dialysis

The dialysis assay was done to determine if a compound binds reversibly or irreversibly to immunoproteasome thereby resulting in reversible or irreversible inhibition of proteasome activity. Compounds exhibiting an irreversible mode of binding will demonstrate no significant return of enzymatic activity following extensive dialysis. Partial or complete recovery of proteasome activity over extended periods of time during dialysis is indicative of slow off-rate kinetics due to formation of a reversible covalent bond. For rapidly reversible compounds complete recovery of proteasome activity upon dialysis should be observed.

A solution containing immunoproteasome was incubated with a compound described herein (test compound) or (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholino-acetamido)-4-phenylbutanamido)-pentanamide (reference compound), an irreversible covalent inhibitor of the immunoproteasome which targets the catalytic threonine of the immunoproteasome subunits (see Kuhn, D. J., et al. 2007. Potent activity of carfilzomib, a novel, irreversible inhibitor of the ubiquitin-proteasome pathway, against preclinical models of multiple myeloma. Blood, 110(9), 3281-3290). Following pre-incubation, the solution containing immunoproteasome and the test compound or reference compound was dialyzed at rt in a buffer of 50 mM Hepes pH 7.5, 0.1% bovine serum albumin, 5 mM magnesium chloride, 1 mM dithiothreitol, and 0.01% Triton X-100 for 1 day, 2 days, and 3 days with a change of dialysis buffer twice daily. Following dialysis, enzymatic activity was measured using the Caliper-based proteasome activity assay (Caliper Life Sciences, Hopkinton, MA). The level of activity of solution with test or reference compound was compared to control samples (i.e., proteasome solution with no inhibitor) also dialyzed for 1 day, 2 days, and 3 days with a change of dialysis buffer twice daily.

Example 5

Durability of Binding in Cells

The durability of binding of proteasome inhibitors was assessed in cells using wash-out assays and the Proteasome-Glo™ Reagent kit. THP-1 cells, HT-29 cells, or PBMC were incubated with an 8-fold dilution series of inhibitor for 2 h. Following 2 h of incubation, cells were washed using 3 occasions of centrifugation followed by resuspension in culture medium. Following inhibitor washout, cells were returned to culture for either 30 minutes, 4 h, or 18 h. Cells were then transferred to white 384 plates, and 20 uL of Proteasome-Glo™ Reagent was added to each well for 10 minutes. Plates were then read on an Analyst HT plate reader using luminescence mode. The percent inhibition of activity was plotted as a function of log compound concentration. The $IC_{50}$ was then calculated for each compound using Prism software from GraphPad.

| Synthetic Ex #2 | PBMC LMP7 IC$_{50}$ (nM) | HT29 β5c IC$_{50}$ (nM) | PBMC LMP2 IC$_{50}$ (nM) |
|---|---|---|---|
| 30 min | 5 | 109 | nd |
| 4 hr | 10 | >5000 | >5000 |
| 18 hr | 126 | >5000 | >5000 |

Example 6

Biochemical Durability of Binding

The durability of binding of proteasome inhibitors was assessed in cells using purified constitutive and immune proteasome and an ELISA-based active site occupancy assay called Pro-CISE. Here, occupancy of a test compound within the active site is measured in a time dependent fashion by blocking binding of a high affinity probe to the proteasome. A buffer of 20 mM Tris-HCl pH 8, 0.5 mM EDTA, 0.03% SDS is utilized for initial steps. 200 nM test compound is incubated with 60 nM proteasome for 1 hr at rt to facilitate compound binding. The mixture is then diluted 50-fold, and a high concentration of 5 uM biotinylated proteasome active binding probe (PABP) is added (See Kirk et al. *Meth Mol Biol* 1172:114 (2014)) at 1, 3, 6, and 24 h following dilution. The probe will bind irreversibly to any proteasome sites that become available following dissociation of the test molecule, providing a read-out of the test compound's durability. The ELISA steps of the procedure utilize a buffer of phosphate buffered saline, 1% bovine serum albumin, 0.1% Tween-20. Streptavidin coated ELISA plates are pre-blocked with ELISA buffer, buffer is removed, and the following are added: 20 uL ELISA buffer, 70 uL 8M guanidine HCl in 20 mM Tris HCl pH 8.0 with 0.5 mM EDTA, and 10 uL of PABP-treated proteasome samples. Mixture is incubated for 1 hr at rt. Plates are washed, incubated with subunit selective immune or constitutive primary antibody overnight at 4° C., washed, incubated with secondary antibody for 2 h at rt, washed, and detected using SuperSignal ELISA Pico Kit solution and luminescence is detected on a Perkin Elmer Envision. The % occupancy at each time point is determined by normalization to conditions with no test compound (maximum signal) or no proteasome (minimum signal) and the compound dissociation half-life (t$_{1/2}$) is determined by fitting the time course to a one-phase exponential decay.

| Synthetic Ex# | LMP7 subunit t$_{1/2}$ (h) | B5c subunit t$_{1/2}$ (h) | LMP2 subunit t$_{1/2}$ (h) |
|---|---|---|---|
| 2 | 15 | <0.5 | 1.6 |
| 3 | 7 | <0.5 | 2.3 |
| 6 | 7 | <0.5 | 1.6 |
| 11 | 14 | <0.5 | <0.5 |
| 14 | 39 | 2.3 | <0.5 |
| 15 | 8 | nd | 0.9 |
| 17 | 14 | nd | 0.6 |
| 19 | 31 | nd | 1.6 |
| 20 | 18 | nd | 0.8 |
| 21 | <0.5 | nd | 0.6 |
| 35 | 9 | <0.5 | <0.5 |
| 50 | 37 | nd | 0.8 |
| 52 | 4.3 | nd | 0.9 |
| 55 | >40 | 1.6 | nd |
| 58 | >40 | <0.5 | nd |
| 60 | 1.9 | <0.5 | nd |
| 67 | 30 | nd | nd |
| 70 | >40 | nd | nd | nd = not determined

The foregoing disclosure has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the disclosure should, therefore, be determined not with reference to the above description, but should instead be determined with reference to the following appended claims, along with the full scope of equivalents to which such claims are entitled.

This application refers to various issued patents, published patent applications, journal articles, and other publications, each of which are incorporated herein by reference.

What is claimed is:

1. A compound of Formula (I):

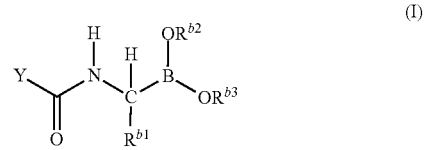

(I)

or a pharmaceutically acceptable salt thereof, wherein:
Y is —OR$^2$, —N(R')R$^2$, or a group of formula

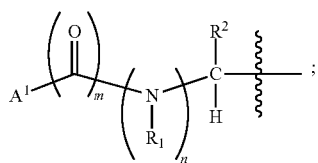

A$^1$ is hydrogen, hydroxy, optionally substituted alkyl, optionally substituted aryl, optionally substituted heteroaryl, optionally substituted heterocyclyl, or —S(=O)$_2$-alkyl, where said alkyl of said —S(=O)$_2$-alkyl is optionally substituted;
R' is H or optionally substituted alkyl;
each R$^1$ is H or optionally substituted alkyl;
each R$^2$ independently is a group of Formula (a) or (b):

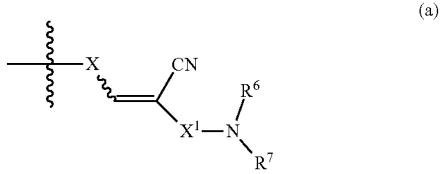

(a)

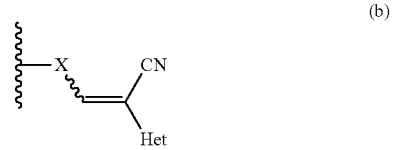

(b)

wherein:
  each X independently is -alkyl-, -alkyl-cycloalkyl-, -alkyl-aryl-, -alkyl-heteroaryl-, -alkyl-heterocyclyl-, -alkyl-heterocyclenyl-, -alkyl-O-alkyl-, -alkyl-O-cycloalkyl-, -alkyl-O-aryl-, -alkyl-O-heteroaryl-, -alkyl-O-heterocyclyl-, -alkyl-O-heterocyclenyl-, -alkyl-N(R)-alkyl-, -alkyl-N(R)-cycloalkyl-, -alkyl-N(R)-aryl-, -alkyl-N(R)-heteroaryl-, -alkyl-N(R)-heterocyclyl-, -alkyl-N(R)-heterocyclenyl-, -alkyl-O-alkyl-cycloalkyl-, -alkyl-O-alkyl-aryl-, -alkyl-O-alkyl-heteroaryl-, -alkyl-O-alkyl-heterocyclyl-, -alkyl-O-alkyl-heterocyclenyl-, -alkyl-N(R)-alkyl-cycloalkyl-, -alkyl-N(R)-alkyl-aryl-, -alkyl-N(R)-alkyl-heteroaryl-, -alkyl-N(R)-alkyl-heterocyclyl-, -alkyl-N(R)-alkyl-heterocyclenyl-, -cycloalkyl-aryl-, -heterocyclyl-alkyl-, -heterocyclyl-cycloalkyl-, -heterocyclyl-aryl-, -heterocyclyl-heteroaryl-, -heterocyclyl-heterocyclyl-, -heterocyclyl-heterocyclenyl-, —O-alkyl-, —O-cycloalkyl-, —O-aryl-, —O-heteroaryl-, —O-heterocyclyl-, —O-heterocyclenyl-, —N(R)-alkyl-, —N(R)-cycloalkyl-, —N(R)-aryl-, —N(R)-heteroaryl-, —N(R)-heterocyclyl-, —N(R)-heterocyclenyl-, —O-alkyl-cycloalkyl-, —O-alkyl-aryl-, —O-alkyl-heteroaryl-, —O— alkyl-heterocyclyl-, —O-alkyl-heterocyclenyl-, —N(R)-alkyl-cycloalkyl-, —N(R)-alkyl-aryl-, —N(R)-alkyl-heteroaryl-, —N(R)-alkyl-heterocyclyl-, —N(R)-alkyl-heterocyclenyl-, -aryl-aryl-, or

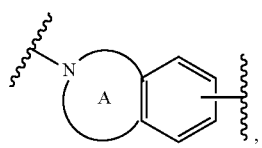

wherein each instance of alkyl, aryl, heteroaryl, cycloalkyl, heterocyclyl, and heterocyclenyl is optionally substituted;
  ring A with the ring nitrogen atom shown is an optionally substituted five- to six-membered heterocyclyl that is benzofused as shown, wherein said benzofused ring A is optionally substituted;
  $X^1$ is —C(=O)— or —S(=O)$_2$—;
  $R^6$ is hydrogen, optionally substituted alkyl, optionally substituted heterocyclyl, or optionally substituted heteroaryl;
  $R^7$ is hydrogen, optionally substituted alkyl, optionally substituted cycloalkyl, optionally substituted aryl, optionally substituted heterocyclyl, or optionally substituted heteroaryl; or
  $R^6$ and $R^7$ together with the nitrogen atom to which they are shown attached form an optionally substituted heterocyclyl or optionally substituted heterocyclenyl;
  Het is an optionally substituted aryl or optionally substituted heteroaryl;
  each R independently is H or optionally substituted alkyl;
  $R^{b1}$ is optionally substituted alkyl, optionally substituted aryl, optionally substituted heteroaryl, optionally substituted cycloalkyl, or optionally substituted heterocyclyl;
  $R^{b2}$ and $R^{b3}$ are independently hydrogen or optionally substituted alkyl; or
  $R^{b2}$ and $R^{b3}$ together with the boron atom to which they are shown attached form a cyclic boronic ester having 2 to 20 carbons, and optionally containing one or two additional cyclic heteroatoms chosen from N, O and S; and
  m and n are independently 0 or 1.

2. A compound of Formula (I'):

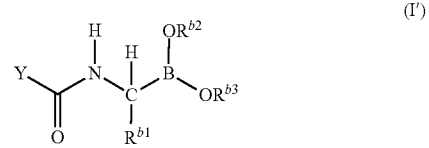

(I')

or a pharmaceutically acceptable salt thereof, wherein:
  Y is —OR$^2$, —N(R')R$^2$, or a group of formula

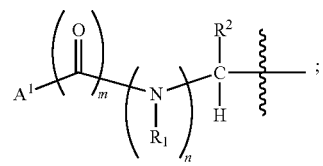

$A^1$ is hydrogen, hydroxy, alkyl, aryl, heteroaryl, heterocyclyl, or —S(=O)$_2$-alkyl, wherein each of said alkyl, aryl, heteroaryl, and heterocyclyl, and the "alkyl" portion of said —S(=O)$_2$-alkyl is optionally substituted with 1-3 substituents independently chosen from halo, hydroxy, alkyl, alkoxy, cyano, haloalkyl, —NH$_2$, —NH(alkyl), —N(alkyl)$_2$, heterocyclyl, aryl, and heteroaryl;
  R' is H or alkyl;
  each $R^1$ is H or alkyl;
  each $R^2$ independently is a group of Formula (a) or (b):

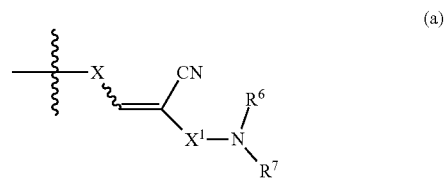

(a)

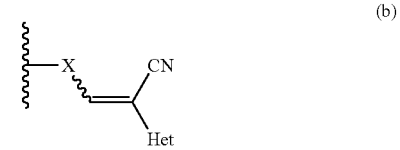

(b)

wherein:
  each X independently is -alkyl-aryl-, -alkyl-O-aryl-, or

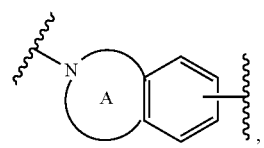

wherein the "aryl" portion of each of said -alkyl-aryl- and -alkyl-O-aryl- is optionally independently substituted with 1-2 substituents chosen from halo, alkoxy, hydoxyalkyl, and cyano;

ring A with the ring nitrogen atom shown is a five- to six-membered heterocyclyl that is benzofused as shown;
$X^1$ is —C(=O)— or —S(=O)$_2$—;
$R^6$ is hydrogen, alkyl, or heterocyclyl;
$R^7$ is alkyl which is optionally substituted with 1-2 substituents chosen from halo and alkoxy; heterocyclyl; or aryl; or
$R^6$ and $R^7$ together with the nitrogen atom to which they are shown attached form a heterocyclyl which is optionally substituted with 1-2 substituents chosen from alkyl and heterocyclyl;
Het is a heteroaryl which is optionally substituted with 1-2 substituents chosen from halo, haloalkyl, alkoxy, and cyano;
$R^{b1}$ is alkyl which is optionally substituted with an aryl or heteroaryl, wherein each of said aryl or heteroaryl is optionally substituted with 1-2 substituents chosen from halo, hydroxy, alkyl, alkoxy, cyano, haloalkyl, —NH$_2$, —NH(alkyl), and —N(alkyl)$_2$;
$R^{b2}$ and $R^{b3}$ are independently hydrogen; and
m and n are independently 0 or 1.

3. The compound or pharmaceutically acceptable salt of claim 1, wherein Y is

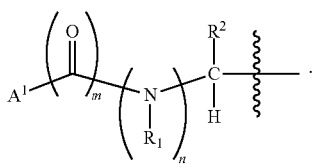

4. The compound or pharmaceutically acceptable salt of claim 1, wherein Y is OR$^2$ or —N(R')R$^2$.

5. The compound or pharmaceutically acceptable salt of claim 3, wherein m and n are each 0.

6. The compound or pharmaceutically acceptable salt of claim 3, wherein m and n are each 1; or m is 0 and n is 1.

7. The compound or pharmaceutically acceptable salt of claim 5, wherein A' is H.

8. The compound or pharmaceutically acceptable salt of claim 6, wherein A' is alkyl, aryl or heteroaryl, each of which is optionally independently substituted with 1-3 substituents independently chosen from halo, hydroxy, alkyl, alkoxy, cyano, haloalkyl, —NH$_2$, —NH(alkyl), —N(alkyl)$_2$, optionally substituted heterocyclyl, optionally substituted aryl, and optionally substituted heteroaryl.

9. The compound or pharmaceutically acceptable salt of claim 1, wherein R$^2$ is a group of Formula (a); each X independently is -alkyl-O-aryl-, -alkyl-aryl-, -alkyl-O-alkyl-aryl-, -alkyl-O-heteroaryl-, -alkyl-heteroaryl-, -alkyl-Oalkyl- heteroaryl-, -alkyl-N(R)-aryl-, -alkyl-N(R)-alkyl-aryl-, -alkyl-N(R)-heteroaryl-, -alkyl- N(R)-alkyl-heteroaryl-, —O-alkyl-aryl-, —O-alkyl-heteroaryl-, —N(R)-alkyl-aryl-, -cycloalkyl-aryl-, -heterocyclyl-aryl-, -aryl-aryl-, -alkyl-heterocyclyl-, -alkyl-heterocyclenyl-, or a benzofused ring A having the structure

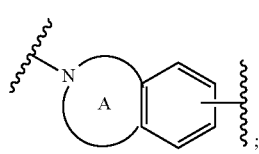

wherein each instance of alkyl, aryl, heteroaryl, cycloalkyl, heterocyclyl, and heterocyclenyl is optionally substituted, and said benzofused ring A is optionally substituted; and X$^1$ is —C(=O).

10. The compound or pharmaceutically acceptable salt of claim 1, wherein R$^2$ is a group of Formula (b).

11. The compound or pharmaceutically acceptable salt of claim 9, wherein said -alkyl-O-aryl- of X is —(CH$_2$)$_{1-2}$—O-phenyl-,

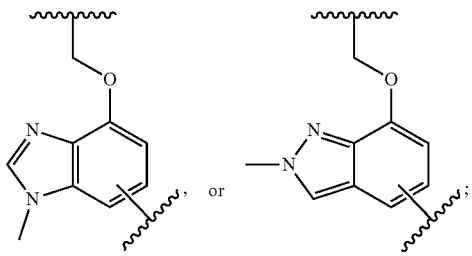

said -alkyl-aryl- of X is —(CH$_2$)$_{1-2}$-phenyl; said -alkyl-O-alkyl-aryl- of X is —(CH$_2$)$_{1-2}$—O—(CH$_2$)$_{1-2}$-phenyl-; said -alkyl-O-heteroaryl- of X is —(CH$_2$)$_{1-2}$—O-pyridyl-; said -alkyl-N(R)-aryl- of X is —(CH$_2$)$_{1-2}$—N(R)-phenyl-; said —N(R)-alkyl-aryl- of X is —N(R)—(CH$_2$)$_{1-2}$-phenyl-; said —O-alkyl-aryl- of X is —O—(CH$_2$)$_{1-2}$-phenyl-; said -cycloalkyl-aryl- of X is -cyclopropyl-phenyl-; said -heterocyclyl-aryl- of X is

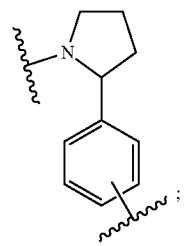

said -aryl-aryl- of X is -phenyl-phenyl-, and said -alkyl-heterocyclenyl- is —(CH$_2$)$_{1-2}$-1,2,3,4-tetrahydroisoquinolinyl-;
wherein each phenyl of X is optionally independently substituted with 1-3 substituents chosen from alkyl, halo, cyano, haloalkyl, and alkoxy.

12. The compound or pharmaceutically acceptable salt of claim 9, wherein X is -alkyl-O-aryl-, -alkyl-aryl-, or -alkyl-O-alkyl-aryl-, wherein each of said aryl independently is phenyl, which is optionally independently substituted with 1-3 substituents chosen from alkyl, halo, cyano, haloalkyl, and alkoxy; wherein said -alkyl-O—, -alkyl-, or -alkyl-O-alkyl-portion respectively of said -alkyl-O-phenyl-, -alkyl-phenyl-, or -alkyl-O-alkyl-phenyl-, and said

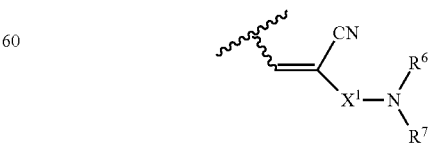

are in 1,3-position with respect to each other on the phenyl ring; and wherein said -alkyl-O—, -alkyl-, or -alkyl-O-alkylportions respectively of said -alkyl-O-phenyl-, -alkyl-phenyl-, or -alkyl-O-alkyl-phenyl, and said

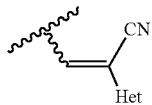

are in 1,3-position with respect to each other on the phenyl ring.

13. The compound or pharmaceutically acceptable salt of claim 9, wherein $R^6$ is hydrogen, alkyl, or optionally substituted heterocyclyl; and $R^7$ is hydrogen, alkyl, haloalkyl, alkoxyalkyl, optionally substituted aryl or optionally substituted heterocyclyl; or $R^6$ and $R^7$ together with the nitrogen atom to which they are shown attached form a optionally substituted heterocyclyl; wherein said optionally substituted heterocyclyl is morpholinyl, 3,5-dimethylmorpholinyl, 3,3-dimethylmopholinyl, azetidinyl, azetidin-1-yl, piperadinyl, piperazinyl, 4-methylpiperazin-1-yl, -piperazinyl-oxetanyl,

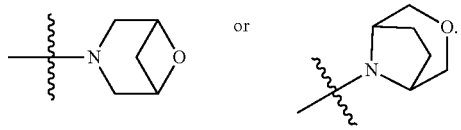 [SMILES: *N1CC2CC(C1)O2 ; "or" ; *N1C2CCC1COC2]

14. The compound or pharmaceutically acceptable salt of claim 10, wherein said Het is a five to ten membered heteroaryl ring, which is optionally substituted with 1-3 substituents chosen from halo, hydroxy, alkyl, alkoxy, cyano, haloalkyl, —NH$_2$, —NH(alkyl), —N(alkyl)$_2$, and heterocyclyl.

15. The compound or pharmaceutically acceptable salt of claim 1, wherein $R^{b1}$ is aryl or alkyl, wherein said alkyl is optionally substituted with —O-aryl, —O-heteroaryl, —N(R)-aryl, —N(R)-heteroaryl, aryl, heterocyclyl, heterocyclenyl, or a heteroaryl, wherein each of said aryl, heteroaryl, heterocyclyl, and heterocyclenyl substituent of said alkyl of $R^{b1}$ is optionally substituted with 1-3 substituents chosen from halo, alkyl, alkoxy, haloalkyl, cyano, —NH$_2$, —NH(alkyl), —N(alkyl)$_2$, and heterocyclyl.

16. The compound or pharmaceutically acceptable salt of claim 1, wherein $R^{b2}$ and $R^{b3}$ are H, or wherein said optionally substituted cyclic boronic ester formed by $R^{b2}$ and $R^{b3}$ together with the boron atom to which they are shown attached is chosen from:

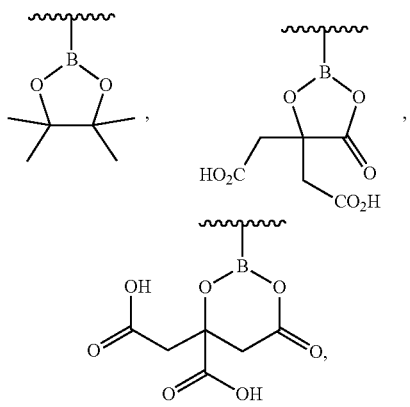

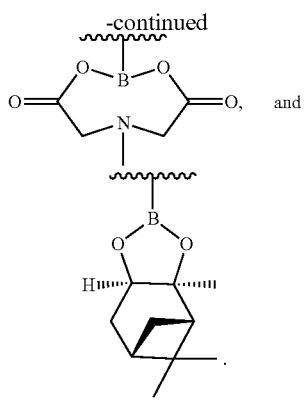

17. The compound or pharmaceutically acceptable salt of claim 1, wherein the compound is chosen from:
- (R)-(1-(3-(3-(3-(tert-butylamino)-2-cyano-3-oxoprop-1-en-1-yl)phenoxy)propanamido)-2-phenylethyl)boronic acid;
- (R)-(1-(3-(3-(3-(tert-butylamino)-2-cyano-3-oxoprop-1-en-1-yl)phenyl)propanamido)-2-phenylethyl)boronic acid;
- (R)-(1-(3-(3-(2-cyano-3-(dimethylamino)-3-oxoprop-1-en-1-yl)phenoxy)propanamido)-2-phenylethyl)boronic acid;
- (R)-(1-(3-(3-(2-cyano-2-(pyridin-2-yl)vinyl)phenoxy)propanamido)-2-phenylethyl)boronic acid;
- (R)-(1-(3-(3-(2-cyano-3-(diethylamino)-3-oxoprop-1-en-1-yl)phenoxy)propanamido)-2-phenylethyl)boronic acid;
- (R)-(1-(3-(3-(3-(tert-butylamino)-2-cyano-3-oxoprop-1-en-1-yl)phenoxy)propanamido)-2-(3-ethylphenyl)ethyl)boronic acid;
- (R)-(1-(3-(3-(2-cyano-3-morpholino-3-oxoprop-1-en-1-yl)phenoxy)propanamido)-2-phenylethyl)boronic acid;
- (R)-(1-(3-(3-(2-cyano-3-oxo-3-((tetrahydro-2H-pyran-4-yl)amino)prop-1-en-1-yl)phenoxy)propanamido)-2-phenylethyl)boronic acid;
- (R)-(1-(3-(3-(3-(tert-butylamino)-2-cyano-3-oxoprop-1-en-1-yl)phenoxy)propanamido)-3-phenylpropyl)boronic acid;
- (R)-(1-(3-(3-(2-cyano-3-(isopropylamino)-3-oxoprop-1-en-1-yl)phenoxy)propanamido)-2-phenylethyl)boronic acid;
- (R)-(1-(3-(3-(3-(tert-butylamino)-2-cyano-3-oxoprop-1-en-1-yl)phenoxy)propanamido)-3,3-dimethylbutyl)boronic acid;
- (R)-(2-(benzofuran-3-yl)-1-(3-(3-(3-(tert-butylamino)-2-cyano-3-oxoprop-1-en-1-yl)phenoxy)propanamido)ethyl)boronic acid;
- (R)-(1-(3-(5-(3-(tert-butylamino)-2-cyano-3-oxoprop-1-en-1-yl)-2-fluorophenoxy)propanamido)-2-phenylethyl)boronic acid;
- (R)-(1-(3-(3-(2-cyano-3-(4-methylpiperazin-1-yl)-3-oxoprop-1-en-1-yl)phenoxy)propanamido)-2-phenylethyl)boronic acid;
- (R)-(1-(3-(3-(2-cyano-3-(methylamino)-3-oxoprop-1-en-1-yl)phenoxy)propanamido)-2-phenylethyl)boronic acid;
- (R)-(1-(3-(3-(2-cyano-2-(pyridin-2-yl)vinyl)phenoxy)propanamido)-3-phenylpropyl)boronic acid;
- (R)-(1-(3-(3-(2-cyano-3-(methyl(phenyl)amino)-3-oxoprop-1-en-1-yl)phenoxy)propanamido)-2-phenylethyl)boronic acid;

(R)-(2-(benzofuran-3-yl)-1-(3-(3-(2-cyano-2-(pyridin-2-yl)vinyl)phenoxy)propanamido)ethyl)boronic acid;
(R)-(1-(4-(3-(2-cyano-3-(dimethylamino)-3-oxoprop-1-en-1-yl)phenyl)butanamido)-2-phenylethyl)boronic acid;
(R)-(1-(4-(3-(2-cyano-2-(1H-1,2,4-triazol-1-yl)vinyl)phenyl)butanamido)-2-phenylethyl)boronic acid;
(R)-(1-(3-(5-(2-cyano-3-(dimethylamino)-3-oxoprop-1-en-1-yl)-2-methoxyphenoxy)propanamido)-2-phenylethyl)boronic acid;
(R)-(1-(3-(5-(2-cyano-3-(dimethylamino)-3-oxoprop-1-en-1-yl)-2-fluorophenoxy)propanamido)-2-phenylethyl)boronic acid;
(R)-(1-(3-(5-(2-cyano-2-(pyridin-2-yl)vinyl)-2-fluorophenoxy)propanamido)-2-phenylethyl)boronic acid;
(R)-(1-(3-(5-(2-cyano-2-(pyridin-2-yl)vinyl)-2-methoxyphenoxy)propanamido)-2-phenylethyl)boronic acid;
(R)-(1-(3-(3-(3-(azetidin-1-yl)-2-cyano-3-oxoprop-1-en-1-yl)phenoxy)propanamido)-2-phenylethyl)boronic acid;
(R)-(1-(3-(3-(2-cyano-3-(ethylamino)-3-oxoprop-1-en-1-yl)phenoxy)propanamido)-2-phenylethyl)boronic acid;
(R)-(1-(3-(3-(2-cyano-3-(4-(oxetan-3-yl)piperazin-1-yl)-3-oxoprop-1-en-1-yl)phenoxy)propanamido)-2-phenylethyl)boronic acid;
(R)-(1-(3-(3-(2-cyano-2-(5-(trifluoromethyl)pyridin-2-yl)vinyl)phenoxy)propanamido)-2-phenylethyl)boronic acid;
(R)-(1-(3-(3-(2-cyano-2-(3-fluoropyridin-2-yl)vinyl)phenoxy)propanamido)-2-phenylethyl)boronic acid;
(R)-(1-(3-(3-(2-cyano-3-(dimethylamino)-3-oxoprop-1-en-1-yl)-2-fluorophenoxy)propanamido)-2-phenylethyl)boronic acid;
(R)-(1-(3-(2,6-dichloro-3-(2-cyano-3-(dimethylamino)-3-oxoprop-1-en-1-yl)phenoxy)propanamido)-2-phenylethyl)boronic acid;
(R)-(1-(3-(2,6-dichloro-3-(2-cyano-2-(pyridin-2-yl)vinyl)phenoxy)propanamido)-2-phenylethyl)boronic acid;
(R)-(1-(3-(3-(2-cyano-2-(pyridin-2-yl)vinyl)-2-fluorophenoxy)propanamido)-2-phenylethyl)boronic acid;
(R)-(1-(3-(3-(2-cyano-3-(dimethylamino)-3-oxoprop-1-en-1-yl)-5-fluorophenoxy)propanamido)-2-phenylethyl)boronic acid;
(R)-(1-(3-(3-(2-cyano-3-(dimethylamino)-3-oxoprop-1-en-1-yl)-4-fluorophenoxy)propanamido)-2-phenylethyl)boronic acid;
(R)-(1-(3-(3-(2-cyano-2-(pyridin-2-yl)vinyl)-4-fluorophenoxy)propanamido)-2-phenylethyl)boronic acid;
(R)-(1-(3-(3-(2-cyano-3-(dimethylamino)-3-oxoprop-1-en-1-yl)phenoxy)propanamido)-2-(2,4-dimethylphenyl)ethyl)boronic acid;
(R)-(1-(3-(3-(2-cyano-2-(pyridin-2-yl)vinyl)phenoxy)propanamido)-2-(2,4-dimethylphenyl)ethyl)boronic acid;
(R)-(1-(3-(3-(2-cyano-3-((2-methoxyethyl)amino)-3-oxoprop-1-en-1-yl)phenoxy)propanamido)-2-phenylethyl)boronic acid;
(R)-(1-(3-(3-(2-cyano-3-((1-methoxy-2-methylpropan-2-yl)amino)-3-oxoprop-1-en-1-yl)phenoxy)propanamido)-2-phenylethyl)boronic acid;
(R)-(1-(3-(3-(2-cyano-3-((2-methoxy-2-methylpropyl)amino)-3-oxoprop-1-en-1-yl)phenoxy)propanamido)-2-phenylethyl)boronic acid;
(R)-(1-(2-((3-(2-cyano-3-(dimethylamino)-3-oxoprop-1-en-1-yl)benzyl)oxy)acetamido)-2-phenylethyl)boronic acid;
(R)-(1-(3-(3-(2-cyano-2-(3-methoxypyridin-2-yl)vinyl)phenoxy)propanamido)-2-phenylethyl)boronic acid;
(R)-(1-(2-(7-(2-cyano-2-(pyridin-2-yl)vinyl)-3,4-dihydroisoquinolin-2(1H)-yl)acetamido)-2-phenylethyl)boronic acid;
(R)-(2-(benzofuran-3-yl)-1-(2-(7-(2-cyano-3-(ethyl(tetrahydro-2H-pyran-4-yl)amino)-3-oxoprop-1-en-1-yl)-3,4-dihydroisoquinolin-2(1H)-yl)acetamido)ethyl)boronic acid;
(R)-(1-(2-(7-(2-cyano-3-(diethyl amino)-3-oxoprop-1-en-1-yl)-3,4-dihydroisoquinolin-2(1H)-yl)acetamido)-2-(p-tolyl)ethyl)boronic acid;
(R)-(1-(2-(7-(2-cyano-3-(diethyl amino)-3-oxoprop-1-en-1-yl)-3,4-dihydroisoquinolin-2(1H)-yl)acetamido)-2-phenylethyl)boronic acid;
(R)-1-(3-(3-(2-cyano-3-(dimethylamino)-3-oxoprop-1-enyl)phenoxy)propanamido)-2-phenylethylboronic acid;
(R)-1-(3-(3-(2-cyano-3-(diethyl amino)-3-oxoprop-1-enyl)phenoxy)propanamido)-2-phenylethylboronic acid;
(R)-1-(3-(3-(2-cyano-3-morpholino-3-oxoprop-1-enyl)phenoxy)propanamido)-2-phenylethylboronic acid;
(R)-1-(3-(3-(2-cyano-3-oxo-3-(tetrahydro-2H-pyran-4-ylamino)prop-1-enyl)phenoxy)propanamido)-2-phenylethylboronic acid;
(R)-1-(3-(3-(3-(tert-butylamino)-2-cyano-3-oxoprop-1-enyl)phenoxy)propanamido)-3-phenylpropylboronic acid;
(R)-1-(3-(3-(2-cyano-3-(isopropylamino)-3-oxoprop-1-enyl)phenoxy)propanamido)-2-phenylethylboronic acid;
(R)-1-(3-(3-(3-(tert-butylamino)-2-cyano-3-oxoprop-1-enyl)phenoxy)propanamido)-3,3-dimethylbutylboronic acid;
(R)-1-((S)-4-(3-(3-(tert-butylamino)-2-cyano-3-oxoprop-1-enyl)phenyl)-2-(2,5-dichlorobenzamido)butanamido)-2-phenylethylboronic acid;
((R)-1-((S)-4-(3-(3-(tert-butylamino)-2-cyano-3-oxoprop-1-en-1-yl)phenyl)-2-(pyrazine-2-carboxamido)butanamido)-2-phenyl ethyl)boronic acid;
((R)-1-((R)-4-(3-(3-(tert-butylamino)-2-cyano-3-oxoprop-1-en-1-yl)phenyl)-2-(2,5-dichlorobenzamido)butanamido)-2-phenyl ethyl)boronic acid;
(R)-(1-((((3-(2-cyano-3-(dimethylamino)-3-oxoprop-1-en-1-yl)benzyl)oxy)carbonyl)amino)-2-phenylethyl)boronic acid;
(R)-(1-((((3-(3-(tert-butylamino)-2-cyano-3-oxoprop-1-en-1-yl)benzyl)oxy)carbonyl)amino)-2-phenylethyl)boronic acid;
(R)-(1-(((3-(2-cyano-3-(dimethylamino)-3-oxoprop-1-en-1-yl)phenethoxy)carbonyl)amino)-2-phenylethyl)boronic acid;
(R)-(2-(benzofuran-3-yl)-1-(((3-(2-cyano-2-(pyridin-2-yl)vinyl)phenethoxy)carbonyl)amino)ethyl)boronic acid;
(R)-(1-(((3-(2-cyano-2-(pyridin-2-yl)vinyl)phenethoxy)carbonyl)amino)-2-phenylethyl)boronic acid;
(R)-(1-(((3-(2-cyano-3-(dimethylamino)-3-oxoprop-1-en-1-yl)phenethoxy)carbonyl)amino)-2-(p-tolyl)ethyl)boronic acid;
(R)-(1-(((3-(2-cyano-3-(diethyl amino)-3-oxoprop-1-en-1-yl)phenethoxy)carbonyl)amino)-2-phenylethyl)boronic acid;
(R)-(2-(benzofuran-3-yl)-1-(((3-(2-cyano-3-(dimethylamino)-3-oxoprop-1-en-1-yl)phenethoxy)carbonyl)amino)ethyl)boronic acid;

(R)-(1-(((3-(2-cyano-2-(3-fluoropyridin-2-yl)vinyl) phenethoxy)carbonyl)amino)-2-phenylethyl)boronic acid;
(R)-(1-(((3-(2-cyano-3-(di ethyl amino)-3-oxoprop-1-en-1-yl)phenethoxy)carbonyl)amino)-2-(p-tolyl)ethyl)b oronic acid;
(R)-(1-(((3-(2-cyano-2-(5-(trifluoromethyl)pyri din-2-yl) vinyl)phenethoxy)carbonyl)amino)-2-phenylethyl)boronic acid;
(R)-(1-(((3-(2-cyano-2-(pyridin-2-yl)vinyl)phenethoxy) carbonyl)amino)-2-(ptolyl)ethyl)boronic acid;
(R)-(2-(benzofuran-3-yl)-1-(((3-(2-cyano-3-(diethylamino)-3-oxoprop-1-en-1-yl)phenethoxy)carbonyl) amino)ethyl)boronic acid;
(R)-(1-(((3-(2-cyano-2-(pyrimidin-4-yl)vinyl) phenethoxy)carbonyl)amino)-2-phenylethyl)boronic acid;
(R)-(1-(((3-(2-cyano-2-(pyrimidin-2-yl)vinyl) phenethoxy)carbonyl)amino)-2-phenylethyl)boronic acid;
(R)-(1-(((3-(2-cyano-2-(pyrazin-2-yl)vinyl)phenethoxy) carbonyl)amino)-2-phenylethyl)boronic acid;
(R)-(1-(((3-(2-cyano-3-(ethyl(isopropyl)amino)-3-oxoprop-1-en-1-yl)phenethoxy)carbonyl)amino)-2-phenylethyl)boronic acid;
((R)-1-(((3-(2-cyano-3-((3R,5R)-3,5-dimethylmorpholino)-3-oxoprop-1-en-1-yl)phenethoxy)carbonyl) amino)-2-phenylethyl)boronic acid;
((1R)-1-(((3-(3-(3-oxa-8-azabicyclo[3.2.1]octan-8-yl)-2-cyano-3-oxoprop-1-en-1-yl)phenethoxy)carbonyl) amino)-2-phenylethyl)boronic acid;
((R)-1-(((3-(2-cyano-3-((3 S, 5 S)-3,5-dimethylmorpholino)-3-oxoprop-1-en-1-yl)phenethoxy)carbonyl) amino)-2-phenylethyl)boronic acid;
(R)-(1-(((3-(3-(tert-butyl(ethyl)amino)-2-cyano-3-oxoprop-1-en-1-yl)phenethoxy)carbonyl)amino)-2-phenylethyl)boronic acid;
(R)-(1-(((3-(2-cyano-3-(ethyl(tetrahydro-2H-pyran-4-yl) amino)-3-oxoprop-1-en-1-yl)phenethoxy)carbonyl) amino)-2-phenylethyl)boronic acid;
(R)-(1-(((3-(3-(tert-butyl(methyl)amino)-2-cyano-3-oxoprop-1-en-1-yl)phenethoxy)carbonyl)amino)-2-phenylethyl)boronic acid;
(R)-(1-(((3-(3-(bis(tetrahydro-2H-pyran-4-yl)amino)-2-cyano-3-oxoprop-1-en-1-yl)phenethoxy)carbonyl) amino)-2-phenylethyl)boronic acid;
(R)-(1-(((3-(2-cyano-3-(diisopropylamino)-3-oxoprop-1-en-1-yl)phenethoxy)carbonyl)amino)-2-phenylethyl) boronic acid;
(R)-(1-(((3-(2-cyano-2-(pyridin-2-yl)vinyl)-5-(hydroxymethyl)phenethoxy)carbonyl)amino)-2-phenylethyl)boronic acid;
(R)-(1-(((3-(2-cyano-2-(5-cyanopyridin-2-yl)vinyl) phenethoxy)carbonyl)amino)-2-phenylethyl)boronic acid;
(R)-(1-(((3-(2-cyano-3-(3,3-dimethylmorpholino)-3-oxoprop-1-en-1-yl)phenethoxy)carbonyl)amino)-2-phenylethyl)boronic acid;
(R)-(1-(((3-(2-cyano-2-(5-(trifluoromethyl)pyri din-2-yl) vinyl)phenethoxy)carbonyl)amino)-2-(p-tolyl)ethyl) boronic acid;
(R)-(1-(((3-(2-cyano-2-(1-methyl-6-oxo-1, 6-dihydropyrimidin-4-yl)vinyl)phenethoxy)carbonyl)amino)-2-phenylethyl)boronic acid;
((R)-1-(((3-(2-cyano-3-((3R,5R)-3,5-dimethylmorpholino)-3-oxoprop-1-en-1-yl)phenethoxy)carbonyl) amino)-2-(p-tolyl)ethyl)b oronic acid;
(R)-(2-(4-chlorophenyl)-1-(((3-(2-cyano-3-(di ethyl amino)-3-oxoprop-1-en-1-yl)phenethoxy)carbonyl) amino)ethyl)boronic acid;
(R)-(1-(((3-(2-cyano-2-(pyrimidin-2-yl)vinyl) phenethoxy)carbonyl)amino)-2-(ptolyl)ethyl)boronic acid;
(R)-(1-(((3-(2-cyano-3-(ethyl(tetrahydro-2H-pyran-4-yl) amino)-3-oxoprop-1-en-1-yl)phenethoxy)carbonyl) amino)-2-(p-tolyl)ethyl)b oronic acid;
((1R)-1-(((3-(3-(3-oxa-8-azabicyclo[3.2.1]octan-8-yl)-2-cyano-3-oxoprop-1-en-1-yl)phenethoxy)carbonyl) amino)-2-(p-tolyl)ethyl)b oronic acid;
(R)-(1-(((3-(2-cyano-3-(ethyl (methyl)amino)-3-oxoprop-1-en-1-yl)phenethoxy)carbonyl)amino)-2-phenylethyl)boronic acid;
(R)-(1-(((3-(2-cyano-3-(methyl(2,2,2-trifluoroethyl) amino)-3-oxoprop-1-en-1-yl)phenethoxy)carbonyl) amino)-2-phenylethyl)boronic acid;
((R)-1-(((3-(2-cyano-3-((3 S, 5 S)-3,5-dimethylmorpholino)-3-oxoprop-1-en-1-yl)phenethoxy)carbonyl) amino)-2-(p-tolyl)ethyl)b oronic acid;
(R)-(2-(benzofuran-3-yl)-1-(((3-(2-cyano-3-(3,3-dimethylmorpholino)-3-oxoprop-1-en-1-yl)phenethoxy)carbonyl)amino)ethyl)boronic acid;
(R)-(2-(benzofuran-3-yl)-1-(((3-(2-cyano-3-(ethyl(tetrahydro-2H-pyran-4-yl)amino)-3-oxoprop-1-en-1-yl) phenethoxy)carbonyl)amino)ethyl)boronic acid;
(R)-(2-(benzofuran-3-yl)-1-(((3-cyano-5-(2-cyano-3-(di ethyl amino)-3-oxoprop-1-en-1-yl)phenethoxy)carbonyl)amino)ethyl)boronic acid;
((R)-2-(benzofuran-3-yl)-1-(((3-(2-cyano-3-((3R,5R)-3, 5-dimethylmorpholino)-3-oxoprop-1-en-1-yl) phenethoxy)carbonyl)amino)ethyl)boronic acid;
(R)-(1-(((3-(2-cyano-2-(1H-1,2,4-triazol-1-yl)vinyl) phenethoxy)carbonyl)amino)-2-phenylethyl)boronic acid;
(R)-(1-(((3-cyano-5-(2-cyano-3-(di ethyl amino)-3-oxoprop-1-en-1-yl)phenethoxy)carbonyl)amino)-2-(p-tolyl)ethyl)b oronic acid;
(R)-(1-(((3-cyano-5-(2-cyano-3-(ethyl(tetrahydro-2H-pyran-4-yl)amino)-3-oxoprop-1-en-1-yl)phenethoxy) carbonyl)amino)-2-phenylethyl)boronic acid;
(R)-(1-(((3-cyano-5-(2-cyano-3-(ethyl(tetrahydro-2H-pyran-4-yl)amino)-3-oxoprop-1-en-1-yl)phenethoxy) carbonyl)amino)-2-(p-tolyl)ethyl)boronic acid;
(R)-(1-(((3-cyano-5-(2-cyano-3-(di ethyl amino)-3-oxoprop-1-en-1-yl)phenethoxy)carbonyl)amino)-2-phenylethyl)boronic acid;
(R)-(1-(((3-(2-cyano-2-(1H-1,2,4-triazol-1-yl)vinyl) phenethoxy)carbonyl)amino)-3-phenylpropyl)boronic acid;
(R)-(1-(3-(3-(2-cyano-3-(di ethyl amino)-3-oxoprop-1-en-1-yl)phenethyl)ureido)-2-phenylethyl)boronic acid;
(R)-(1-(3-(3-(2-cyano-2-(pyridin-2-yl)vinyl)phenethyl) ureido)-2-phenylethyl)boronic acid;
(R)-(1-(3-(3-(2-cyano-2-(5-(trifluoromethyl)pyridin-2-yl) vinyl)phenethyl)ureido)-2-phenylethyl)boronic acid;
(R)-(1-(3-(3-(2-cyano-2-(pyridin-2-yl)vinyl)phenethyl) ureido)-2-(p-tolyl)ethyl)boronic acid;
(R)-(1-(3-(3-(2-cyano-2-(5-(trifluoromethyl)pyridin-2-yl) vinyl)phenethyl)ureido)-2-(ptolyl) ethyl)boronic acid;
(R)-(1-(3-(3-(2-cyano-3-(di ethyl amino)-3-oxoprop-1-en-1-yl)phenethyl)ureido)-2-(ptolyl) ethyl)boronic acid;
(R)-(1-(3-(3-(2-cyano-2-(pyrimidin-2-yl)vinyl)phenethyl)ureido)-2-(p-tolyl)ethyl)boronic acid;

(R)-(2-(benzofuran-3-yl)-1-(3-(3-(2-cyano-2-(pyrimidin-2-yl)vinyl)phenethyl)ureido)ethyl)boronic acid;

(R)-(2-(benzofuran-3-yl)-1-(3-(3-(2-cyano-3-(diethyl amino)-3-oxoprop-1-en-1-yl)phenethyl)ureido)ethyl) boronic acid;

(R)-(2-(benzofuran-3-yl)-1-(3-(3-(2-cyano-3-(ethyl(tetrahydro-2H-pyran-4-yl)amino)-3-oxoprop-1-en-1-yl) phenethyl)ureido)ethyl)b oronic acid; and (R)-(1-(3-(3-(2-cyano-2-(1H-1,2,4-triazol-1-yl)vinyl) phenethyl)ureido)-2-(ptolyl)ethyl)b oronic acid;

an individual E or Z isomer thereof; or a pharmaceutically acceptable salt of any of the foregoing compounds.

18. A pharmaceutical composition comprising at least one compound of claim 1, or a pharmaceutical acceptable salt thereof, and a pharmaceutically acceptable excipient.

19. A method of inhibiting Large Multifunctional Protease 2 (LMP2) or Large Multifunctional Protease 7 (LMP7) in a subject comprising administering to said subject in need of said inhibition a therapeutically effective amount of a compound of claim 1, or a pharmaceutically acceptable salt thereof, and thereby inhibiting Large Multifunctional Protease 2 (LMP2) or Large Multifunctional Protease 7 (LMP7).

20. A method of treating a hematological malignancy in a patient in need of such treatment, comprising administering to the patient a therapeutically effective amount of a compound of claim 1, or a pharmaceutically acceptable salt thereof.

21. The method of claim 20, wherein the disease is chosen from multiple myeloma.

\* \* \* \* \*